United States Patent
Jung et al.

(10) Patent No.: US 10,155,724 B2
(45) Date of Patent: Dec. 18, 2018

(54) CONDENSED CYCLIC COMPOUND, COMPOSITION INCLUDING THE SAME, AND ORGANIC LIGHT-EMITTING DEVICE INCLUDING THE CONDENSED CYCLIC COMPOUND

(71) Applicants: SAMSUNG ELECTRONICS CO., LTD., Suwon-si, Gyeonggi-do (KR); Samsung SDI Co., Ltd., Yongin-si, Gyeonggi-do (KR)

(72) Inventors: Yongsik Jung, Yongin-si (KR); Dalho Huh, Suwon-si (KR); Jhunmo Son, Yongin-si (KR); Eunsuk Kwon, Suwon-si (KR); Sangmo Kim, Hwaseong-si (KR); Saeyoun Lee, Suwon-si (KR); Soonok Jeon, Seoul (KR); Yeonsook Chung, Seoul (KR); Jongsoo Kim, Suwon-si (KR); Sooghang Ihn, Hwaseong-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/631,043

(22) Filed: Jun. 23, 2017

(65) Prior Publication Data
US 2017/0369439 A1    Dec. 28, 2017

(30) Foreign Application Priority Data

Jun. 27, 2016 (KR) .................. 10-2016-0080236

(51) Int. Cl.
C07D 209/82 (2006.01)
C07D 405/10 (2006.01)
C09K 11/06 (2006.01)
H01L 51/00 (2006.01)

(52) U.S. Cl.
CPC ......... C07D 209/82 (2013.01); C07D 405/10 (2013.01); C09K 11/06 (2013.01); H01L 51/0032 (2013.01); H01L 51/0072 (2013.01)

(58) Field of Classification Search
CPC ................. C07D 209/82; C07D 405/10
See application file for complete search history.

(56) References Cited

U.S. PATENT DOCUMENTS

| | | |
|---|---|---|
| 2012/0161617 A1 | 6/2012 | Fukuzaki |
| 2014/0131686 A1* | 5/2014 | Kawakami .......... C07D 495/22 257/40 |
| 2014/0284581 A1 | 9/2014 | Zheng |
| 2015/0170226 A1 | 6/2015 | Higgins et al. |
| 2017/0186973 A1 | 6/2017 | Ren et al. |
| 2017/0194570 A1 | 7/2017 | Kang et al. |
| 2017/0365796 A1 | 12/2017 | Kim et al. |

FOREIGN PATENT DOCUMENTS

| | | |
|---|---|---|
| CN | 105418486 A | 3/2016 |
| EP | 3113239 A1 | 12/2015 |
| EP | 2966146 A1 | 1/2016 |
| EP | 3109247 A1 | 12/2016 |
| EP | 3190164 A1 | 7/2017 |
| JP | 2007-091719 A | 4/2007 |
| JP | 2011-054696 A | 3/2011 |
| JP | 2011-176258 A | 9/2011 |
| KR | 10-2011-0088427 A | 8/2011 |
| KR | 10-2011-0117513 A | 10/2011 |
| KR | 10-2014-0145451 A | 12/2014 |
| KR | 2017-0076474 A | 7/2017 |
| KR | 2017-0142066 A | 12/2017 |
| WO | 2017005699 A1 | 1/2017 |

OTHER PUBLICATIONS

Oshiyama, et al. Document No. 141:304397, retrieved from STN; Sep. 30, 2004.*
Extended Search Report dated Nov. 1, 2017, issued by the European Patent Office for European Patent Application No. 17177730.3-1452.
Ming-Shiang Lin et al. "Incorporation of a CN group into mCP: a new bipolar host material for highly efficient blue and white electrophosphorescent devices", J. Mater. Chem., 2012, 22(31), p. 16114.

* cited by examiner

Primary Examiner — Shawquia Jackson
(74) Attorney, Agent, or Firm — Cantor Colburn LLP

(57) ABSTRACT

A condensed cyclic compound represented by Formula 1:

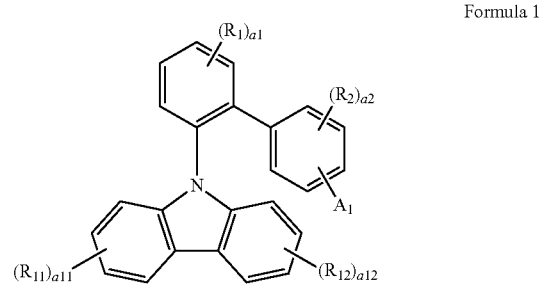

Formula 1 wherein in Formula 1 groups and variables are the same as described in the specification.

22 Claims, 1 Drawing Sheet

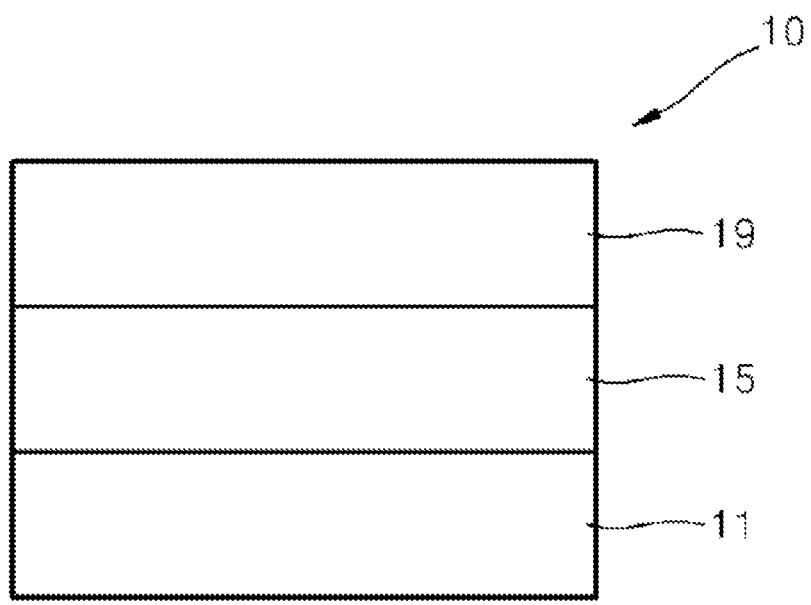

CONDENSED CYCLIC COMPOUND, COMPOSITION INCLUDING THE SAME, AND ORGANIC LIGHT-EMITTING DEVICE INCLUDING THE CONDENSED CYCLIC COMPOUND

CROSS-REFERENCE TO RELATED APPLICATION

This application claims priority to Korean Patent Application No. 10-2016-0080236, filed on Jun. 27, 2016, in the Korean Intellectual Property Office, and all the benefits accruing therefrom under 35 U.S.C. § 119, the content of which is incorporated herein in its entirety by reference.

BACKGROUND

1. Field

The present disclosure relates to a condensed cyclic compound, a composition including the same, and an organic light-emitting device including the condensed cyclic compound.

2. Description of the Related Art

Organic light-emitting devices (OLEDs) are self-emission devices that have wide viewing angles, high contrast ratios, and short response times. In addition, OLEDs display excellent brightness, driving voltage, and response speed characteristics, and produce full-color images.

In an example, an organic light-emitting device includes an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons are changed from an excited state to a ground state, thereby generating light.

Various types of organic light emitting devices are known. However, there still remains a need in OLEDs having low driving voltage, high efficiency, high brightness, and long lifespan.

SUMMARY

Provided are a novel condensed cyclic compound, a composition including the same, and an organic light-emitting device including the condensed cyclic compound.

Additional aspects will be set forth in part in the description which follows and, in part, will be apparent from the description, or may be learned by practice of the presented embodiments.

According to an aspect of an embodiment, a condensed cyclic compound is represented Formula 1:

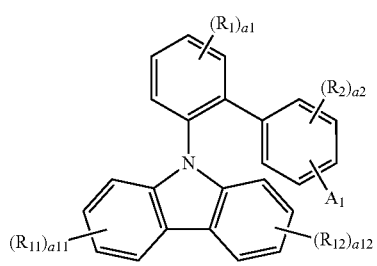

Formula 1

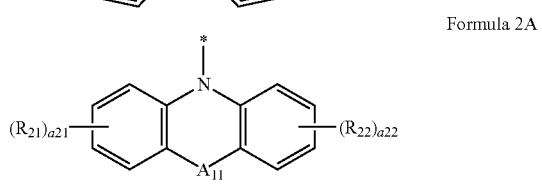

Formula 2A

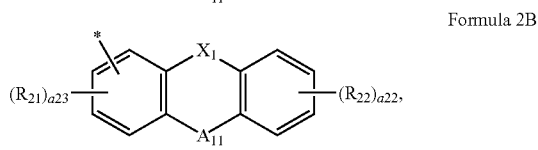

Formula 2B wherein, in Formulae 1, 2A, and 2B, $A_1$ may be a group represented by Formula 2A or 2B,
$A_{11}$ may be a single bond or *—$C(R_{27})(R_{28})$—*',
$X_1$ may be $N(R_{29})$, O, or S,
$R_1$, and $R_2$ may each independently be selected from: hydrogen, deuterium, —F, —Cl, —Br, —I, a cyano group, a $C_1$-$C_{60}$ alkyl group, and a $C_1$-$C_{60}$ alkoxy group; and a $C_1$-$C_{60}$ alkyl group and a $C_1$-$C_{60}$ alkoxy group, each substituted with at least one selected from deuterium, —F, —Cl, —Br, —I, and a cyano group, a1 and a2 may each independently an integer selected from 0 to 4, wherein a sum a1+a2 may be 1 or more, 1, 2, 3, or 4 groups selected from $R_1$ in the number of a1 and $R_2$ in the number of a2 may be a cyano group, $R_{11}$, $R_{12}$, $R_{21}$, $R_{22}$, and $R_{27}$ to $R_{29}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_4)(Q_5)$, and —$B(Q_6)(Q_7)$, a11, a12, a21, and a22 may each independently be an integer selected from 0 to 4, and a23 may be an integer selected from 0 to 3,

* and *' each indicate a binding site to a neighboring atom in a corresponding formula, at least one substituent selected from substituent(s) of the substituted $C_1$-$C_{60}$ alkyl group, the substituted $C_2$-$C_{60}$ alkenyl group, the substituted $C_2$-$C_{60}$ alkynyl group, the substituted $C_2$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, and —$B(Q_{26})(Q_{27})$; and —$Si(Q_{31})(Q_{32})(Q_{33})$, —$N(Q_{34})(Q_{35})$, and —$B(Q_{36})(Q_{37})$, wherein $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one of a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

According to an aspect of another embodiment, a composition includes:

a first compound and a second compound, wherein the first compound is the condensed cyclic compound represented by Formula 1, and wherein the second compound includes at least one selected from a carbazole-containing ring, a dibenzofuran-containing ring, a dibenzothiophene-containing ring, an indenocarbazole-containing ring, an indolocarbazole-containing ring, a benzofurocarbazole-containing ring, a benzothienocarbazole-containing ring, an acridine-containing ring, a dihydroacridine-containing ring, and a triindolobenzene-containing ring and does not include an electron withdrawing group, wherein the electron withdrawing group is selected from:
—F, —$CFH_2$, —$CF_2H$, —$CF_3$, —CN, and —$NC_2$;

a $C_1$-$C_{60}$ alkyl group substituted with at least one selected from —F, —$CF_2H$, —$CF_3$, —CN, and —$NC_2$;

a $C_1$-$C_{60}$ heteroaryl group and a divalent non-aromatic condensed polycyclic heterocyclic group that each includes *=N—*' as a ring-forming moiety; and a $C_1$-$C_{60}$ heteroaryl group and a divalent non-aromatic condensed polycyclic heterocyclic group that are each substituted with at least one selected from deuterium, —F, —$CFH_2$, —$CF_2H$, —$CF_3$, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group and that each includes *=N—*' as a ring-forming moiety.

According to an aspect of another embodiment, a thin film includes the aforementioned composition.

According to an aspect of another embodiment, an organic light-emitting device includes:
- a first electrode;
- a second electrode; and
- an organic layer disposed between the first electrode and the second electrode,
  - wherein the organic layer including an emission layer, and
  - wherein the organic layer includes at least one condensed cyclic compound represented by Formula 1.

BRIEF DESCRIPTION OF THE DRAWINGS

These and/or other aspects will become apparent and more readily appreciated from the following description of the embodiments, taken in conjunction with the FIGURE, which is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

According to an aspect of the present inventive concept, a condensed cyclic compound is represented by Formula 1:

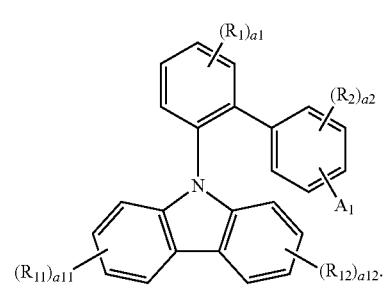

Formula 1

In Formula 1, $A_1$ is a group represented by Formula 2A or 2B:

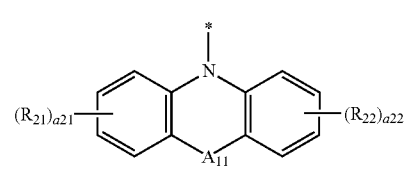

Formula 2A

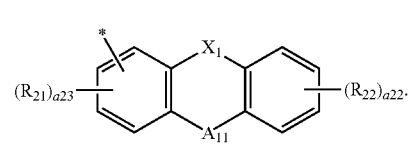

Formula 2B

Formulae 2A and 2B are each independently as defined herein in the present specification.

In Formulae 2A and 2B, $A_{11}$ may be a single bond or *—$C(R_{27})(R_{29})$—*', $X_1$ may be $N(R_{29})$, O, or S, * and *' may each indicate a binding site to a neighboring atom, and $R_{27}$ to $R_{29}$ are each independently as defined herein in the present specification.

In an embodiment, $A_1$ in Formula 1 may be a group represented by Formula 2A, and $A_{11}$ in Formula 2A may be a single bond, but embodiments are not limited thereto.

In Formula 1, $R_1$ and $R_2$ may each independently be selected from:

hydrogen, deuterium, —F, —Cl, —Br, —I, a cyano group, a $C_1$-$C_{60}$ alkyl group, and a $C_1$-$C_{60}$ alkoxy group; and a $C_1$-$C_{60}$ alkyl group and a $C_1$-$C_{60}$ alkoxy group, each substituted with at least one selected from deuterium, —F, —Cl, —Br, —I, and a cyano group.

In various embodiments, in Formula 1, $R_1$ and $R_2$ may each independently be selected from:

hydrogen, deuterium, —F, a cyano group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, and a cyano group, but embodiments are not limited thereto.

In Formula 1, a1 and a2 each indicate the number of groups $R_1$ and the number of groups $R_2$, and a1 and a2 may each independently be an integer selected from 0 to 4, wherein the sum of a1+a2 may be 1 or more.

In an embodiment, in Formula 1, a1 and a2 may each independently be 0, 1, or 2, wherein the sum of a1+a2 may be 1, 2, or 3.

In various embodiments, in Formula 1, a1 and a2 may each independently be 0 or 1, wherein the sum of a1+a2 may be 1 or 2.

In Formula 1, 1, 2, 3, or 4 groups selected from $R_1$ in the number of a1 and $R_2$ in the number of a2 may be a cyano group.

In an embodiment, in Formula 1, 1, 2, or 3 groups selected from $R_1$ in the number of a1 and $R_2$ in the number of a2 may be a cyano group.

In various embodiments, in Formula 1, i) 1 or 2 among $R_1$ in the number of a1 may be a cyano group, and $R_2$ may be a cyano group;

ii) 1 or 2 among $R_1$ in the number of a1 may be a cyano group, and 1 or 2 among $R_2$ in the number of a2 may be a cyano group; or iii) $R_1$ may not be a cyano group, and 1 or 2 among $R_2$ in the number of a2 may be a cyano group, but embodiments are not limited thereto.

In Formulae 1, 2A, and 2B, $R_{11}$, $R_{12}$, $R_{21}$, $R_{22}$, and $R_{27}$ to $R_{29}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_4)(Q_5)$, and —$B(Q_6)(Q_7)$, wherein $Q_1$ to $Q_7$ are each independently as defined herein in the present specification.

In an embodiment, in Formulae 1, 2A, and 2B, $R_{11}$, $R_{12}$, $R_{21}$, $R_{22}$, and $R_{27}$ to $R_{29}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzoxazinyl group, and a pyridobenzothiazinyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzoxazinyl group, and a pyridobenzothiazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —Si($Q_{31}$)($Q_{32}$)($Q_{33}$), —N($Q_{34}$)($Q_{35}$), and —B($Q_{36}$)($Q_{37}$); and —Si($Q_1$)($Q_2$)($Q_3$), —N($Q_4$)($Q_5$), and —B($Q_6$)($Q_7$), wherein $Q_1$ to $Q_7$ and $Q_{31}$ to $Q_{37}$ may each independently be selected from hydrogen, a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group.

In various embodiments, in Formulae 1, 2A, and 2B, $R_{11}$, $R_{12}$, $R_{21}$, $R_{22}$, and $R_{27}$ to $R_{29}$ may each independently be selected from:

hydrogen, deuterium, —F, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a cyano group, —F, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, —F, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from hydrogen, a $C_1$-$C_{20}$ alkyl group, a $C_1$-$C_{20}$ alkoxy group, a phenyl group, a biphenyl group, a terphenyl group, and a naphthyl group.

In various embodiments, $R_{29}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In various embodiments, $R_{29}$ may be selected from:

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group; and a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$), wherein $Q_{31}$ to $Q_{33}$ are each independently as defined herein in the present specification.

In an embodiment, the total number of cyano group(s) in the condensed cyclic compound represented by Formula 1 may be selected from 1 to 4. For example, the total number of cyano group(s) in the condensed cyclic compound represented by Formula 1 may be 1, 2, or 3, but embodiments are not limited thereto.

In various embodiments, $A_1$ in Formula 1 may be selected from groups represented by Formulae 2A-1 and 2B-1 to 2B-4:

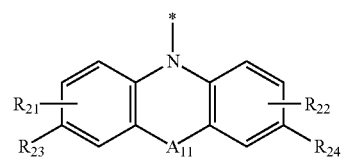

Formula 2A-1

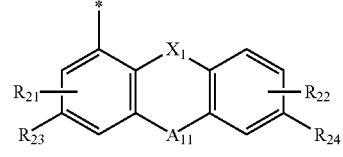

Formula 2B-1

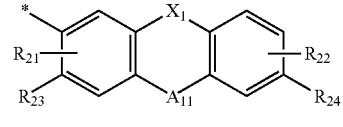

Formula 2B-2

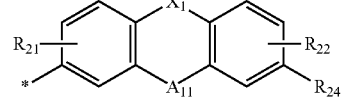

Formula 2B-3

-continued

Formula 2B-4

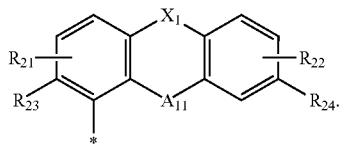

In Formulae 2A-1 and 2B-1 to 2B-4, $A_{11}$, $X_1$, $R_{21}$, $R_{22}$, and * are each independently as defined herein in the present specification, $R_{23}$ is the same as defined herein in connection with $R_{21}$, and $R_{24}$ is the same as defined herein in connection with $R_{22}$.

For example, in Formulae 2A-1 and 2B-1 to 2B-4, at least one of $R_{23}$ and $R_{24}$ may be a cyano group, but embodiments are not limited thereto.

In various embodiments, the condensed cyclic compound may be represented by one selected from Formulae 1A to 1C:

Formula 1A

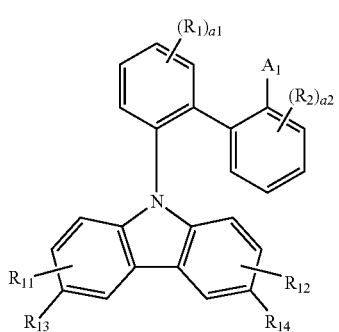

Formula 1B

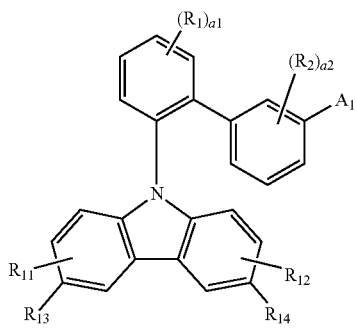

Formula 1C

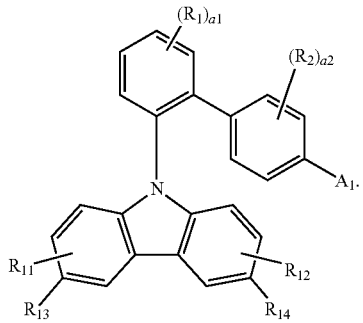

In Formulae 1A to 1C, $A_1$, $R_1$, $R_2$, a1, a2, $R_{11}$, and $R_{12}$ are each independently as defined herein in the present specification, $R_{13}$ is the same as defined herein in connection with $R_{11}$, and $R_{14}$ is the same as defined herein in connection with $R_{12}$.

For example, in Formulae 1A to 1C, at least one of $R_{13}$ and $R_{14}$ may be a cyano group, but embodiments are not limited thereto.

In Formulae 1A to 1C, $A_1$ may be selected from groups represented by Formulae 2A-1 and 2B-1 to 2B-4.

In an embodiment, in Formulae 1A to 1C, $A_1$ may be selected from groups represented by Formulae 2A-1, 2B-1, 2B-2, and 2B-4, and at least one selected from $R_{13}$, $R_{14}$, $R_{23}$, and $R_{24}$ (for example, 1 or 2 among $R_{13}$, $R_{14}$, $R_{23}$, and $R_{24}$) may be a cyano group; or in Formulae 1A to 1C, $A_1$ may be a group represented by Formula 2B-3, and at least one selected from $R_{13}$, $R_{14}$, and $R_{24}$ (for example, 1 or 2 among $R_{13}$, $R_{14}$, and $R_{24}$) may be a cyano group, but embodiments are not limited thereto.

In various embodiments, $A_1$ in Formula 1 (for example, Formulae 1A to 1C) may be identical to a first carbazole ring ("first carbazole ring" is the same as defined herein in connection with Formula 1') included in Formula 1 (for example, Formulae 1A to 1C).

In various embodiments, $A_1$ in Formula 1 (for example, Formulae 1A to 1C) may be different from a first carbazole ring ("first carbazole" is the same as defined herein in connection with Formula 1') included in Formula 1 (for example, Formulae 1A to 1C).

In various embodiments, the condensed cyclic compound represented by Formula 1 (for example, Formulae 1A to 1C) may have a symmetrical structure.

In various embodiments, the condensed cyclic compound represented by Formula 1 (for example, Formulae 1A to 1C) may have an asymmetrical structure.

In various embodiments, the condensed cyclic compound may be represented by one selected from Formulae 1A-1 to 1A-76, 1B-1 to 1B-76, and 1C-1 to 1C-76, but embodiments are not limited thereto:

Formula 1A-1

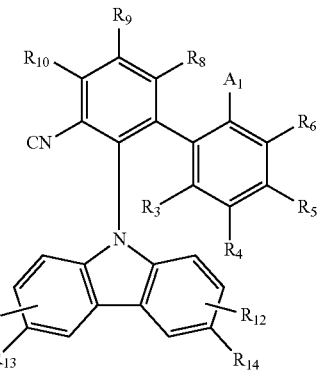

Formula 1A-2

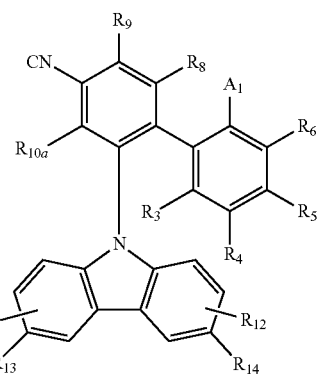

-continued
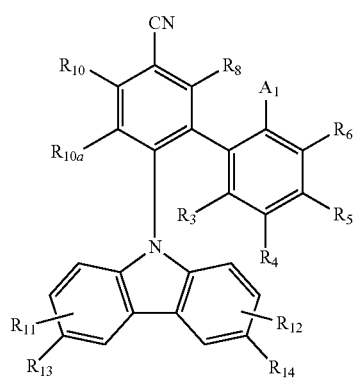
Formula 1A-3

Formula 1A-4
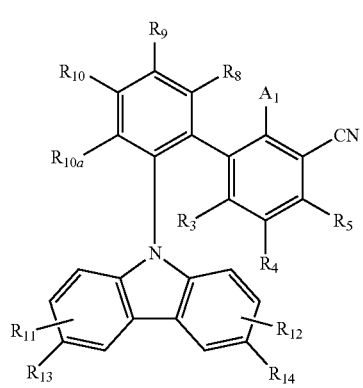
Formula 1A-5

Formula 1A-6
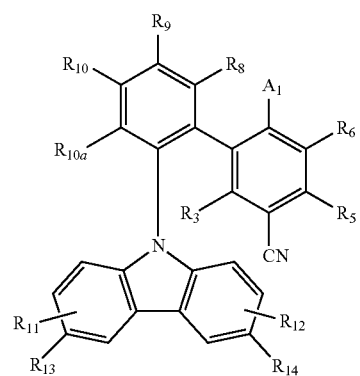
Formula 1A-7
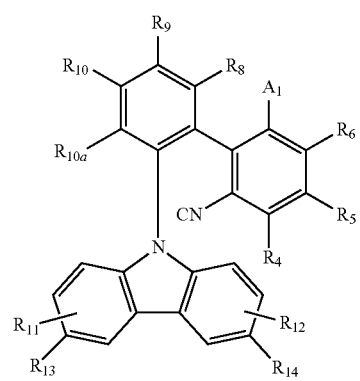
Formula 1A-8
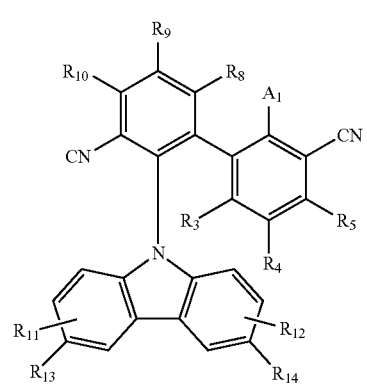
Formula 1A-9
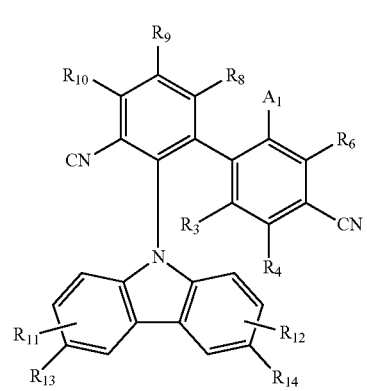
Formula 1A-10

Formula 1A-11
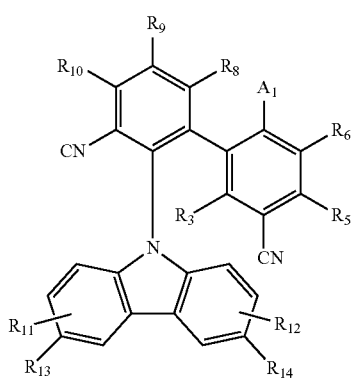
Formula 1A-12
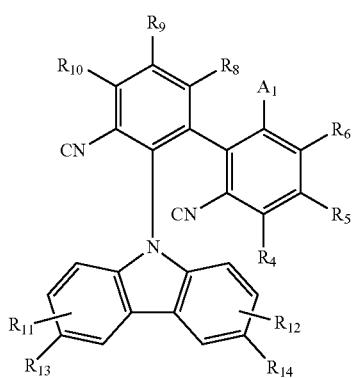
Formula 1A-13
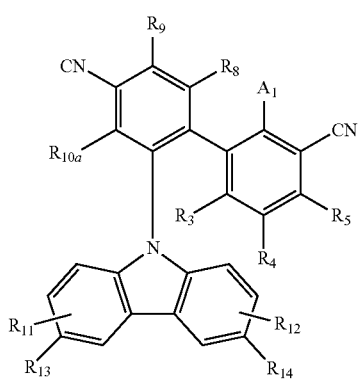
Formula 1A-14
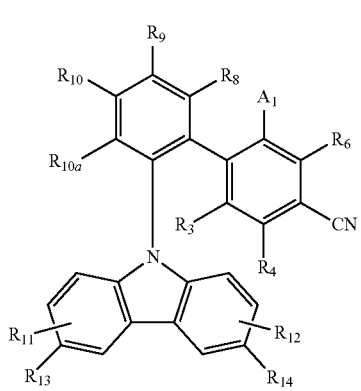
Formula 1A-15
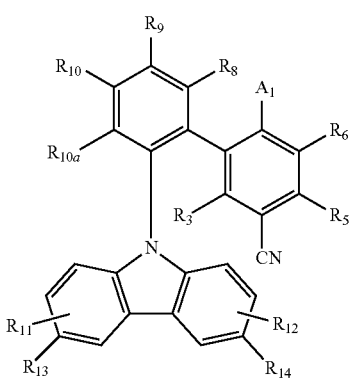
Formula 1A-16
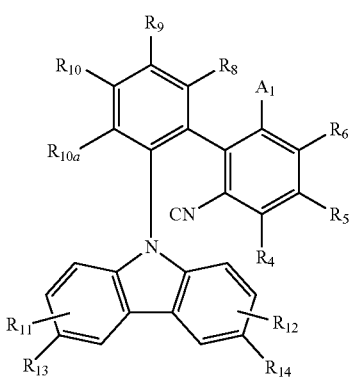
Formula 1A-17
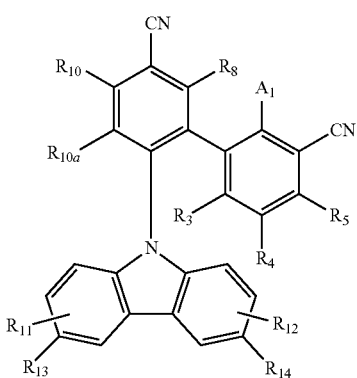
Formula 1A-18
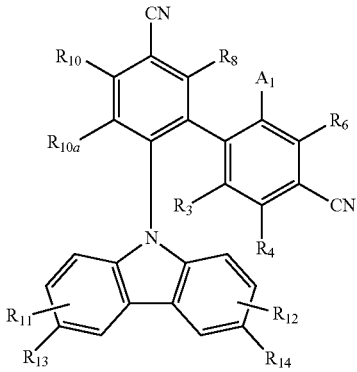

Formula 1A-19

Formula 1A-20

Formula 1A-21

Formula 1A-22

Formula 1A-23

Formula 1A-24

Formula 1A-25

Formula 1A-26

-continued
Formula 1A-27
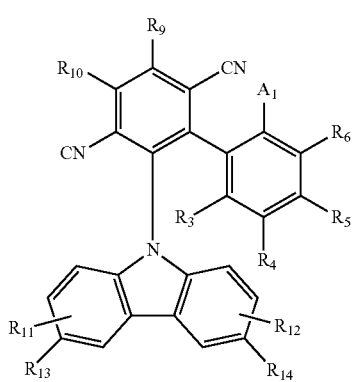
Formula 1A-28
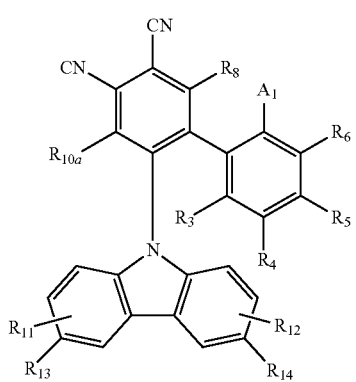
Formula 1A-29
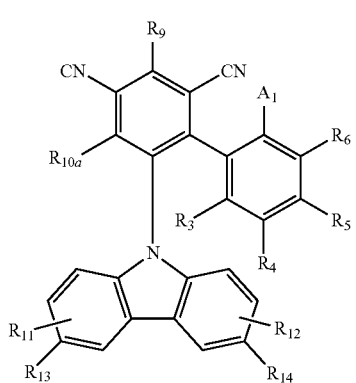
Formula 1A-30
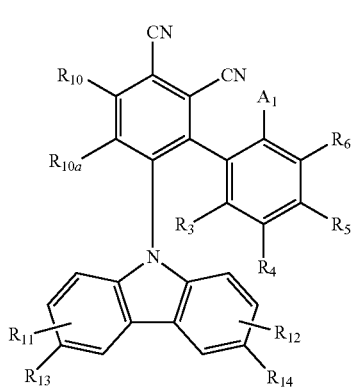
Formula 1A-31
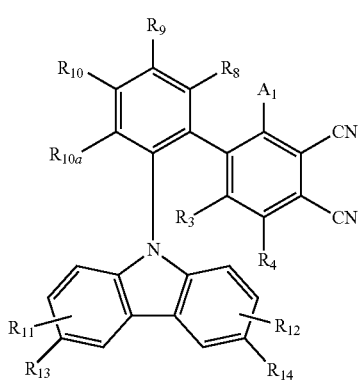
Formula 1A-32
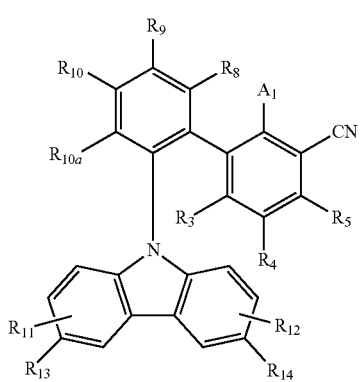
Formula 1A-33
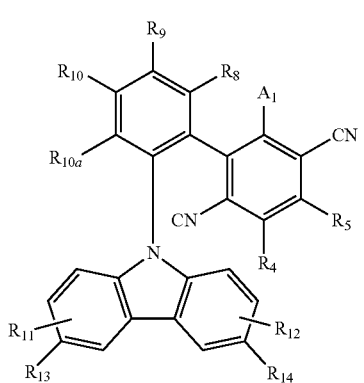
Formula 1A-34
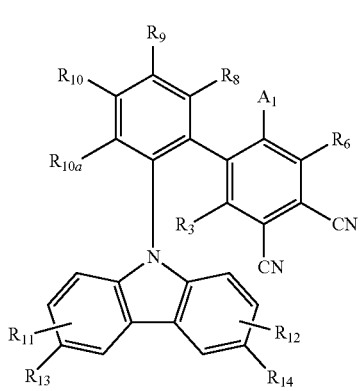

Formula 1A-35
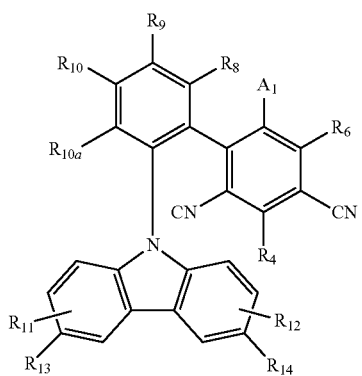
Formula 1A-36
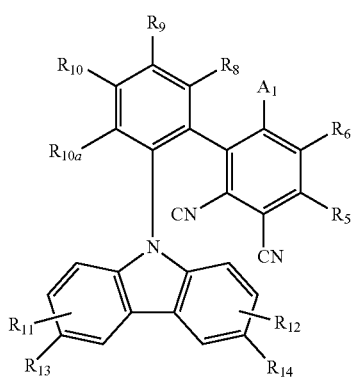
Formula 1A-37
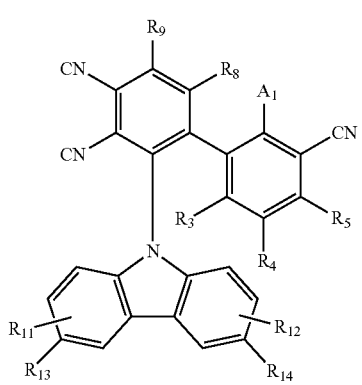
Formula 1A-38
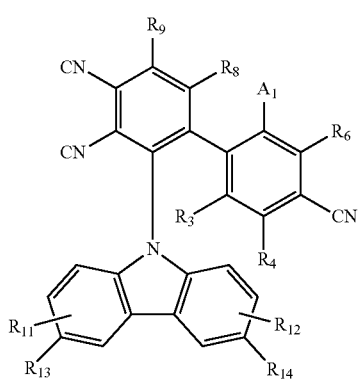
Formula 1A-39
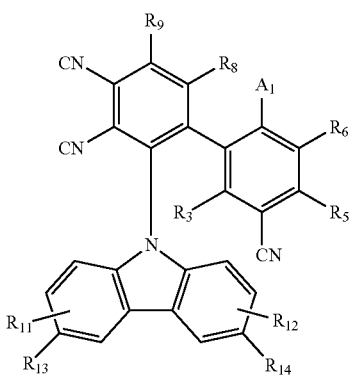
Formula 1A-40
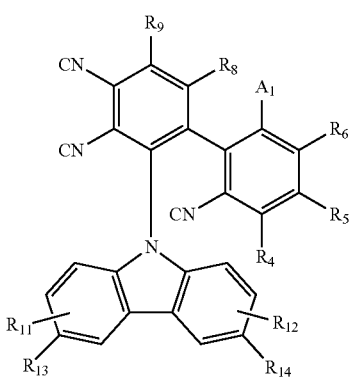
Formula 1A-41
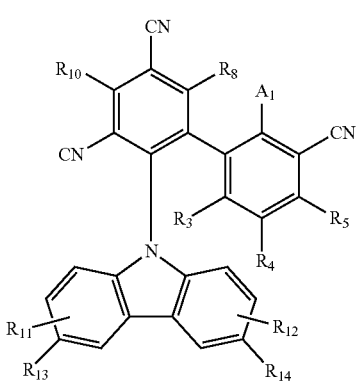
Formula 1A-42
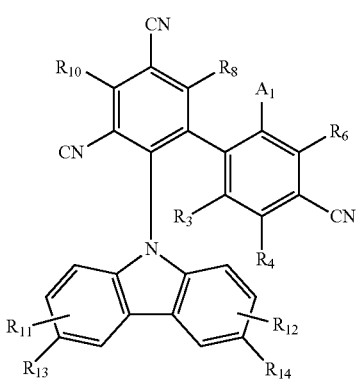

Formula 1A-43
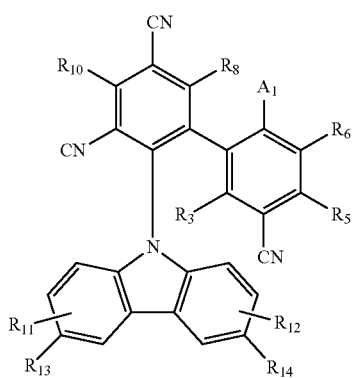
Formula 1A-44
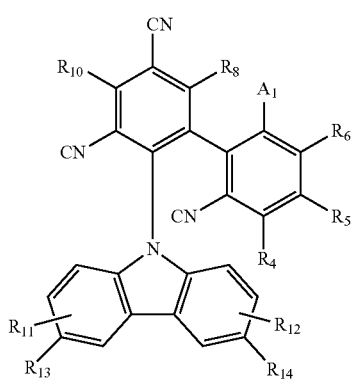
Formula 1A-45
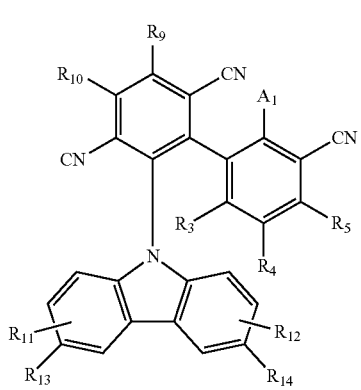
Formula 1A-46
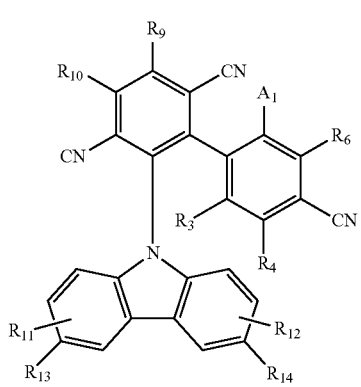
Formula 1A-47
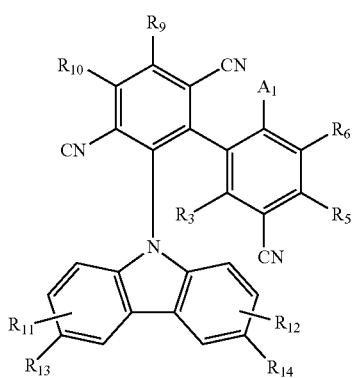
Formula 1A-48
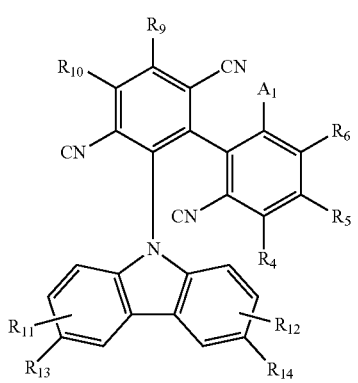
Formula 1A-49
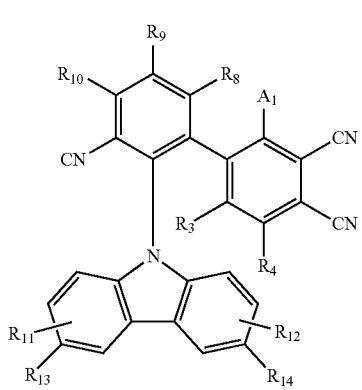
Formula 1A-50
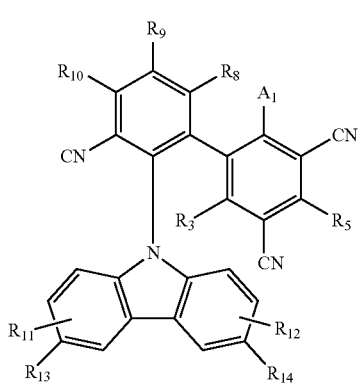

Formula 1A-51
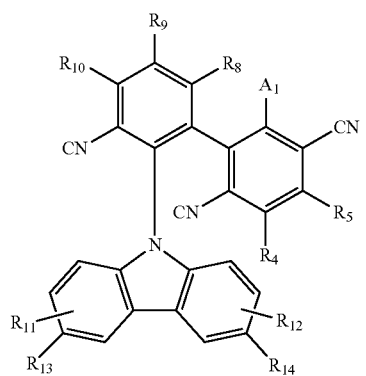
Formula 1A-52
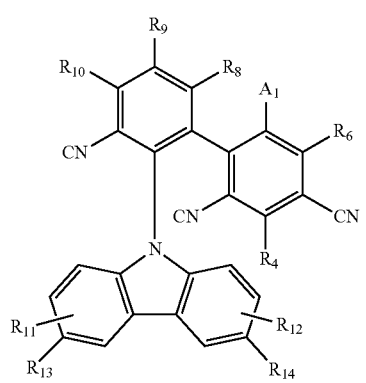
Formula 1A-53
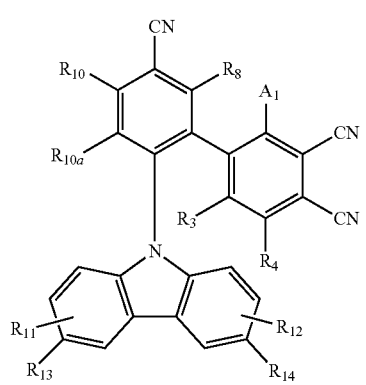
Formula 1A-54
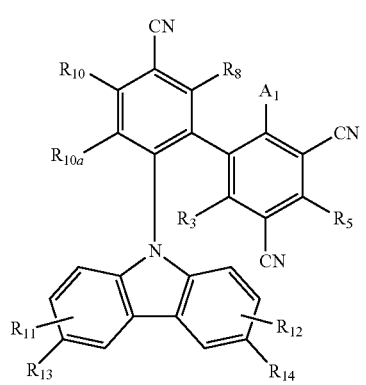
Formula 1A-55
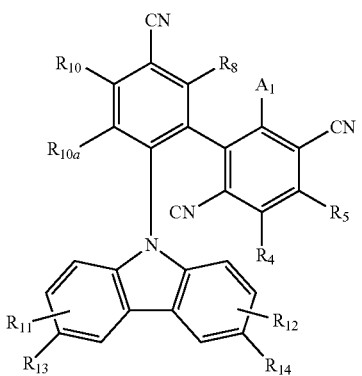
Formula 1A-56
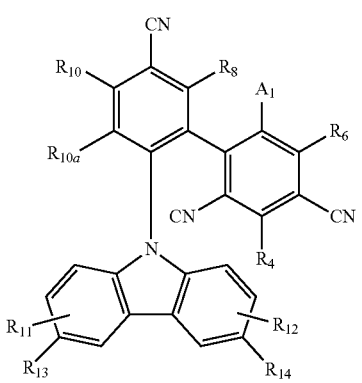
Formula 1A-57
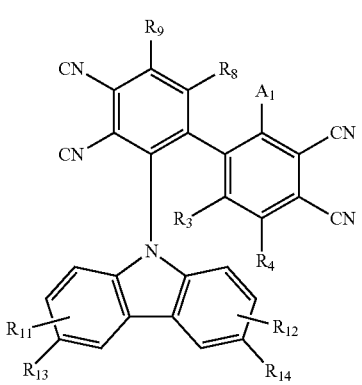
Formula 1A-58
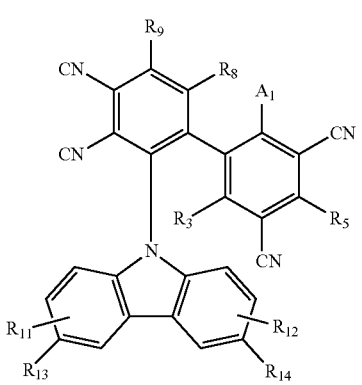

Formula 1A-59
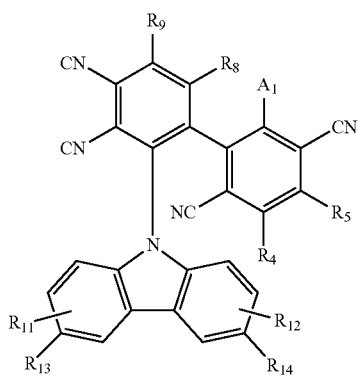
Formula 1A-60
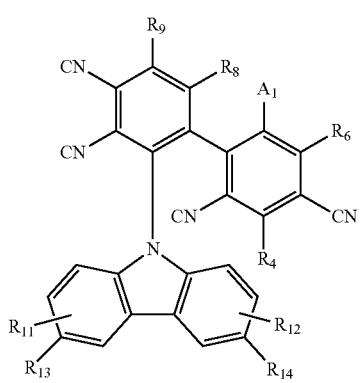
Formula 1A-61
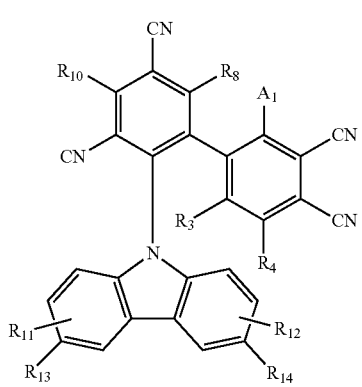
Formula 1A-62
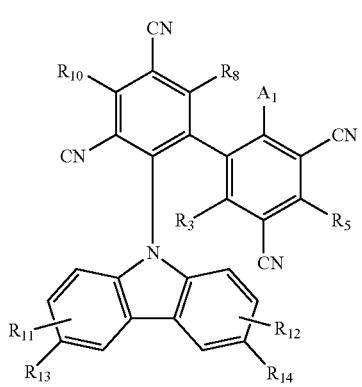
Formula 1A-63
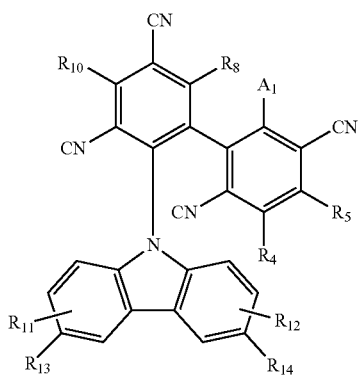
Formula 1A-64
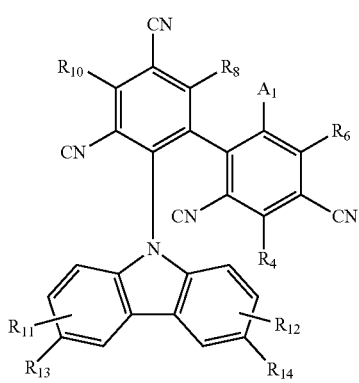
Formula 1A-65
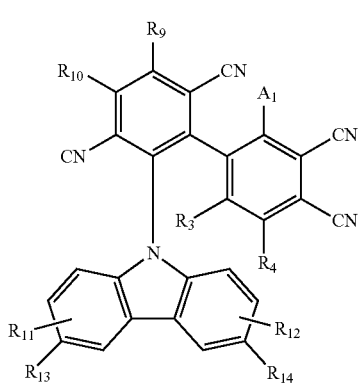
Formula 1A-66
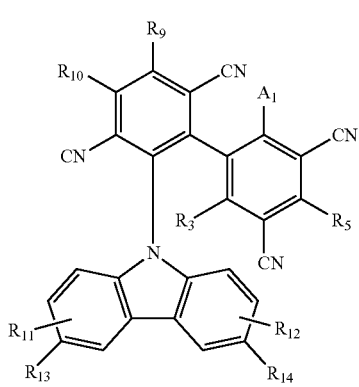

Formula 1A-67
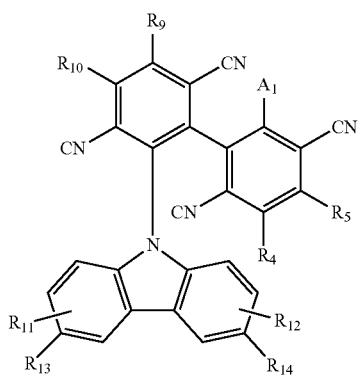
Formula 1A-68
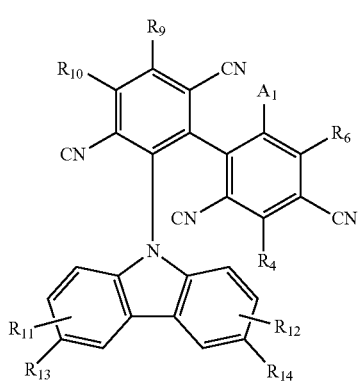
Formula 1A-69
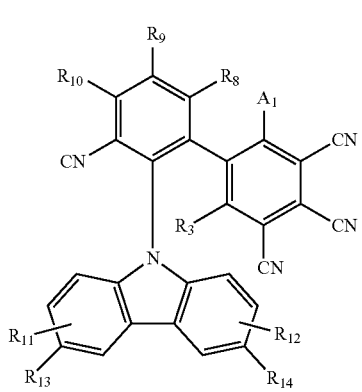
Formula 1A-70
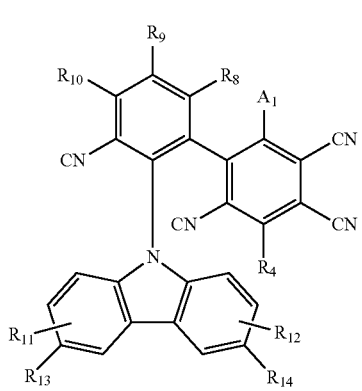
Formula 1A-71
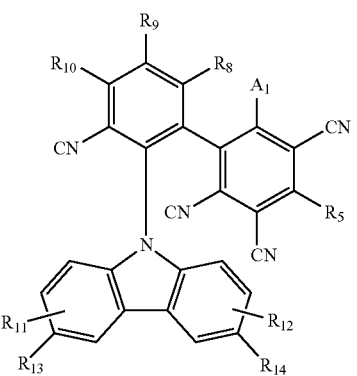
Formula 1A-72
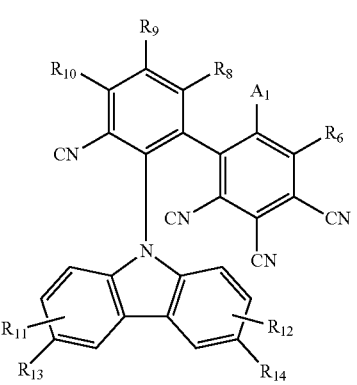
Formula 1A-73
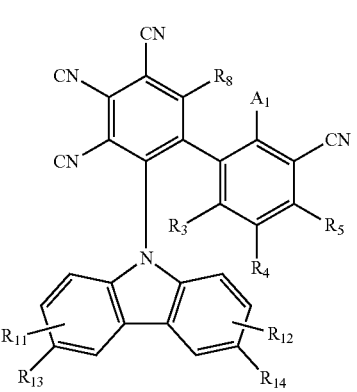
Formula 1A-74
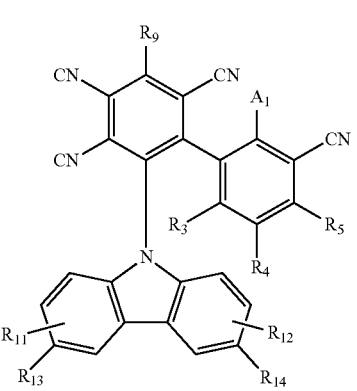

Formula 1A-75
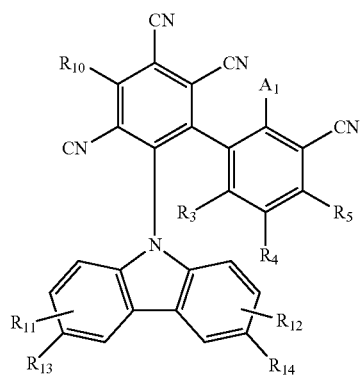
Formula 1A-76
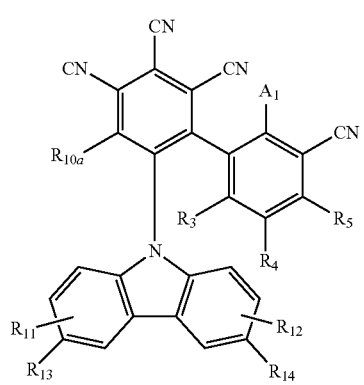
Formula 1B-1
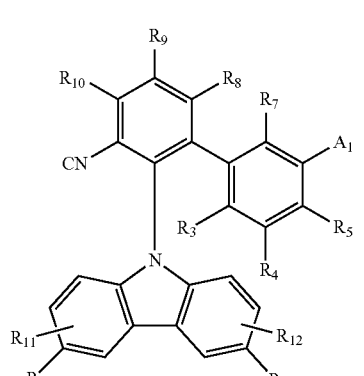
Formula 1B-2
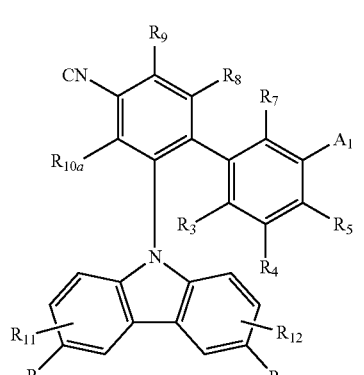
Formula 1B-3
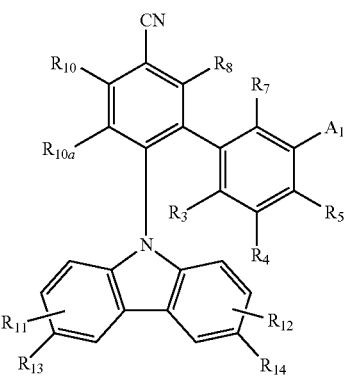
Formula 1B-4
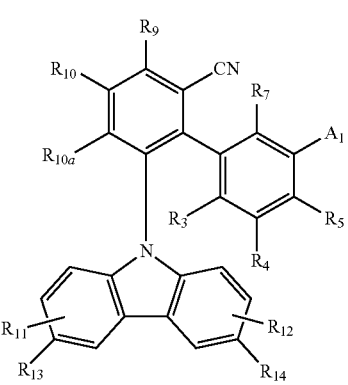
Formula 1B-5
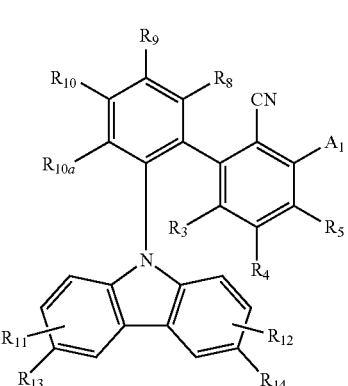
Formula 1B-6
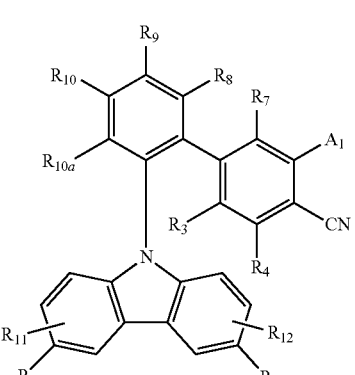

Formula 1B-7
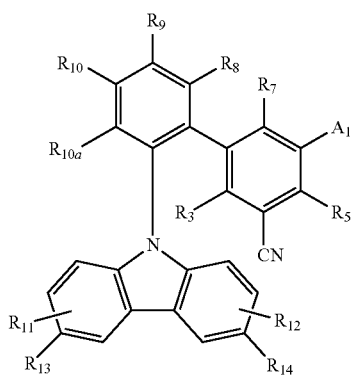
Formula 1B-8
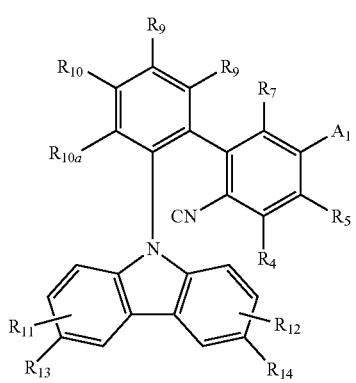
Formula 1B-9
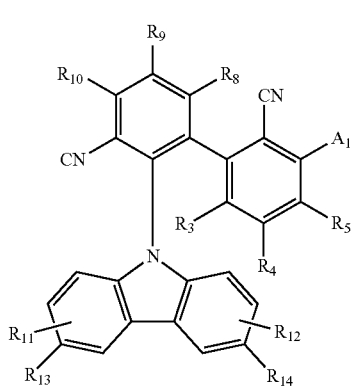
Formula 1B-10
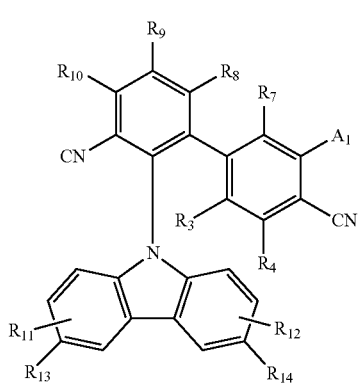
Formula 1B-11
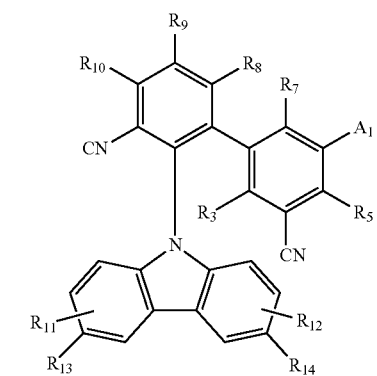
Formula 1B-12
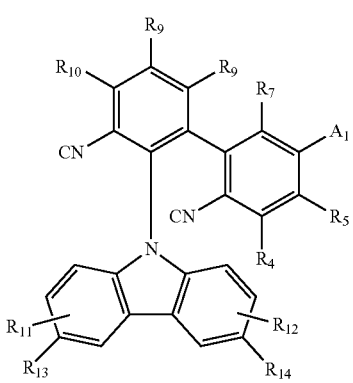
Formula 1B-13
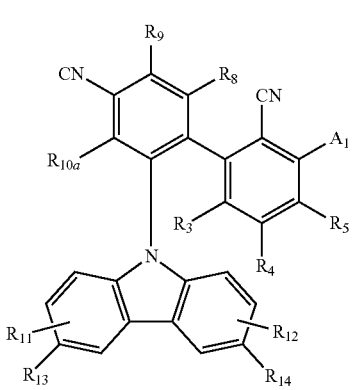
Formula 1B-14
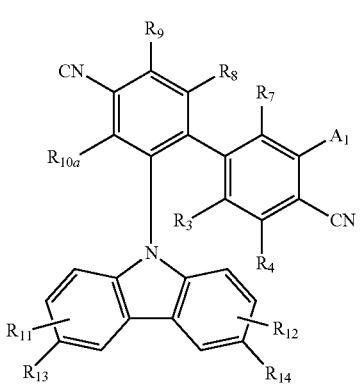

Formula 1B-15
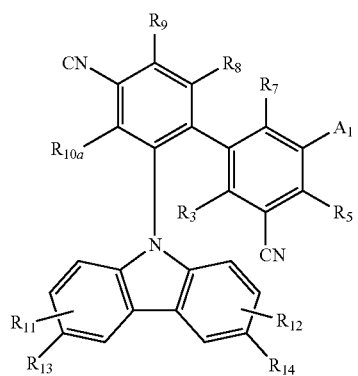
Formula 1B-16
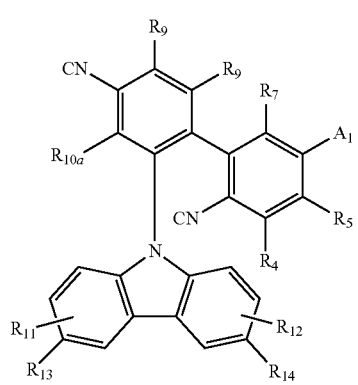
Formula 1B-17
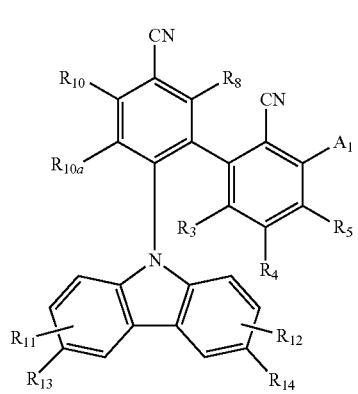
Formula 1B-18
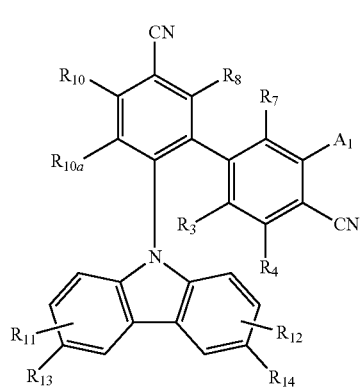
Formula 1B-19
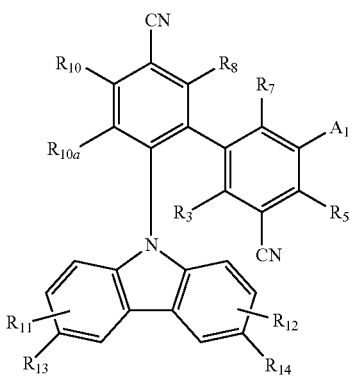
Formula 1B-20
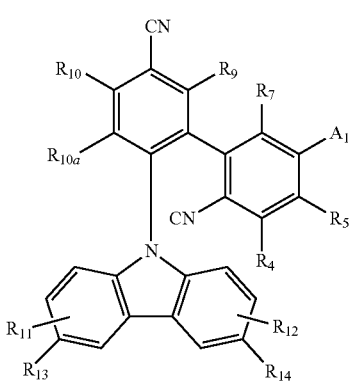
Formula 1B-21
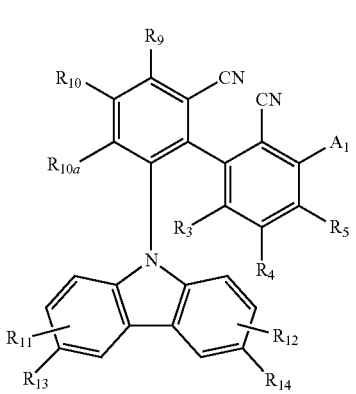
Formula 1B-22
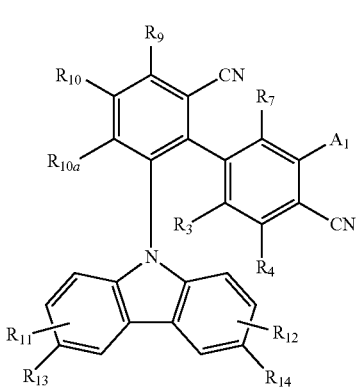

Formula 1B-23
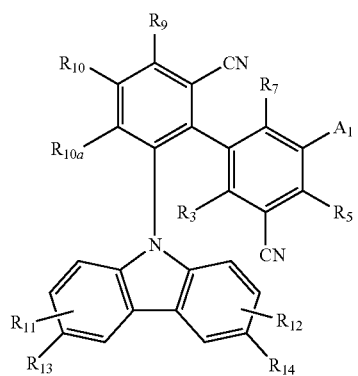
Formula 1B-24
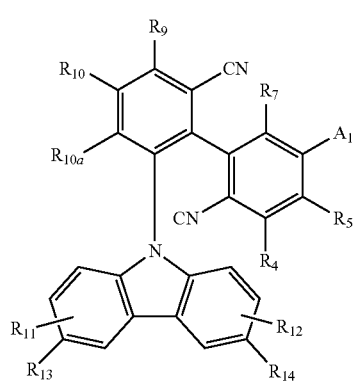
Formula 1B-25
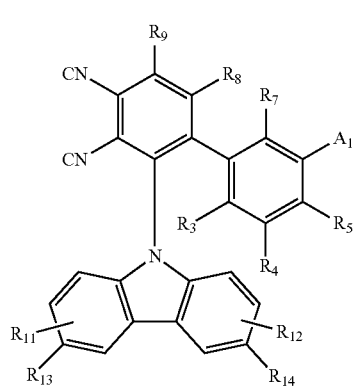
Formula 1B-26
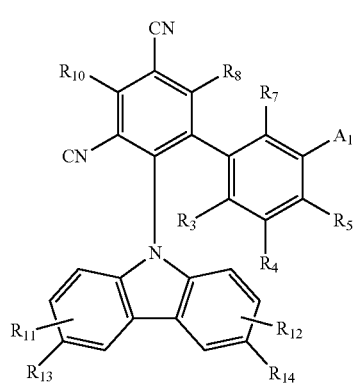
Formula 1B-27
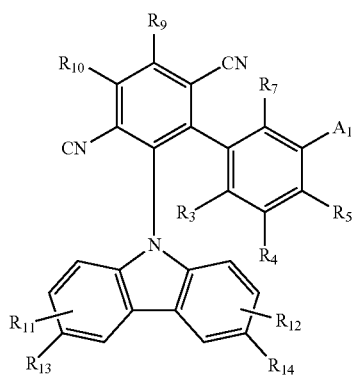
Formula 1B-28
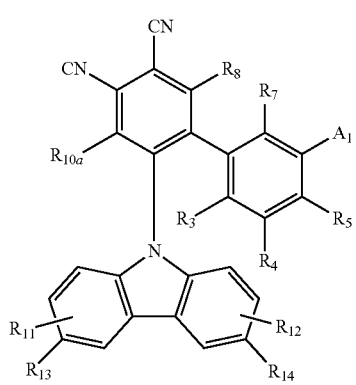
Formula 1B-29
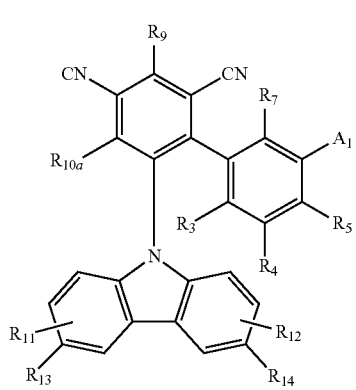
Formula 1B-30
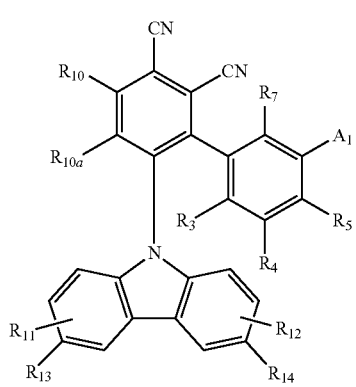

Formula 1B-31
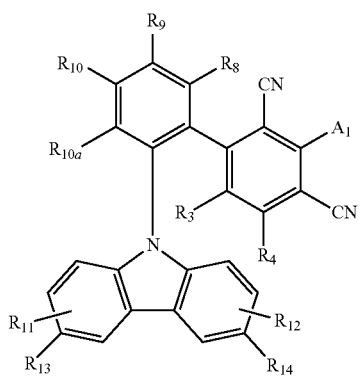
Formula 1B-32
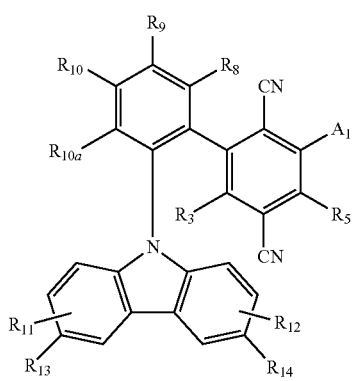
Formula 1B-33
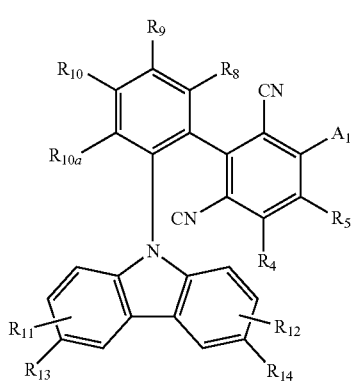
Formula 1B-34
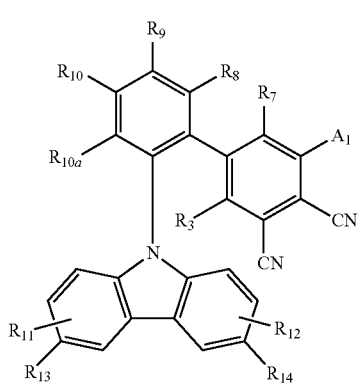
Formula 1B-35
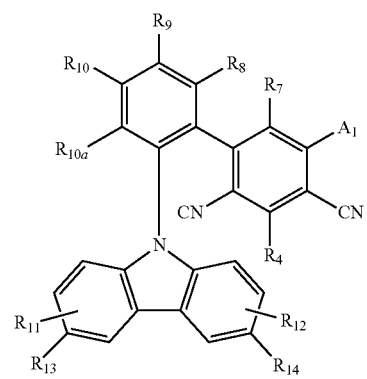
Formula 1B-36
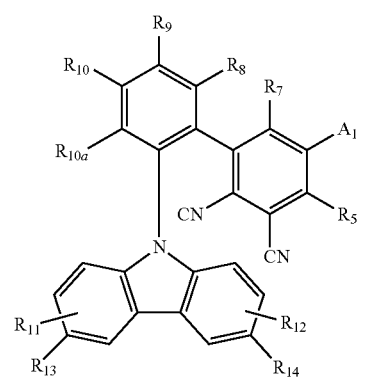
Formula 1B-37
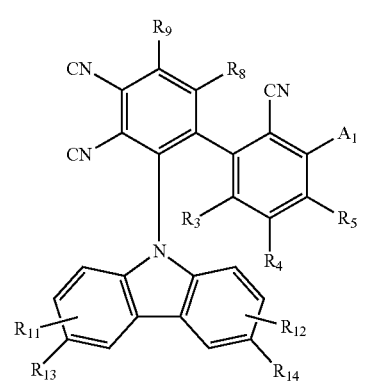
Formula 1B-38
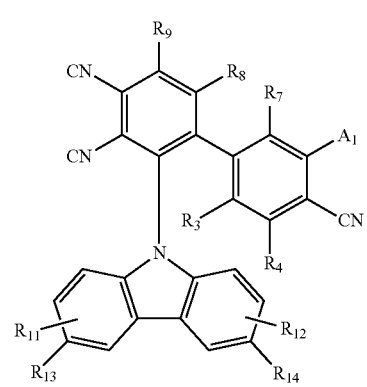

| Formula 1B-39 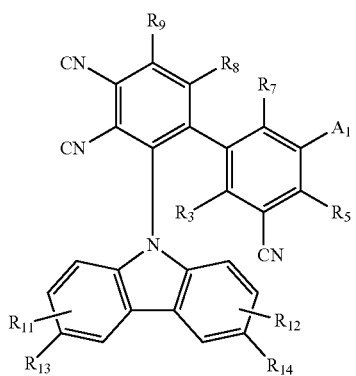 | Formula 1B-43 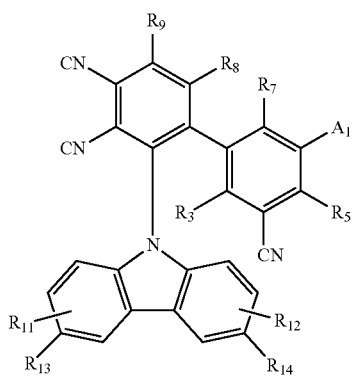 |
| Formula 1B-40 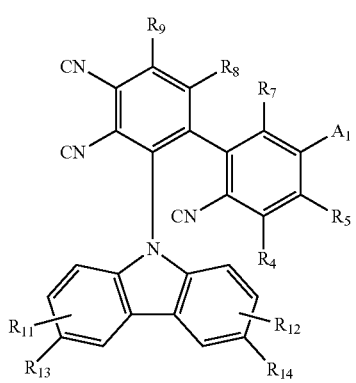 | Formula 1B-44 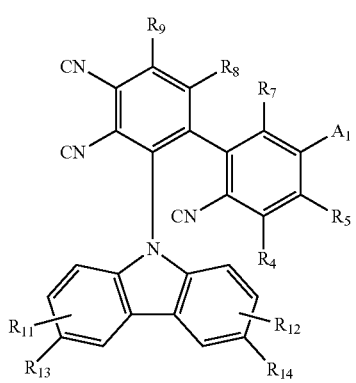 |
| Formula 1B-41 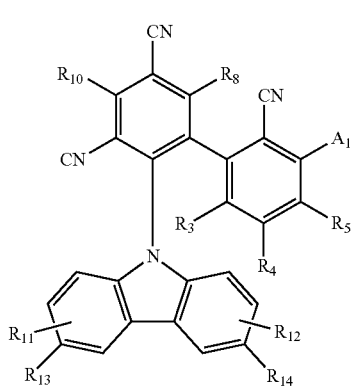 | Formula 1B-45 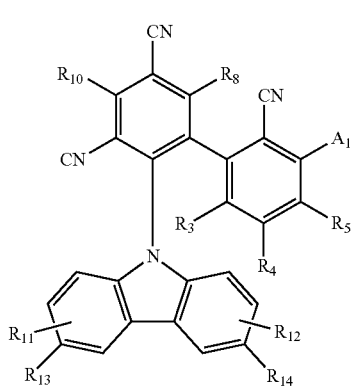 |
| Formula 1B-42 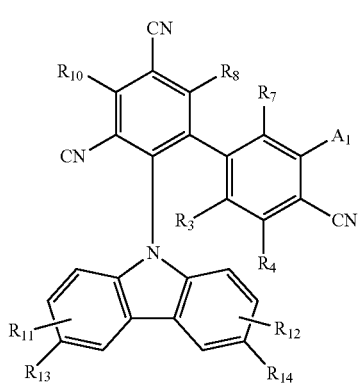 | Formula 1B-46 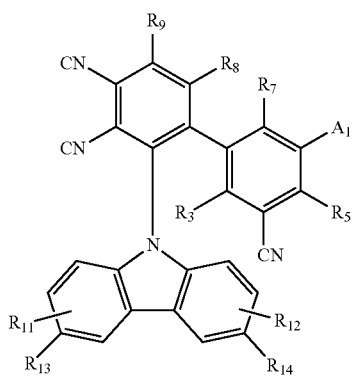 |

Formula 1B-47
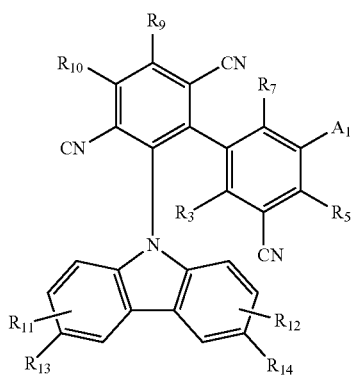
Formula 1B-48
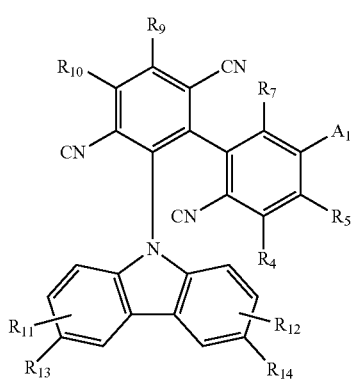
Formula 1B-49
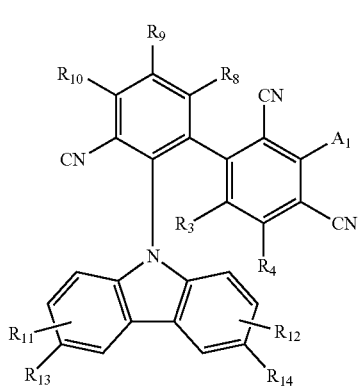
Formula 1B-50
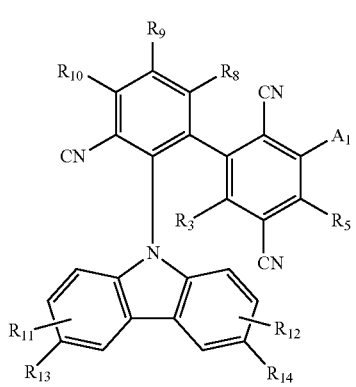
Formula 1B-51
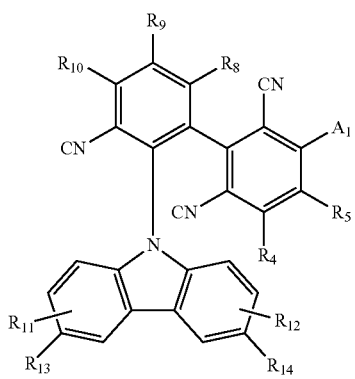
Formula 1B-52
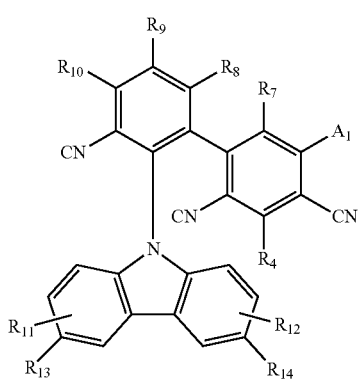
Formula 1B-53
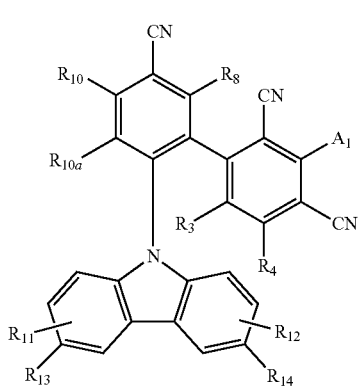
Formula 1B-54
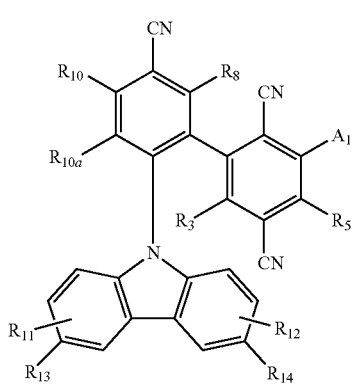

Formula 1B-55
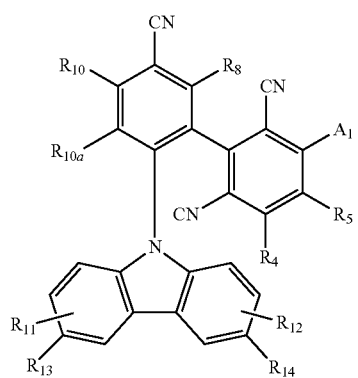
Formula 1B-56
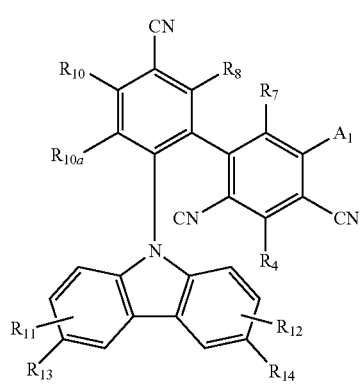
Formula 1B-57
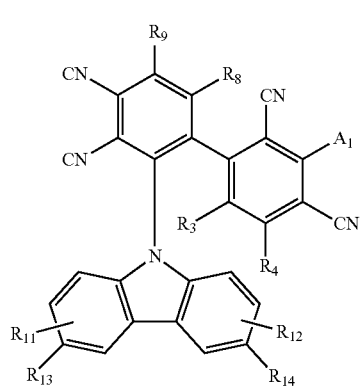
Formula 1B-58
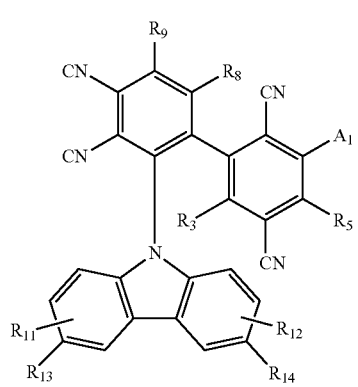
Formula 1B-59
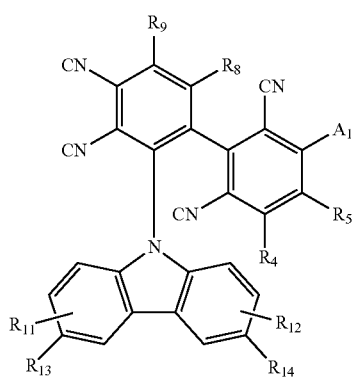
Formula 1B-60
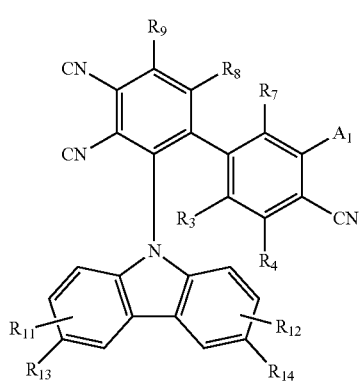
Formula 1B-61
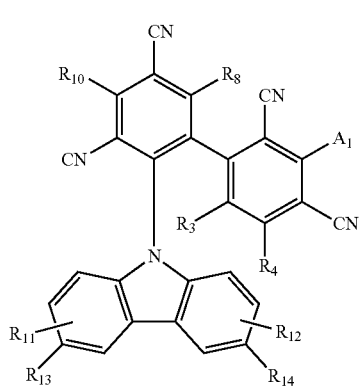
Formula 1B-62
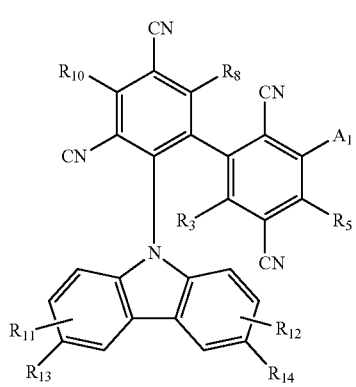

Formula 1B-63
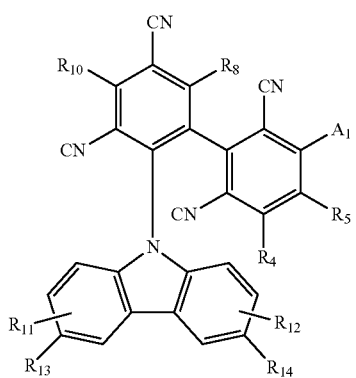
Formula 1B-64
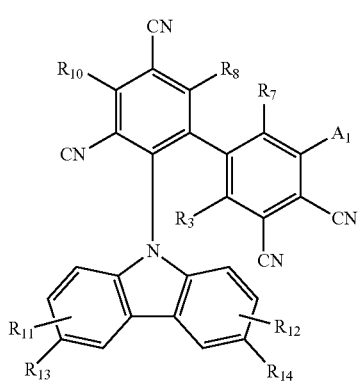
Formula 1B-65
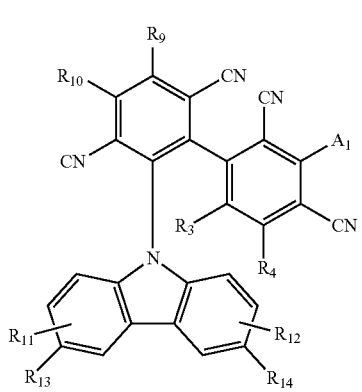
Formula 1B-66
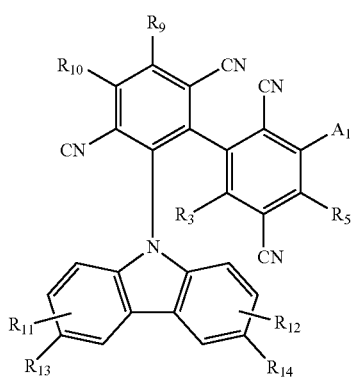
Formula 1B-67
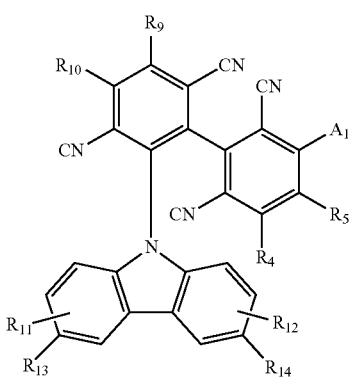
Formula 1B-68
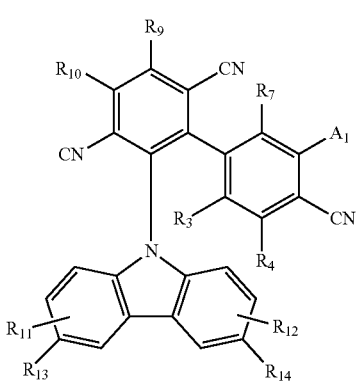
Formula 1B-69
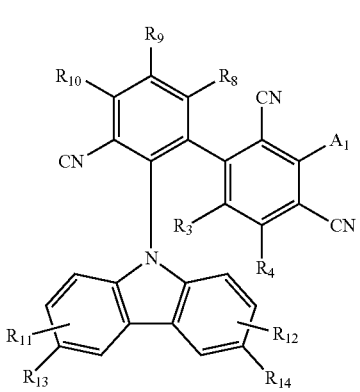
Formula 1B-70
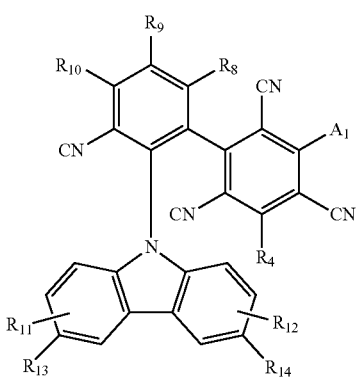

Formula 1B-71
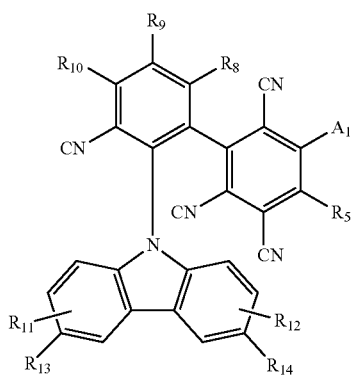
Formula 1B-72
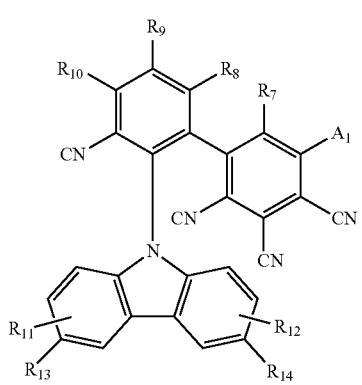
Formula 1B-73
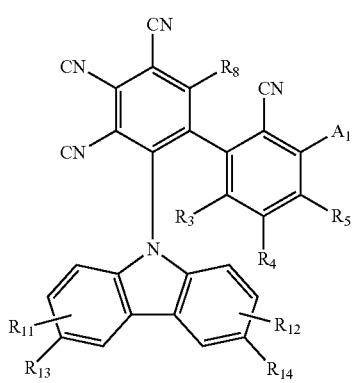
Formula 1B-74
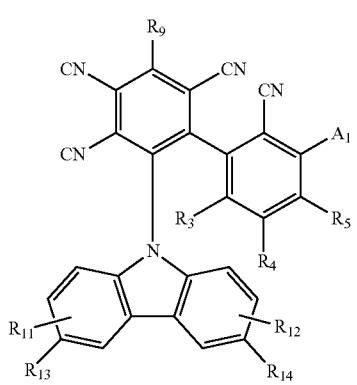
Formula 1B-75
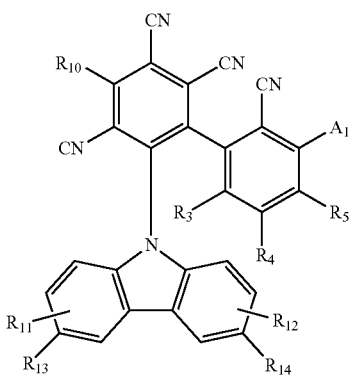
Formula 1B-76
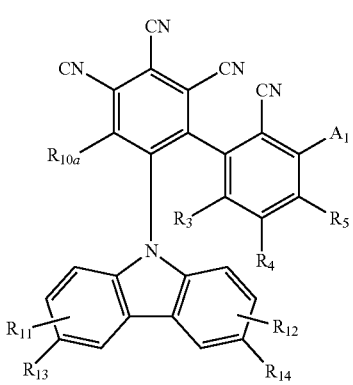
Formula 1C-1
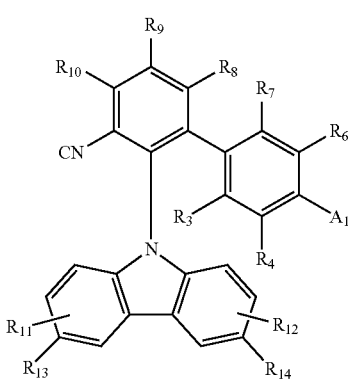
Formula 1C-2
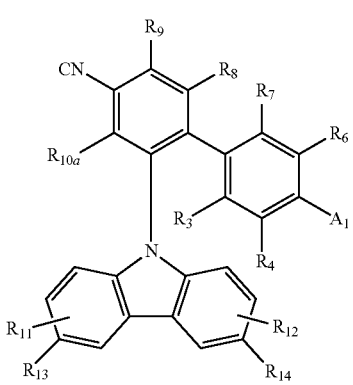

Formula 1C-3
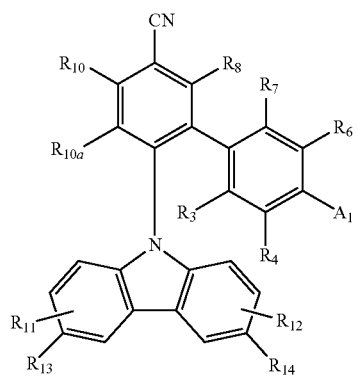
Formula 1C-4
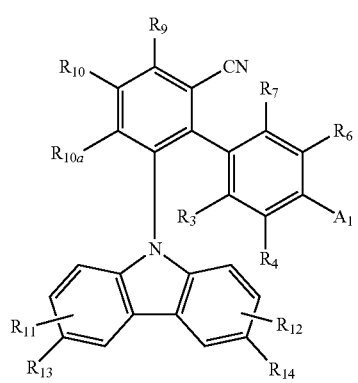
Formula 1C-5
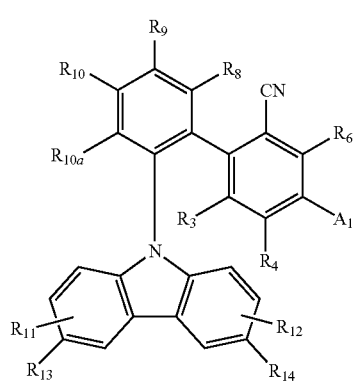
Formula 1C-6
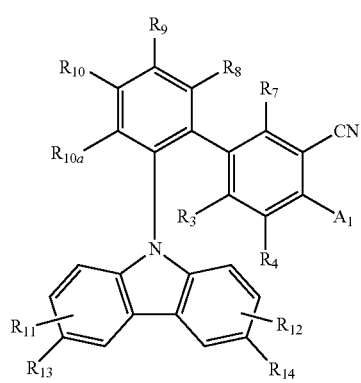
Formula 1C-7
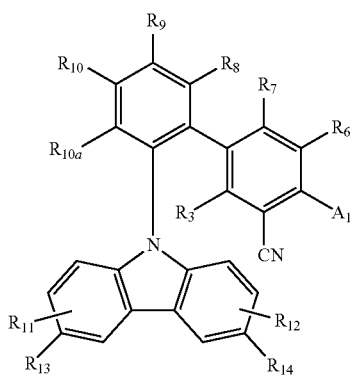
Formula 1C-8
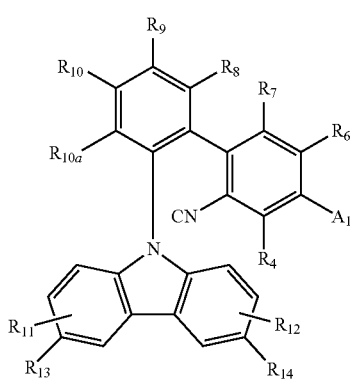
Formula 1C-9
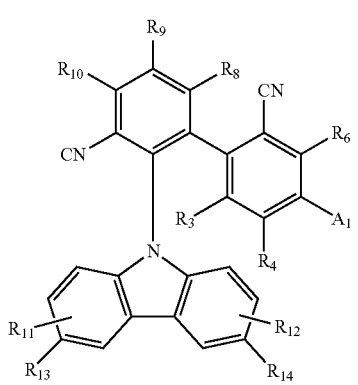
Formula 1C-10
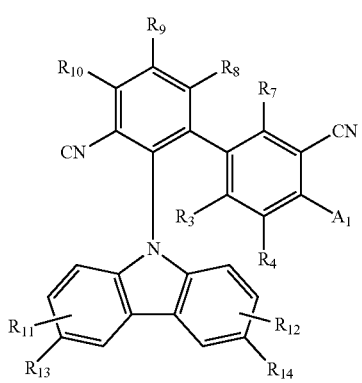

-continued
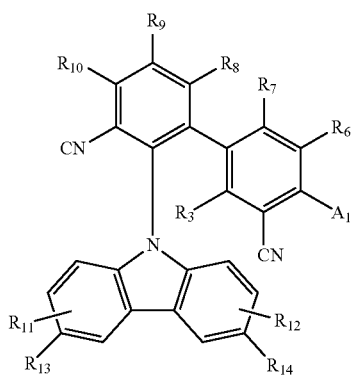
Formula 1C-11
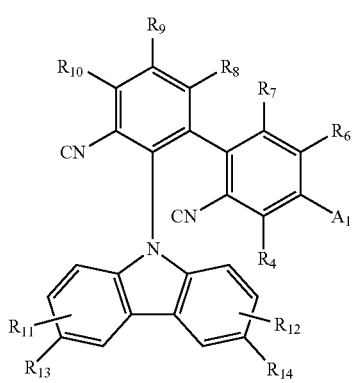
Formula 1C-12
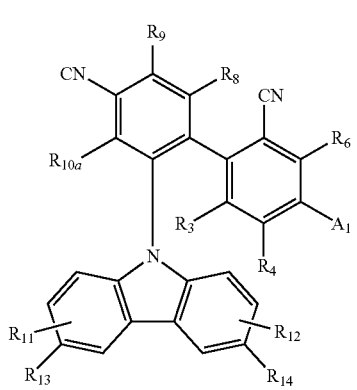
Formula 1C-13
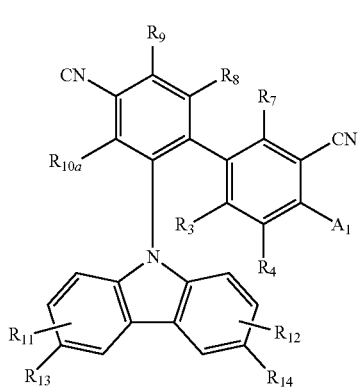
Formula 1C-14
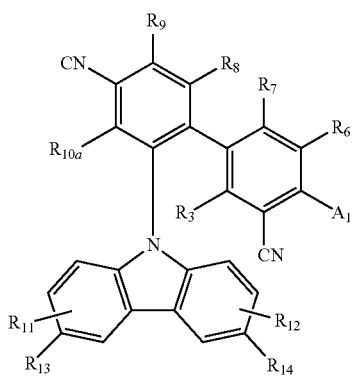
Formula 1C-15
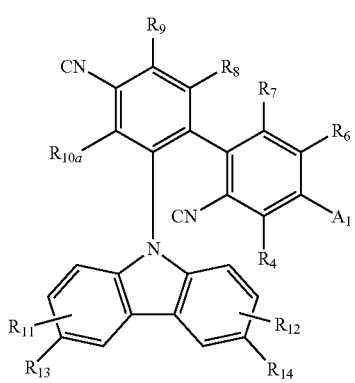
Formula 1C-16
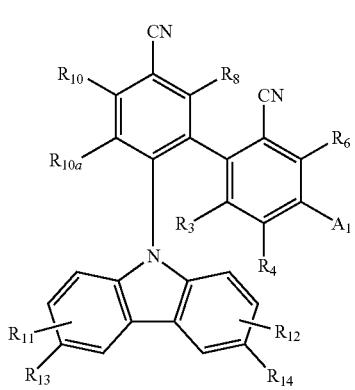
Formula 1C-17
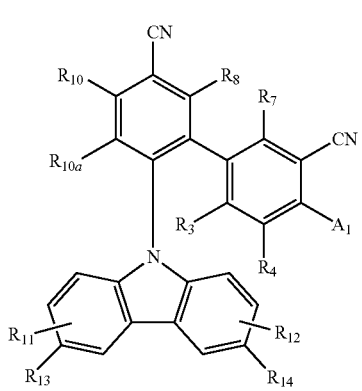
Formula 1C-18

Formula 1C-19
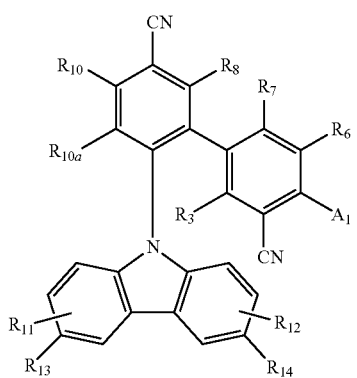
Formula 1C-20
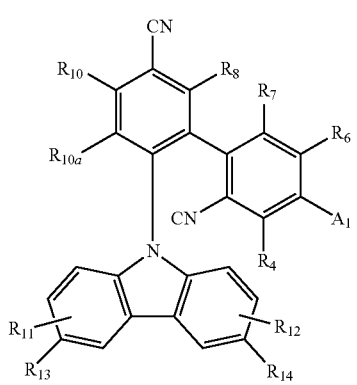
Formula 1C-21
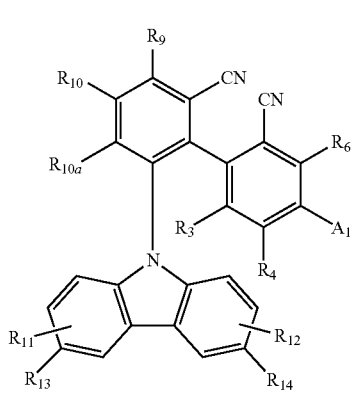
Formula 1C-22
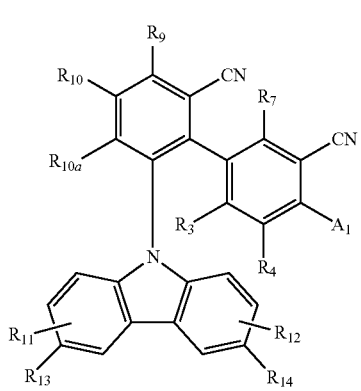
Formula 1C-23
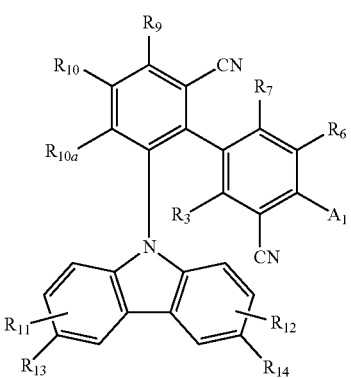
Formula 1C-24
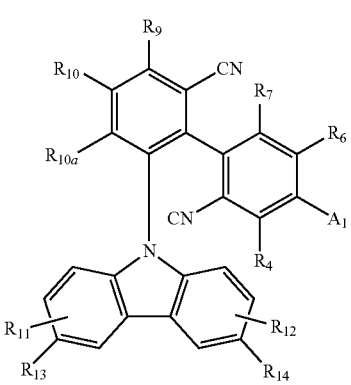
Formula 1C-25
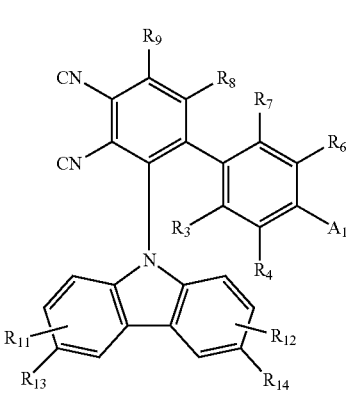
Formula 1C-26
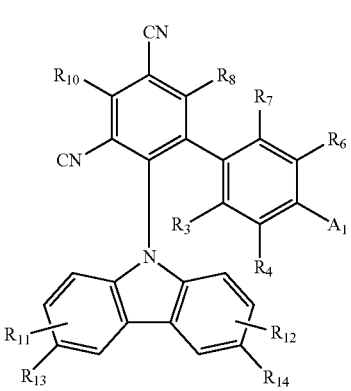

Formula 1C-27

Formula 1C-28

Formula 1C-29

Formula 1C-30

Formula 1C-31

Formula 1C-32

Formula 1C-33

Formula 1C-34

Formula 1C-35
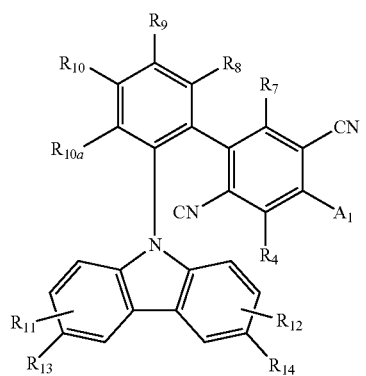
Formula 1C-36
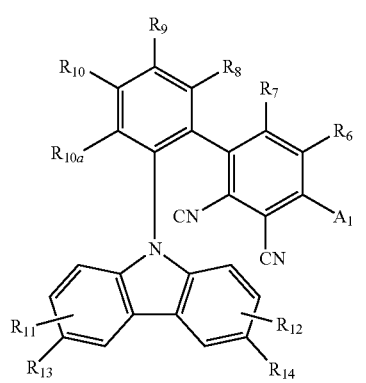
Formula 1C-37
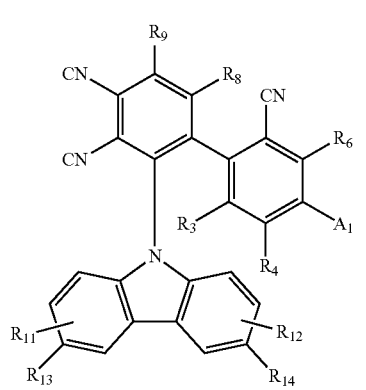
Formula 1C-38
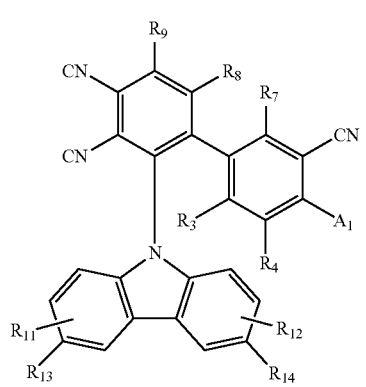
Formula 1C-39
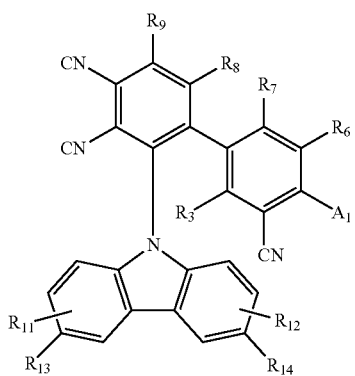
Formula 1C-40
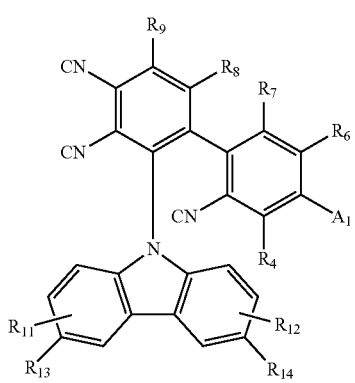
Formula 1C-41
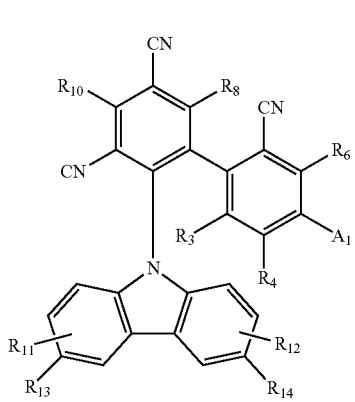
Formula 1C-42
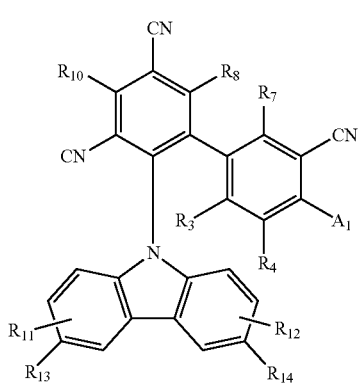

Formula 1C-43
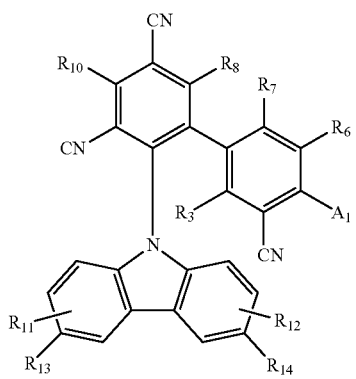
Formula 1C-44
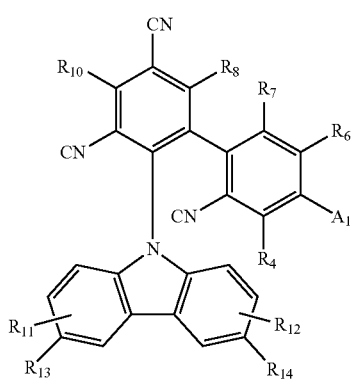
Formula 1C-45
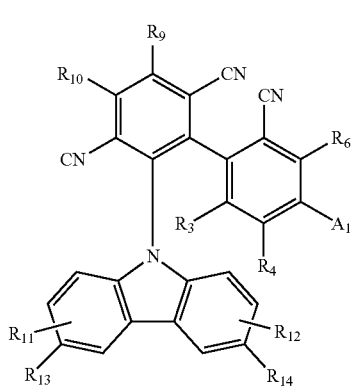
Formula 1C-46
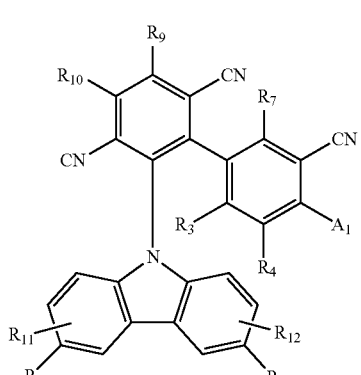
Formula 1C-47
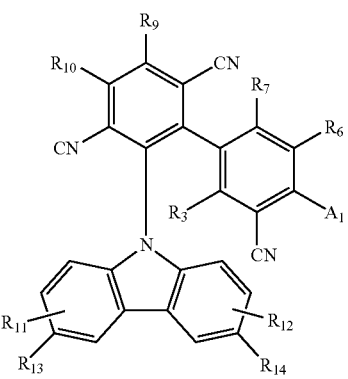
Formula 1C-48
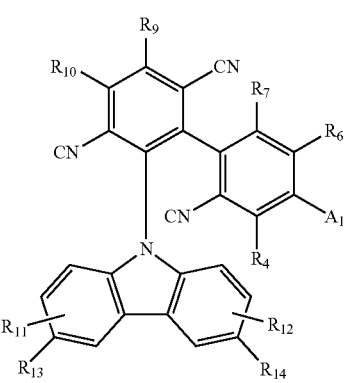
Formula 1C-49
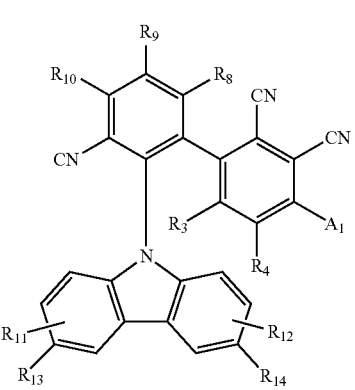
Formula 1C-50
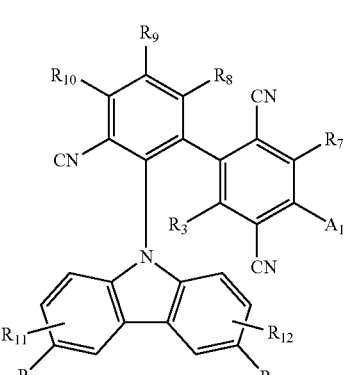

Formula 1C-51
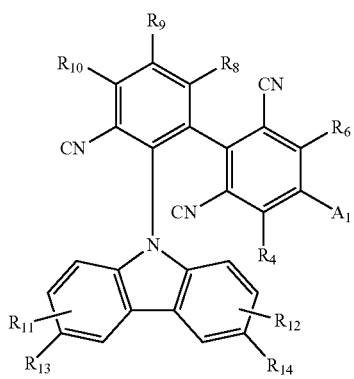
Formula 1C-52
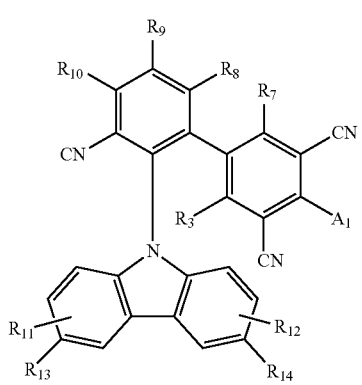
Formula 1C-53
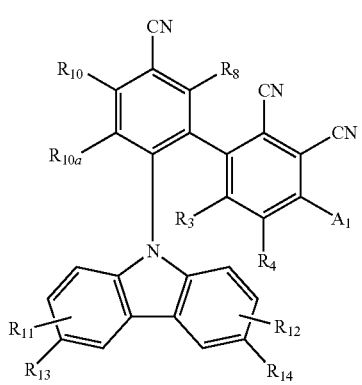
Formula 1C-54
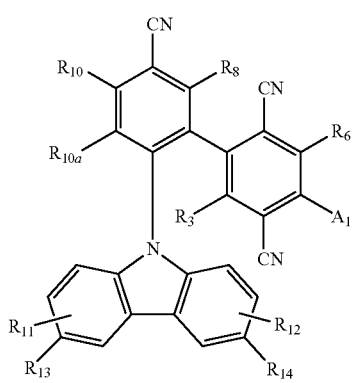
Formula 1C-55
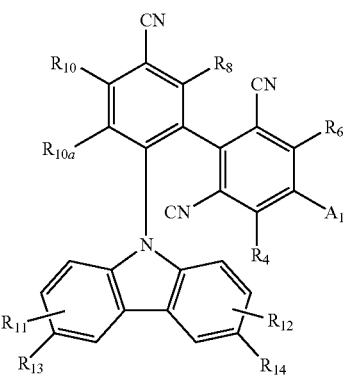
Formula 1C-56
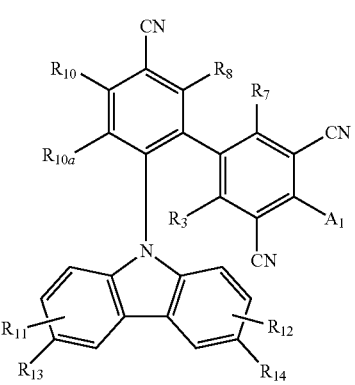
Formula 1C-57
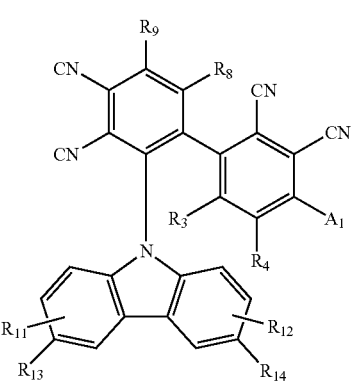
Formula 1C-58
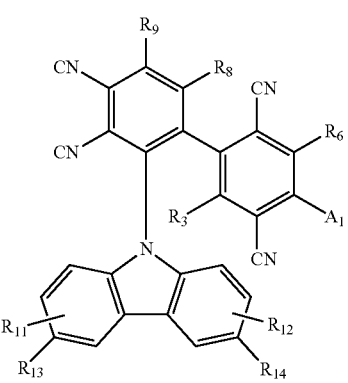

Formula 1C-59
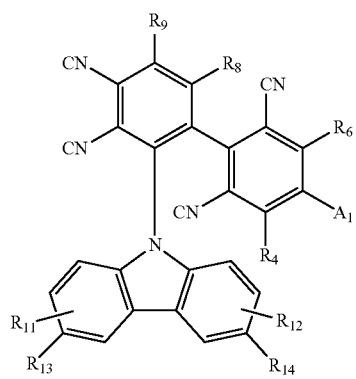
Formula 1C-60
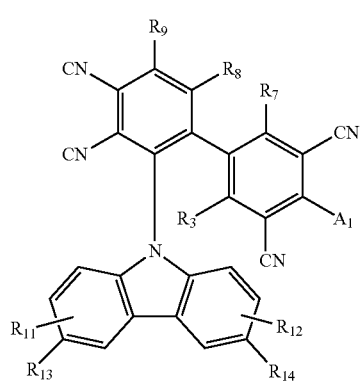
Formula 1C-61
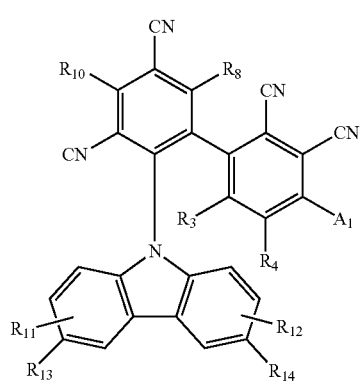
Formula 1C-62
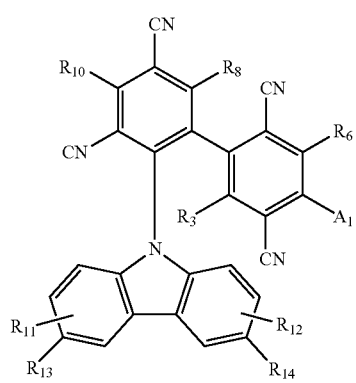
Formula 1C-63
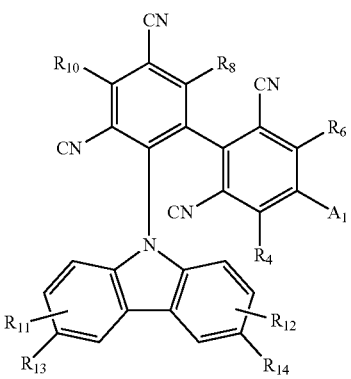
Formula 1C-64
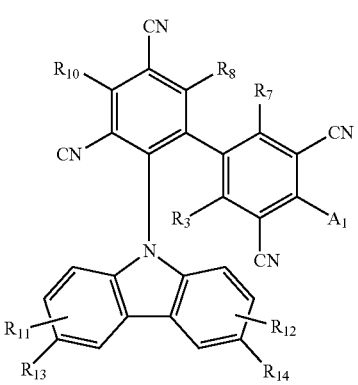
Formula 1C-65
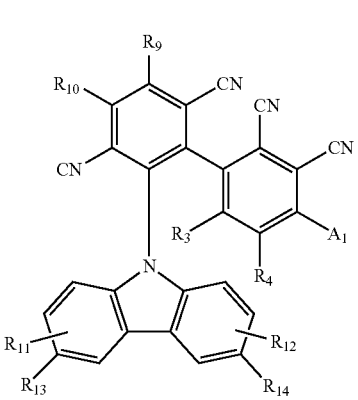
Formula 1C-66
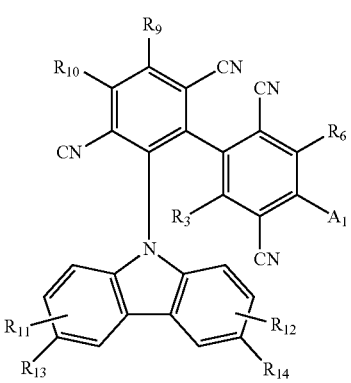

Formula 1C-67
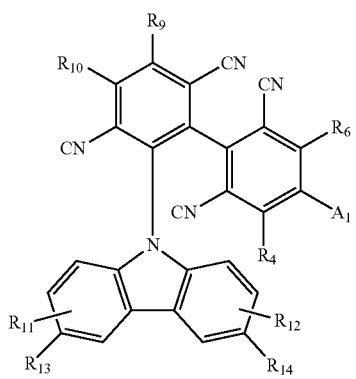
Formula 1C-68
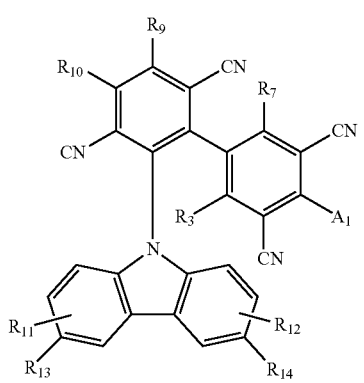
Formula 1C-69
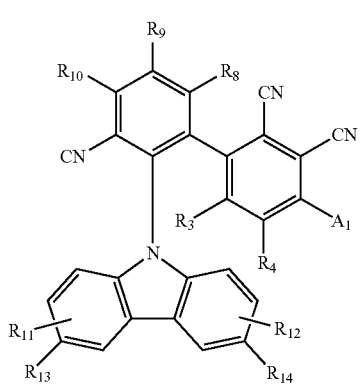
Formula 1C-70
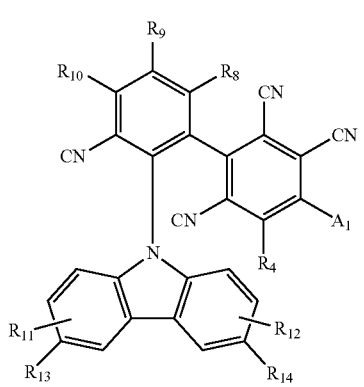
Formula 1C-71
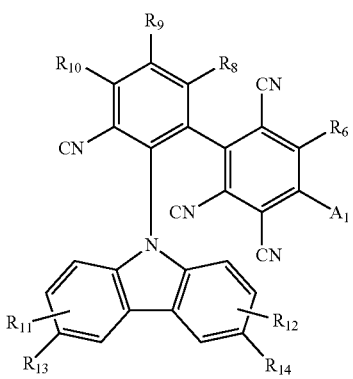
Formula 1C-72
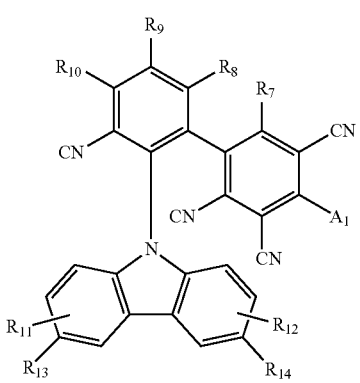
Formula 1C-73
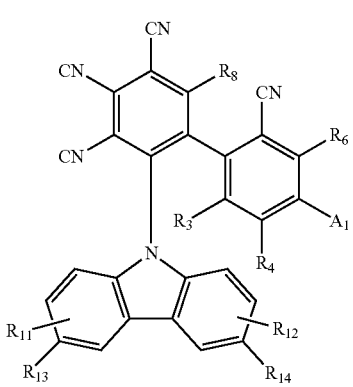
Formula 1C-74
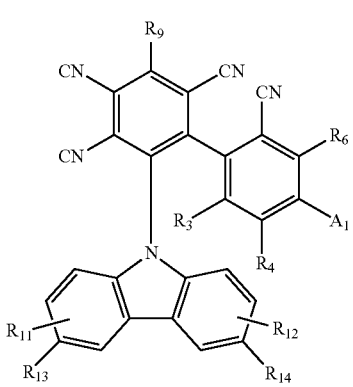

-continued

Formula 1C-75

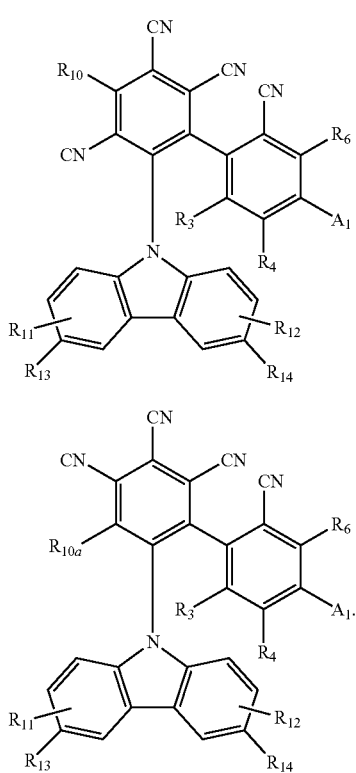

Formula 1C-76

In Formulae 1A-1 to 1A-76, 1B-1 to 1B-76, and 1C-1 to 1C-76, $A_1$, $R_{11}$, and $R_{12}$ are each independently as defined herein in the present specification, $R_8$ to $R_{10}$ and $R_{10a}$ are each independently the same as defined herein in connection with $R_1$, $R_3$ to $R_7$ are each independently the same as defined herein in connection with $R_2$, $R_{13}$ is the same as defined herein in connection with $R_{11}$, and $R_{14}$ is the same as defined herein in connection with $R_{12}$.

For example, in Formulae 1A-1 to 1A-76, 1B-1 to 1B-76, and 1C-1 to 1C-76, $R_3$ to $R_{10}$ and $R_{10a}$ may not be a cyano group.

In various embodiments, in Formulae 1A-1 to 1A-76, 1B-1 to 1B-76, and 1C-1 to 1C-76, $R_3$ to $R_{10}$ and $R_{10a}$ may each independently be selected from:

hydrogen, deuterium, —F, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one of deuterium and —F, but embodiments are not limited thereto.

For example, in Formulae 1A-1 to 1A-76, 1B-1 to 1B-76, and 1C-1 to 1C-76, $A_1$ may be selected from groups represented by Formulae 2A-1 and 2B-1 to 2B-4, but embodiments are not limited thereto.

In various embodiments, in Formula 1, $R_{11}$, $R_{12}$, $R_{21}$, $R_{22}$, and $R_{27}$ to $R_{29}$ may not be a substituted or unsubstituted carbazolyl group.

For example, the condensed cyclic compound may be selected from Compounds 1 to 330, but embodiments are not limited thereto:

1

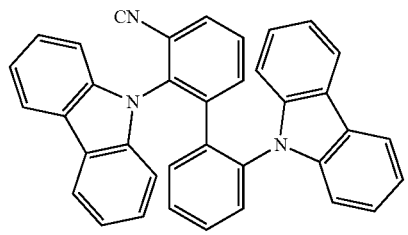

2

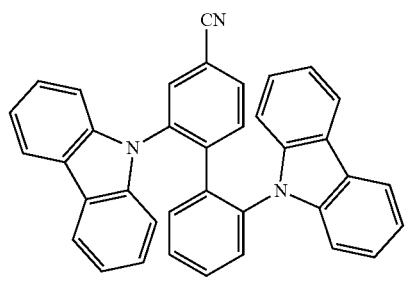

3

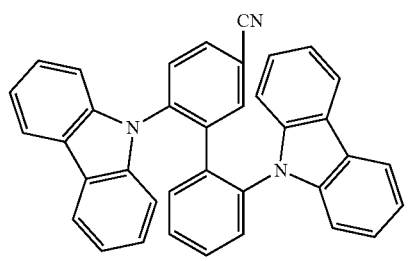

4

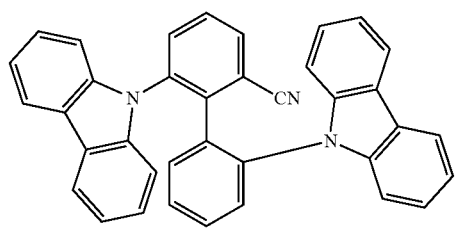

5

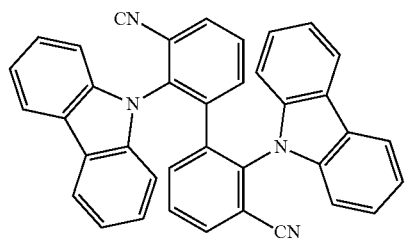

6

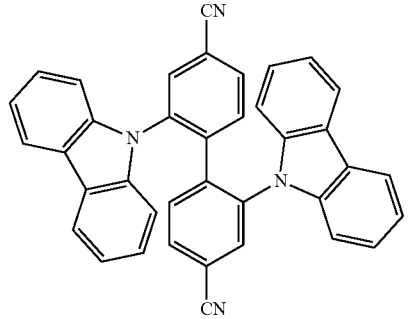

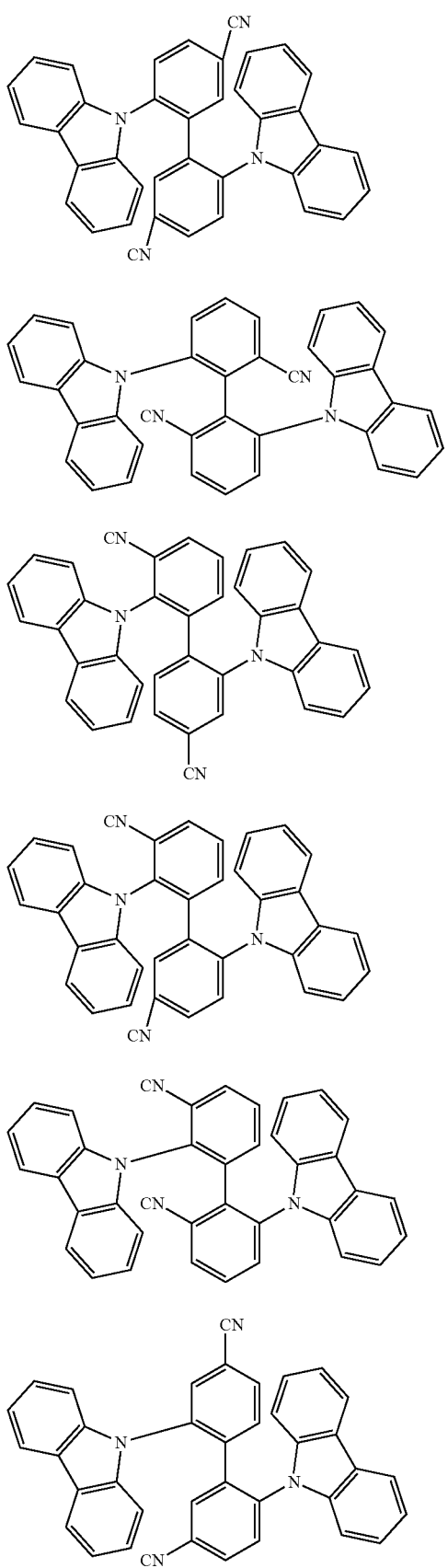
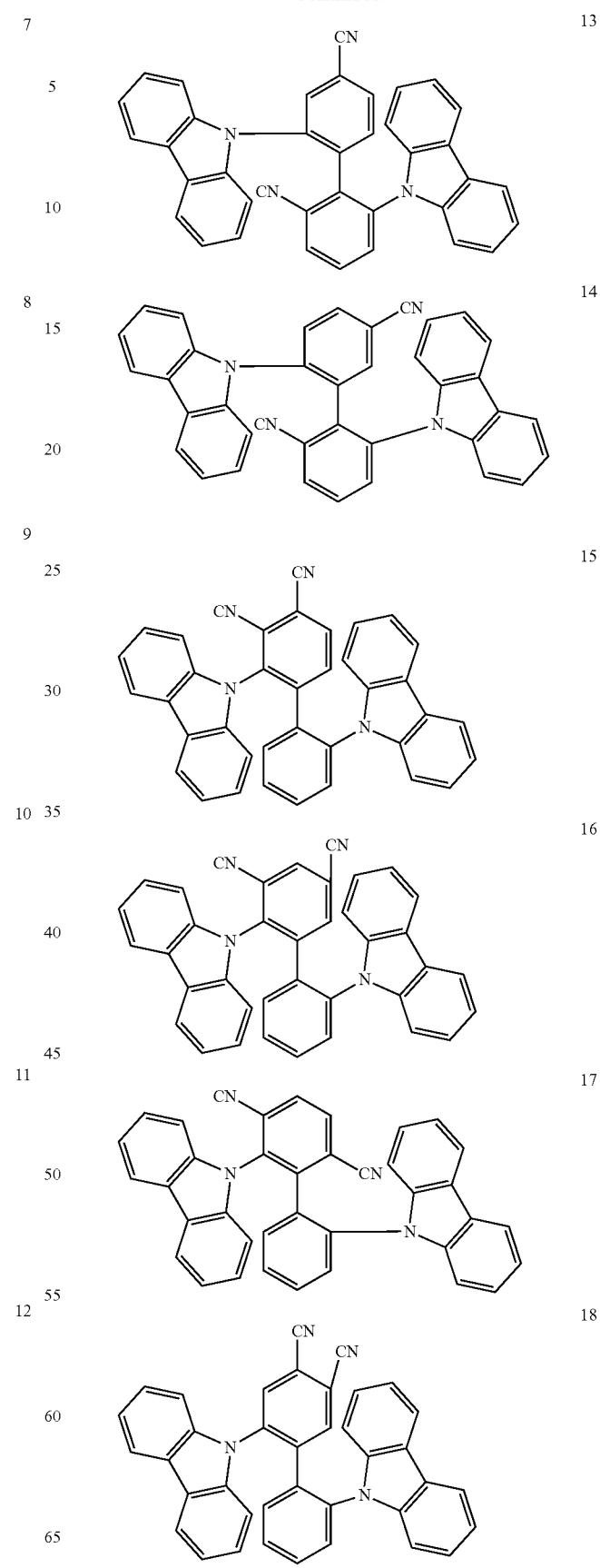

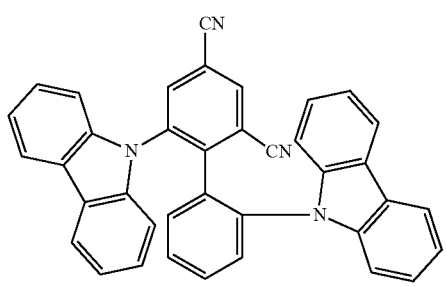
19
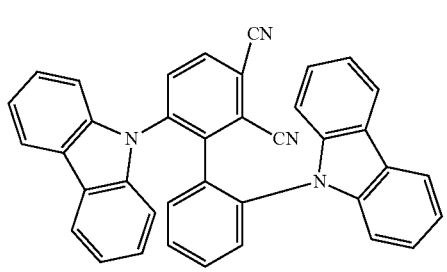
20
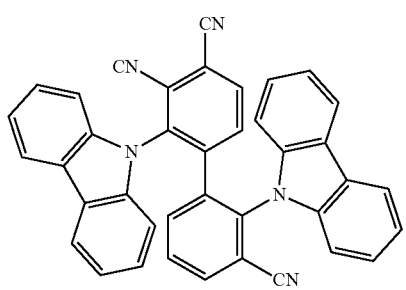
21
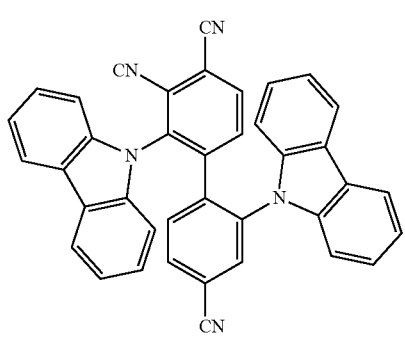
22
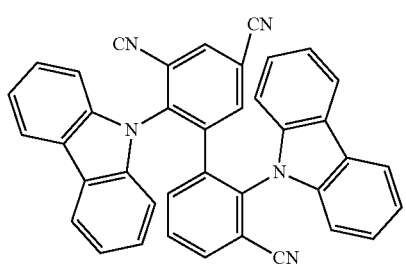
23
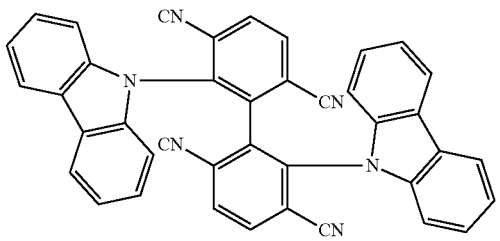
24
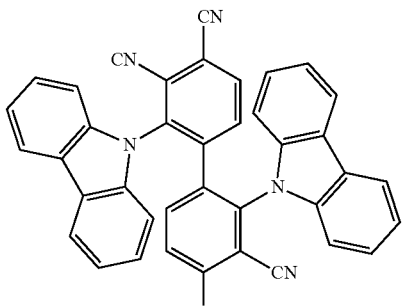
25
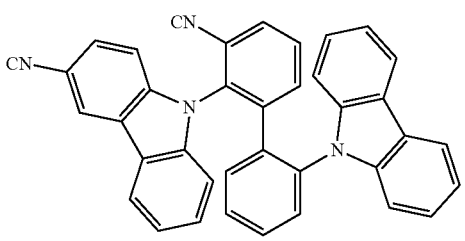
26
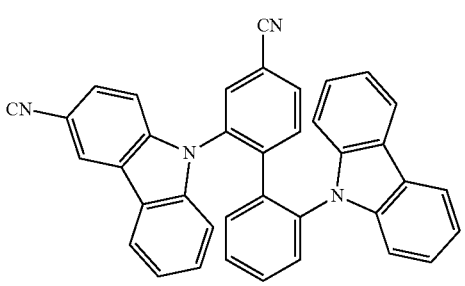
27
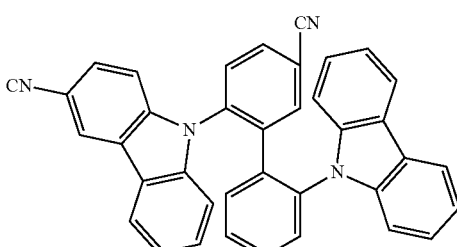
28
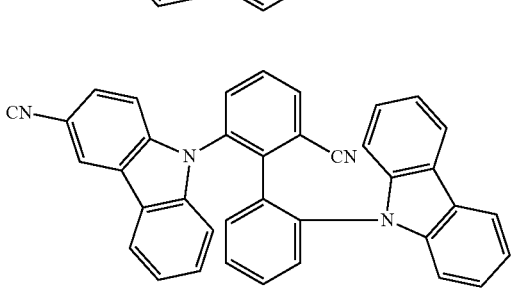
29

-continued
30
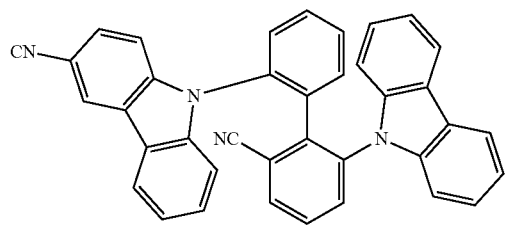
31
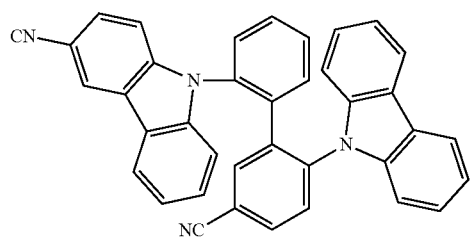
32
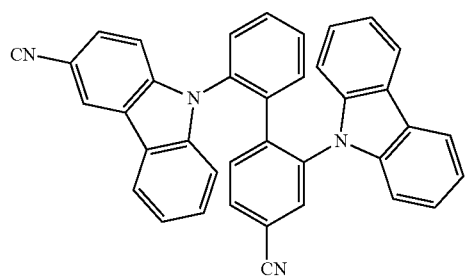
33
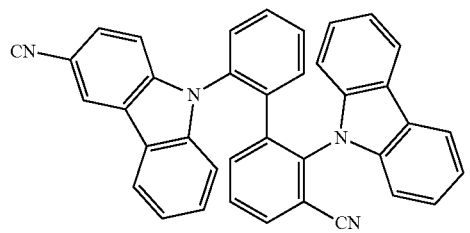
34
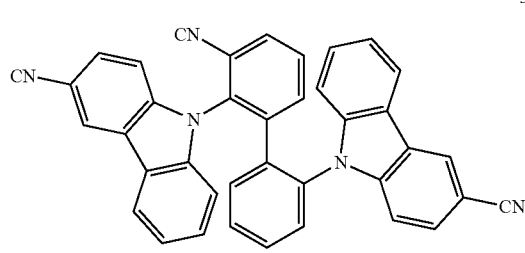
35
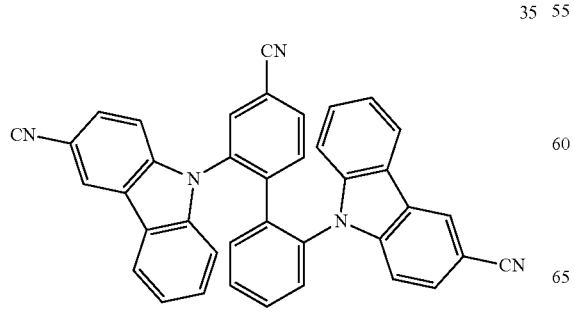
-continued
36
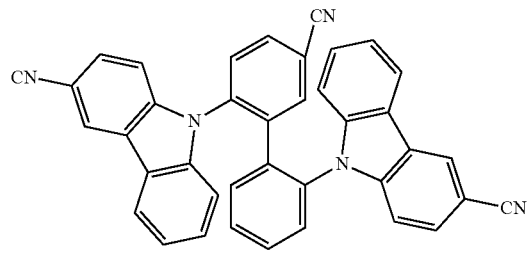
37
38
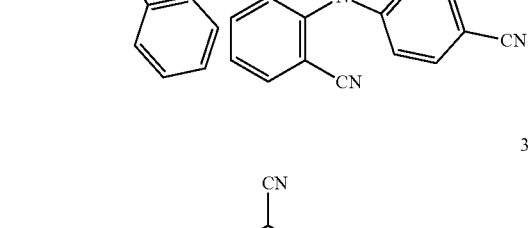
39
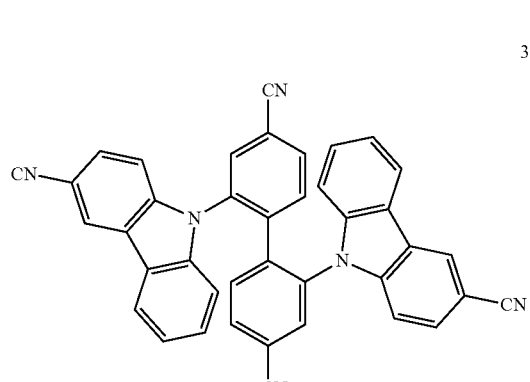
40
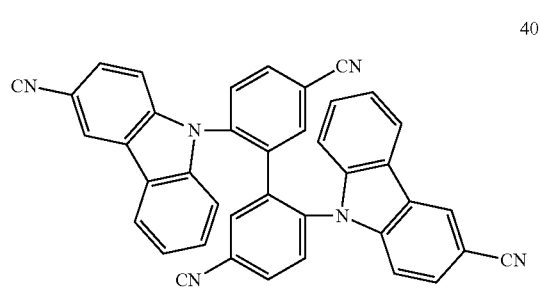

41
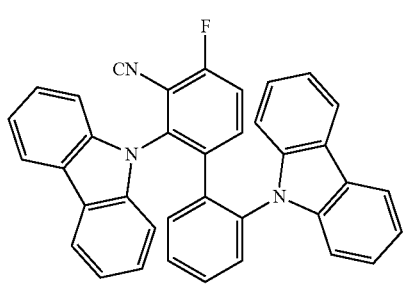
42
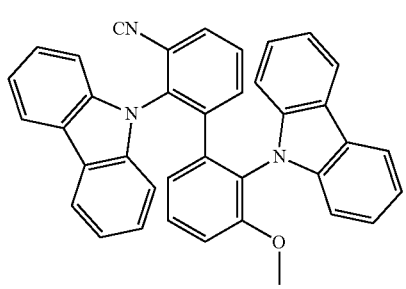
43
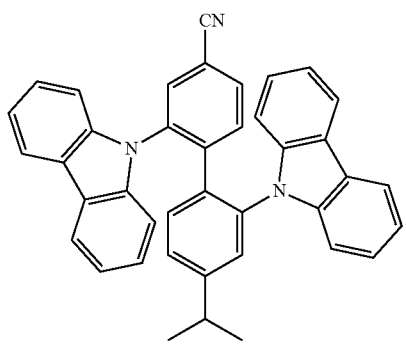
44
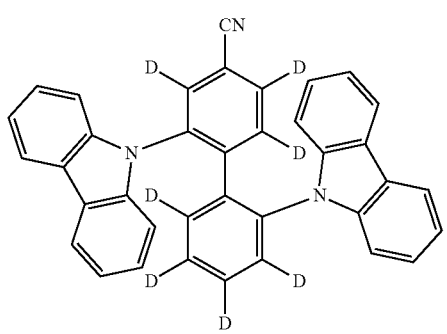
45
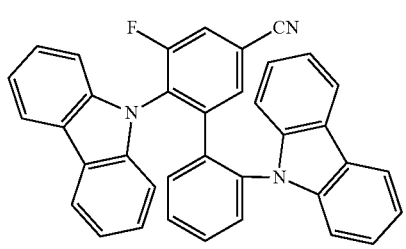
46
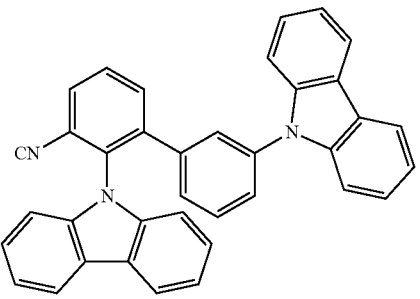
47
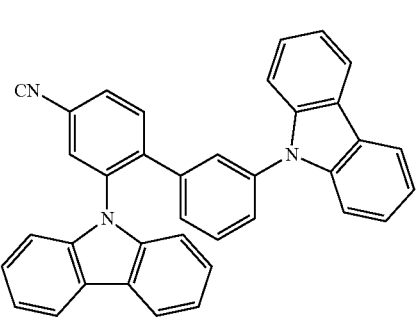
48
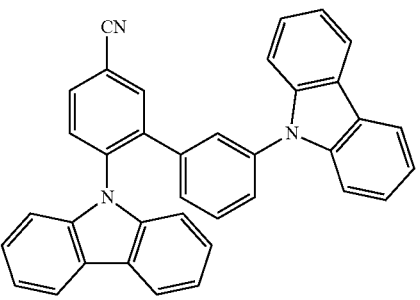
49
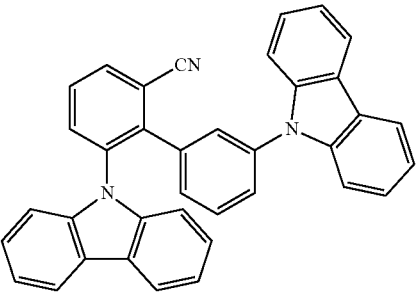
50
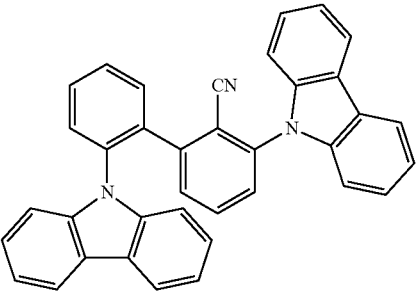

51
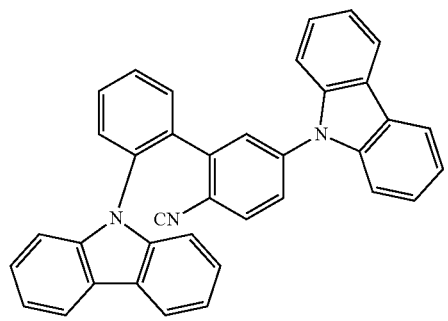
52
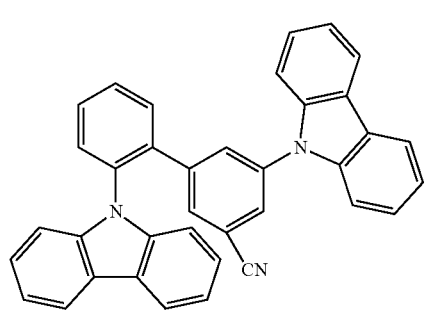
53
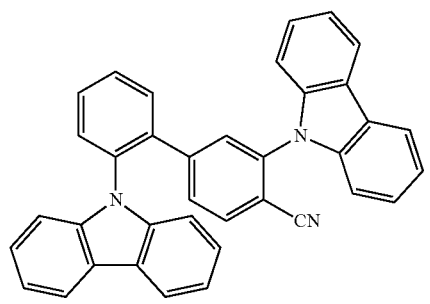
54
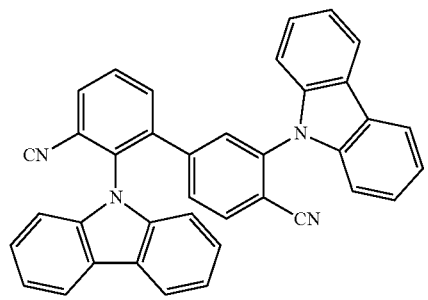
55
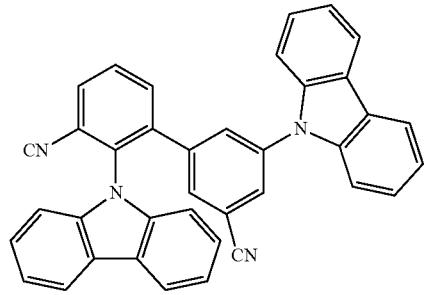
56
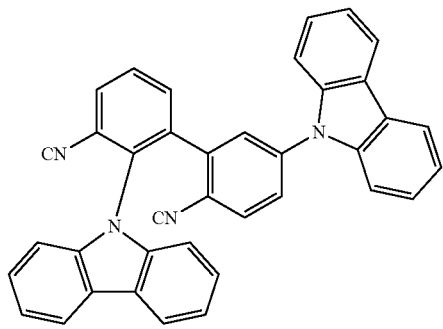
57
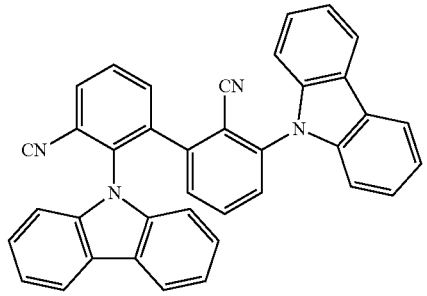
58
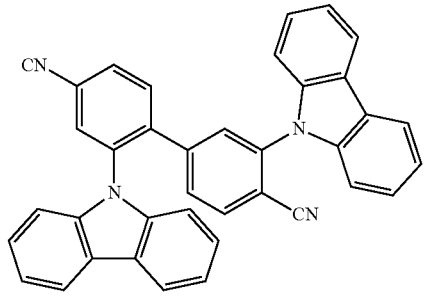
59
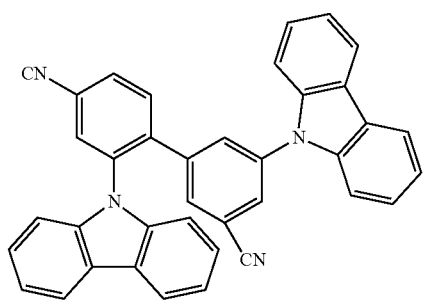
60
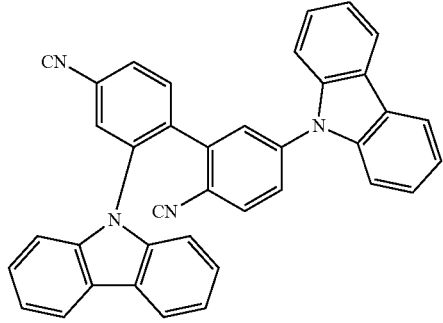

61
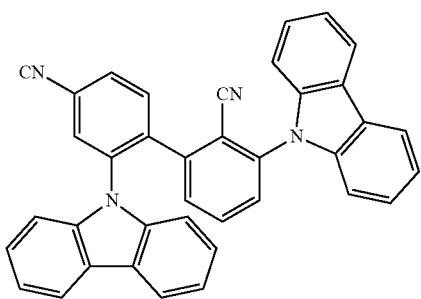
62
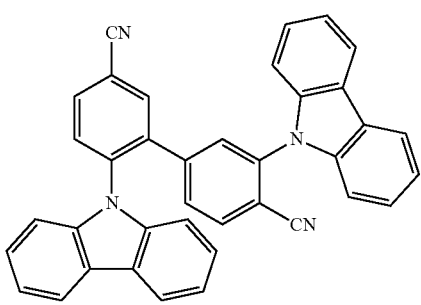
63
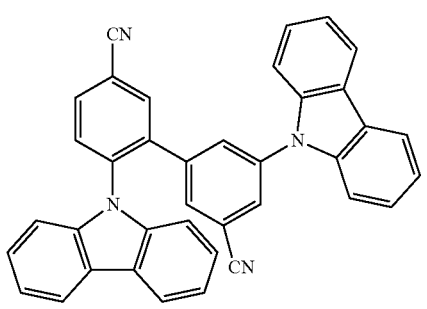
64
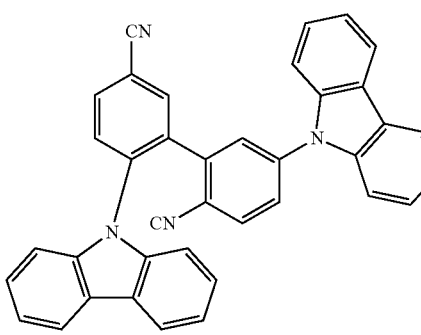
65
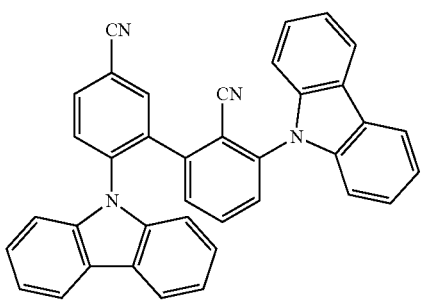
66
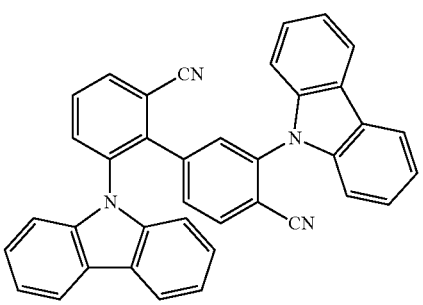
67
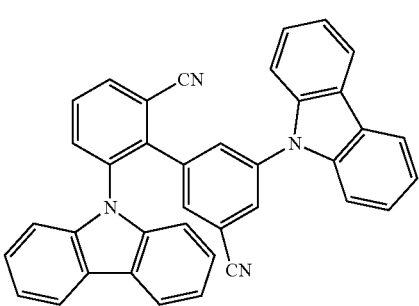
68
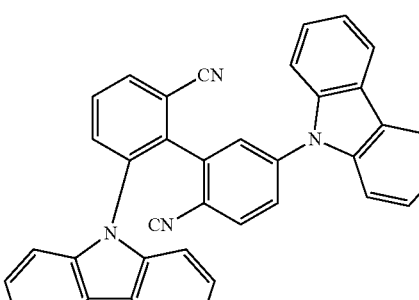
69
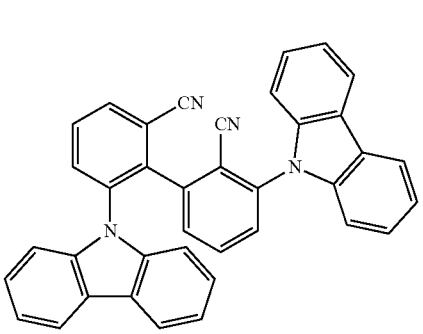
70
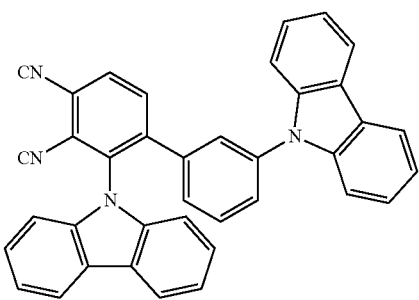

71 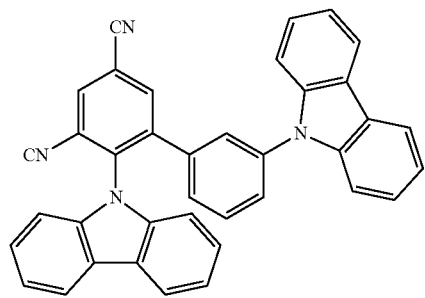
72 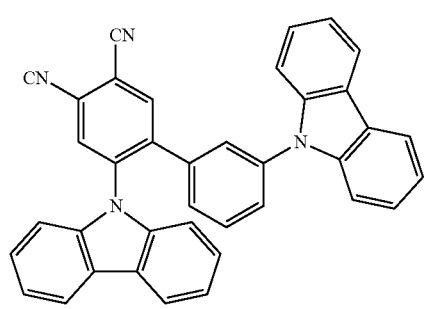
73 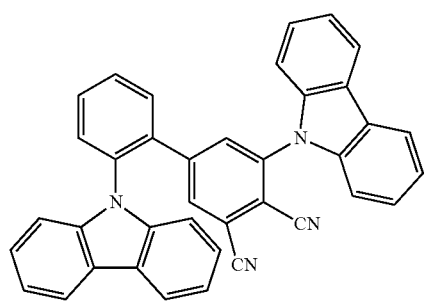
74 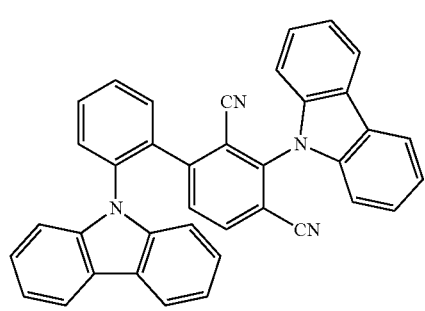
75 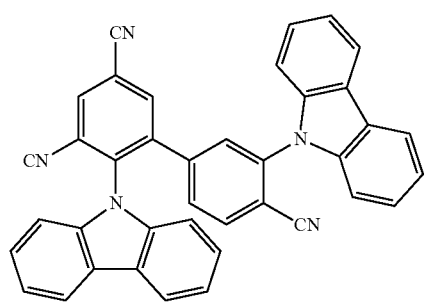
76 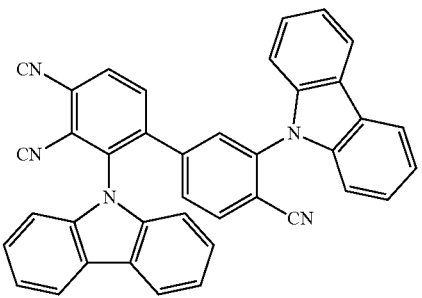
77 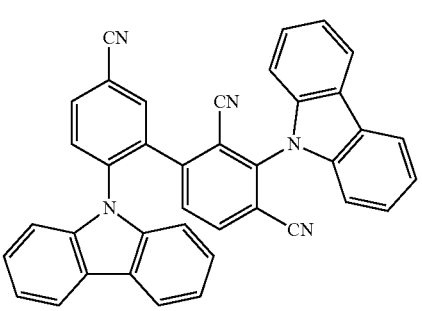
78 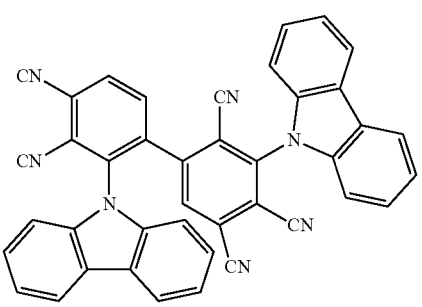
79 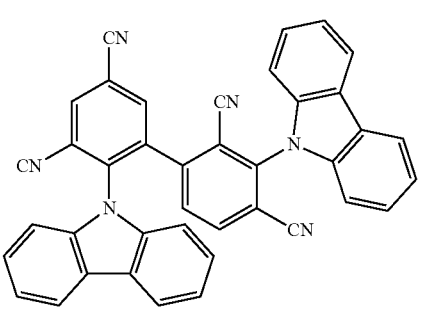
80 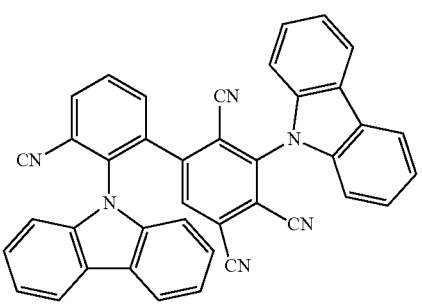

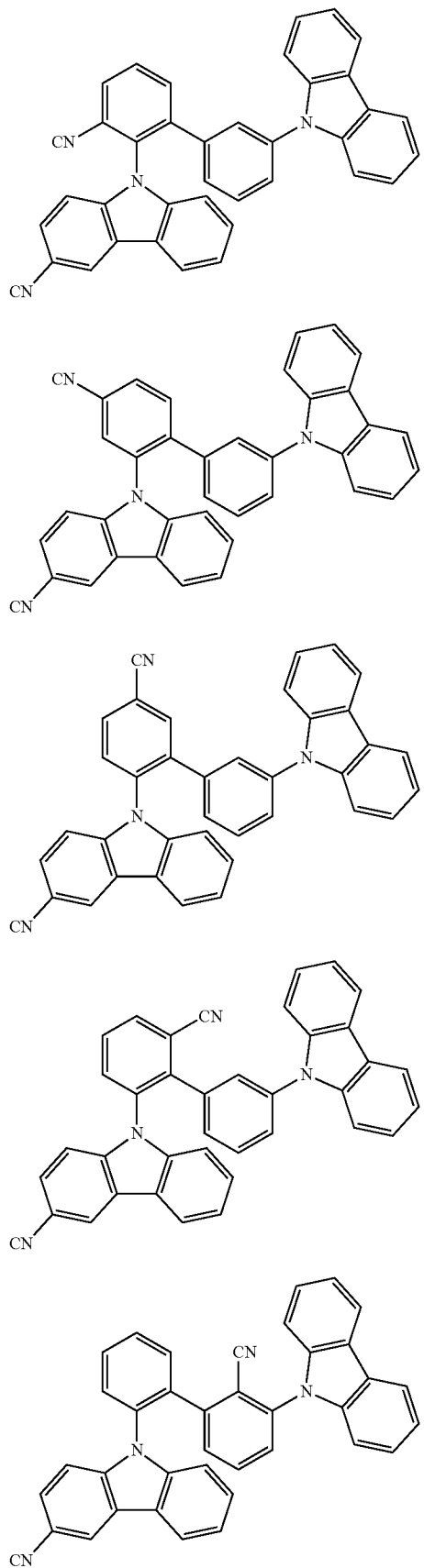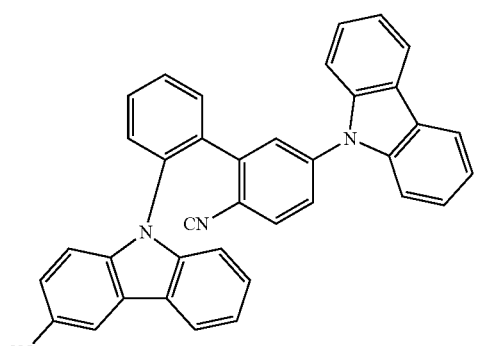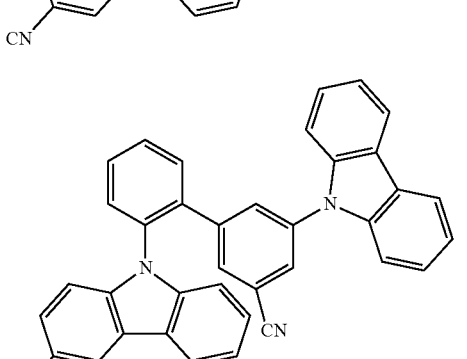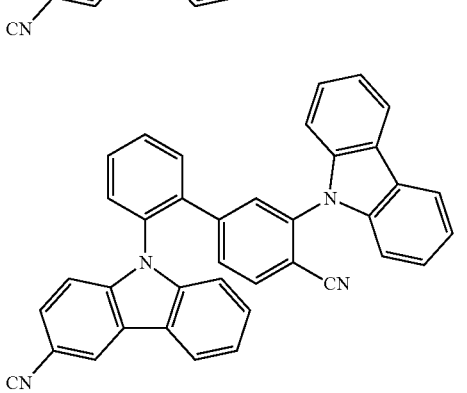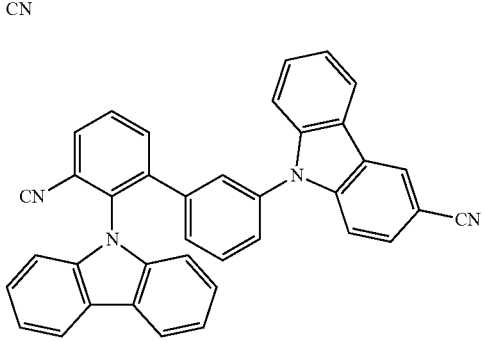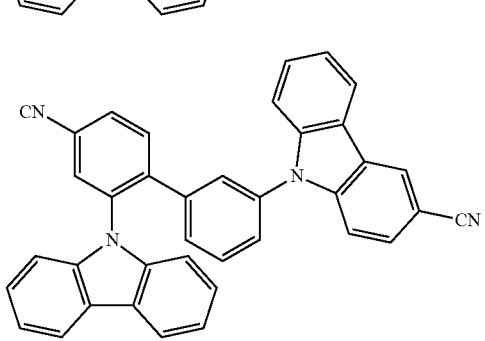

91
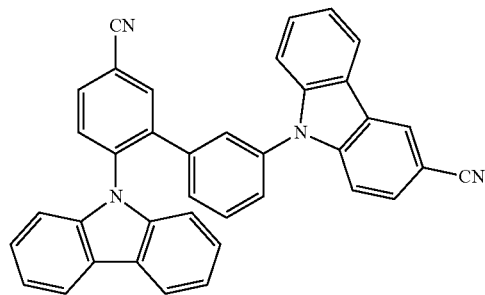
92
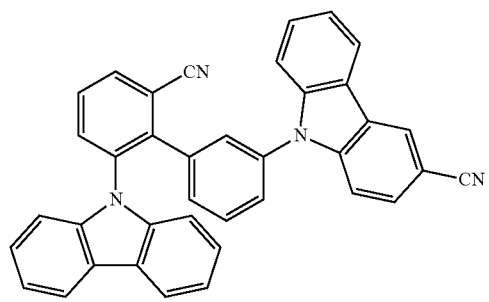
93
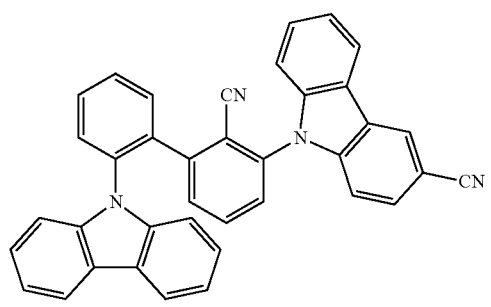
94
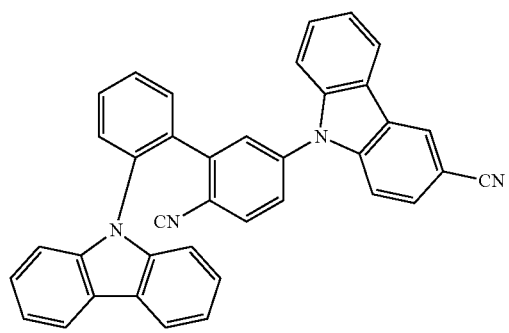
95
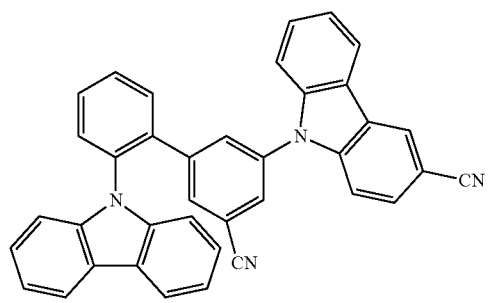
96
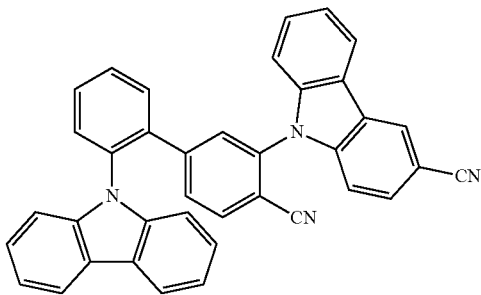
97
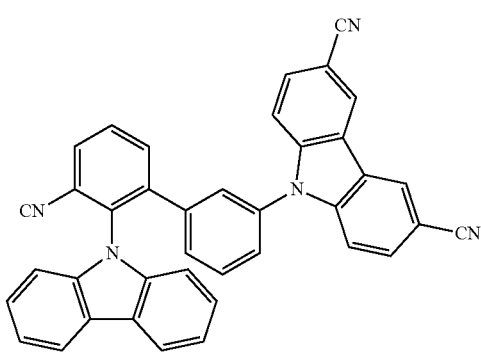
98
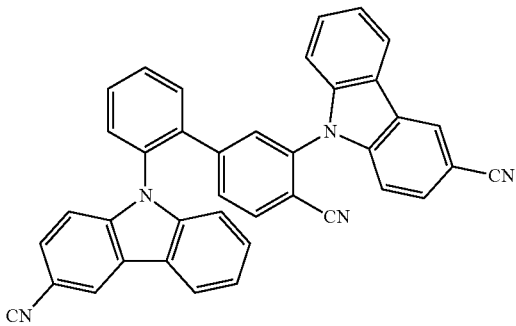
99
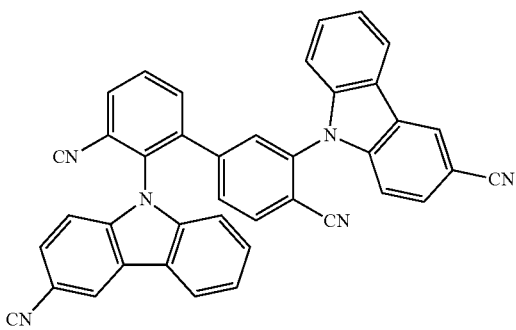

-continued
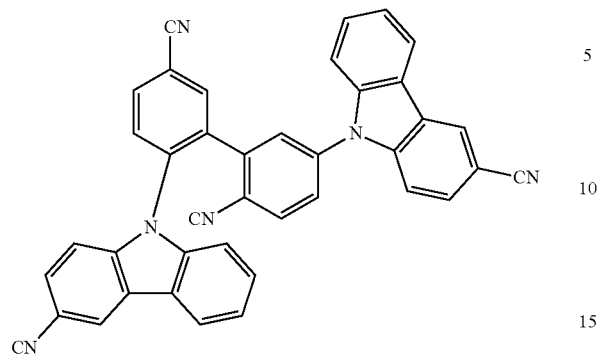
100
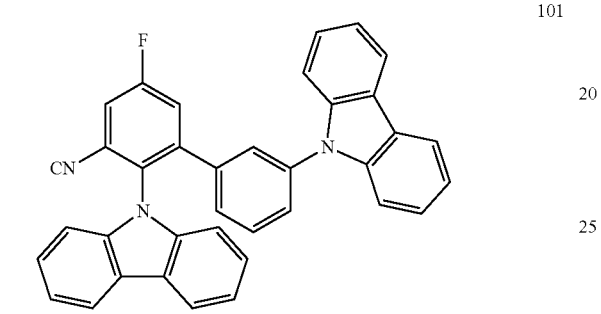
101
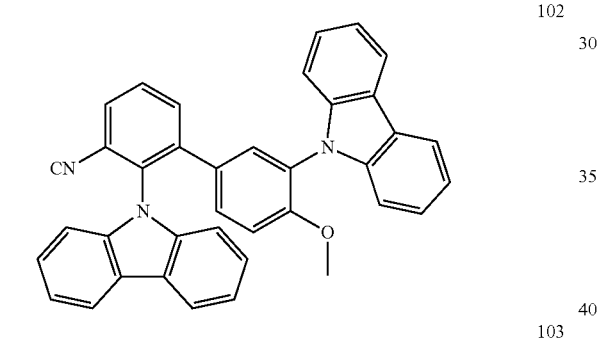
102

103
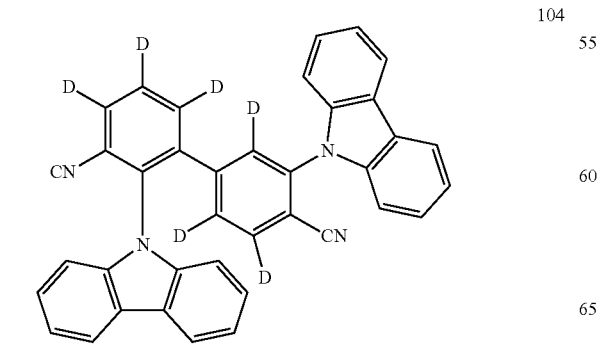
104
-continued
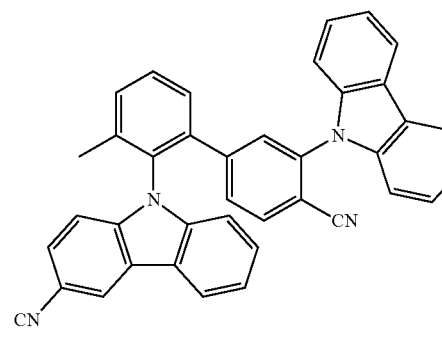
105
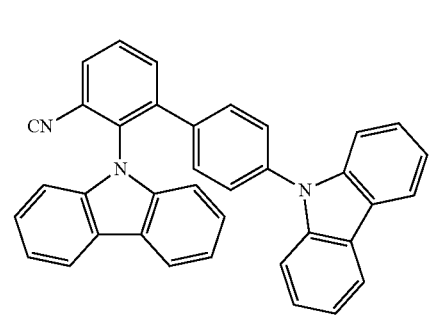
106
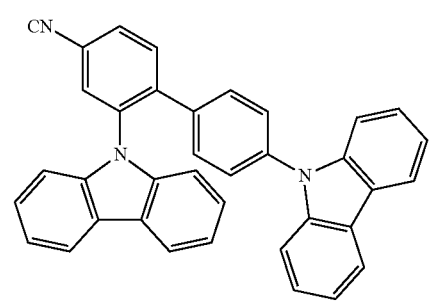
107
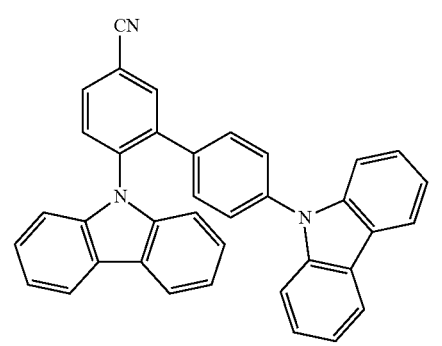
108
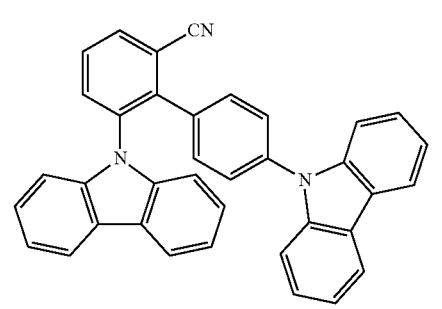
109

91
-continued
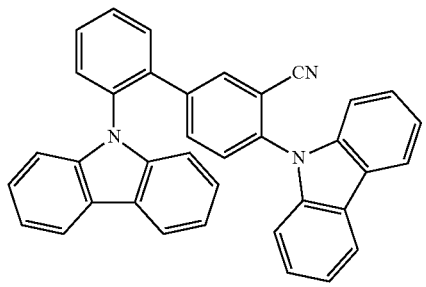
110
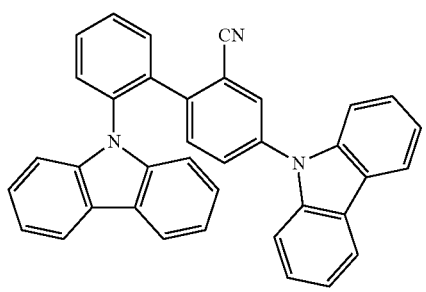
111
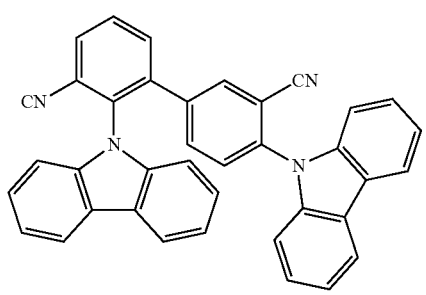
112
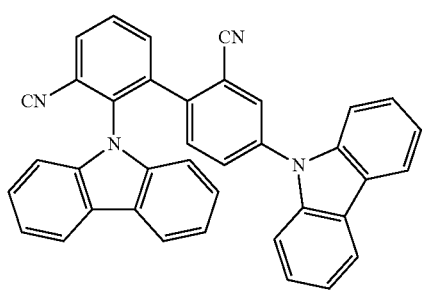
113
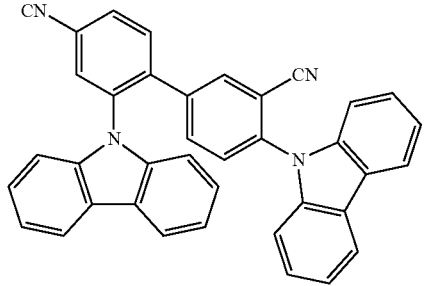
114
92
-continued
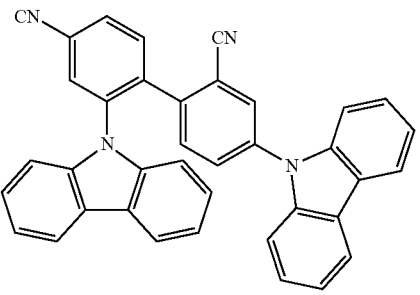
115
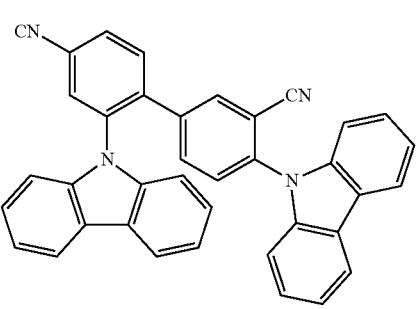
116
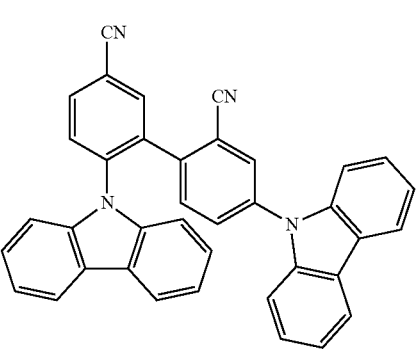
117
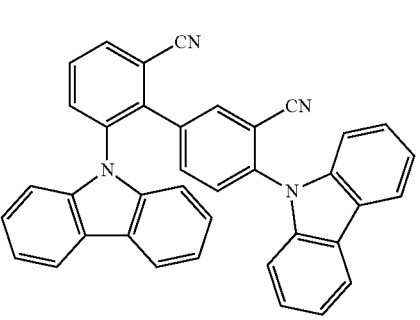
118
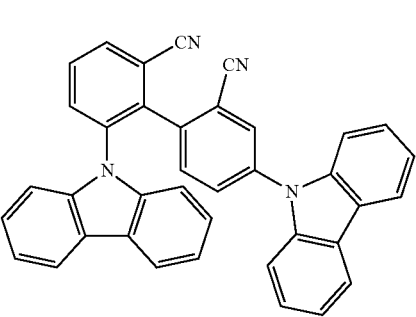
119

120
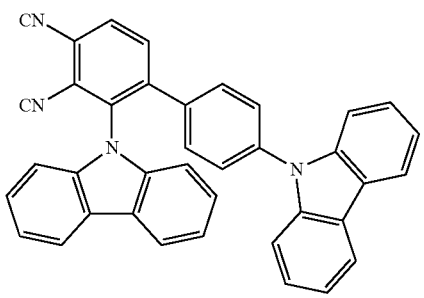
121
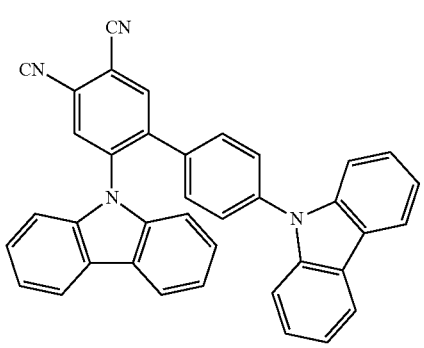
122
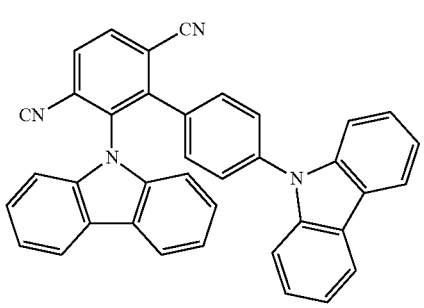
123
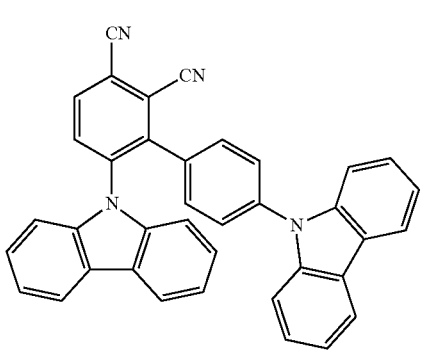
124
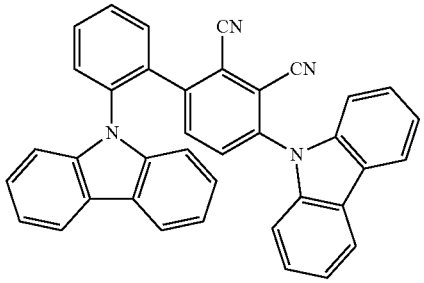
125
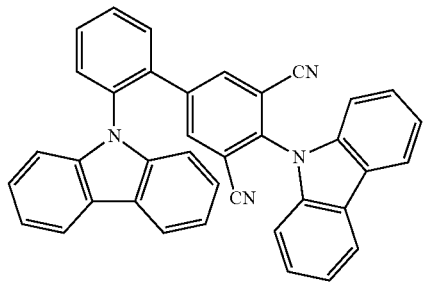
126
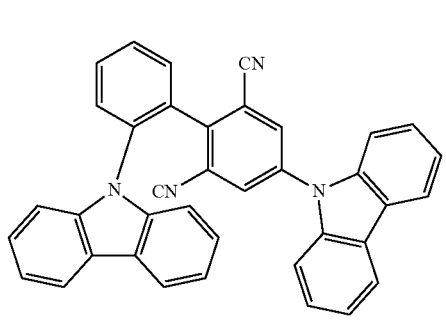
127
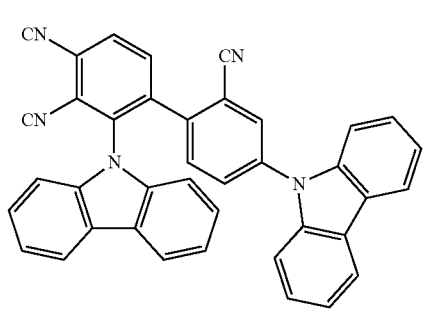
128
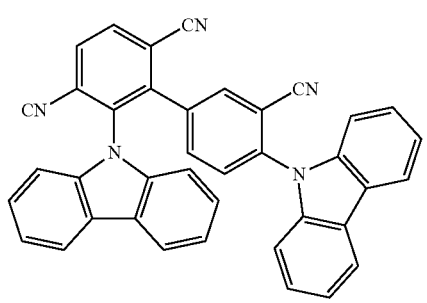
129
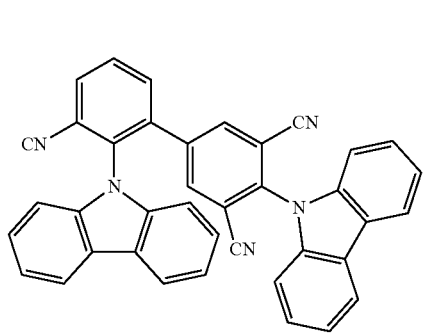

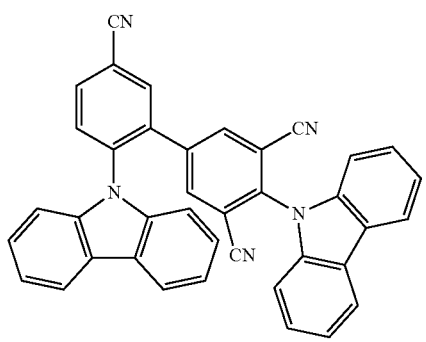
130
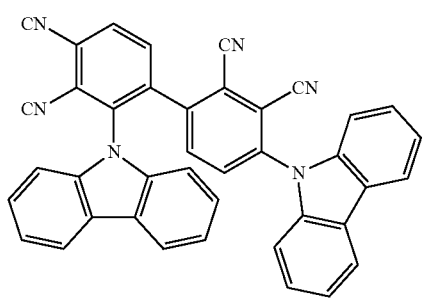
131
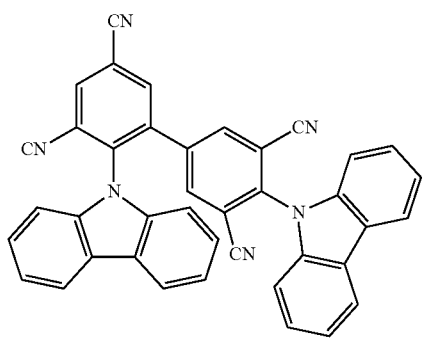
132
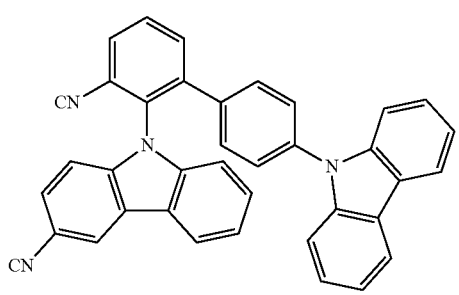
133
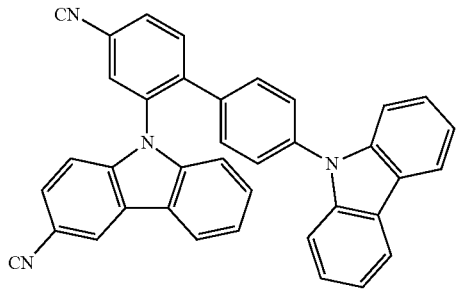
134
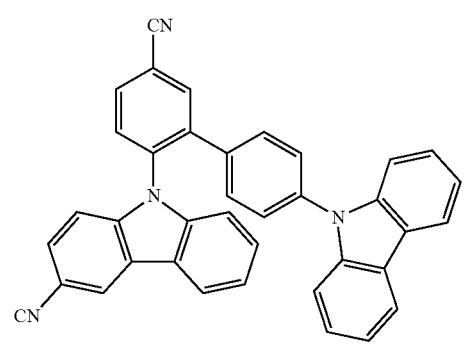
135
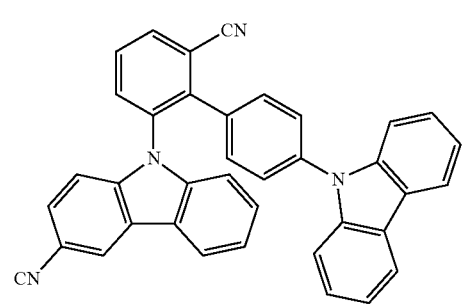
136
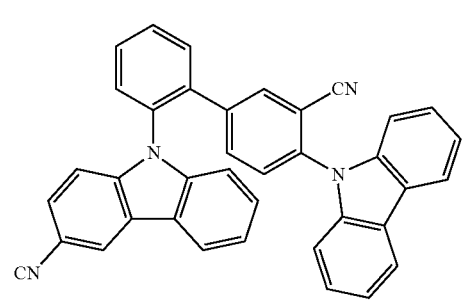
137
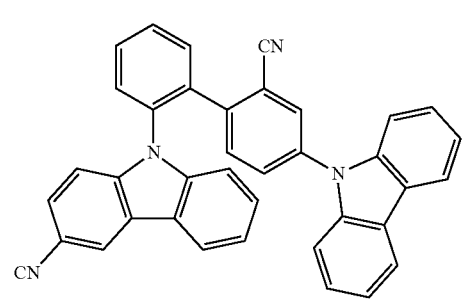
138
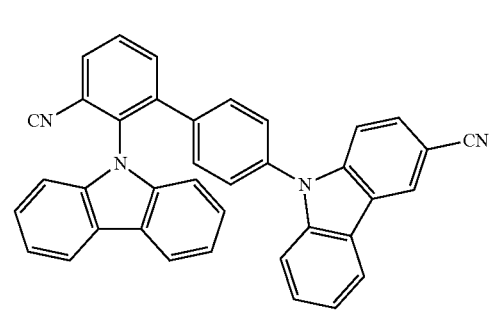
139

140 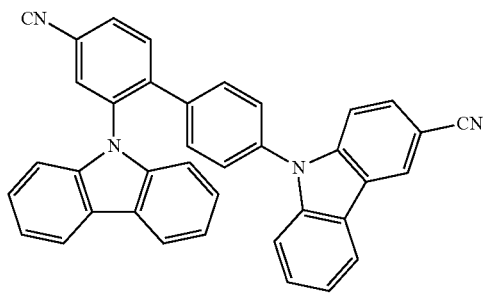
141 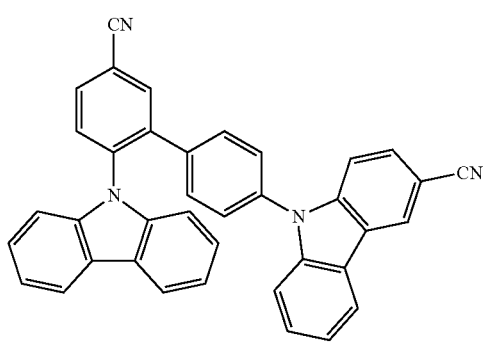
142 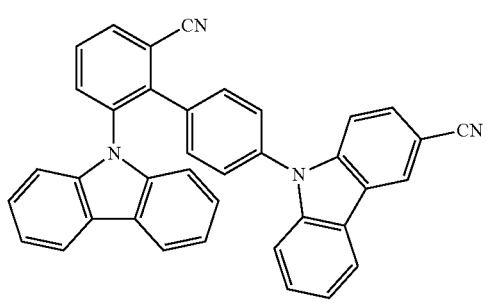
143 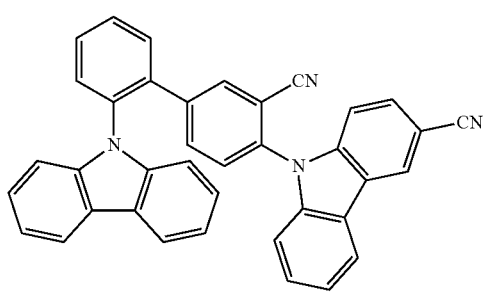
144 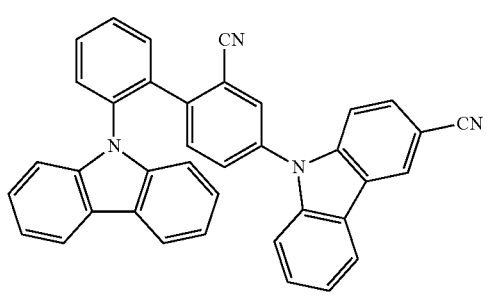
145 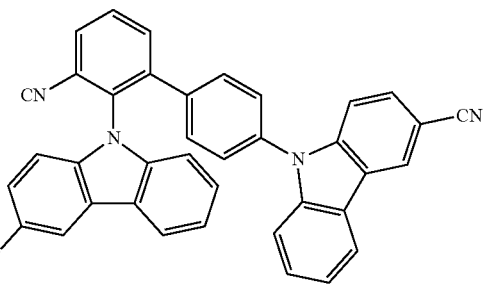
146 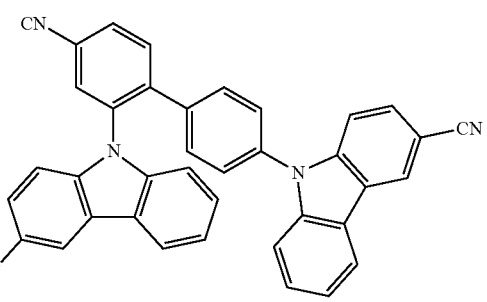
147 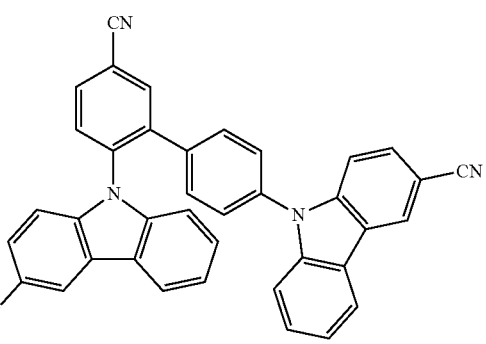
148 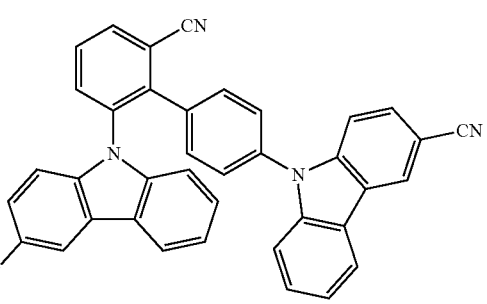
149 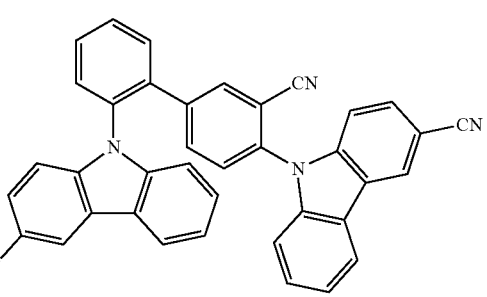

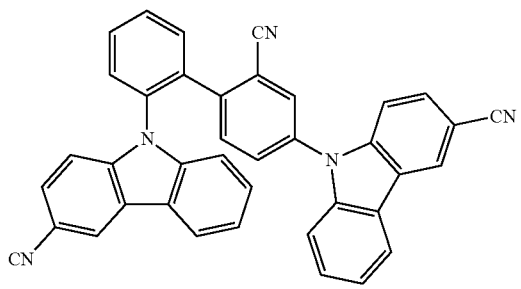
150
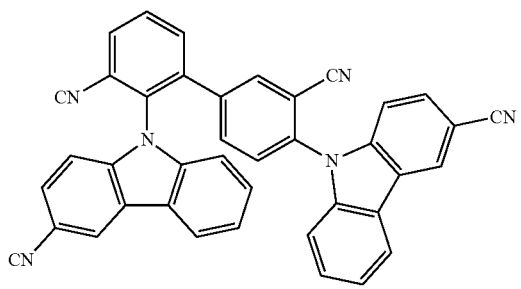
151
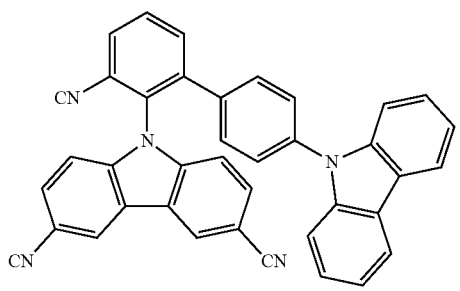
152
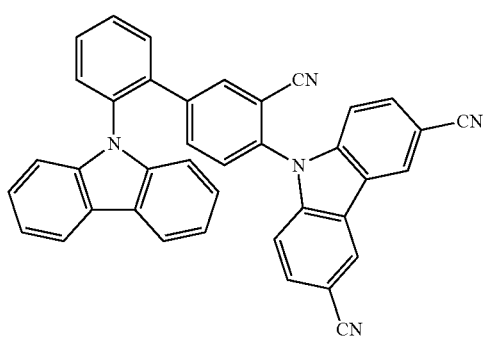
153
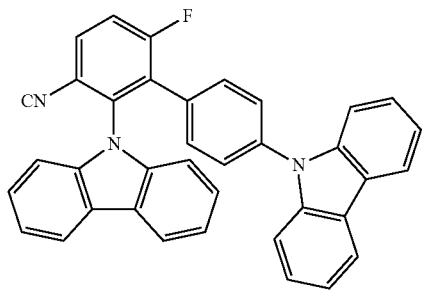
154
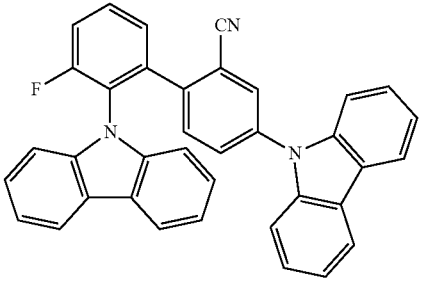
155
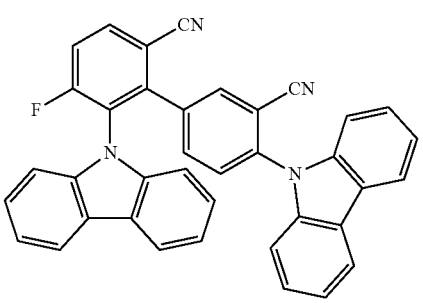
156
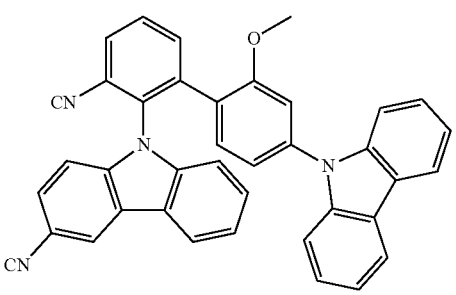
157
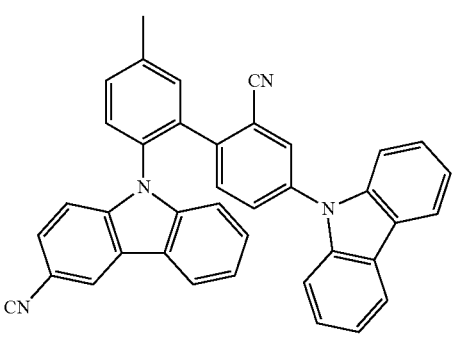
158
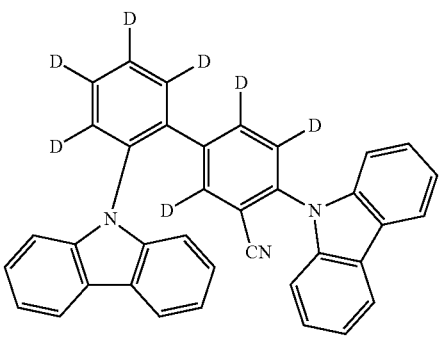
159

160
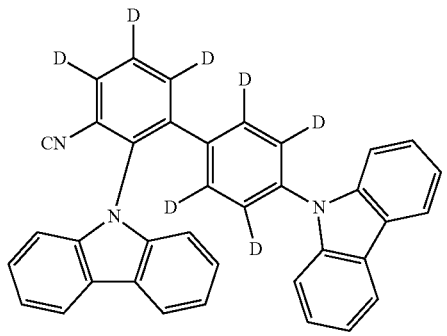
161
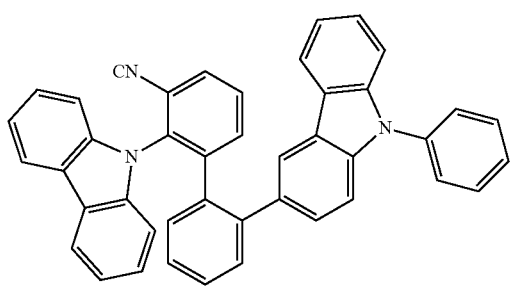
162
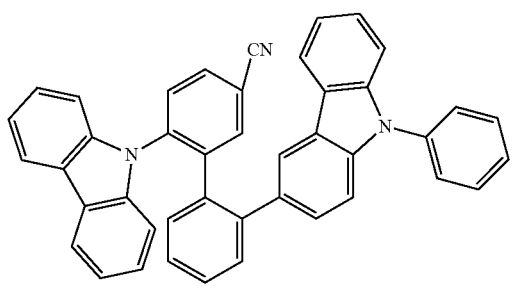
163
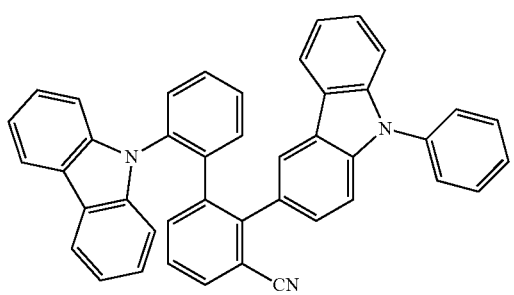
164
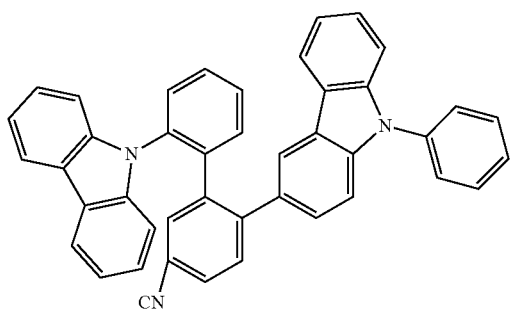
165
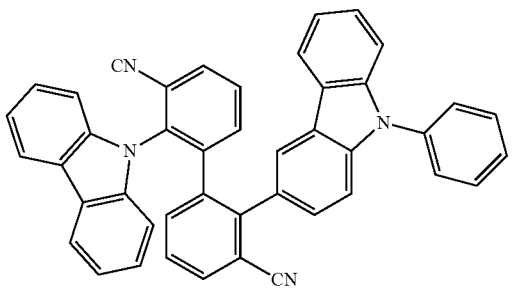
166
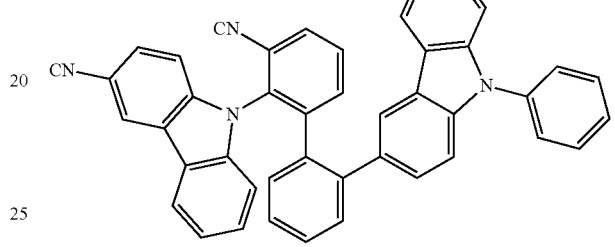
167
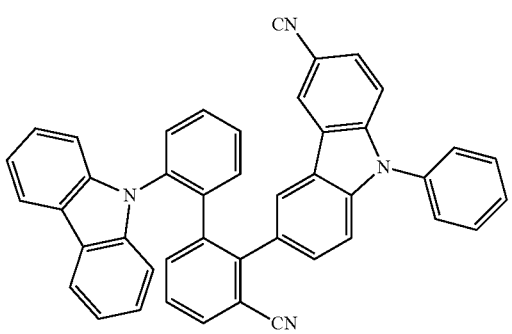
168
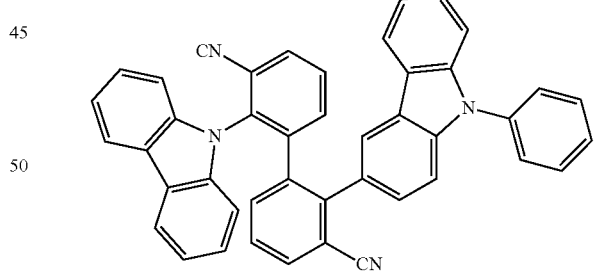
169
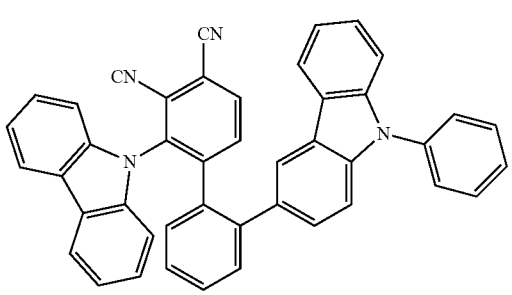

103
-continued
170
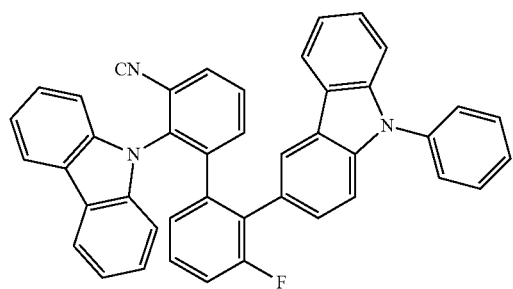
171
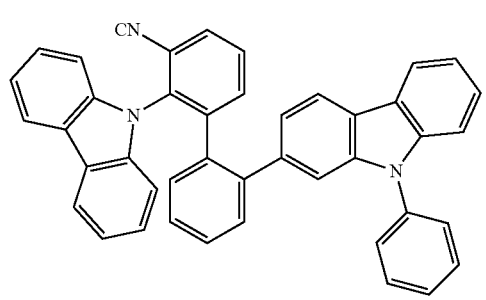
172
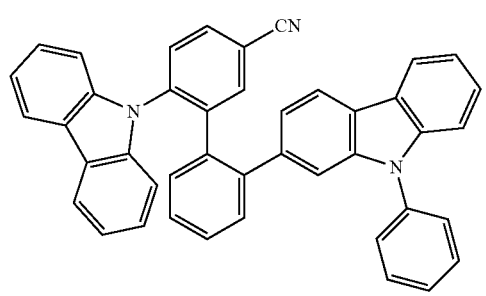
173
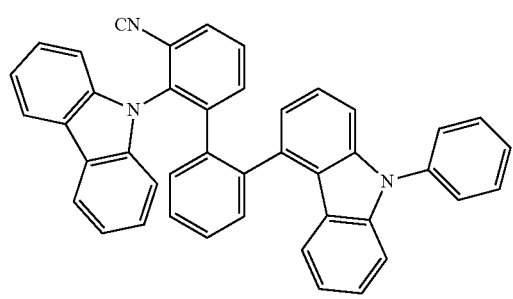
174
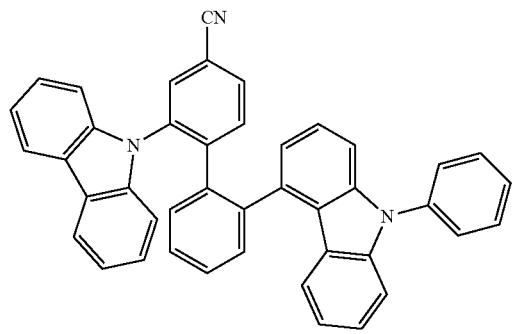
104
-continued
175
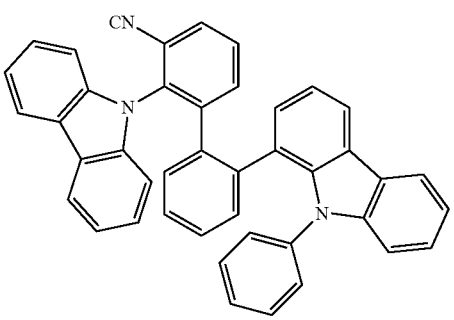
176
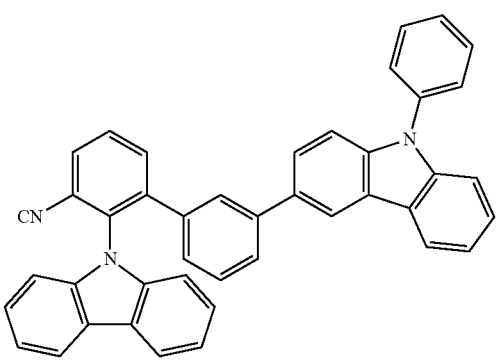
177
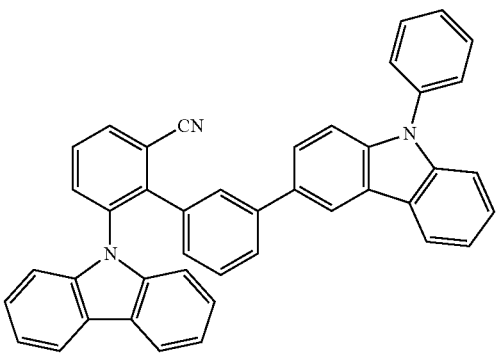
178
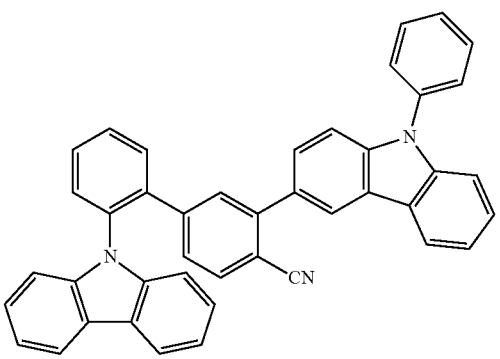

179
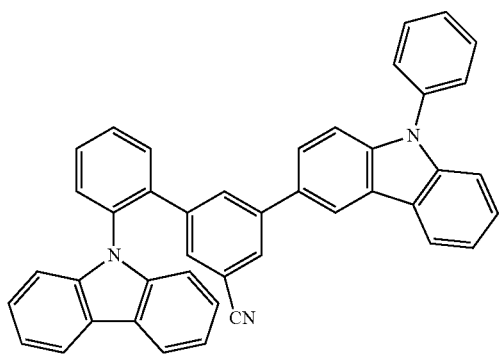
180
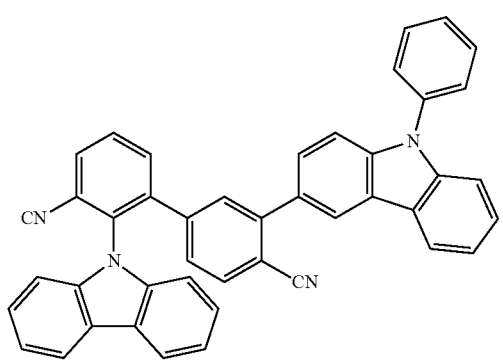
181
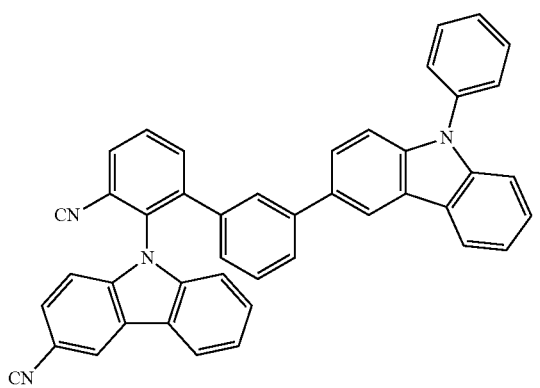
182
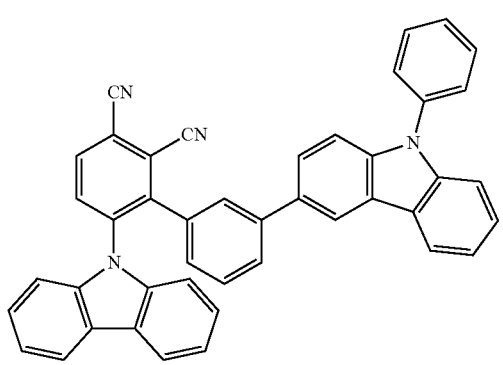
183
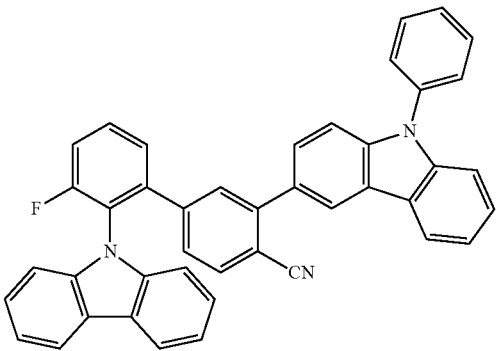
184
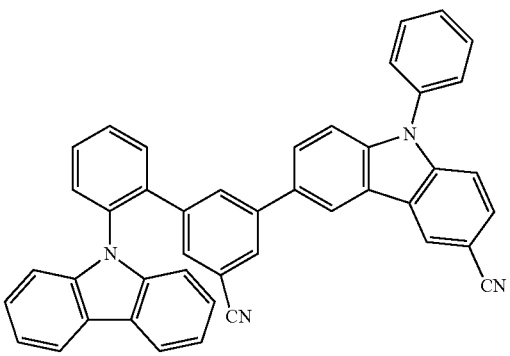
185
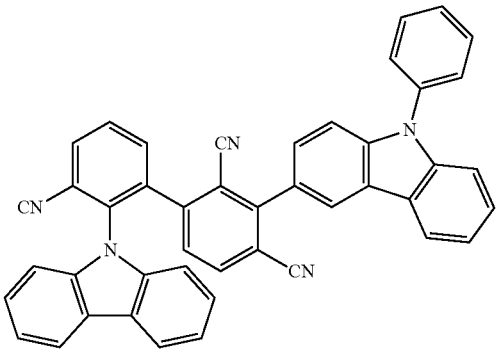
186
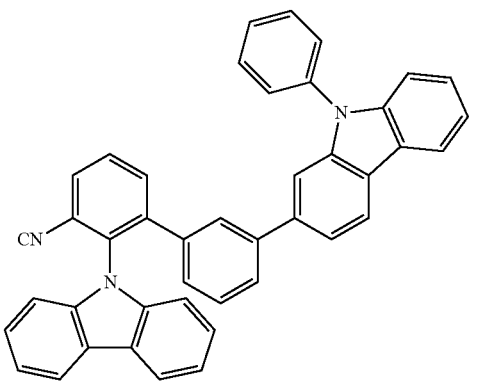

187
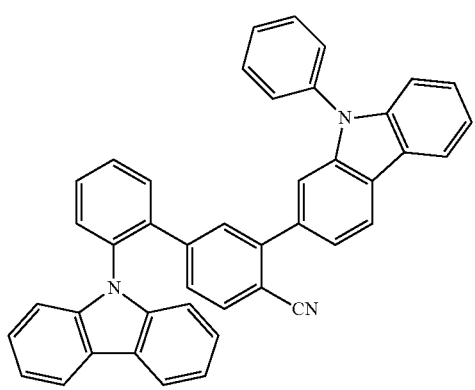
188
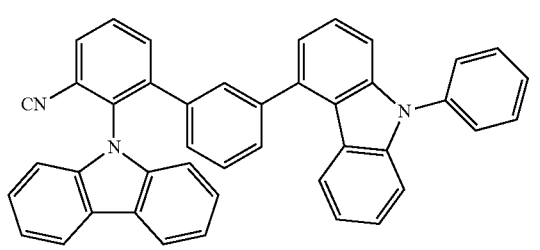
189
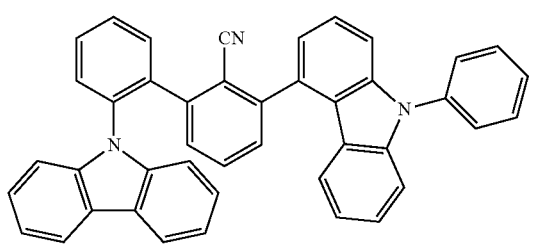
190
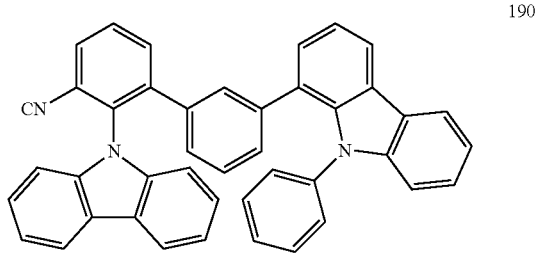
191
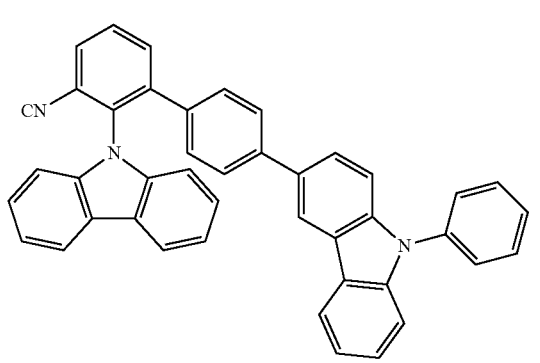
192
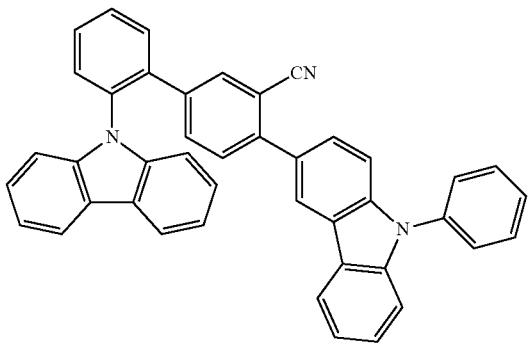
193
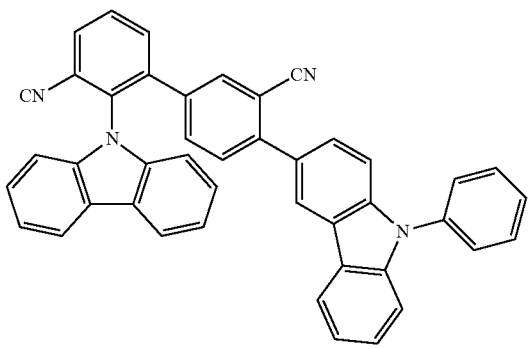
194
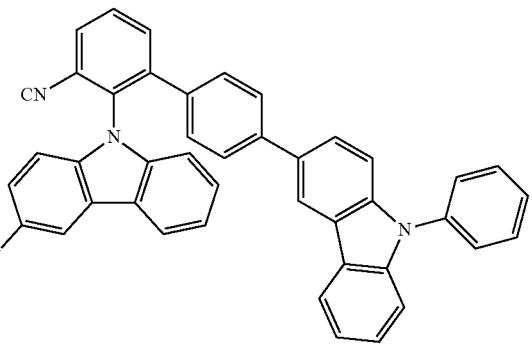
195
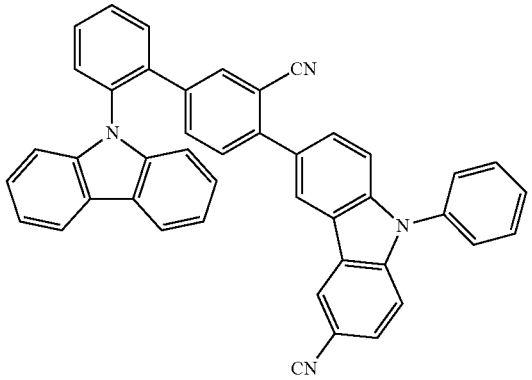

-continued
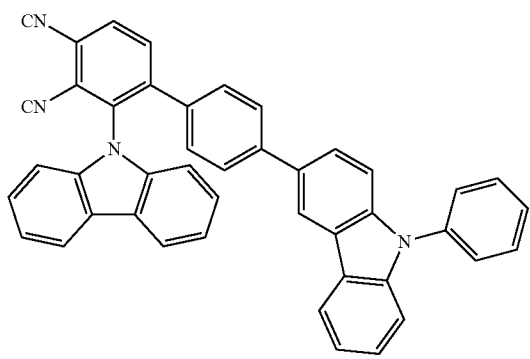
196
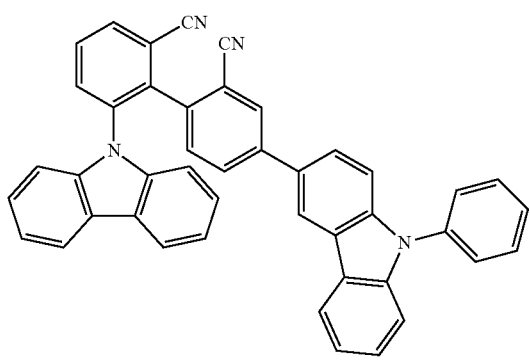
197
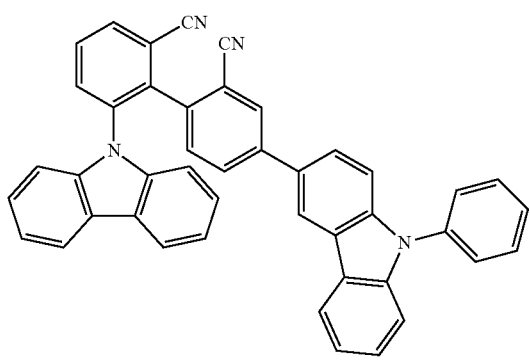
198
199
200
-continued
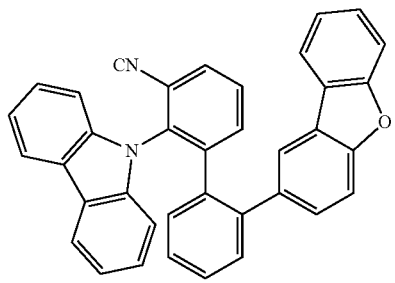
201
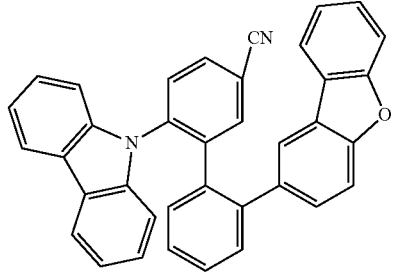
202
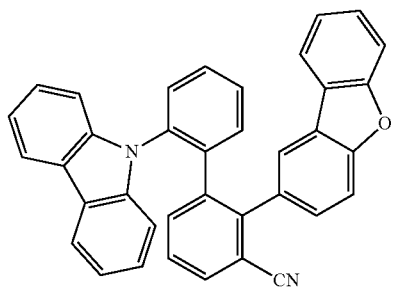
203
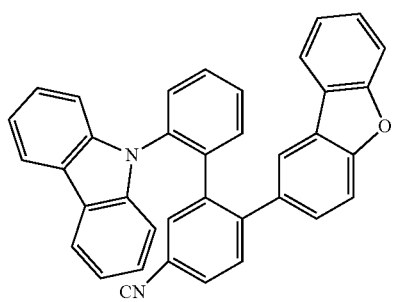
204
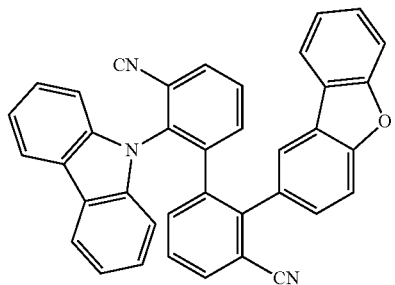
205

-continued
206
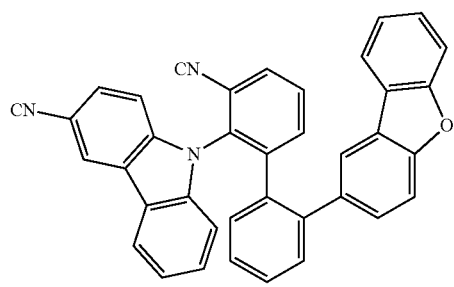
207
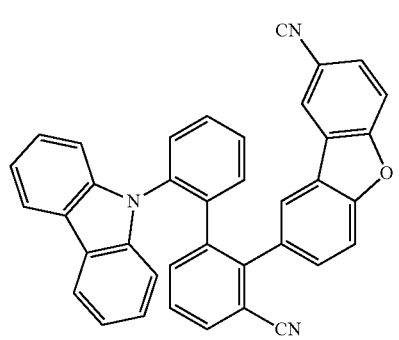
208
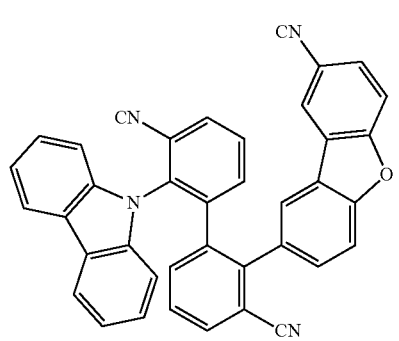
209
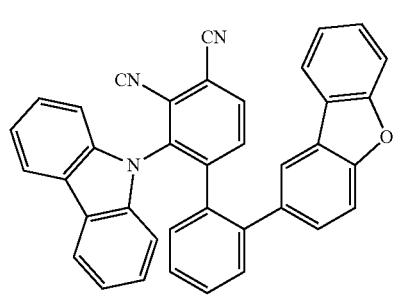
210
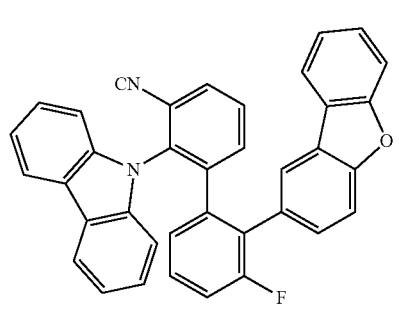
-continued
211
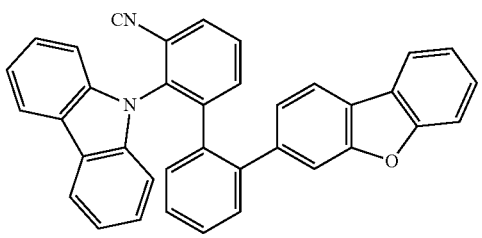
212
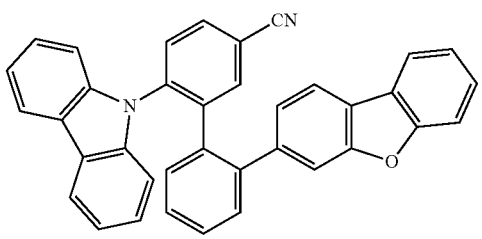
213
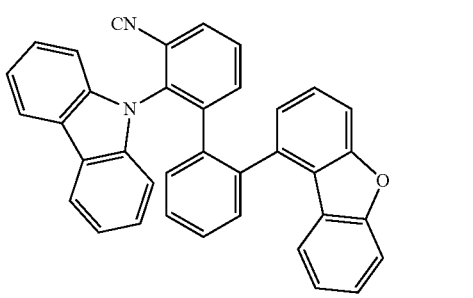
214
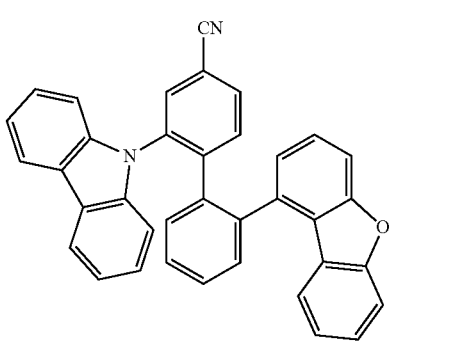
215
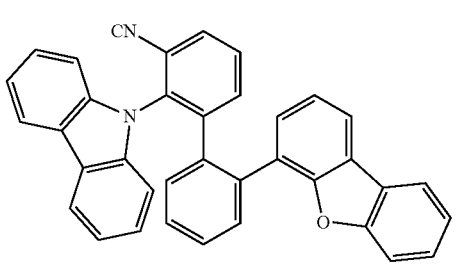
216
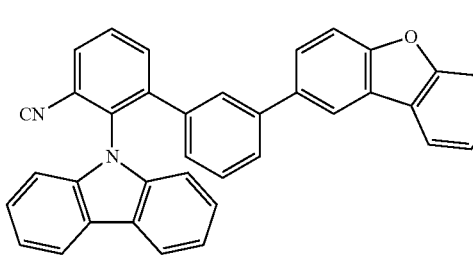

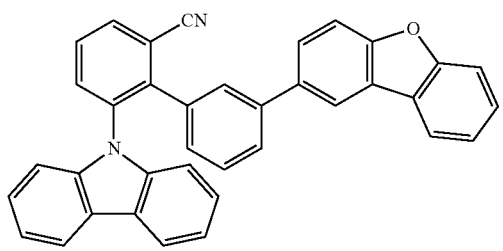
217
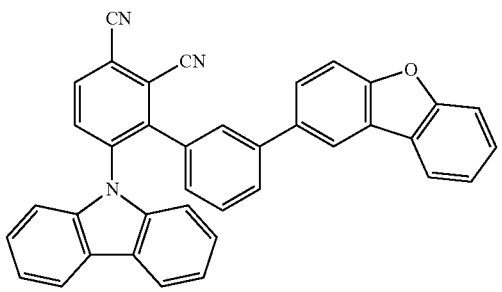
222
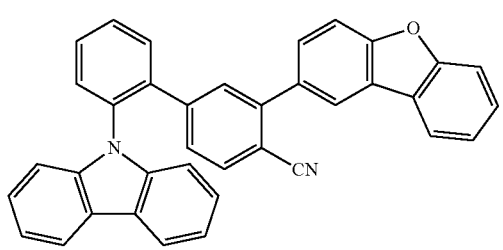
218
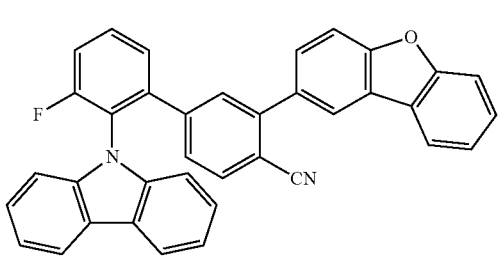
223
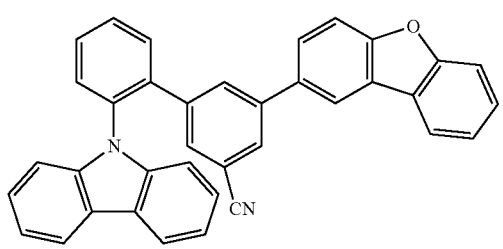
219
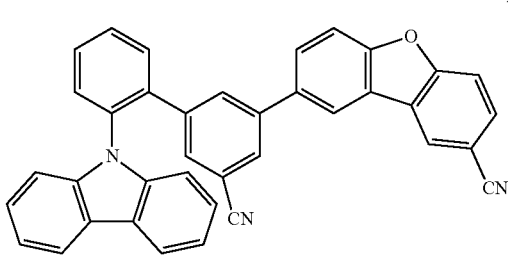
224
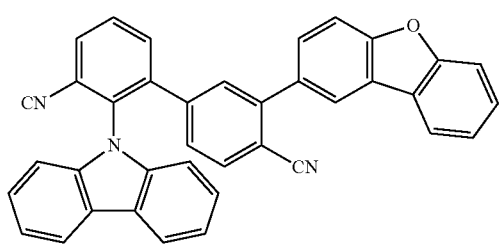
220
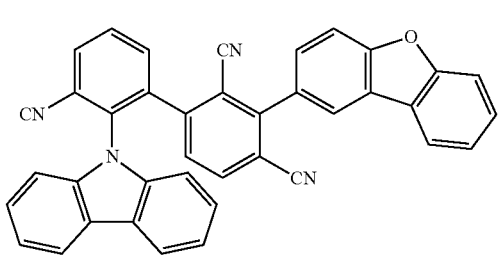
225
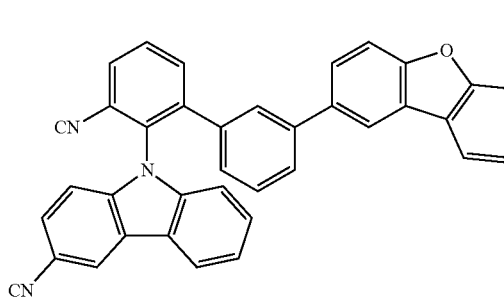
221
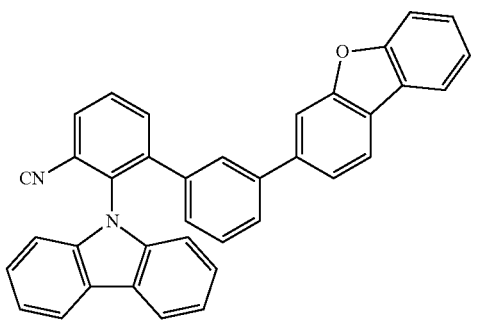
226

227 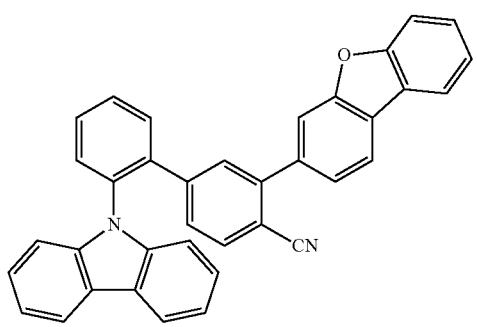
228 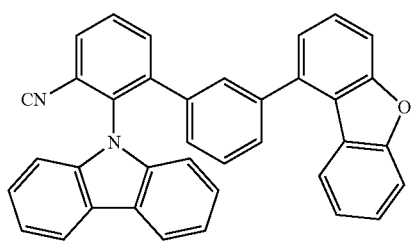
229 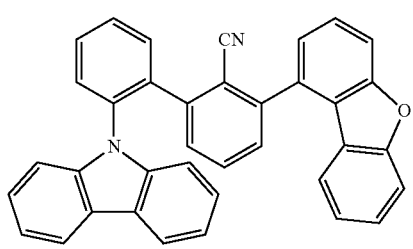
230 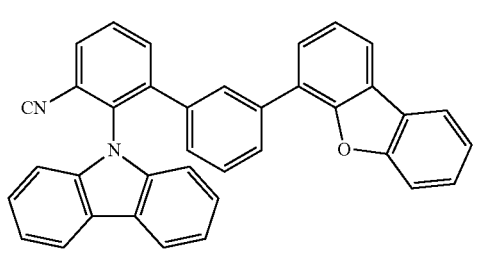
231 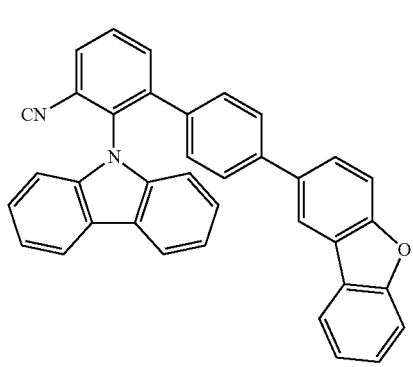
232 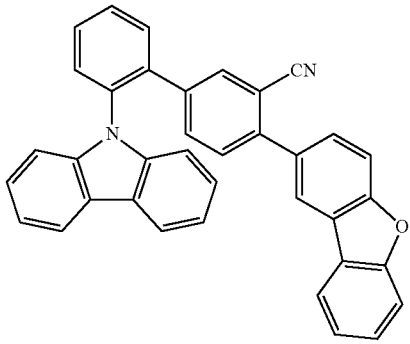
233 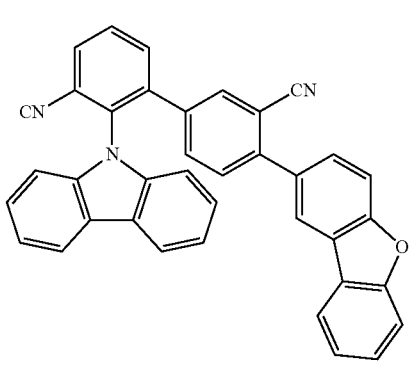
234 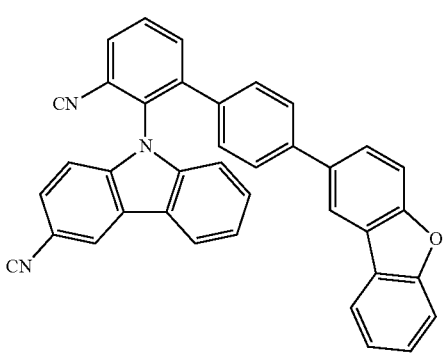
235 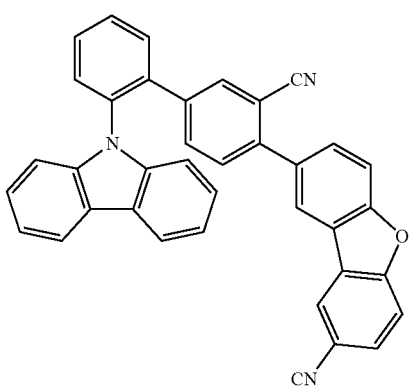

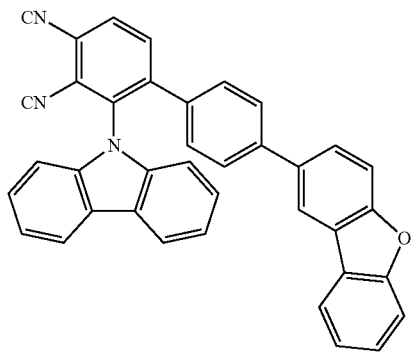 236
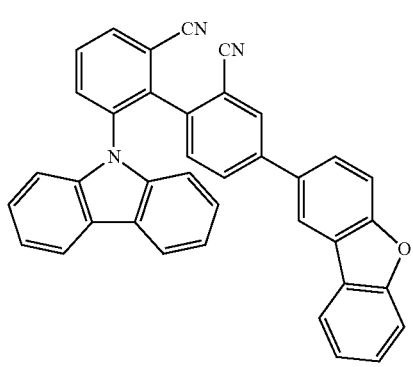 237
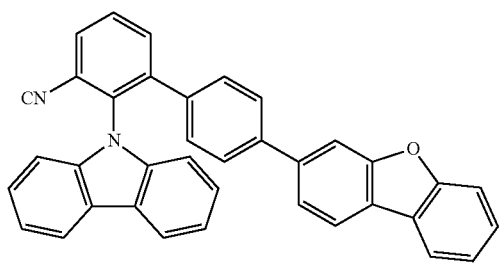 238
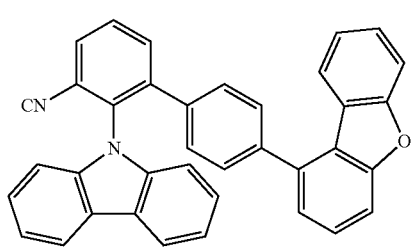 239
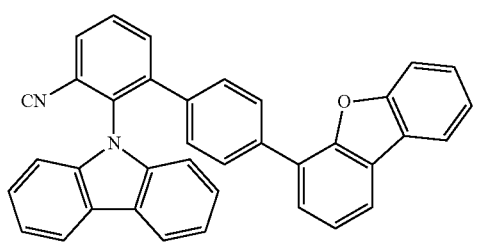 240

246
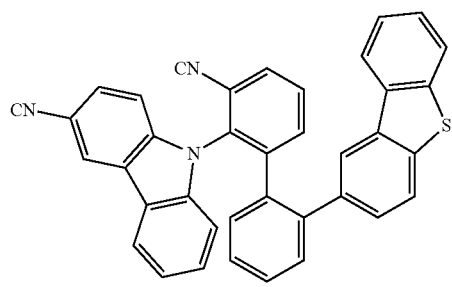
247
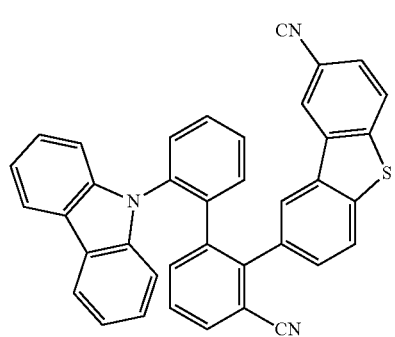
248
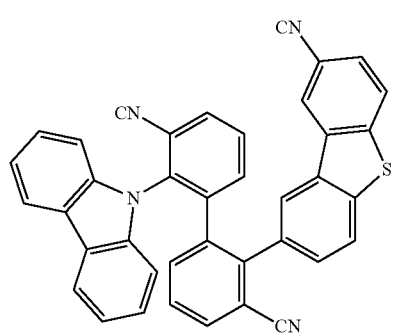
249
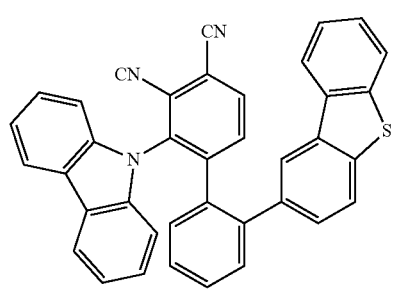
250
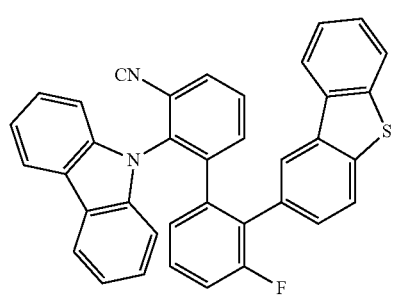
251
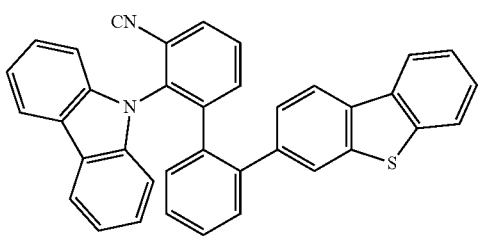
252
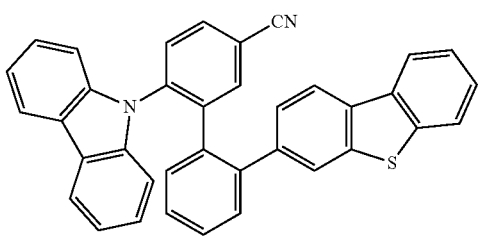
253
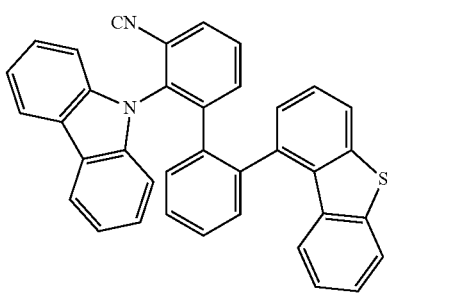
254
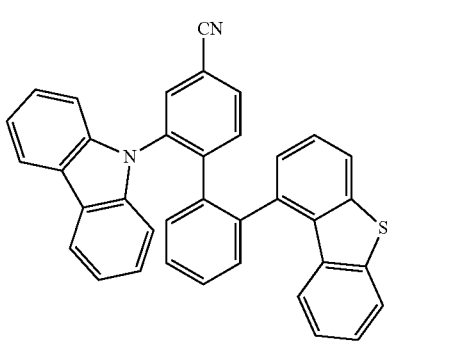
255
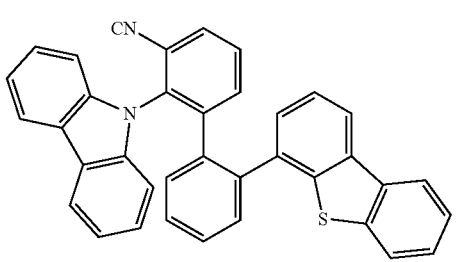
256
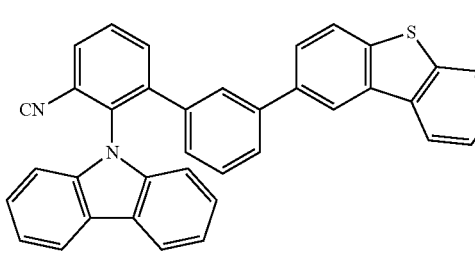

257
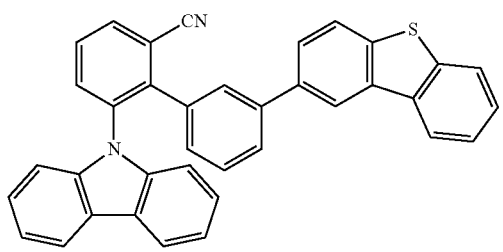
258
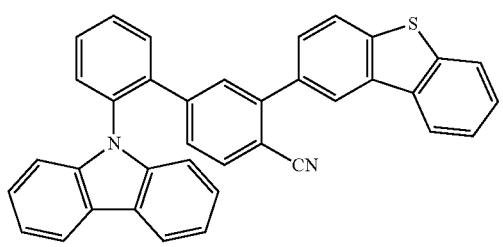
259
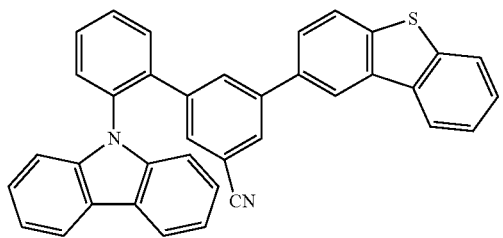
260
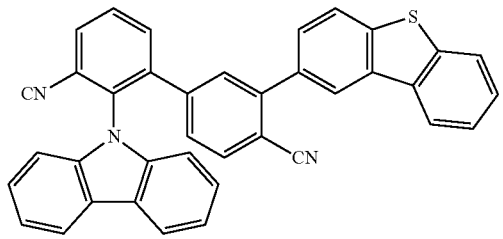
261
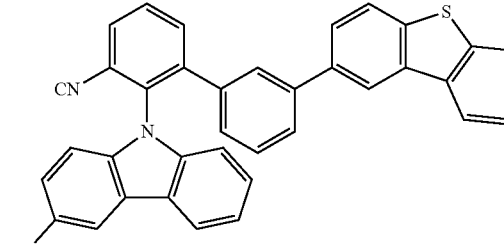
262
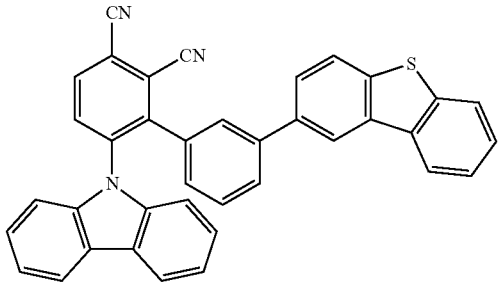
263
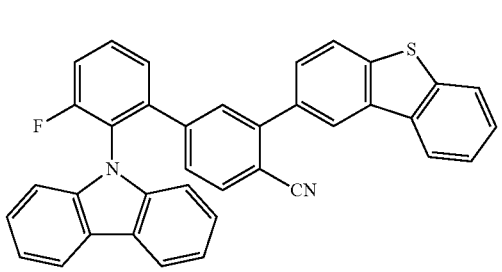
264
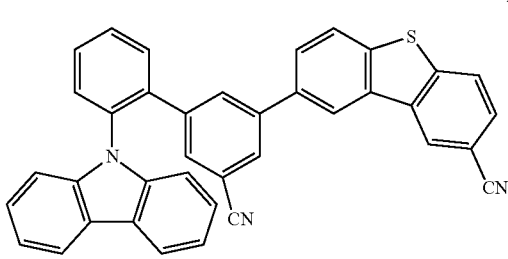
265
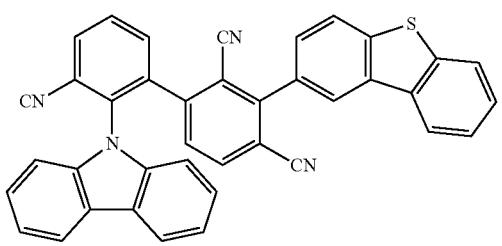
266
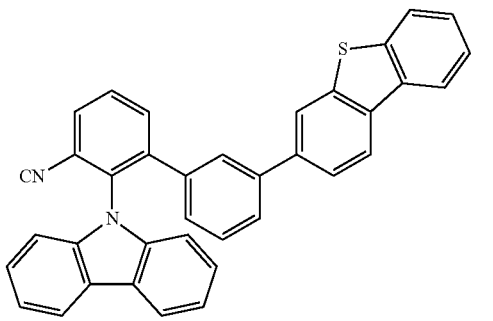

267 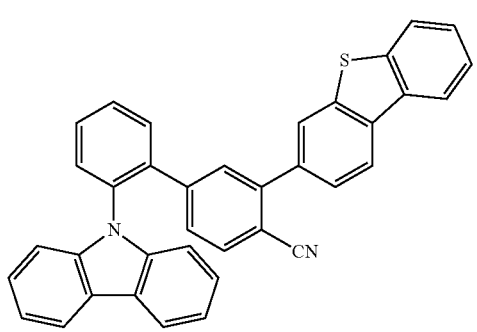
268 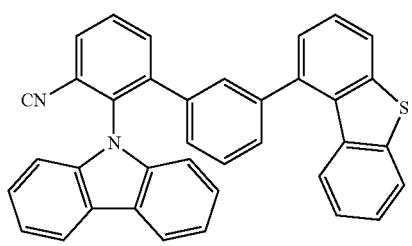
269 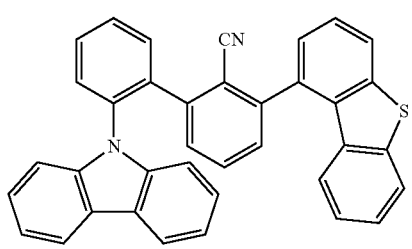
270 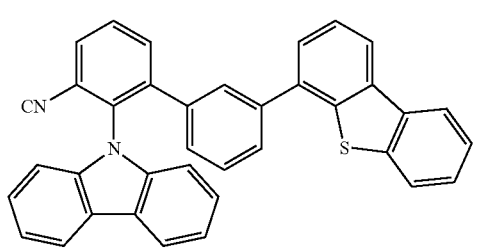
271 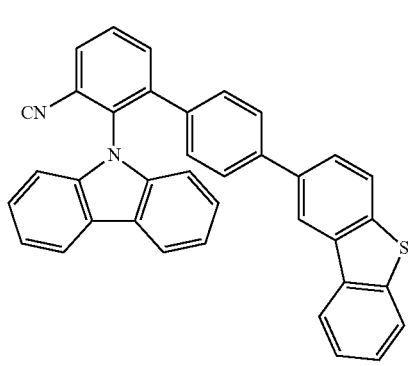
272 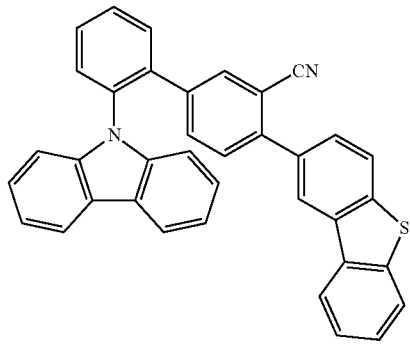
273 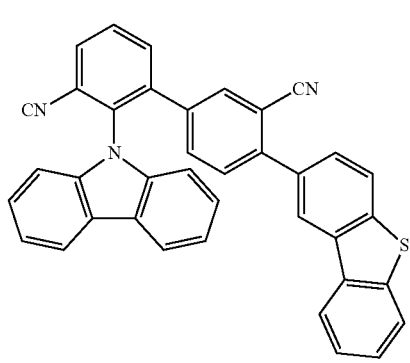
274 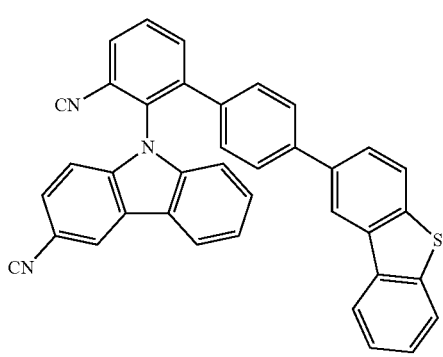
275 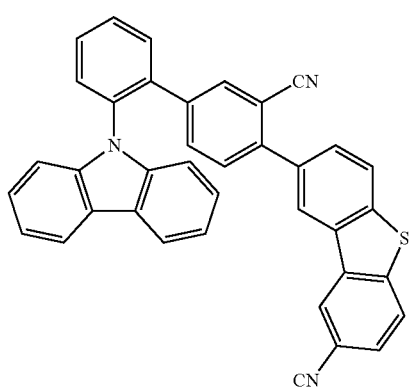

125
-continued
276
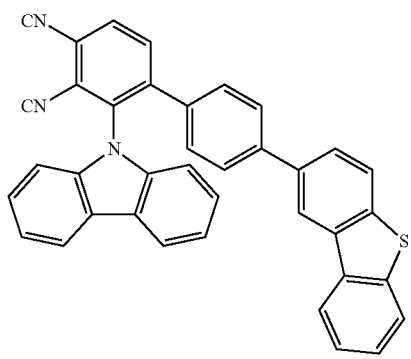
277
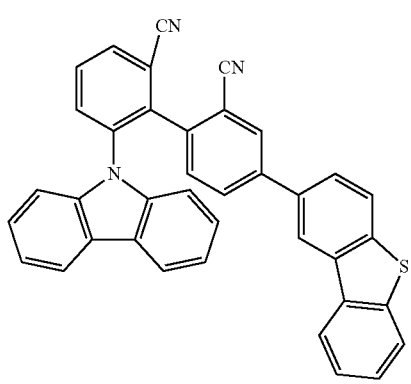
278
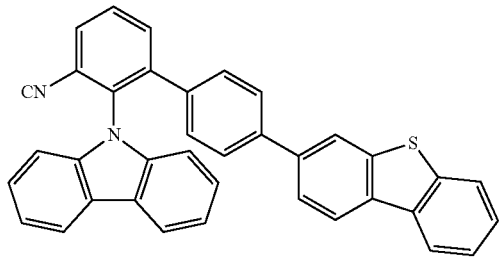
279
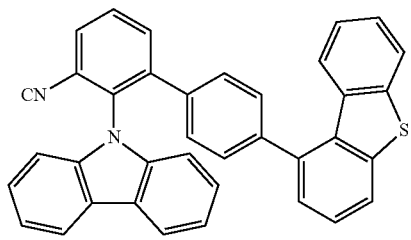
280
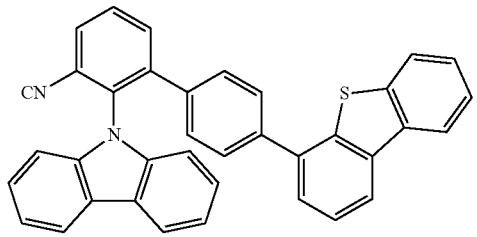
126
-continued
281
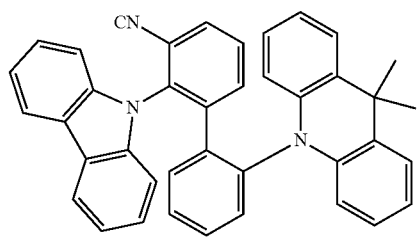
282
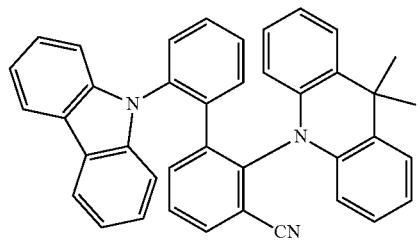
283
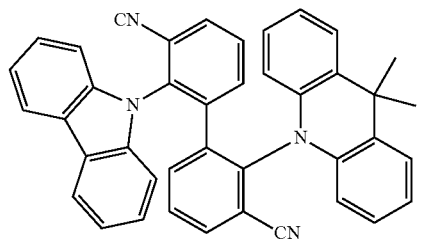
284
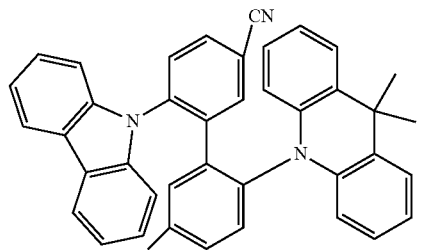
285
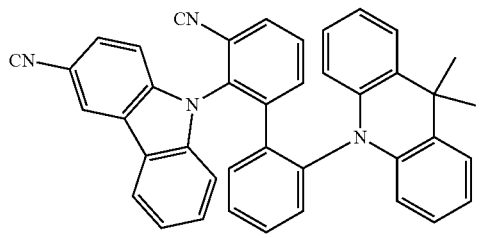
286
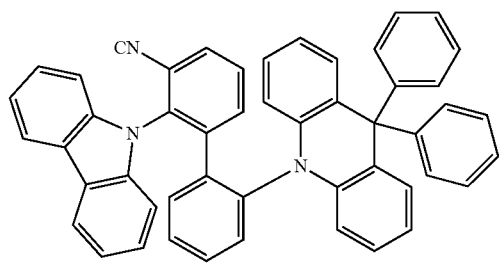

287
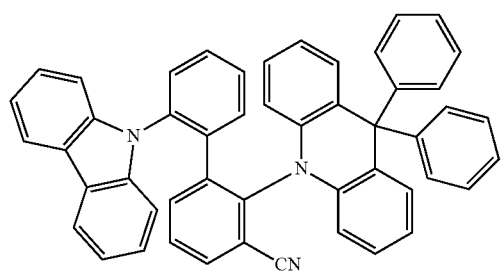
288
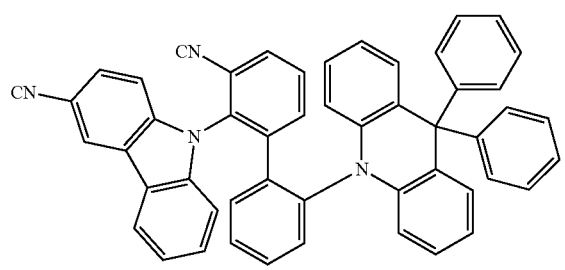
289
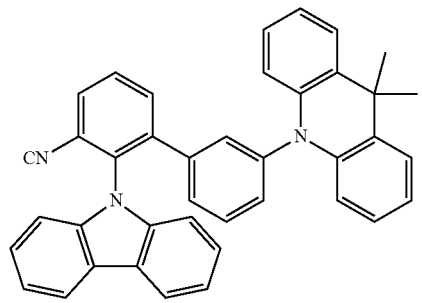
290
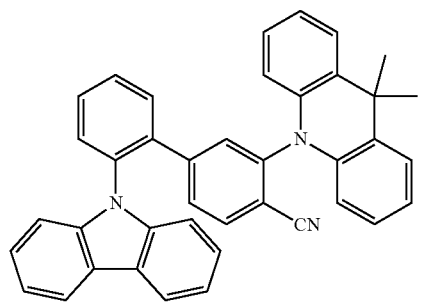
291
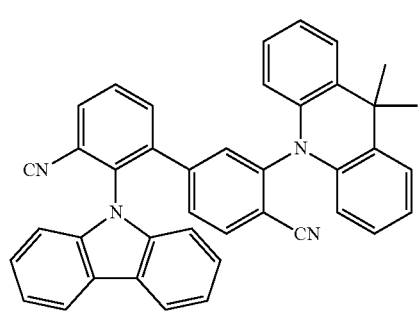
292
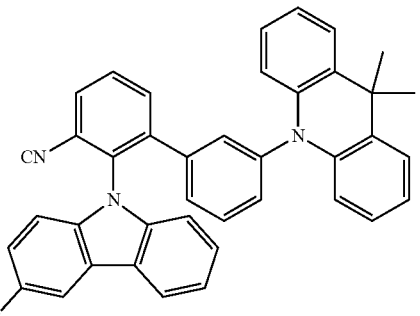
293
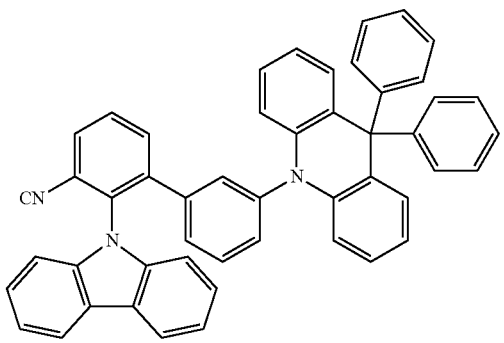
294
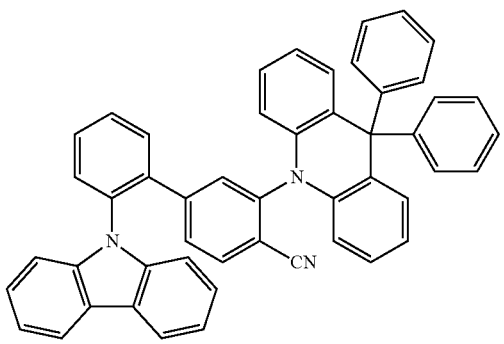
295
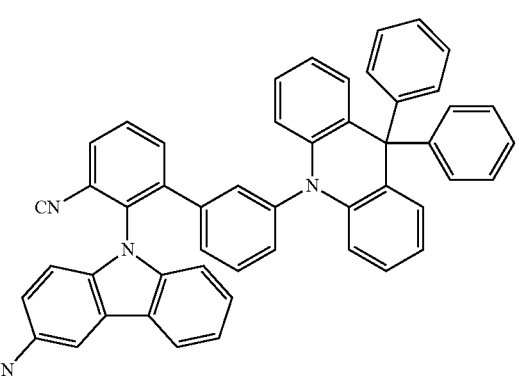

129
-continued
296
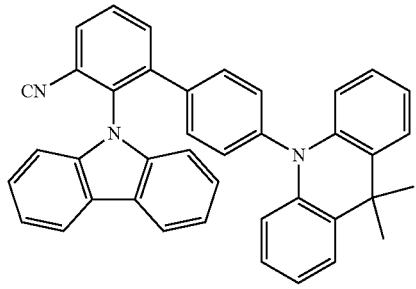
297
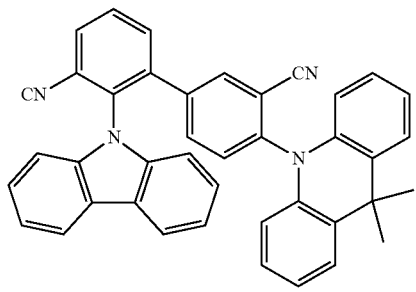
298
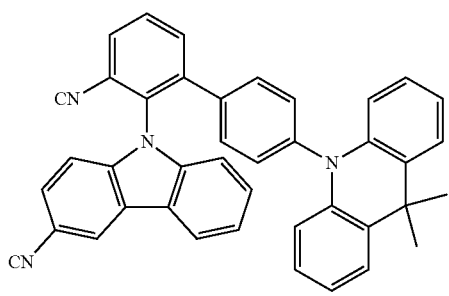
299
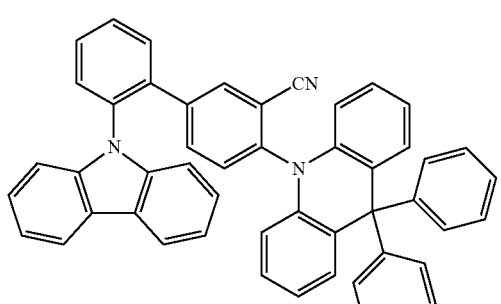
300
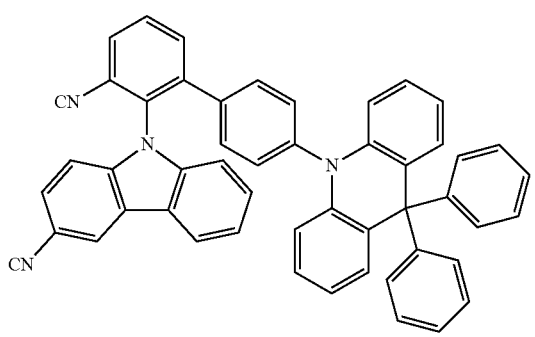
130
-continued
301
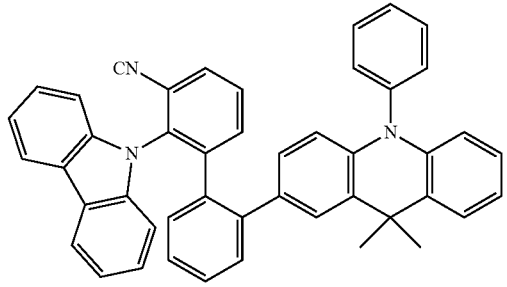
302
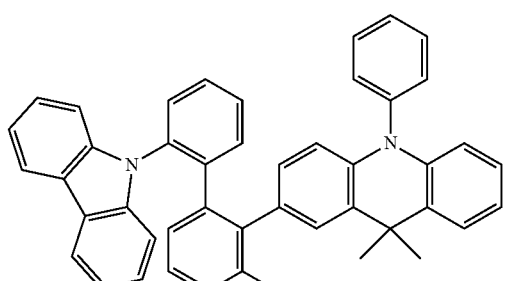
303
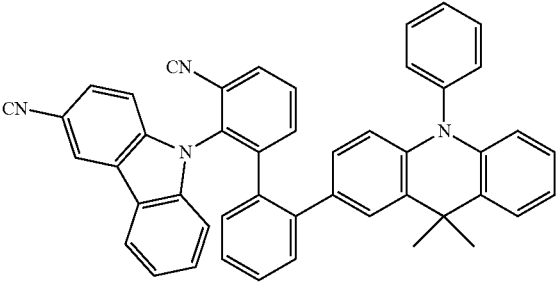
304
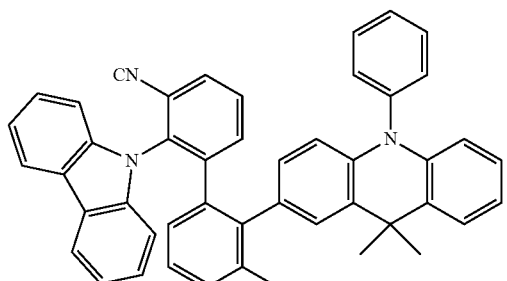
305
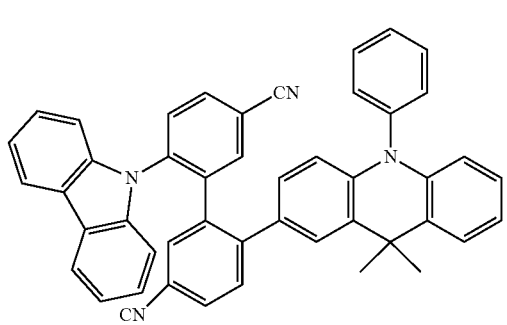

131
-continued
306
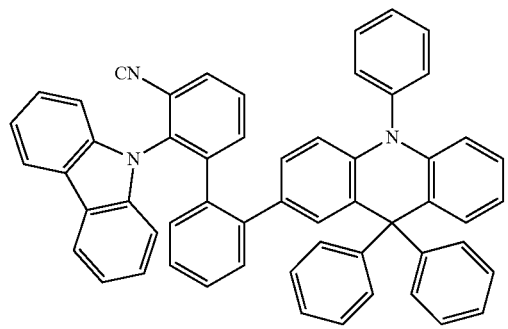
307
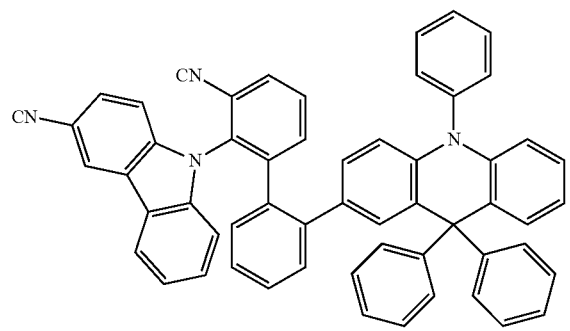
308
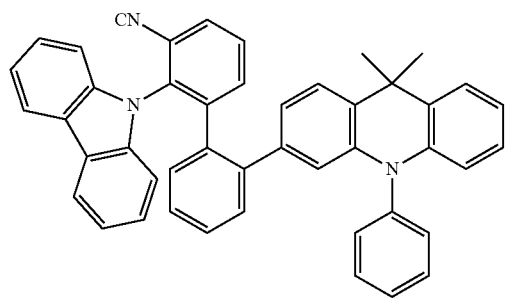
309
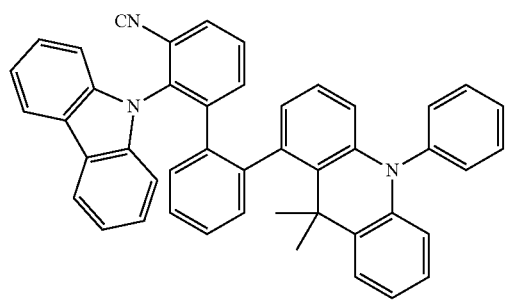
132
-continued
310
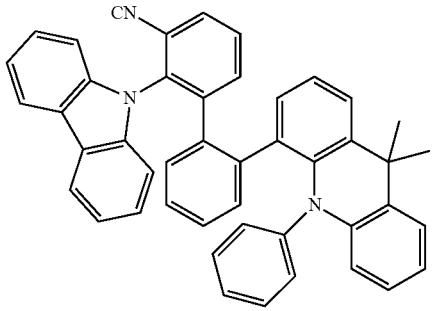
311
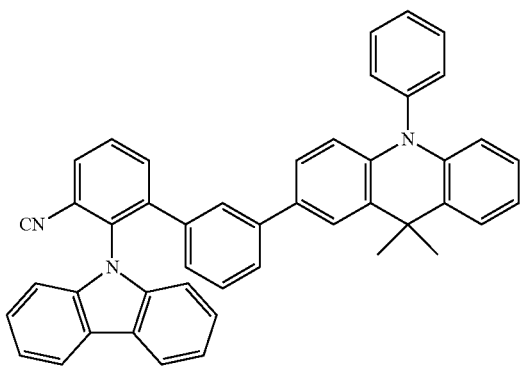
312
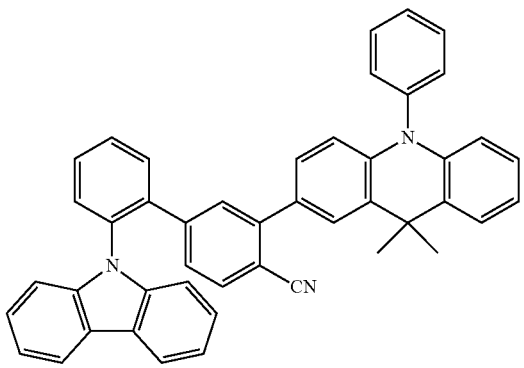
313
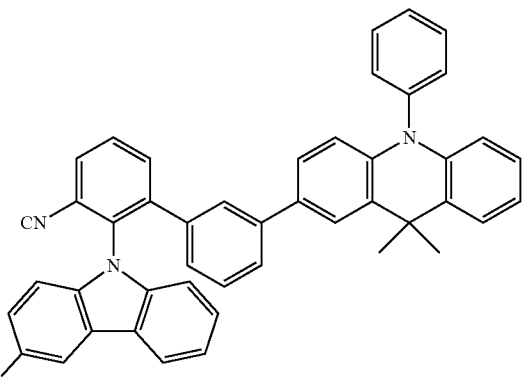

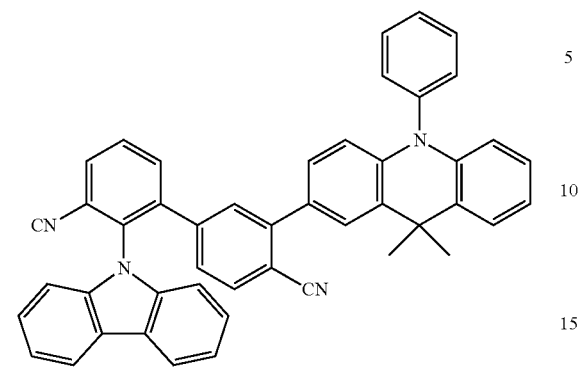
314
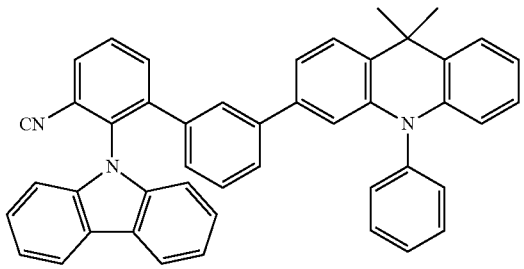
318
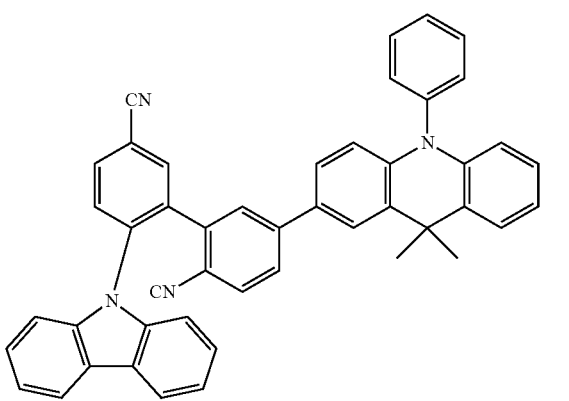
315
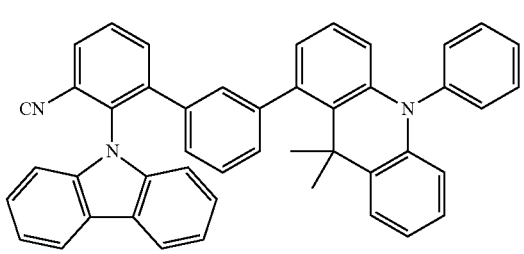
319
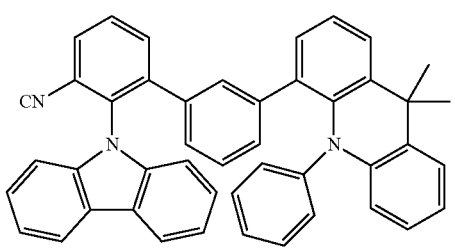
320
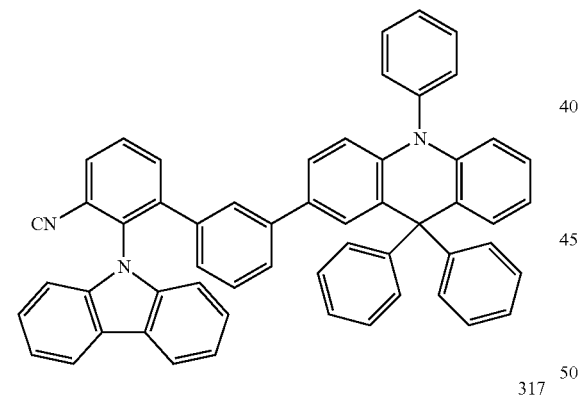
316
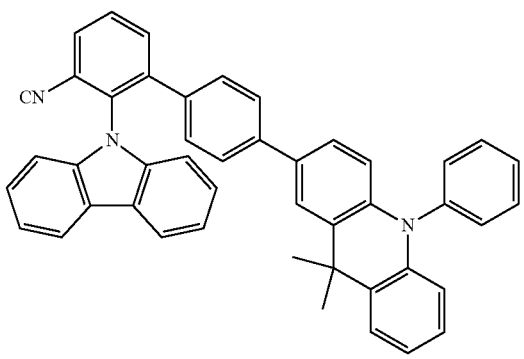
321
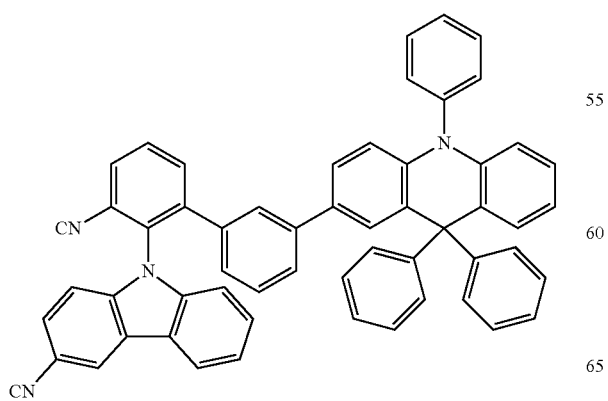
317
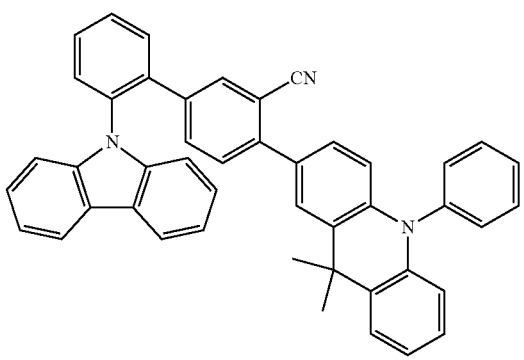
322

-continued

323

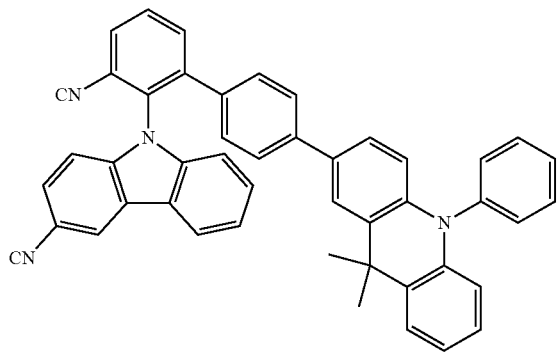

324

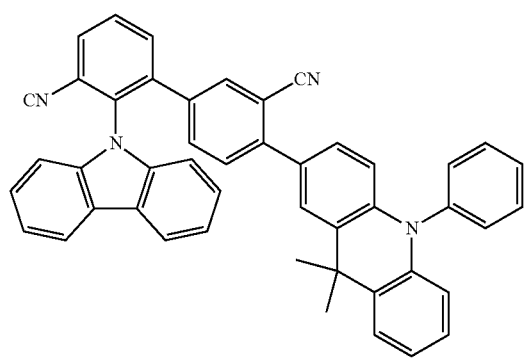

325

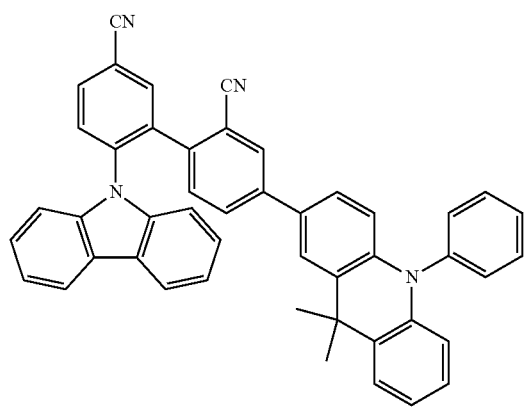

326

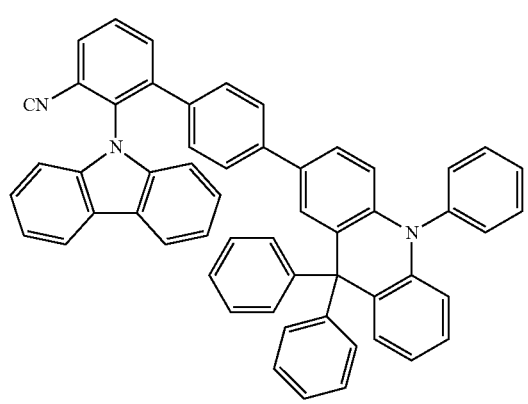

-continued

327

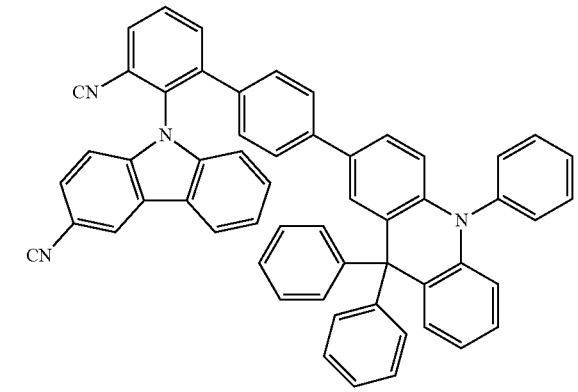

328

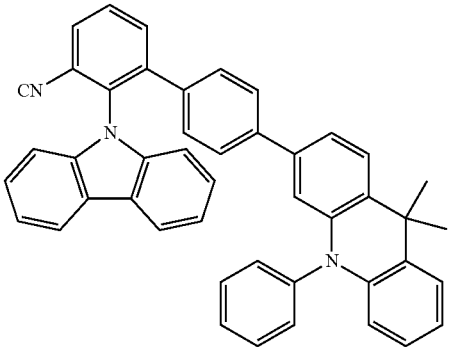

329

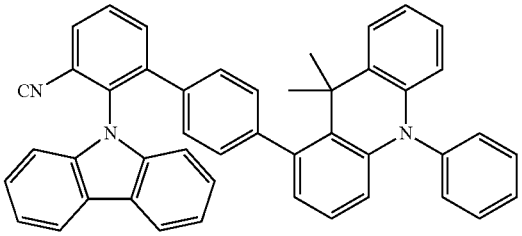

330

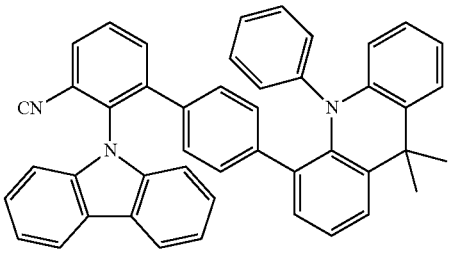

In Formula 1, a first carbazole ring is combined with a carbon atom at an "ortho-position" with respect to a carbon atom combined with a second benzene ring of a first benzene ring (see Formula 1'). In this regard, the condensed cyclic compound represented by Formula 1 may have a relatively high triplet state ($T_1$) energy level, compared to a compound structure combined with a carbon atom at a "para-position" or a "meta-position". Accordingly, a material, such as a host material included in an emission layer, for forming an organic light-emitting device may have suitable electric characteristics to be applied to a blue light-emitting device. Therefore, an organic light-emitting device including the condensed cyclic compound may exhibit high efficiency and long lifespan.

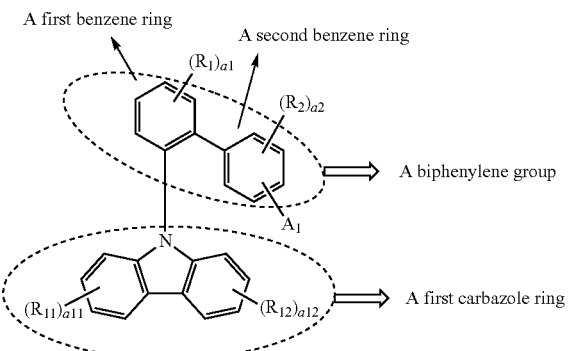

Formula 1'

In addition, in Formula 1, 1, 2, 3, or 4 groups selected from $R_1$ in the number of a1 and $R_2$ in the number of a2 may be a cyano group. That is, in a biphenylene group of Formula 1 is substituted with 1 to 4 cyano group(s) (see Formula 1'). In addition, in Formula 1, $R_1$ and $R_2$ are not a "cyclic group". Thus, the condensed cyclic compound may have a relatively low lowest unoccupied molecular orbital (LUMO) energy level (i.e., a relatively large absolute value of the LUMO energy level) and excellent electron mobility. Accordingly, a material, such as a host material included in an emission layer, for forming an organic light-emitting device may have suitable electric characteristics. Therefore, an organic light-emitting device including the condensed cyclic compound may exhibit high efficiency and long lifespan.

For example, the highest occupied molecular orbital (HOMO), the lowest unoccupied molecular orbital (LUMO), triplet state ($T_1$) energy level, and singlet state ($S_1$) energy level of Compounds 1, 3, 5, 7, 26, 46, 52, 55, 95, 97, 106, 176, 179, 216, and 219 and Compounds A and B evaluated through simulations using DFT methods of Gaussian programs (molecular structures are optimized at the B3LYP, 6-31G(d,p) levels), and the evaluation results are shown in Table 1:

TABLE 1

| Compound No. | HOMO (eV) | LUMO (eV) | $T_1$ (eV) | $S_1$ (eV) |
|---|---|---|---|---|
| 1 | −5.577 | −1.604 | 3.164 | 3.285 |
| 3 | −5.555 | −1.750 | 3.134 | 3.212 |
| 5 | −5.735 | −1.880 | 3.132 | 3.237 |
| 7 | −5.780 | −2.096 | 2.987 | 3.033 |
| 26 | −5.780 | −1.859 | 3.119 | 3.355 |
| 46 | −5.394 | −1.722 | 3.034 | 3.128 |
| 52 | −5.570 | −1.642 | 3.098 | 3.331 |
| 55 | −5.719 | −1.956 | 3.021 | 3.109 |
| 95 | −5.722 | −1.887 | 3.118 | 3.256 |
| 97 | −5.898 | −2.052 | 3.058 | 3.161 |
| 106 | −5.442 | −1.730 | 3.035 | 3.172 |
| 176 | −5.321 | −1.564 | 3.037 | 3.166 |
| 179 | −5.404 | −1.329 | 2.992 | 3.483 |
| 216 | −5.497 | −1.632 | 3.062 | 3.164 |
| 219 | −5.474 | −1.444 | 3.068 | 3.439 |

TABLE 1-continued

| Compound No. | HOMO (eV) | LUMO (eV) | $T_1$ (eV) | $S_1$ (eV) |
|---|---|---|---|---|
| A | −5.799 | −2.144 | 2.936 | 3.098 |
| B | −5.273 | −1.090 | 3.166 | 3.644 |

Compound A

Compound B

Referring to Table 1, it was confirmed that the condensed cyclic compound represented by Formula 1 had a higher $T_1$ energy level than that of Compound A, and a lower LUMO energy level than that of Compound B, wherein such a low LUMO energy level is advantageous for movement of electrons within an emission layer. That is, it was confirmed that the condensed cyclic compound represented by Formula 1 having a relatively high $T_1$ energy level and a low LUMO energy level was suitable for use in an emission layer of an electronic device, such as an organic light-emitting device.

Synthesis methods of the condensed cyclic compound represented by Formula 1 may be understood by those of ordinary skill in the art by referring to Synthesis Examples that will described below.

According to another aspect of the present inventive concept, a composition includes a first compound and a second compound, wherein the first compound is the condensed cyclic compound represented by Formula 1, and the second compound includes at least one selected from a carbazole-containing ring, a dibenzofuran-containing ring, a dibenzothiophene-containing ring, an indenocarbazole-containing ring, an indolocarbazole-containing ring, a benzofurocarbazole-containing ring, a benzothienocarbazole-containing ring, an acridine-containing ring, a dihydroacridine-containing ring, and a triindolobenzene-containing ring, and does not include an electron withdrawing group, wherein the electron withdrawing group is selected from:
—F, —CFH$_2$, —CF$_2$H, —CF$_3$, —CN, and —NC$_2$;
a C$_1$-C$_{60}$ alkyl group substituted with at least one selected from —F, —CF$_2$H, —CF$_3$, —CN, and —NC$_2$;
a C$_1$-C$_{60}$ heteroaryl group and a monovalent non-aromatic condensed polycyclic heterocyclic group that each includes *=N—*' as a ring-forming moiety; and a $C_1$-$C_{60}$ heteroaryl group and a monovalent non-aromatic condensed polycyclic heterocyclic group that are each substituted with at least one selected from deuterium, —F, —CFH$_2$, —CF$_2$H, —CF$_3$, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group and that each includes *=N—*' as a ring-forming moiety.

The composition may be suitable for use in preparation of an organic layer of an electronic device (such as an organic light-emitting device).

In the composition, the first compound may be an electron transport material, and the second compound may be a hole transport material.

In an embodiment, the composition may consist of the first compound and the second compound, but embodiments are not limited thereto.

In the composition, the condensed cyclic compound that is represented by Formula 1 may be the first compound as defined herein in the present specification.

For example, the second compound in the composition may be selected from a compound represented by Formula H-1:

Formula H-1

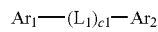

Formula 11

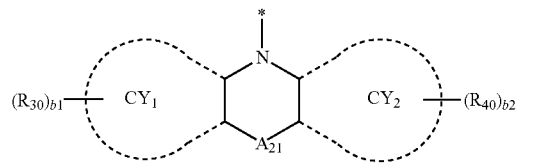

Formula 12

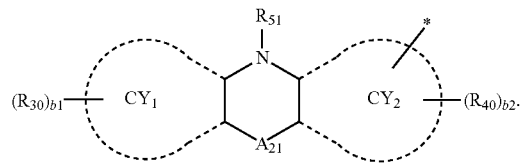

In Formulae H-1, 11, and 12, $L_1$ may be selected from:

a single bond, a phenylene group, a naphthylene group, a fluorenylene group, a carbazolylene group, a dibenzofuranylene group, and a dibenzothiophenylene group; and a phenylene group, a naphthylene group, a fluorenylene group, a carbazolylene group, a dibenzofuranylene group, and a dibenzothiophenylene group, each substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a biphenyl group, and —Si($Q_{11}$)($Q_{12}$)($Q_{13}$), c1 may be an integer selected from 1 to 10, wherein, when c1 is 2 or more, 2 or more $L_1$ may be identical to or different from each other, $Ar_1$ may be selected from groups represented by Formulae 11 and 12, $Ar_2$ may be selected from:

groups represented by Formulae 11 and 12, a phenyl group, and a naphthyl group; and a phenyl group and a naphthyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, and a biphenyl group, $CY_1$ and $CY_2$ may each independently be selected from a benzene group, a naphthalene group, a fluorene group, a carbazole group, a benzocarbazole group, an indolocarbazole group, a dibenzofuran group, and a dibenzothiophene group, $A_{21}$ may be selected from:

a single bond, a $C_1$-$C_4$ alkylene group, and a $C_2$-$C_4$ alkenylene group; and a $C_1$-$C_4$ alkylene group and a $C_2$-$C_4$ alkenylene group, each substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a biphenyl group, and —Si($Q_{21}$)($Q_{22}$)($Q_{23}$), $R_{30}$, $R_{40}$, and $R_{51}$ may each independently be selected from:

hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, and a dibenzothiophenyl group;

a phenyl group, a naphthyl group, a fluorenyl group, a carbazolyl group, a dibenzofuranyl group, and a dibenzothiophenyl group;

a phenyl group, a naphthyl group, a fluorenyl group, a carbazolyl group, a dibenzofuranyl group, and a dibenzothiophenyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, and a biphenyl group; and —Si($Q_1$)($Q_2$)($Q_3$), b1 and b2 may each independently be an integer selected from 0 to 10, $Q_1$ to $Q_3$, $Q_{11}$ to $Q_{13}$, and $Q_{21}$ to $Q_{23}$ may each independently be selected from hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, a dibenzothiophenyl group, and a biphenyl group, and \* indicates a binding site to a neighboring atom.

For example, in Formula H-1, c1 indicates the number of groups $L_1$, and may be 1, 2, 3, or 4.

In various embodiments, in Formulae 11 and 12, at least one of $CY_1$ and $CY_2$ may be a benzene group, but embodiments are not limited thereto.

In an embodiment, in Formula H-1, $Ar_1$ may be selected from groups represented by Formulae 11-1 to 11-8 and 12-1 to 12-16, and $Ar_2$ may be selected from:

groups represented by Formulae 11-1 to 11-8 and 12-1 to 12-16, a phenyl group, and a naphthyl group; and a phenyl group and a naphthyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, and a biphenyl group, but embodiments are not limited thereto:

Formula 11-1

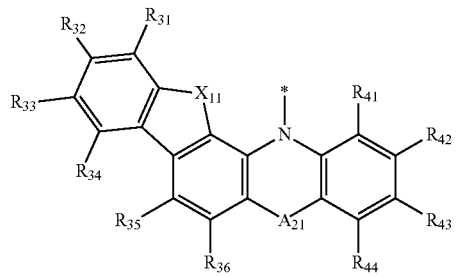

Formula 11-2

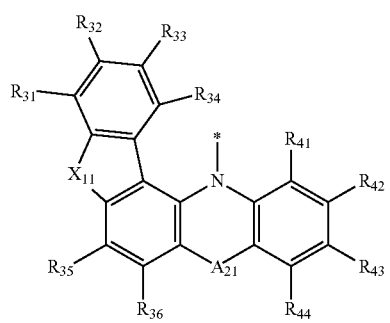

Formula 11-3

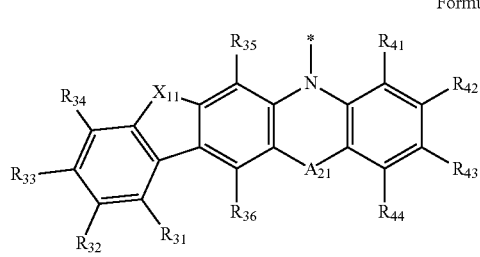

Formula 11-4

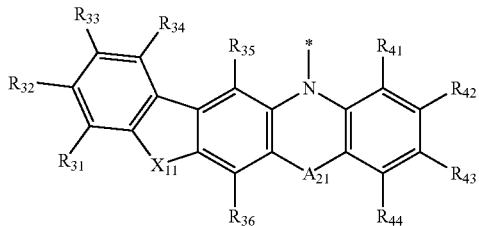

Formula 11-5

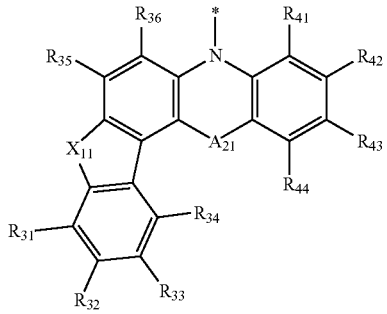

Formula 11-6

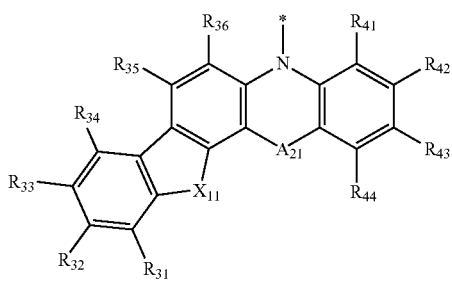

Formula 11-7

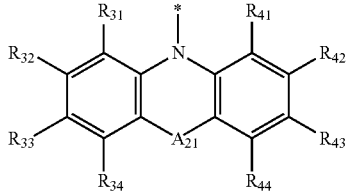

Formula 11-8

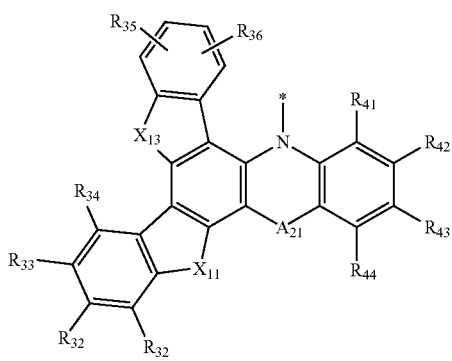

Formula 12-1
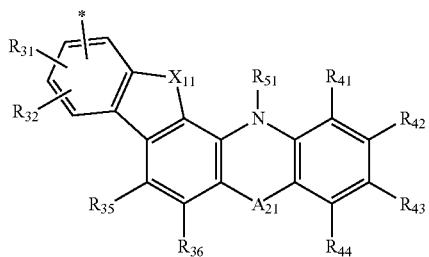
Formula 12-2
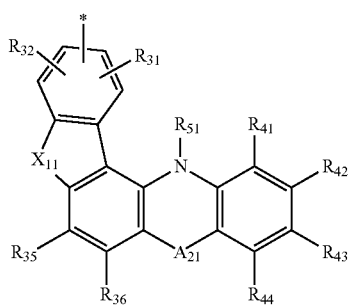
Formula 12-3
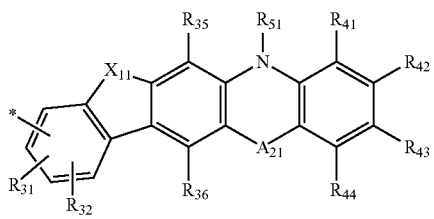
Formula 12-4
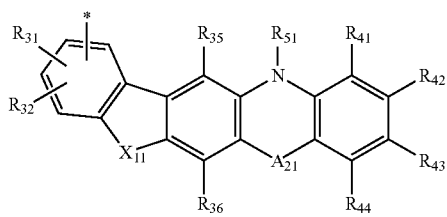
Formula 12-5
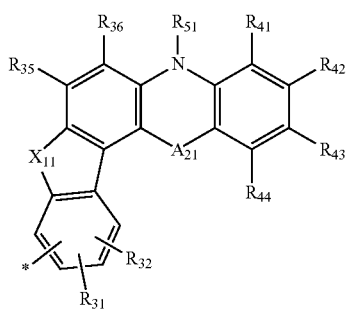
Formula 12-6
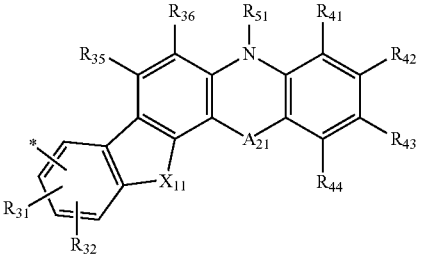
Formula 12-7
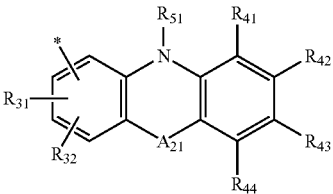
Formula 12-8
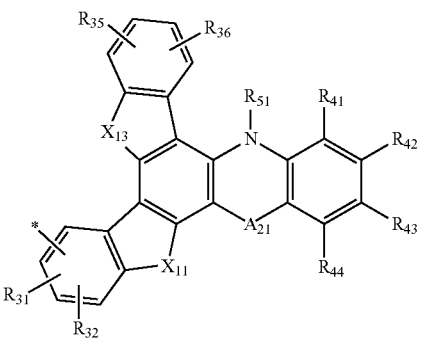
Formula 12-9
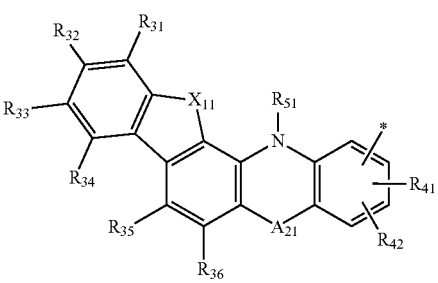
Formula 12-10
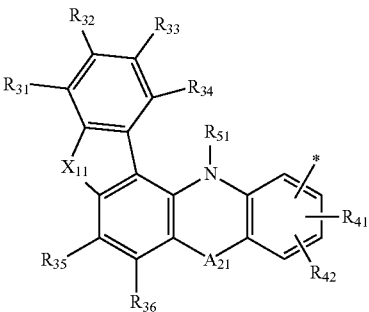

Formula 12-11
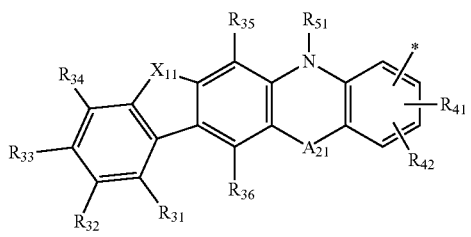

Formula 12-12
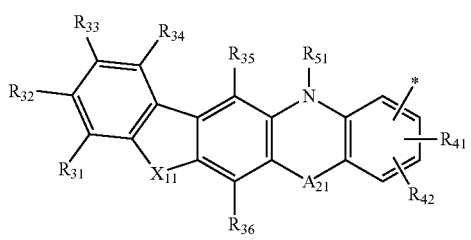

Formula 12-13
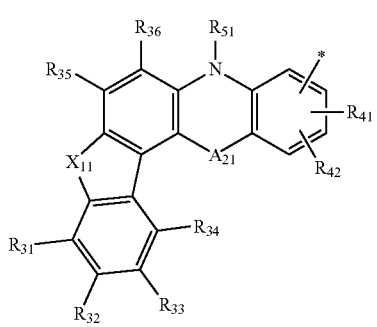

Formula 12-14
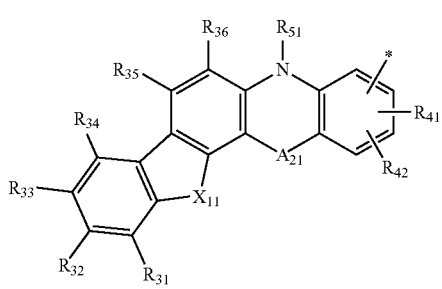

Formula 12-15
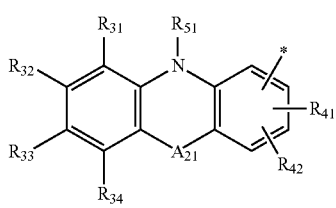

Formula 12-16
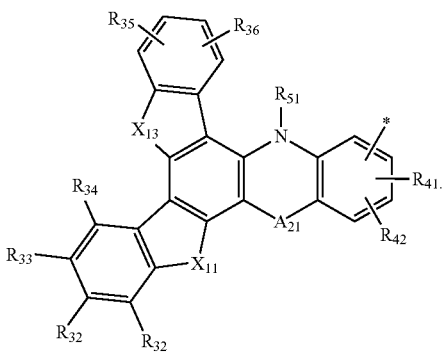

In Formulae 11-1 to 11-8 and 12-1 to 12-16, $X_{11}$ and $X_{13}$ may each independently be $C(R_{37})(R_{38})$, $N(R_{39})$, O, or S, $A_{21}$, $R_{51}$, and * are each independently as defined herein in the present specification, $R_{31}$ to $R_{39}$ are each independently the same as defined herein in connection with $R_{30}$, and $R_{41}$ to $R_{44}$ are each independently the same as defined herein in connection with $R_{40}$.

In various embodiments, in Formulae 11 and 12, $A_{21}$ may be selected from:

a single bond, a $C_1$-$C_2$ alkylene group, and a $C_2$ alkenylene group; and a $C_1$-$C_2$ alkylene group and a $C_2$ alkenylene group, each substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a biphenyl group, and —Si($Q_{21}$)($Q_{22}$)($Q_{23}$), but embodiments are not limited thereto. Here, $Q_{21}$ to $Q_{23}$ are each independently the same as defined herein in the present specification.

In various embodiments, in the composition, i) the second compound may be selected from compounds represented by Formula H-1, wherein $L_1$ in Formula H-1 may be a single bond; or ii) the second compound may be selected from compounds represented by Formulae H-1(1) to H-1(52), but embodiments are not limited thereto:

Formula H-1(1)
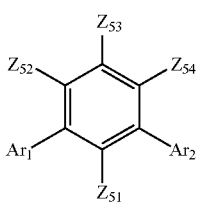

Formula H-1(2)
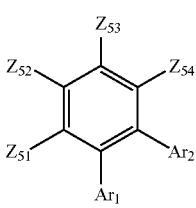

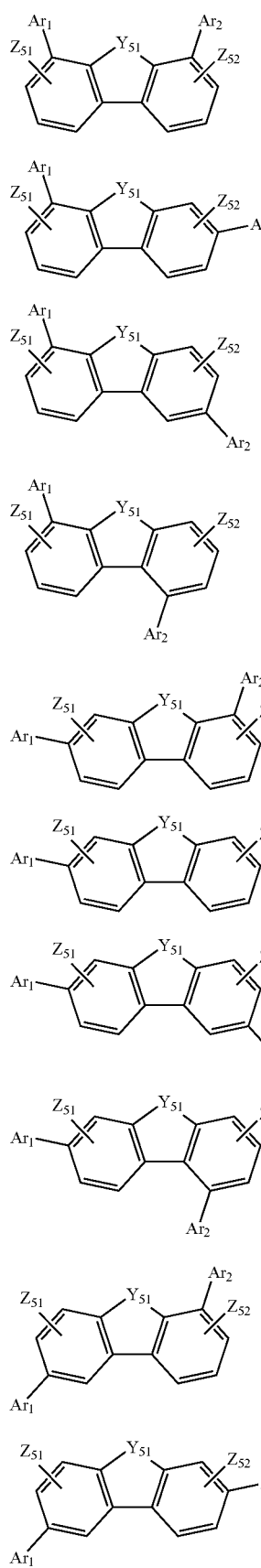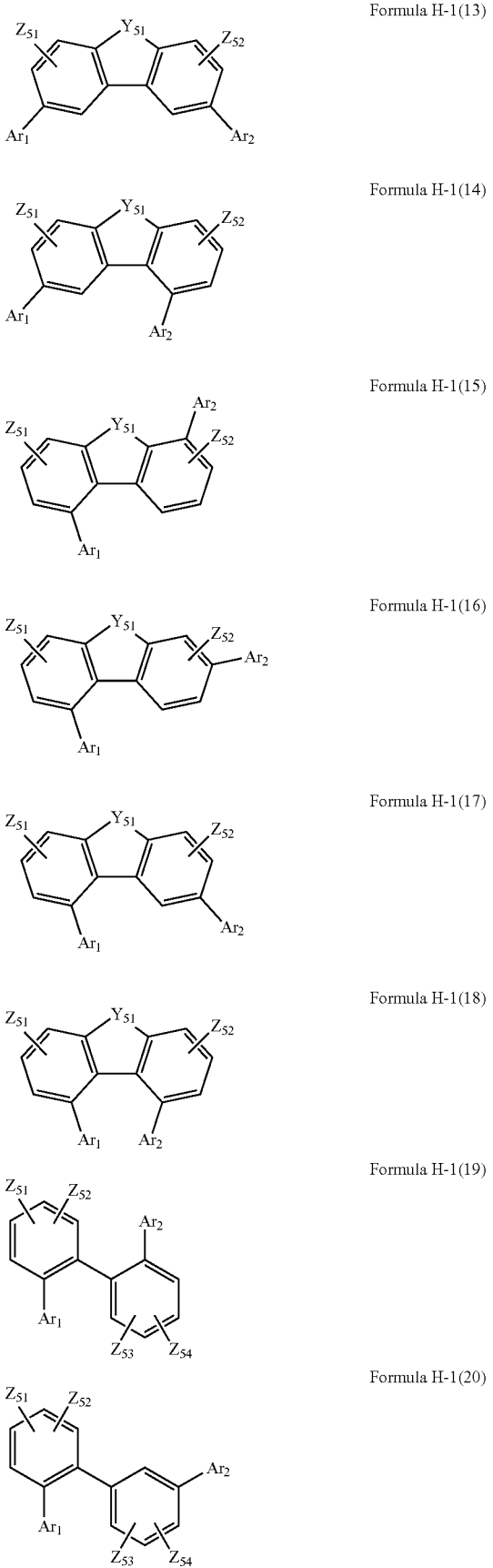
Formula H-1(3)
Formula H-1(4)
Formula H-1(5)
Formula H-1(6)
Formula H-1(7)
Formula H-1(8)
Formula H-1(9)
Formula H-1(10)
Formula H-1(11)
Formula H-1(12)
Formula H-1(13)
Formula H-1(14)
Formula H-1(15)
Formula H-1(16)
Formula H-1(17)
Formula H-1(18)
Formula H-1(19)
Formula H-1(20)

Formula H-1(21)
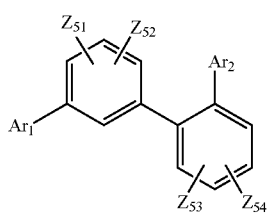
Formula H-1(22)
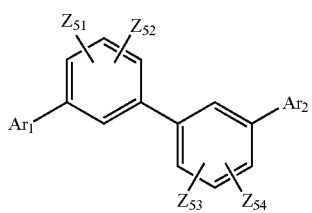
Formula H-1(23)
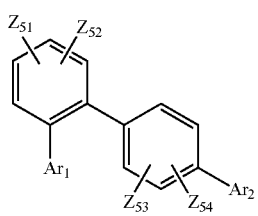
Formula H-1(24)
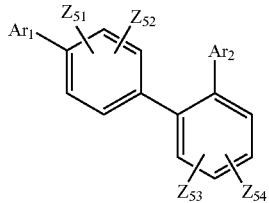
Formula H-1(25)
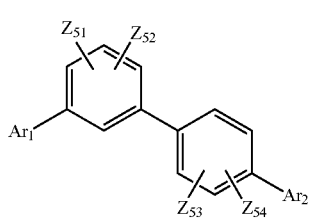
Formula H-1(26)
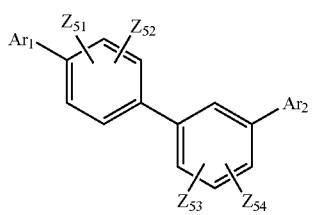
Formula H-1(27)
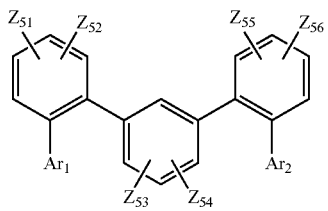
Formula H-1(28)
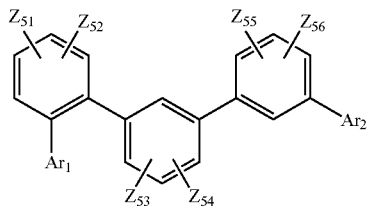
Formula H-1(29)
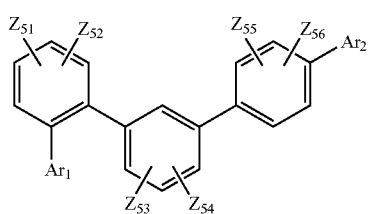
Formula H-1(30)
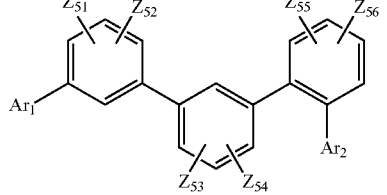
Formula H-1(31)
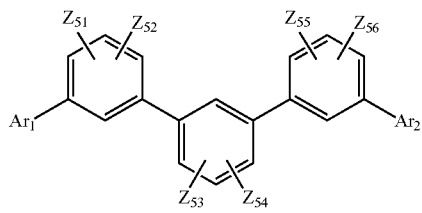
Formula H-1(32)
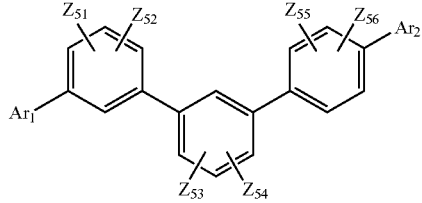
Formula H-1(33)
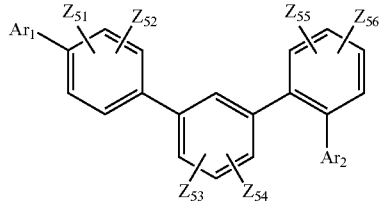
Formula H-1(34)
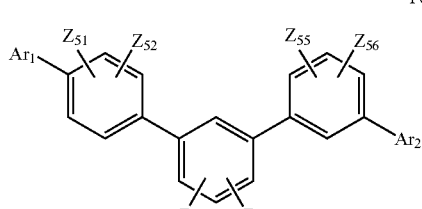

Formula H-1(35)
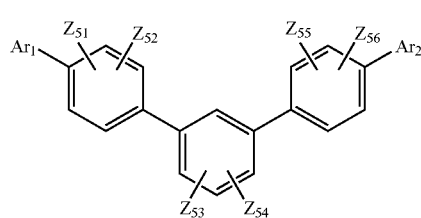
Formula H-1(36)
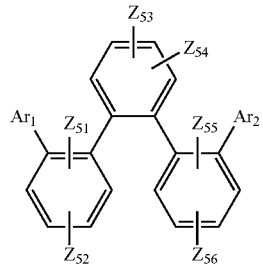
Formula H-1(37)
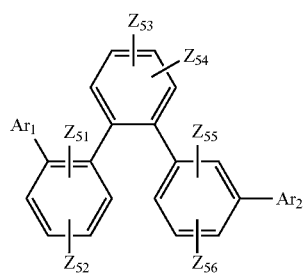
Formula H-1(38)
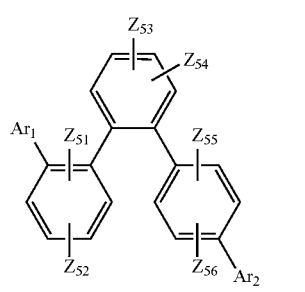
Formula H-1(39)
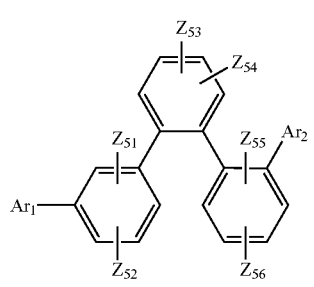
Formula H-1(40)
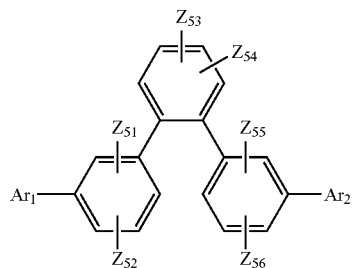
Formula H-1(41)
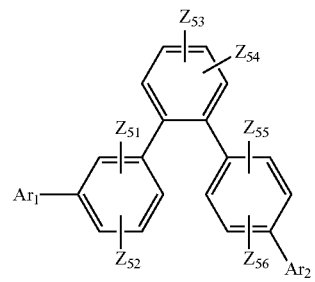
Formula H-1(42)
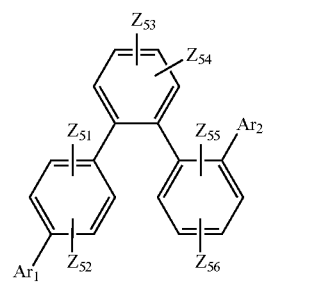
Formula H-1(43)
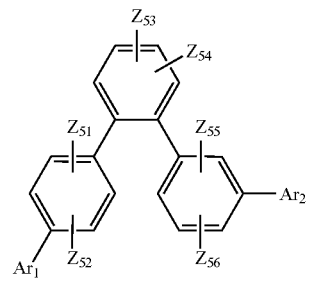
Formula H-1(44)
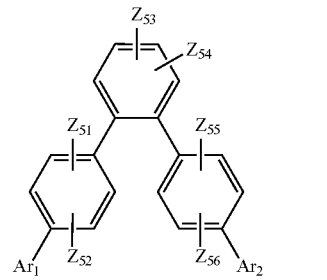
Formula H-1(45)

Formula H-1(46)
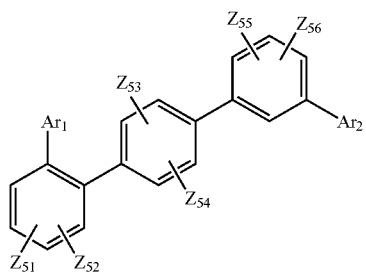

Formula H-1(47)
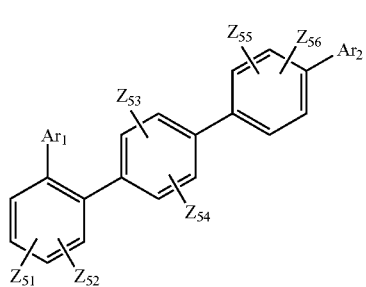

Formula H-1(48)
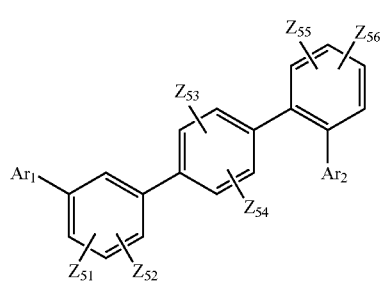

Formula H-1(49)
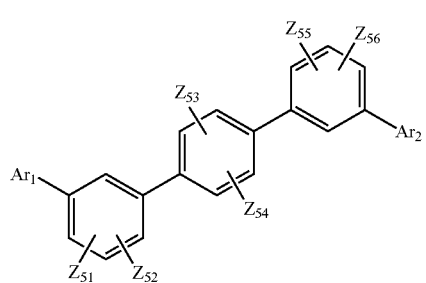

Formula H-1(50)
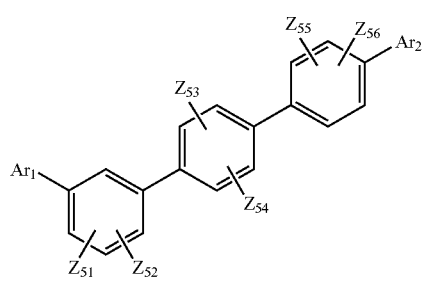

Formula H-1(51)
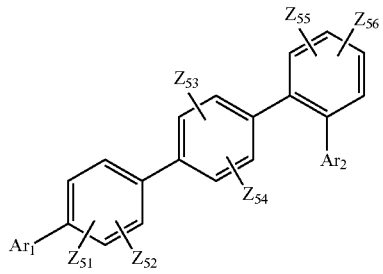

Formula H-1(52)
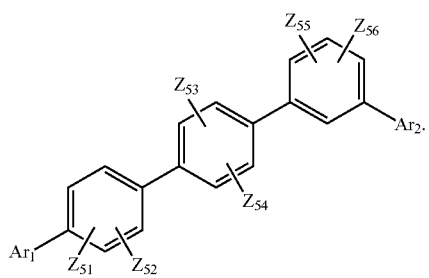

In Formulae H-1(1) to H-1(52), $Ar_1$ and $Ar_2$ are each independently as defined herein in the present specification, $Y_{51}$ may be $C(Z_{53})(Z_{54})$, $N(Z_{55})$, O, or S, $Z_{51}$ to $Z_{56}$ may each independently be selected from hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a biphenyl group, and —$Si(Q_{11})(Q_{12})(Q_{13})$, wherein $Q_{11}$ to $Q_{13}$ may each independently be selected from hydrogen, a $C_1$-$C_{10}$ alkyl group, a $C_1$-$C_{10}$ alkoxy group, a phenyl group, and a naphthyl group, but embodiments are not limited thereto.

In the composition, the second compound may be selected from Compounds H-1 to H-32, but embodiments are not limited thereto:

H-1
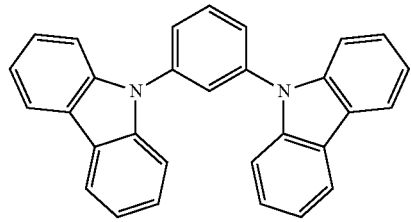

H-2
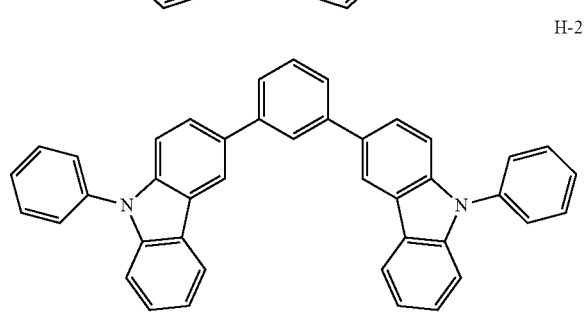

H-3
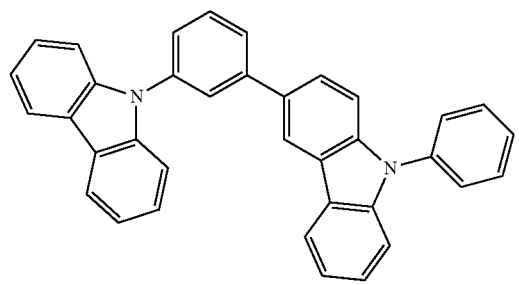
H-4
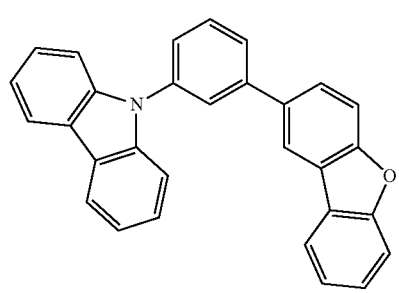
H-5
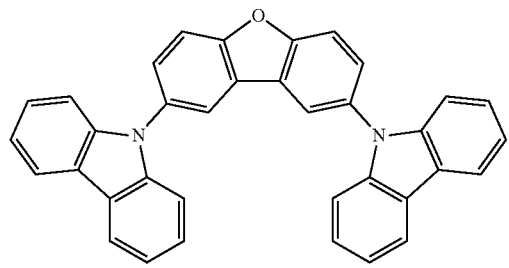
H-6
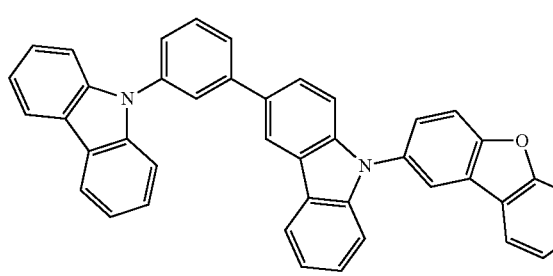
H-7
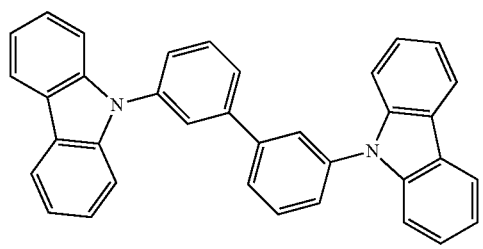
H-8
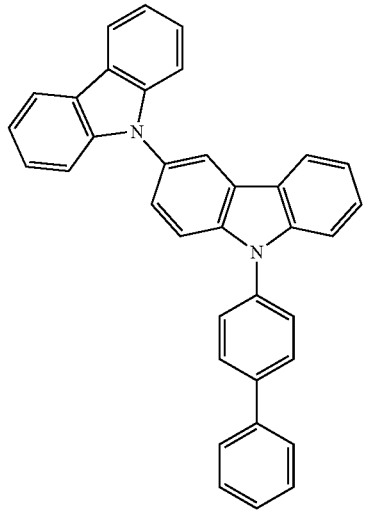
H-9
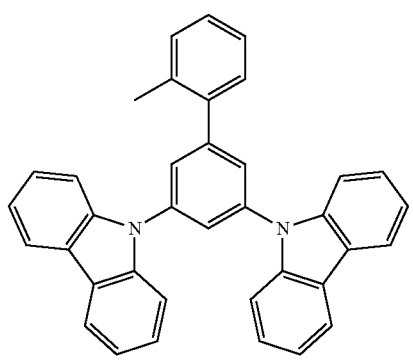
H-10
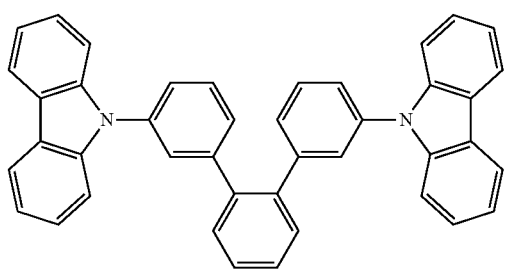
H-11
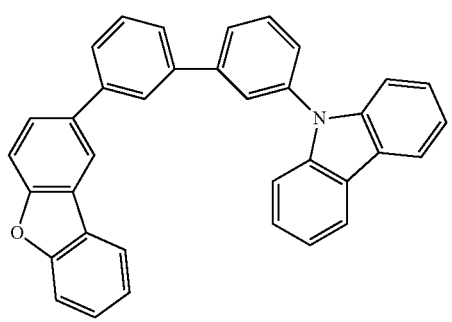

H-12
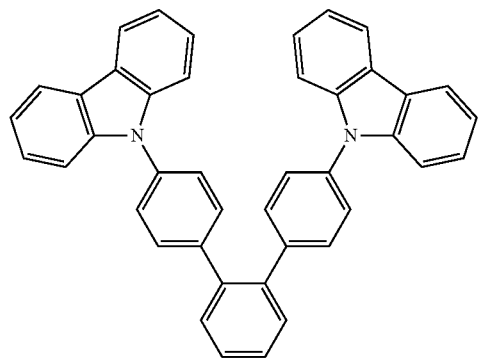
H-13
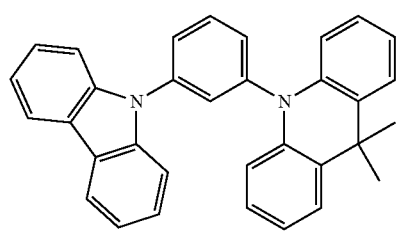
H-14
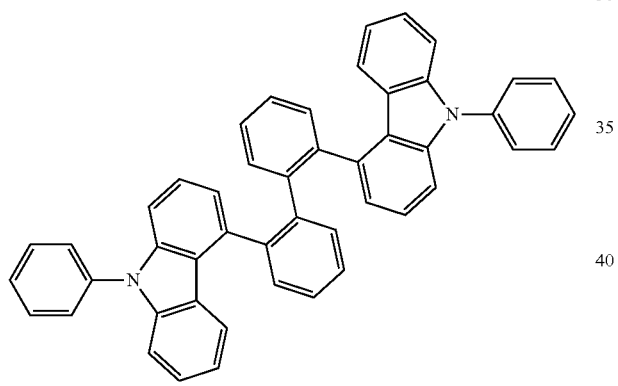
H-15
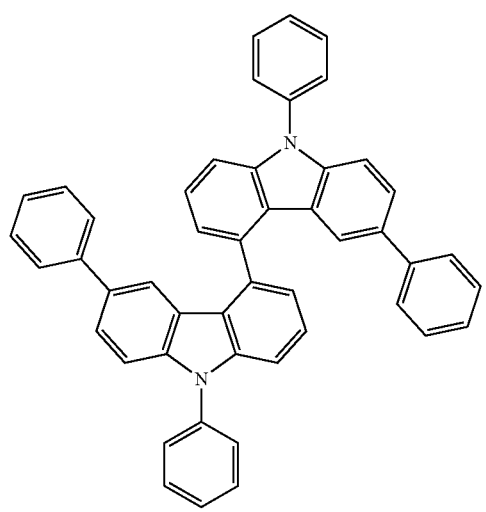
H-16
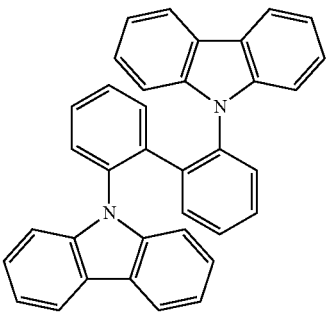
H-17
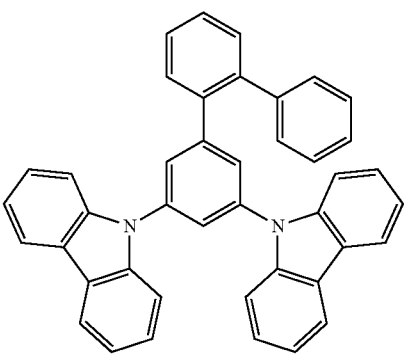
H-18
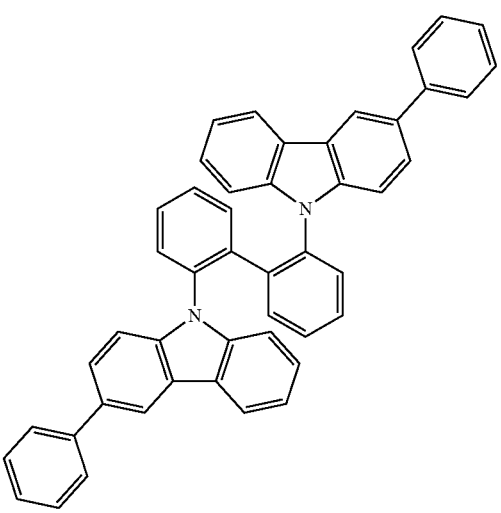
H-19
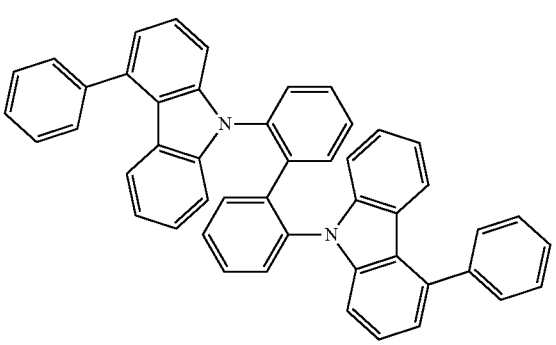

H-20
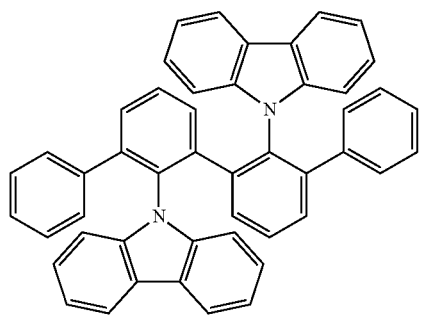
H-21
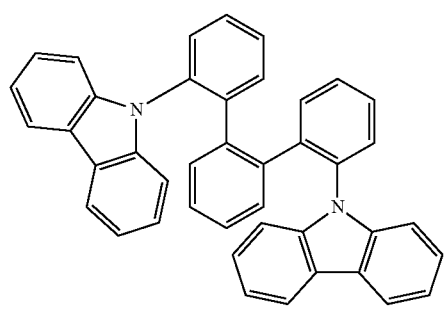
H-22
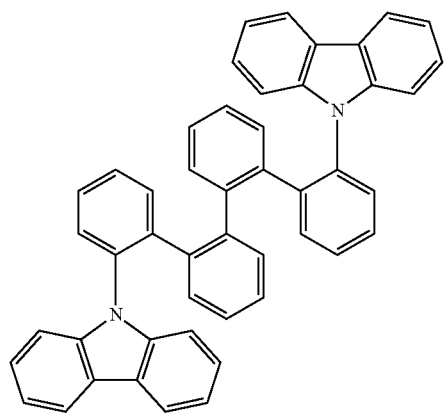
H-23
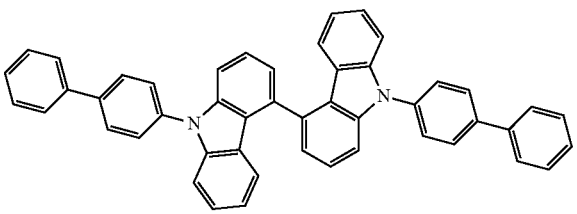
H-24
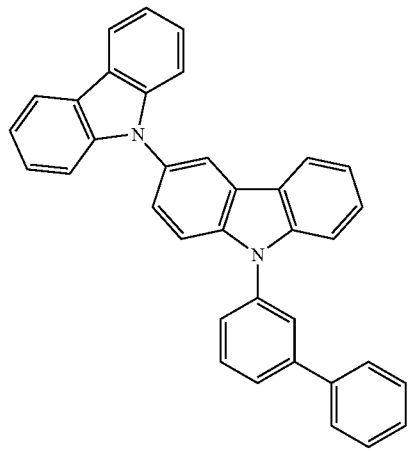
H-25
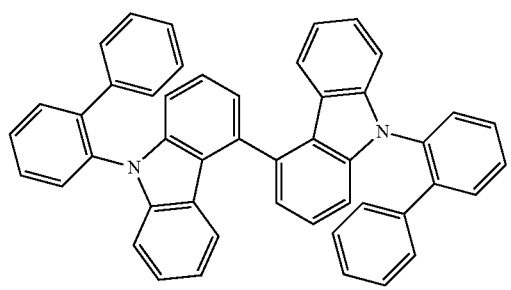
H-26
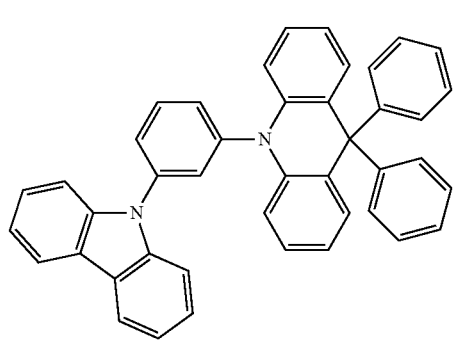
H-27
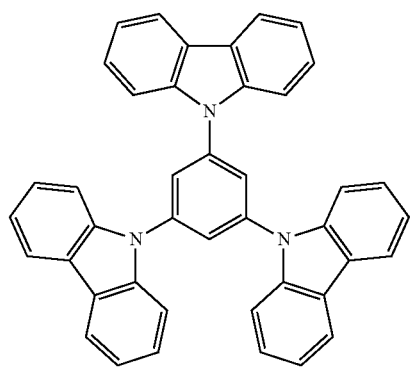

-continued

H-28

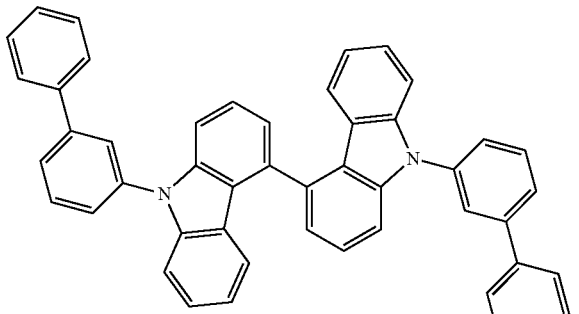

H-29

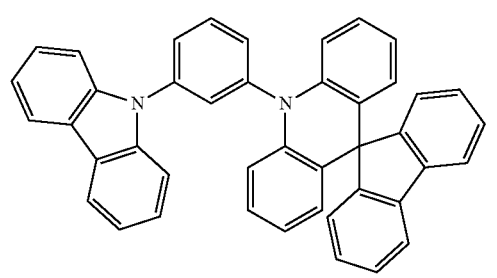

H-30

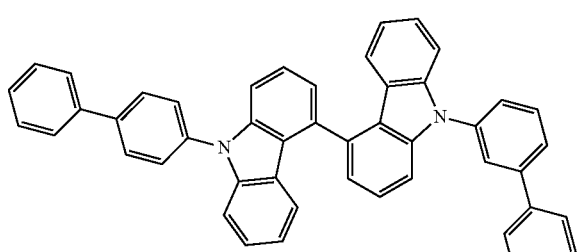

H-31

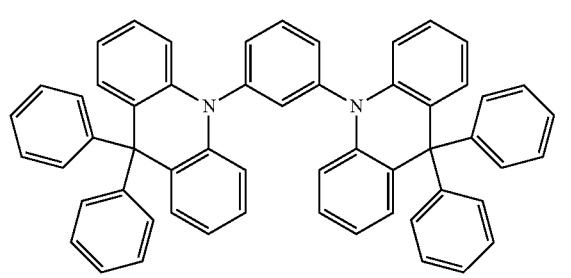

H-32

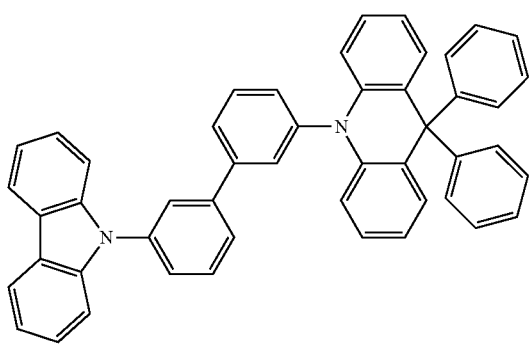

In the composition, a weight ratio of the first compound and the second compound may be selected from ranges of 1:99 to 99:1, for example, ranges of 70:30 to 30:70. For example, in the composition, the weight ratio of the first compound and the second compound may be selected from ranges of 40:60 to 60:40, but embodiments are not limited thereto. While not wishing to be bound by theory, it is understood that when the weight ratio of the first compound and the second compound in the composition is within any of these ranges, the composition may provide excellent charge transport balance.

The condensed cyclic compound represented by Formula 1 may be suitable for use in an organic layer of an organic light-emitting device, for example, in an emission layer and/or an electron transport region of the organic layer.

According to another aspect of the present inventive concept, an organic light-emitting device includes:

a first electrode, a second electrode, and an organic layer disposed between the first electrode and the second electrode, wherein the organic layer includes an emission layer, and wherein the organic layer includes at least one condensed cyclic compound represented by Formula 1.

The organic light-emitting device including the organic layer including the condensed cyclic compound represented by Formula 1 may exhibit low driving voltage, high emission efficiency, high luminance, high quantum emission efficiency, and long lifespan.

In an embodiment, in the organic light-emitting device, the first electrode may be an anode, the second electrode may be a cathode, the organic layer may include a hole transport region disposed between the first electrode and the emission layer and an electron transport region disposed between the emission layer and the second electrode, wherein the hole transport region may include at least one selected from a hole injection layer, a hole transport layer, and an electron blocking layer, and wherein the electron transport region may include at least one selected from a hole blocking layer, an electron transport layer, and an electron injection layer, but embodiments are not limited thereto.

For example, the emission layer may include the condensed cyclic compound represented by Formula 1.

In various embodiments, the emission layer may include the condensed cyclic compound represented by Formula 1, which may be used as a delayed fluorescence material.

In an embodiment, the emission layer may include a host and a dopant (wherein an amount of the host may be greater than that of the dopant), and the host may include the condensed cyclic compound represented by Formula 1. The condensed cyclic compound, which serves as the host, may deliver energy to a dopant according to the delayed fluorescence mechanism. Here, the dopant may include at least one of a fluorescent dopant and a phosphorescent dopant. The dopant may be selected from known dopants in the art. The host may further include, in addition to the condensed cyclic compound represented by Formula 1, a host selected from known hosts in the art.

In various embodiments, the emission layer may include a host and a dopant (wherein an amount of the host may be greater than that of the dopant), and the dopant may include the condensed cyclic compound represented by Formula 1. The condensed cyclic compound, which serves as the dopant, may emit delayed fluorescence according to the delayed fluorescence mechanism. Here, the host may further include, in addition to the condensed cyclic compound represented by Formula 1, a dopant selected from known dopants in the art.

The emission layer may emit red light, green light, or blue light.

In an embodiment, the emission layer may be a blue emission layer including a phosphorescent dopant, but embodiments are not limited thereto.

In various embodiments, the emission layer may include a host and a dopant, wherein the host may include the condensed cyclic compound represented by Formula 1 and the dopant may include a phosphorescent dopant.

In various embodiments, the electron transport region may include the condensed cyclic compound represented by Formula 1.

For example, the electron transport region of the organic light-emitting device may include at least one of a hole blocking layer and an electron transport layer, wherein the at least one of the electron blocking layer and the electron transport layer may include the condensed cyclic compound represented by Formula 1.

In an embodiment, the electron transport region of the organic light-emitting device may include a hole blocking layer, wherein the hole blocking layer may include the condensed cyclic compound represented by Formula 1. Here, the hole blocking layer may directly contact the emission layer.

In various embodiments, the organic layer of the organic light-emitting device may further include, in addition to the condensed cyclic compound represented by Formula 1,
i) the second compound;
ii) an organometallic compound represented by Formula 81; or
iii) any combination of i) and ii):

$$M(L_{81})_{n81}(L_{82})_{n82}$$ Formula 81

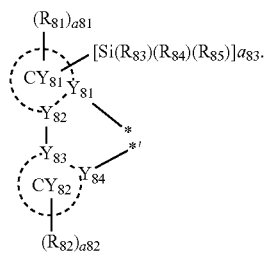

Formula 81A

In Formulae 81 and 81A,

M may be selected from iridium (Ir), platinum (Pt), osmium (Os), titanium (Ti), zirconium (Zr), hafnium (Hf), europium (Eu), terbium (Tb), thulium (Tm), and rhodium (Rh), $L_{81}$ may be a ligand represented by Formula 81A, and n81 may be an integer selected from 1 to 3, wherein, when n81 is 2 or more, 2 or more $L_{81}$ may be identical to or different from each other, $L_{82}$ may be an organic ligand, and n82 may be an integer selected from 0 to 4, wherein, when n82 is 2 or more, 2 or more $L_{82}$ may be identical to or different from each other, $Y_{81}$ to $Y_{84}$ may each independently be C or N, $Y_{81}$ and $Y_{82}$ may be linked via a single bond or a double bond, and $Y_{83}$ and $Y_{84}$ may be linked via a single bond or a double bond, $CY_{81}$ and $CY_{82}$ may each independently be selected from a $C_5$-$C_{30}$ carbocyclic group and a $C_3$-$C_{30}$ heterocarbocyclic group, $CY_{81}$ and $CY_{82}$ may be optionally further linked via an organic linking group, $R_{81}$ to $R_{85}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q$_{81}$)(Q$_{82}$)(Q$_{83}$), —N(Q$_{84}$)(Q$_{85}$), —B(Q$_{86}$)(Q$_{87}$), and —P(=O)(Q$_{88}$)(Q$_{89}$), a81 to a83 may each independently be an integer selected from 0 to 5, wherein, when a81 is 2 or more, 2 or more $R_{81}$ may be identical to or different from each other, when a82 is 2 or more, 2 or more $R_{82}$ may be identical to or different from each other, when a81 is 2 or more, two adjacent $R_{81}$ may be optionally linked to form a saturated or unsaturated $C_2$-$C_{30}$ ring (for example, a benzene ring, a cyclopentane ring, a cyclohexane ring, a cyclopentene ring, a cyclohexene ring, a norbornane ring, a (bicyclo[2.2.1]heptanes) ring, a naphthalene ring, a benzoindene ring, a benzoindole ring, a benzofuran ring, a benzothiophene ring, a pyridine ring, a pyrimidine ring, or a pyrazine ring), or a saturated or unsaturated $C_2$-$C_{30}$ ring substituted with at least one $R_{88}$ (for example, a benzene ring, a cyclopentane ring, a cyclohexane ring, a cyclopentene ring, a cyclohexene ring, a norbornane ring, a (bicyclo[2.2.1]heptanes) ring, a naphthalene ring, a benzoindene ring, a benzoindole ring, a benzofuran ring, a benzothiophene ring, a pyridine ring, a pyrimidine ring, or a pyrazine ring, each substituted with at least one $R_{88}$), when a82 is 2 or more, two adjacent $R_{82}$ may be optionally linked to form a saturated or unsaturated $C_2$-$C_{30}$ ring (for example, a benzene ring, a cyclopentane ring, a cyclohexane ring, a cyclopentene ring, a cyclohexene ring, a norbornane ring, a (bicyclo[2.2.1]heptanes) ring, a naphthalene ring, a benzoindene ring, a benzoindole ring, a benzofuran ring, a benzothiophene ring, a pyridine ring, a pyrimidine ring, or a pyrazine ring), or a saturated or unsaturated $C_2$-$C_3$ ring substituted with at least one $R_{89}$ (for example, a benzene ring, a cyclopentane ring, a cyclohexane ring, a cyclopentene ring, a cyclohexene ring, a norbornane ring, a (bicyclo[2.2.1]heptanes) ring, a naphthalene ring, a benzoindene ring, a benzoindole ring, a benzofuran ring, a benzothiophene ring, a pyridine ring, a pyrimidine ring, or a pyrazine ring, each substituted with at least one $R_{89}$), $R_{88}$ is the same as defined herein in connection with $R_{81}$,
$R_{89}$ is the same as defined herein in connection with $R_{82}$,
* and *' in Formula 81A each indicate a binding site to M of Formula 81, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{91}$)($Q_{92}$)($Q_{93}$), and $Q_{81}$ to $Q_{89}$ and $Q_{91}$ to $Q_{93}$ may each independently be selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In an embodiment, in Formula 81A, a83 may be 1 or 2, $R_{83}$ to $R_{85}$ may each independently be selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, but embodiments are not limited thereto.

In various embodiments, in Formula 81A, $Y_{81}$ may be N, $Y_{82}$ and $Y_{83}$ may each independently be C, and $Y_{84}$ may be N or C, $CY_{81}$ and $CY_{82}$ may each independently be selected from a cyclopentadiene group, a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, a hexacene group, a pentacene group, a rubicene group, a corozene group, an ovalene group, a pyrrole group, an isoindole group, an indole group, an indazole group, a pyrazole group, an imidazole group, a triazole group, an oxazole group, an isoxazole group, an oxadiazole group, a thiazole group, an isothiazole group, thiadiazole group, a purine group, a furan group, a thiophene group, a pyridine group, a pyrimidine group, a quinoline group, an isoquinoline group, a benzoquinoline group, a phthalazine group, a naphthyridine group, a quinoxaline group, a quinazoline group, a cinnoline group, a phenanthrididine group, an acridine group, a phenanthroline group, a phenazine group, a benzimidazole group, a benzofuran group, a benzothiophene group, an isobenzothiazole group, a benzoxazole group, an isobenzoxazole group, a benzocarbazole group, a dibenzocarbazole group, an imidazopyridine group, an imidazopyrimidine group, a dibenzofuran group, a dibenzothiophene group, a dibenzothiophene sulfone group, a carbazole group, a dibenzosilol group, and a 2,3-dihydro-1H-imidazole group.

In various embodiments, in Formula 81A, $Y_{81}$ may be N, $Y_{82}$ to $Y_{84}$ may each independently be C, $CY_{81}$ may be selected from 5-membered ring including two nitrogen atoms as ring-forming atoms, and $CY_{82}$ may be selected from a benzene group, a naphthalene group, a fluorene group, a dibenzofuran group, and a dibenzothiophene group, but embodiments are not limited thereto.

In various embodiments, in Formula 81A, $Y_{81}$ may be N, $Y_{82}$ to $Y_{84}$ may each independently be C, $CY_{81}$ may be an imidazole group or a 2,3-dihydro-1H-imidazole group, and $CY_{82}$ may be selected from a benzene group, a naphthalene group, a fluorene group, a dibenzofuran group, and a dibenzothiophene group, but embodiments are not limited thereto.

In various embodiments, in Formula 81A, $Y_{81}$ may be N, $Y_{82}$ to $Y_{84}$ may each independently be C, $CY_{81}$ may be selected from a pyrrole group, a pyrazole group, an imidazole group, a triazole group, an oxazole group, an isoxazole group, an oxadiazole group, a thiazole group, an isothiazole group, a thiadiazole group, a pyridine group, a pyrimidine group, a quinoline group, an isoquinoline group, a benzoquinoline group, a phthalazine group, a naphthyridine group, a quinoxaline group, a quinazoline group, a cinnoline group, a benzimidazole group, an isobenzothiazole group, a benzoxazole group, and an isobenzoxazole group, and $CY_{82}$ may be selected from a cyclopentadiene group, a benzene group, a naphthalene group, a fluorene group, a benzofluorene group, a dibenzofluorene group, a phenanthrene group, an anthracene group, a triphenylene group, a pyrene group, a chrysene group, a perylene group, a benzofuran group, a benzothiophene group, a benzocarbazole group, a dibenzocarbazole group, a dibenzofuran group, a dibenzothiophene group, a dibenzothiophene sulfone group, a carbazole group, and a dibenzosilol group.

In various embodiments, in Formula 81A, $R_{81}$ and $R_{82}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group (adamantyl), a norbornanyl group (norbornyl), a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B(Q$_{86}$)(Q$_{87}$) and —P(=O)(Q$_{88}$)(Q$_{89}$), wherein Q$_{86}$ to Q$_{89}$ may each independently be selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group and a phenyl group.

In various embodiments, in Formula 81A, R$_{81}$ and R$_{82}$ may each independently be selected from:

hydrogen, deuterium, —F, a cyano group, a nitro group, —SF$_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from deuterium, —F, —CD$_3$, —CD$_2$H, —CDH$_2$, —CF$_3$, —CFH$_2$, a cyano group, a nitro group, a C$_1$-C$_{10}$ alkyl group, a C$_1$-C$_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group; and —B(Q$_{86}$)(Q$_{87}$) and —P(=O)(Q$_{88}$)(Q$_{89}$), wherein Q$_{86}$ to Q$_{89}$ may each independently be selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group.

In various embodiments, in Formula 81A, R$_{81}$ and R$_{82}$ may each independently be selected from hydrogen, deuterium, —F, a cyano group, a nitro group, —SF$_5$, —CH$_3$, —CD$_3$, —CD$_2$H, —CDH$_2$, —CF$_3$, —CFH$_2$, groups represented by Formulae 9-1 to 9-19, and groups represented by Formulae 10-1 to 10-30, but embodiments are not limited thereto:

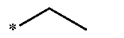

Formula 9-1

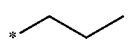

Formula 9-2

Formula 9-3

Formula 9-4

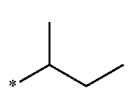

Formula 9-5

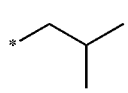

Formula 9-6

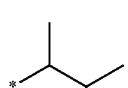

Formula 9-7

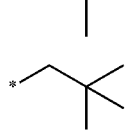

Formula 9-8


Formula 9-9

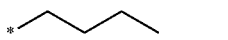

Formula 9-10

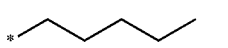

Formula 9-11

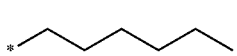

Formula 9-12

Formula 9-13

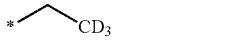

Formula 9-14

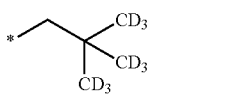

Formula 9-15

Formula 9-16

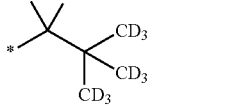

Formula 9-17

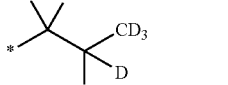

Formula 9-18

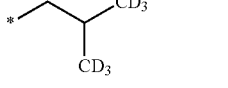

Formula 9-19

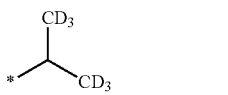

Formula 10-1

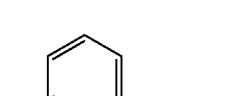

Formula 10-2

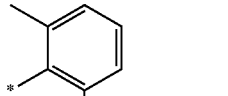

Formula 10-3

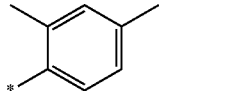

Formula 10-4

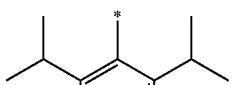

Formula 10-5

171
-continued
Formula 10-6
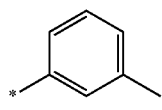
Formula 10-7
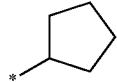
Formula 10-8
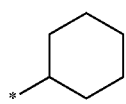
Formula 10-9
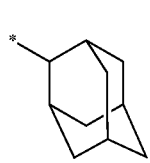
Formula 10-10
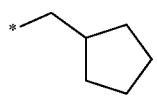
Formula 10-11
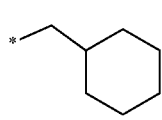
Formula 10-12
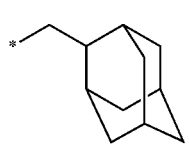
Formula 10-13
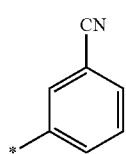
Formula 10-14
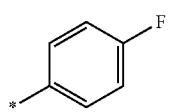
Formula 10-15
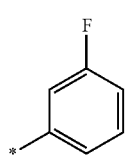
Formula 10-16
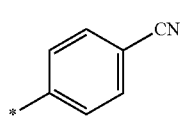
Formula 10-17
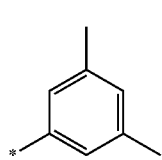
172
-continued
Formula 10-18
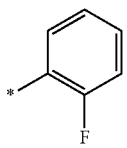
Formula 10-19
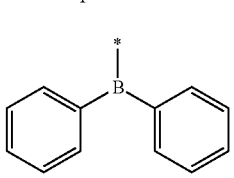
Formula 10-20
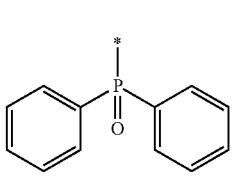
Formula 10-21
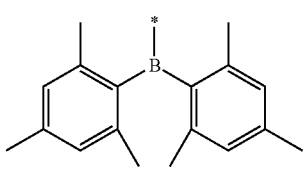
Formula 10-22
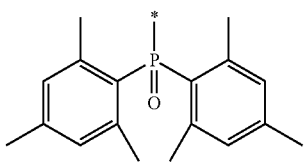
Formula 10-23
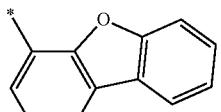
Formula 10-24
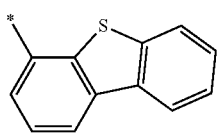
Formula 10-25
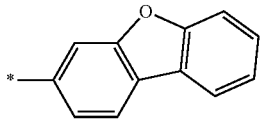
Formula 10-26
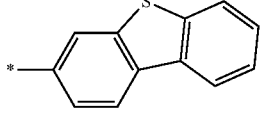
Formula 10-27
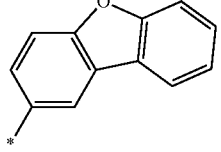

-continued

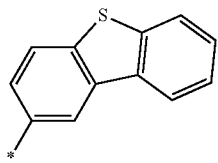

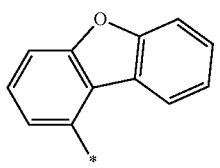

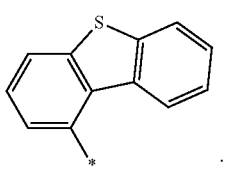

In Formulae 9-1 to 9-17 and 10-1 to 10-30, * indicates a binding site to a neighboring atom.

In various embodiments, in Formula 81A, at least one selected from $R_{81}$ in the number of a81 and $R_{82}$ in the number of a82 may be a cyano group.

In various embodiments, in Formula 81A, at least one selected from $R_{82}$ in the number of a82 may be a cyano group.

In various embodiments, in Formula 81A, at least one selected from $R_{81}$ in the number of a81 and $R_{82}$ in the number of a82 may be deuterium.

In various embodiments, in Formula 81, $L_{82}$ may be selected from ligands represented by Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114):

Formula 3-1(1)

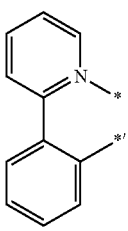

Formula 3-1(2)

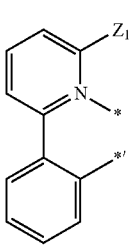

Formula 10-28

Formula 3-1(3)

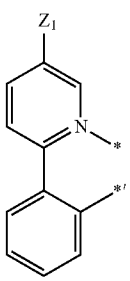

Formula 10-29

Formula 3-1(4)

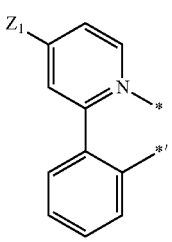

Formula 10-30

Formula 3-1(5)

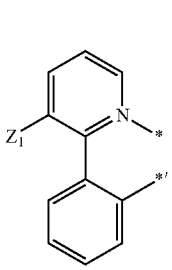

Formula 3-1(6)

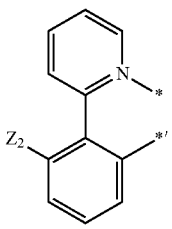

Formula 3-1(7)

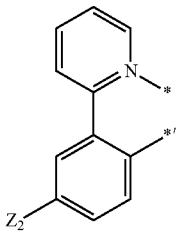

Formula 3-1(8)

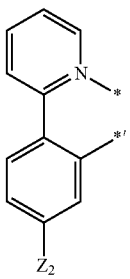

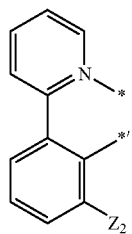
Formula 3-1(9)
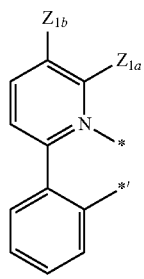
Formula 3-1(10)
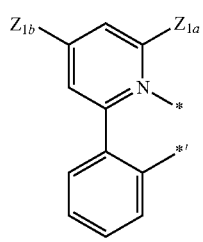
Formula 3-1(11)
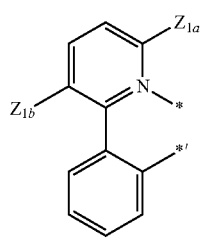
Formula 3-1(12)
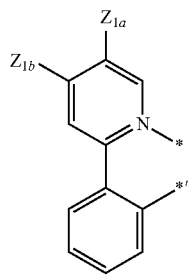
Formula 3-1(13)
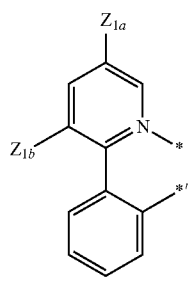
Formula 3-1(14)
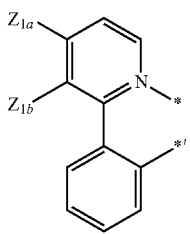
Formula 3-1(15)
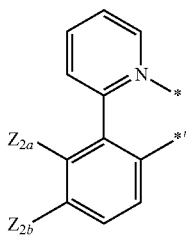
Formula 3-1(16)
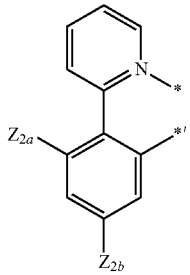
Formula 3-1(17)
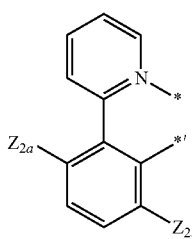
Formula 3-1(18)
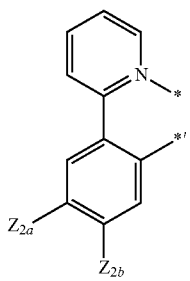
Formula 3-1(19)
Formula 3-1(20)

Formula 3-1(21)
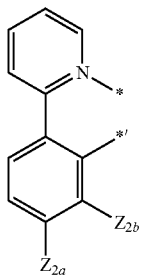
Formula 3-1(22)
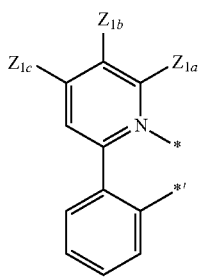
Formula 3-1(23)
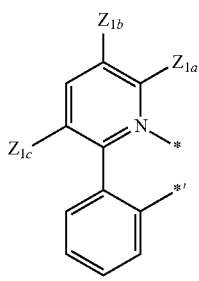
Formula 3-1(24)
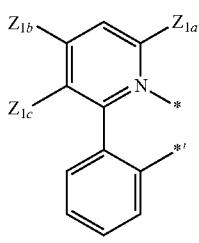
Formula 3-1(25)
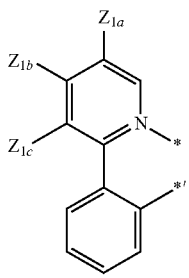
Formula 3-1(26)
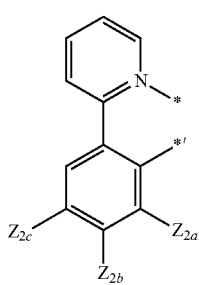
Formula 3-1(27)
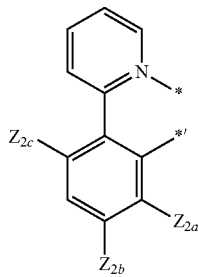
Formula 3-1(28)
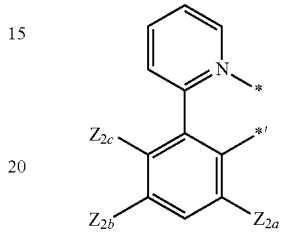
Formula 3-1(29)
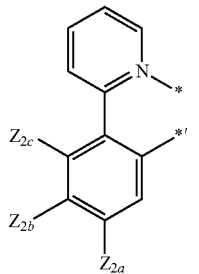
Formula 3-1(30)
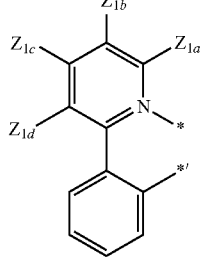
Formula 3-1(31)
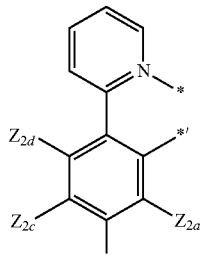
Formula 3-1(32)
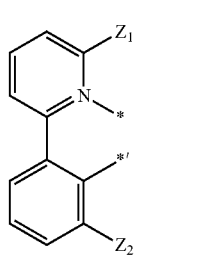

Formula 3-1(33)
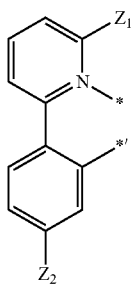
Formula 3-1(34)
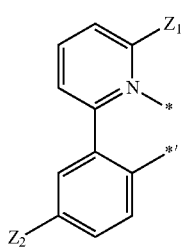
Formula 3-1(35)
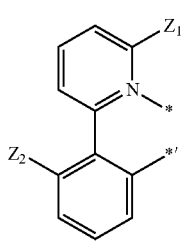
Formula 3-1(36)
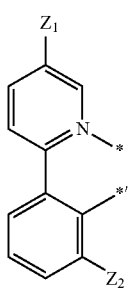
Formula 3-1(37)
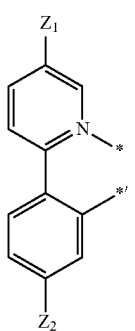
Formula 3-1(38)
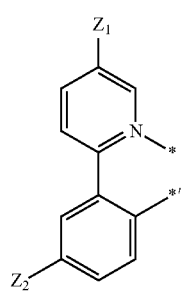
Formula 3-1(39)
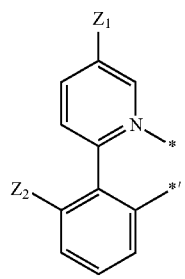
Formula 3-1(40)
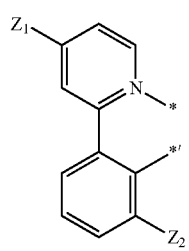
Formula 3-1(41)
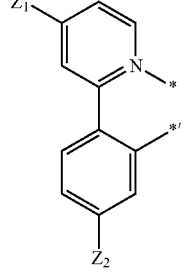
Formula 3-1(42)
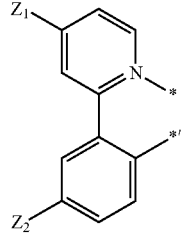
Formula 3-1(43)

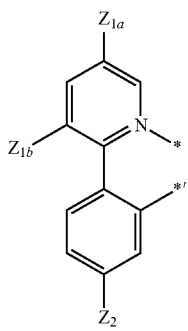 Formula 3-1(44)
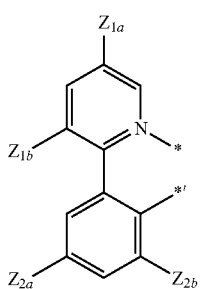 Formula 3-1(45)
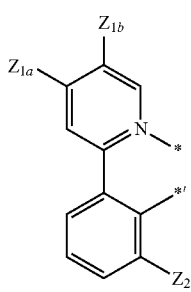 Formula 3-1(46)
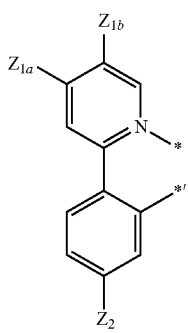 Formula 3-1(47)
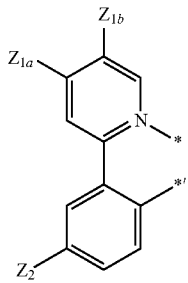 Formula 3-1(48)
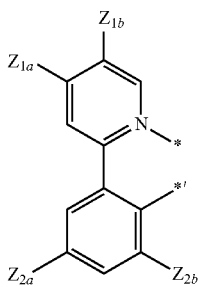 Formula 3-1(49)
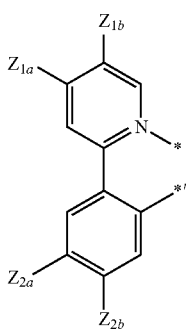 Formula 3-1(50)
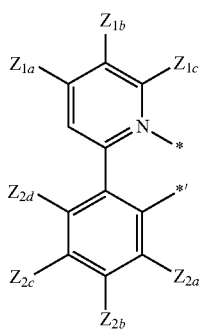 Formula 3-1(51)
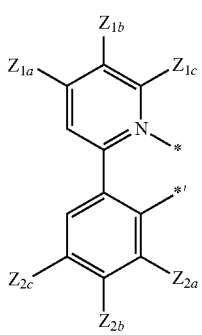 Formula 3-1(52)
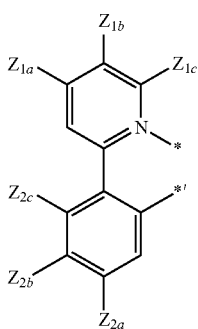 Formula 3-1(53)

-continued
Formula 3-1(54)
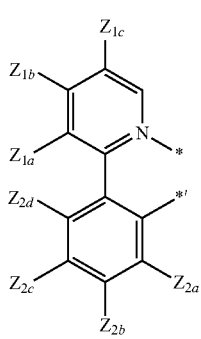
Formula 3-1(55)
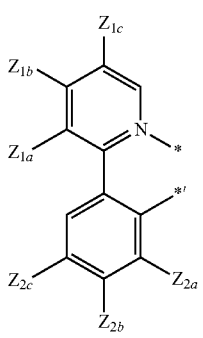
Formula 3-1(56)
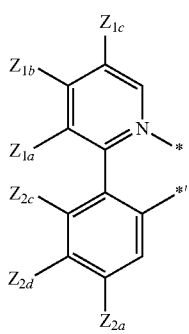
Formula 3-1(57)
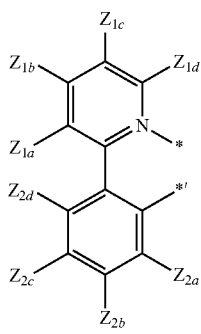
Formula 3-1(58)
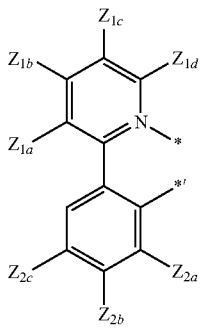
-continued
Formula 3-1(59)
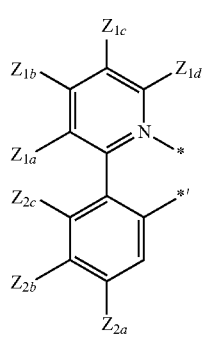
Formula 3-1(60)
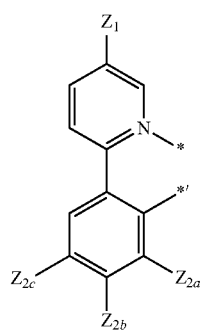
Formula 3-1(61)
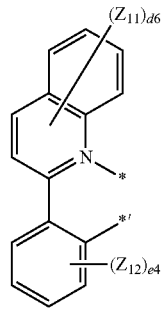
Formula 3-1(62)
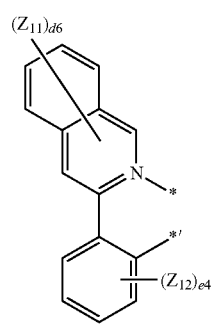
Formula 3-1(63)
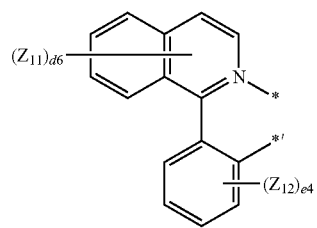

185
-continued
Formula 3-1(64)
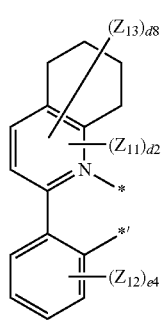
Formula 3-1(65)
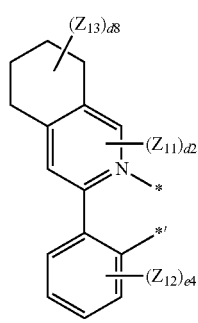
Formula 3-1(66)
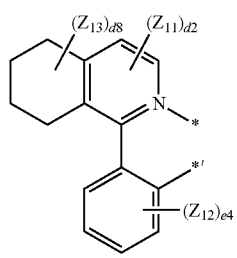
Formula 3-1(67)
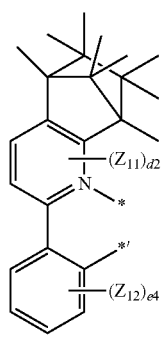
Formula 3-1(68)
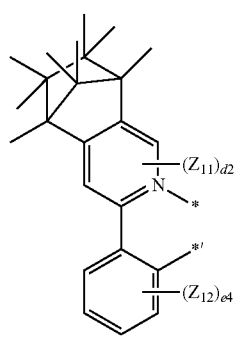
186
-continued
Formula 3-1(69)
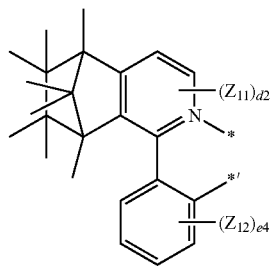
Formula 3-1(71)
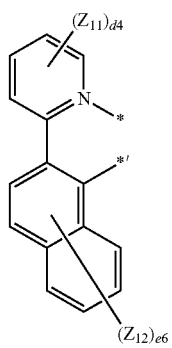
Formula 3-1(72)
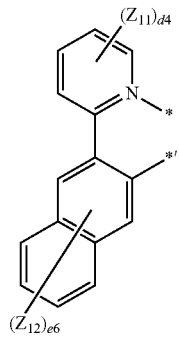
Formula 3-1(73)
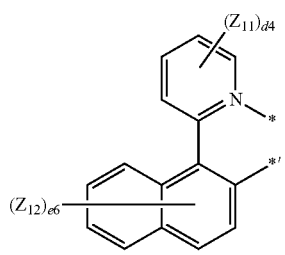
Formula 3-1(74)
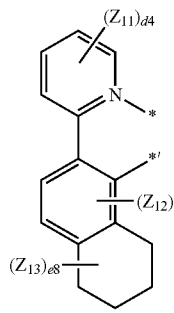

Formula 3-1(75) 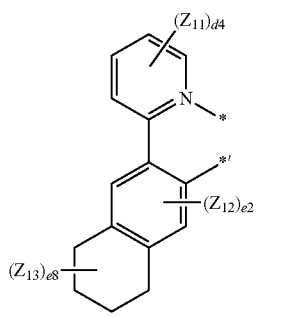
Formula 3-1(76) 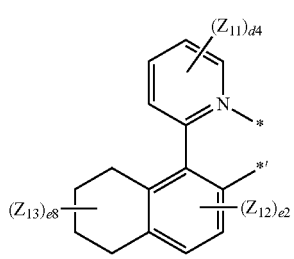
Formula 3-1(77) 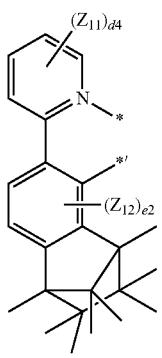
Formula 3-1(78) 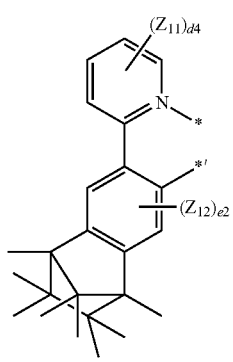
Formula 3-1(79) 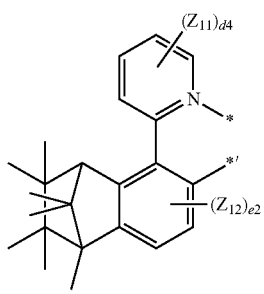
Formula 3-1(81) 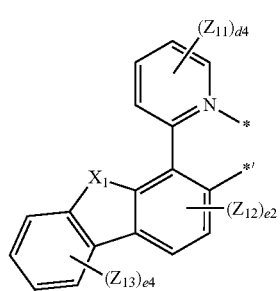
Formula 3-1(82) 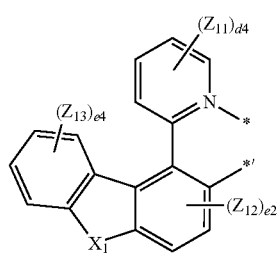
Formula 3-1(83) 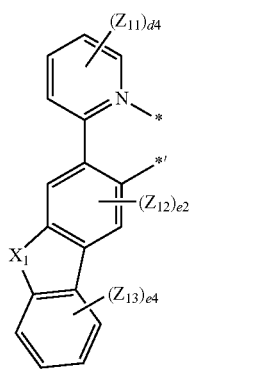
Formula 3-1(84) 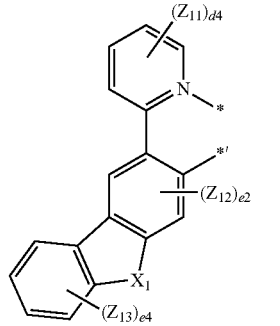
Formula 3-1(85) 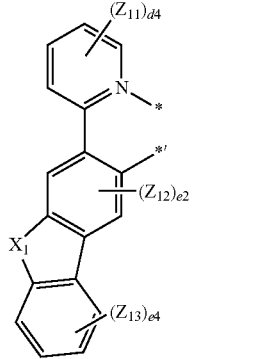

-continued
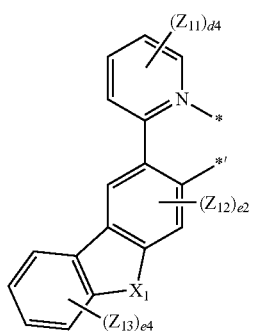
Formula 3-1(86)
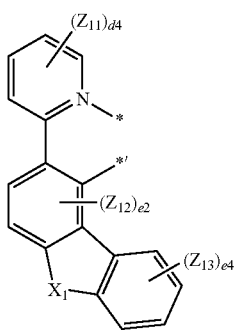
Formula 3-1(87)
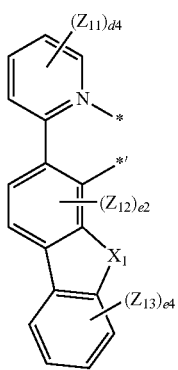
Formula 3-1(88)
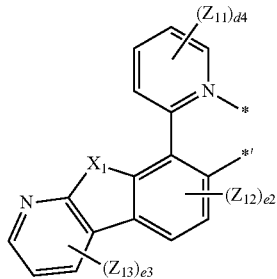
Formula 3-1(91)
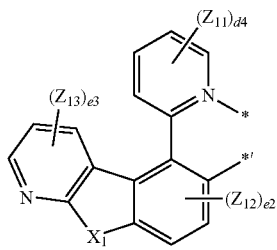
Formula 3-1(92)
-continued
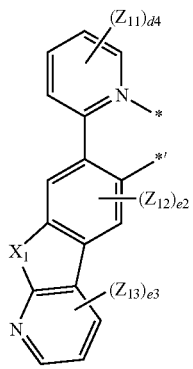
Formula 3-1(93)
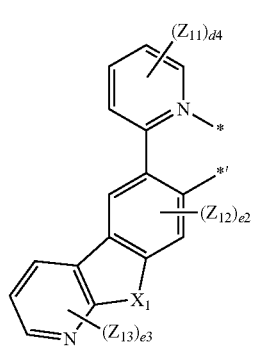
Formula 3-1(94)
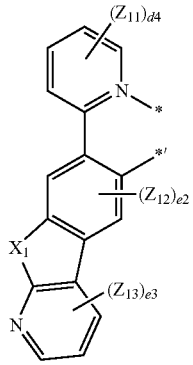
Formula 3-1(95)
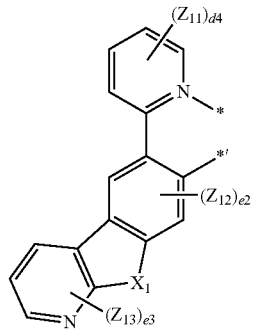
Formula 3-1(96)

-continued
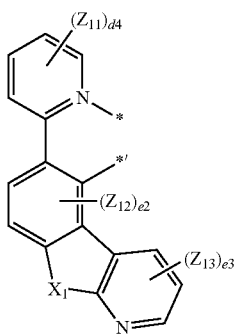
Formula 3-1(97)
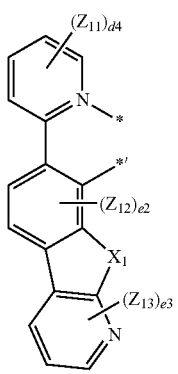
Formula 3-1(98)
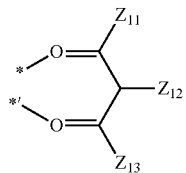
Formula 3-1(101)
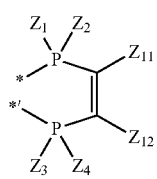
Formula 3-1(102)
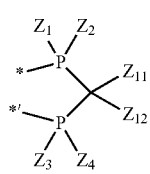
Formula 3-1(103)
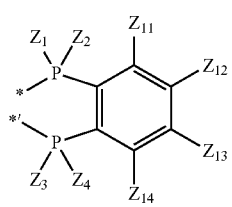
Formula 3-1(104)
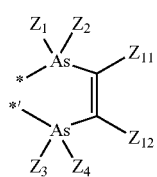
Formula 3-1(105)
-continued
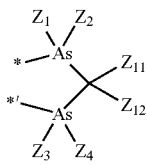
Formula 3-1(106)
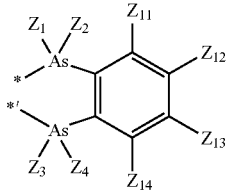
Formula 3-1(107)
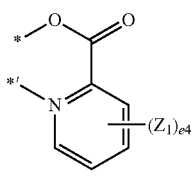
Formula 3-1(108)
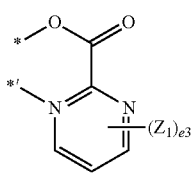
Formula 3-1(109)
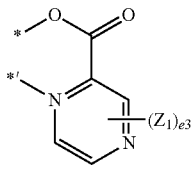
Formula 3-1(110)
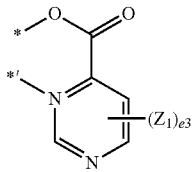
Formula 3-1(111)

Formula 3-1(112)
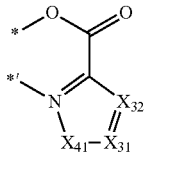
Formula 3-1(113)
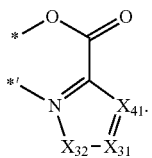
Formula 3-1(114)

In Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114), $X_1$ may be O, S, $C(Z_{21})(Z_{22})$, or $N(Z_{23})$, $X_{31}$ may be N or $C(Z_{1a})$, $X_{32}$ may be N or $C(Z_{1b})$, $X_{41}$ may be O, S, $N(Z_{1a})$, or $C(Z_{1a})(Z_{1b})$, $Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, and $Z_{21}$ to $Z_{23}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —$B(Q_{86})(C)_{87}$ and —$P(=O)(C)_{88})(Q_{89})$, wherein $Q_{86}$ to $Q_{89}$ may each independently be selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, d2 and e2 may each independently be 0 or 2, e3 may be an integer selected from 0 to 3, d4 and e4 may each independently an integer selected from 0 to 4, d6 and e6 may each independently an integer selected from 0 to 6, d8 and e8 may each independently an integer selected from 0 to 8, and

* and *' each indicate a binding site to M of Formula 1.

For example, $Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, and $Z_{21}$ to $Z_{23}$ may each independently be selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, and groups represented by Formulae 10-1 to 10-30, but embodiments are not limited thereto.

In various embodiments, in Formula 81, M may be Ir and the sum of n81+n82 may be 3; or M may be Pt and the sum of n81+n82 may be 2.

In various embodiments, the organometallic compound represented by Formula 81 may neutral, rather than being a salt consisting of a pair of a cation and an anion.

In various embodiments, the organometallic compound represented by Formula 81 may include at least one selected from Compounds PD1 to PD78 and FIr$_6$, but embodiments are not limited thereto:

PD1
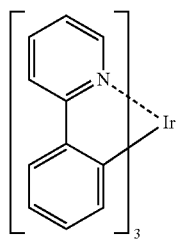

PD2
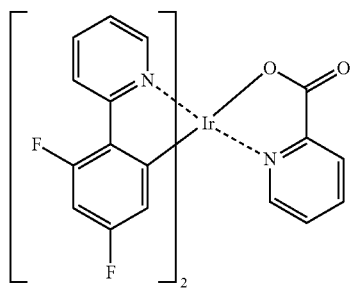

PD3
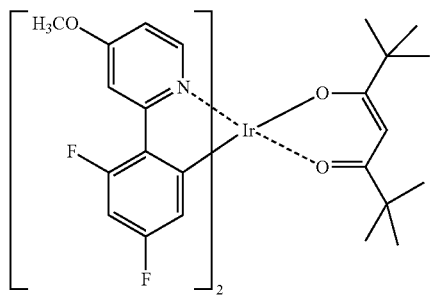

PD4
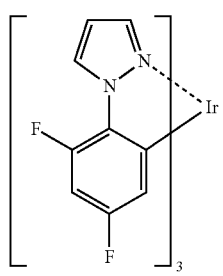

PD5
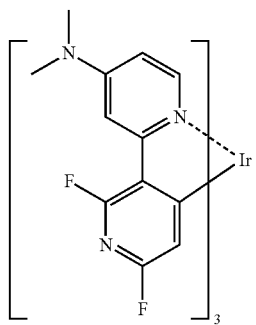

PD6
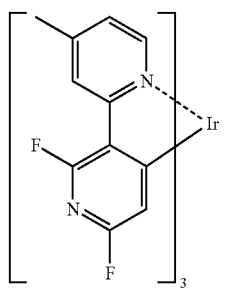

PD7
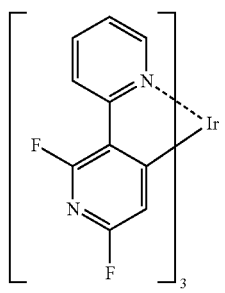

PD8
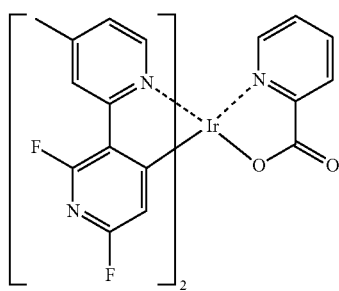

PD9
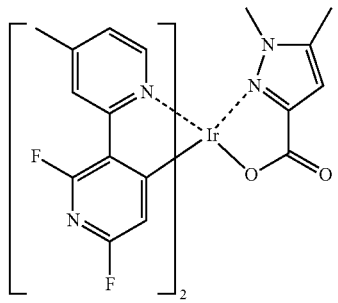

PD10 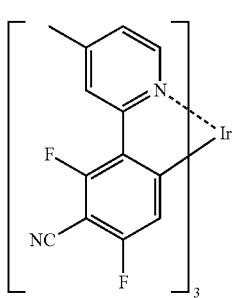
PD11 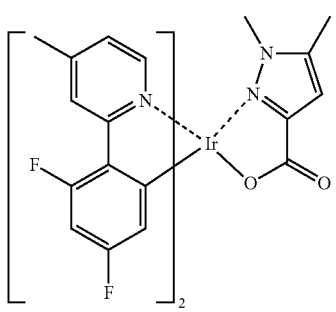
PD12 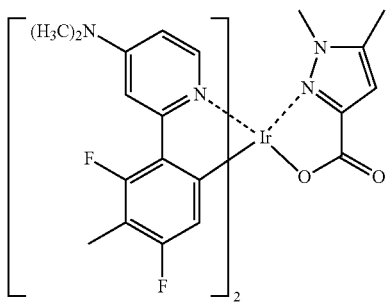
PD13 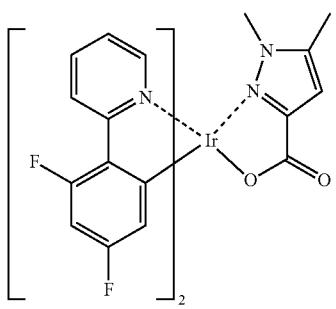
PD14 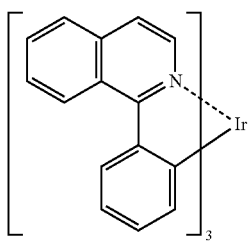
PD15 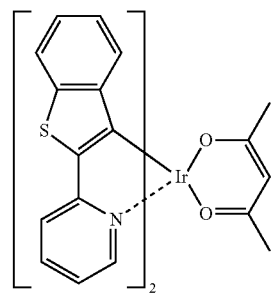
PD16 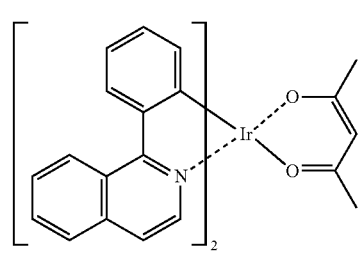
PD17 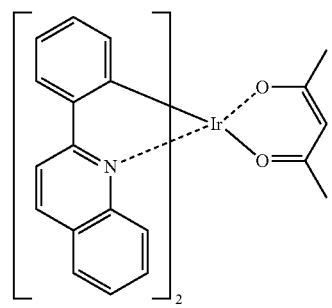
PD18 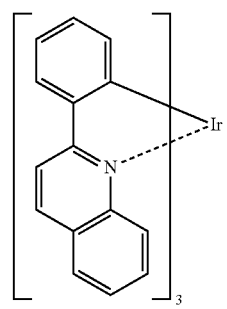
PD19 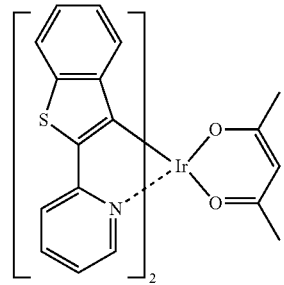

PD20
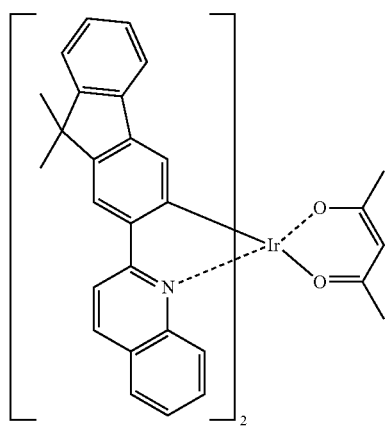
PD21
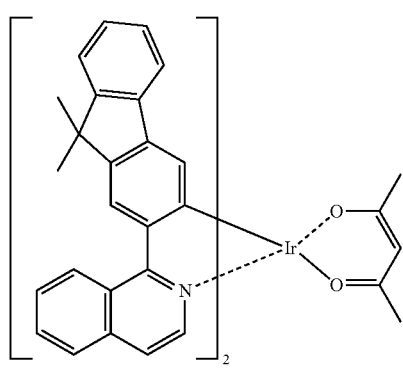
PD22
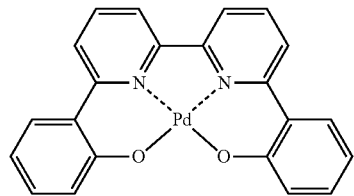
PD23
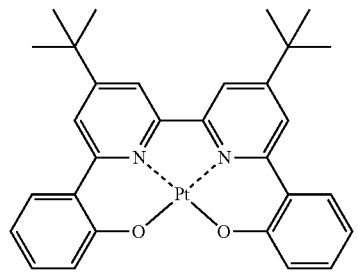
PD24
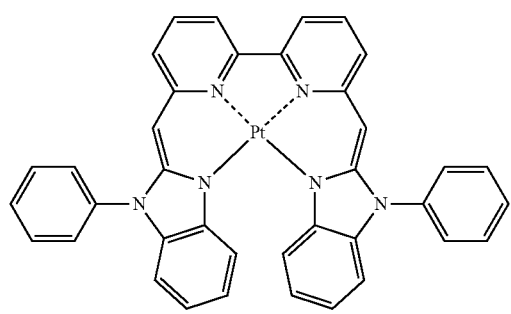
PD25
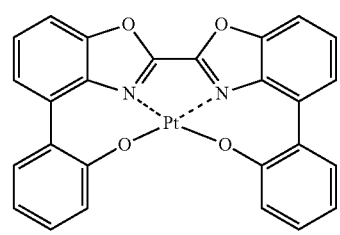
PD26
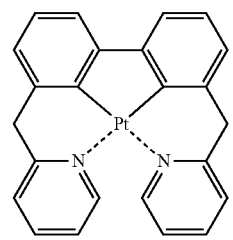
PD27
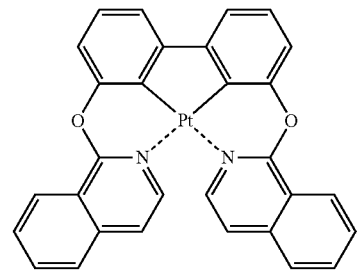
PD28
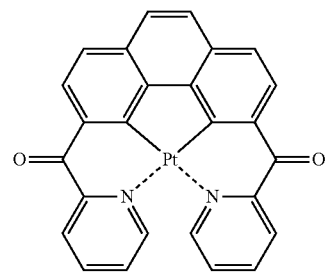
PD29
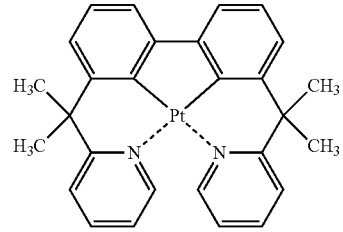
PD30
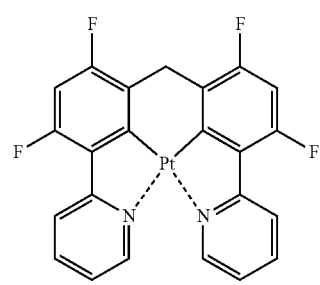

PD31 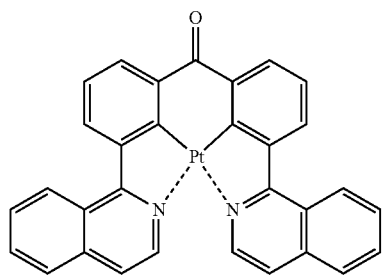
PD32 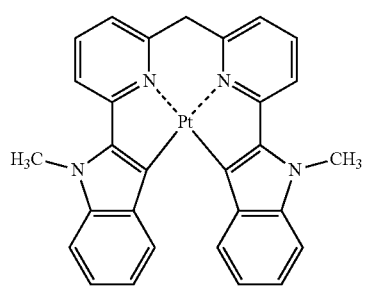
PD33 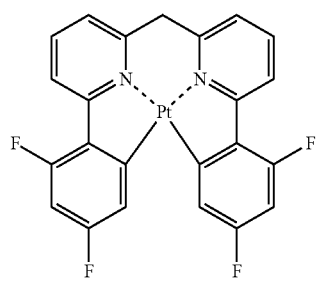
PD34 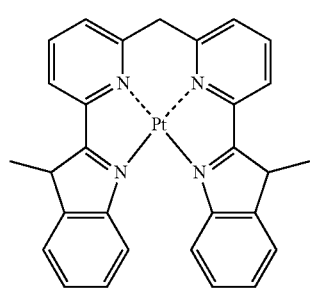
PD35 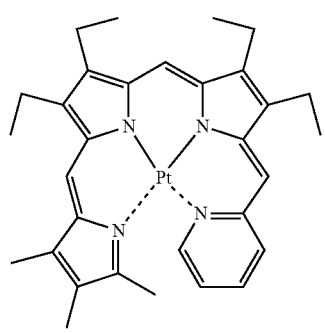
PD36 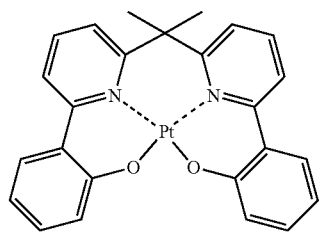
PD37 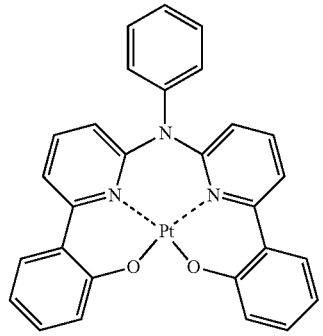
PD38 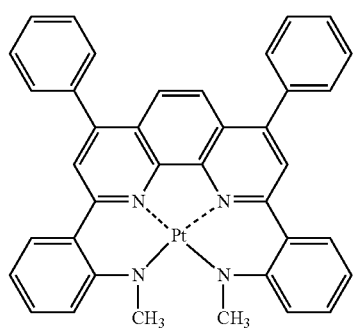
PD39 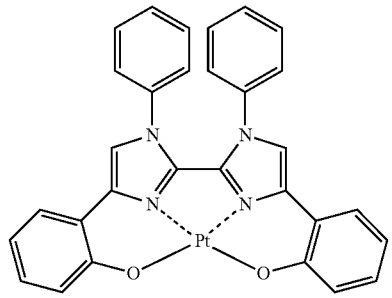
PD40 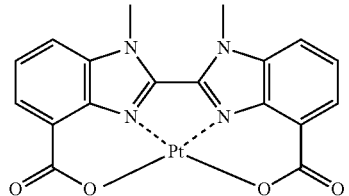
PD41 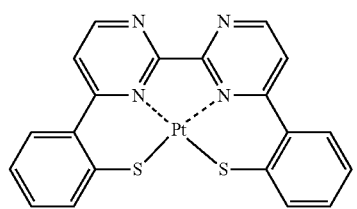

203
-continued
PD42
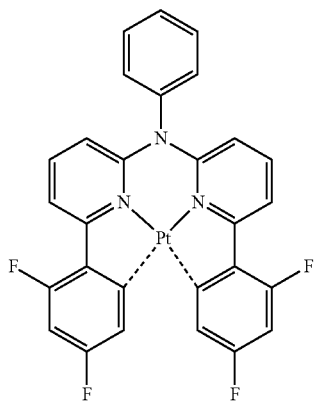
PD43
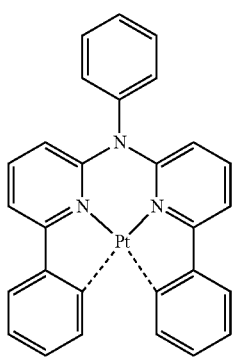
PD44
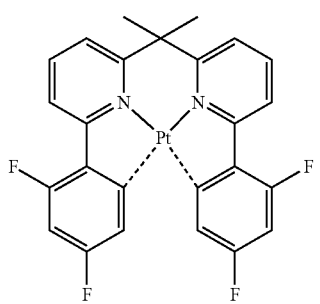
PD45
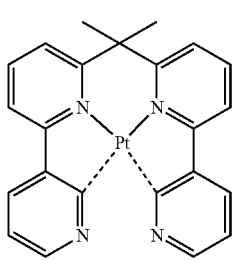
PD46
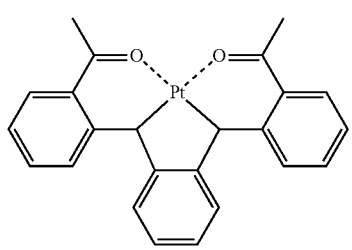
204
-continued
PD47
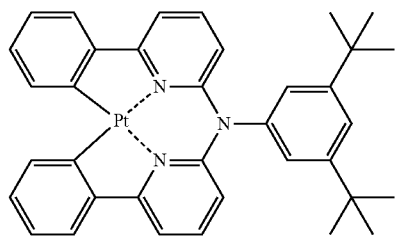
PD48
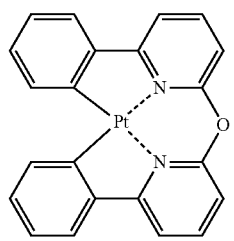
PD49
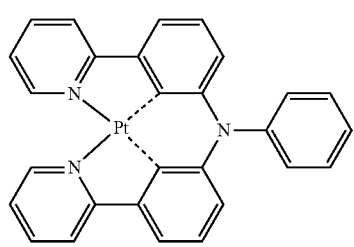
PD50
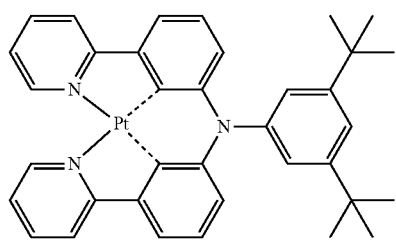
PD51
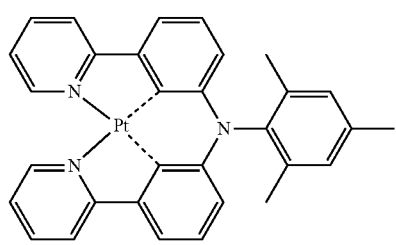
PD52
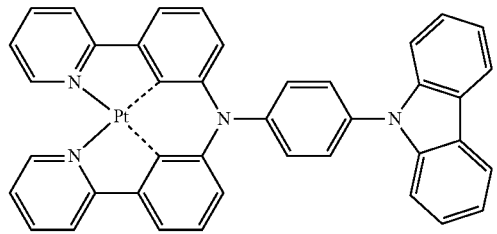

PD53 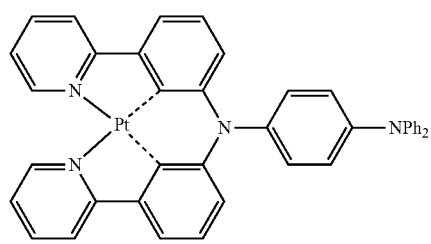
PD54 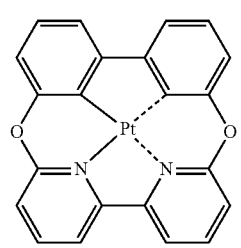
PD55 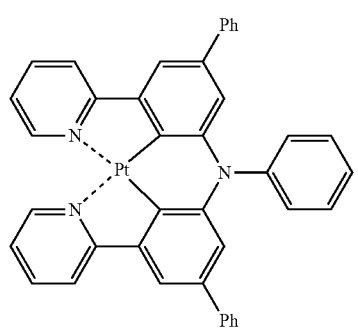
PD56 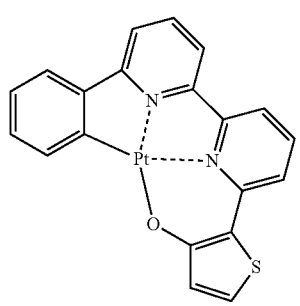
PD57 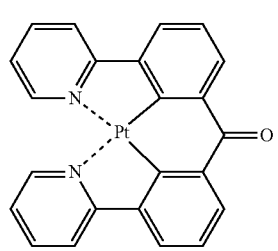
PD58 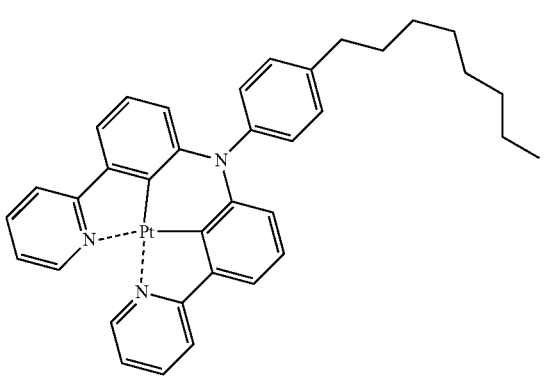
PD59 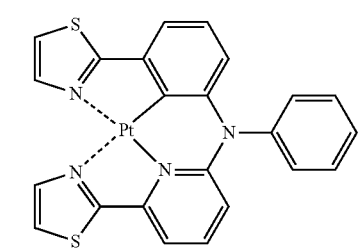
PD60 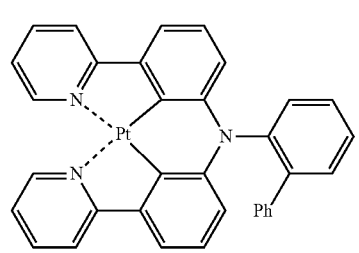
PD61 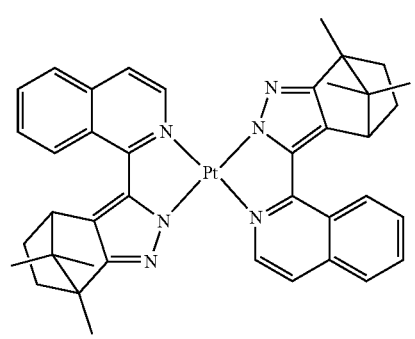
PD62 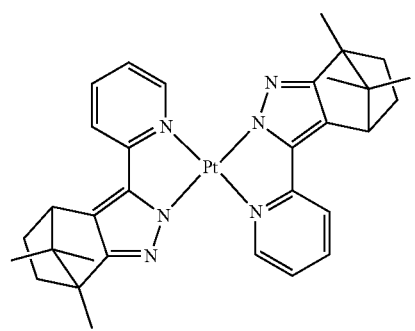

-continued
PD63
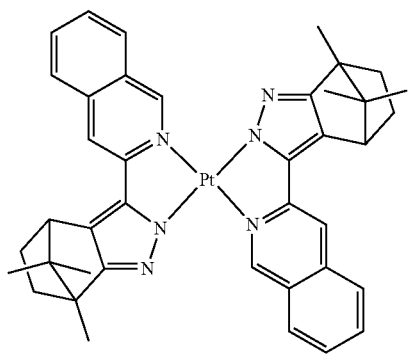
PD64
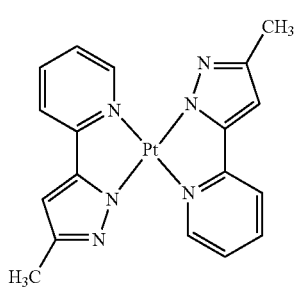
PD65
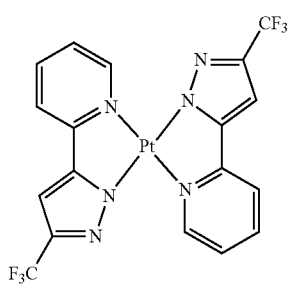
PD66
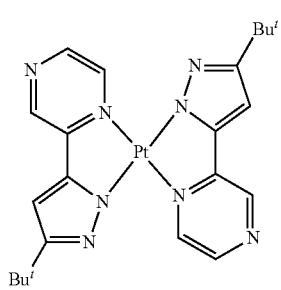
PD67
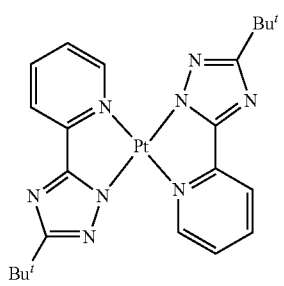
-continued
PD68
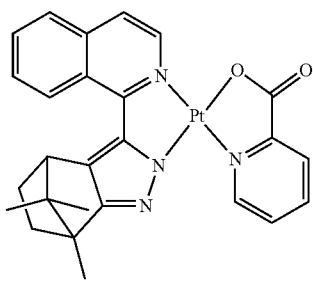
PD69
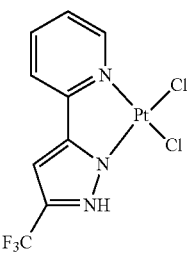
PD70
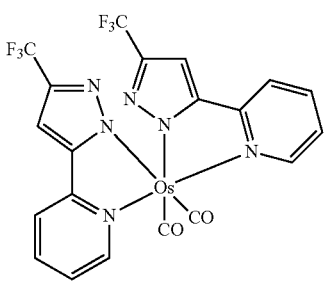
PD71
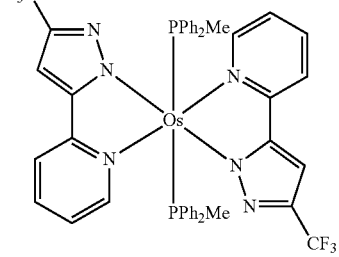
PD72
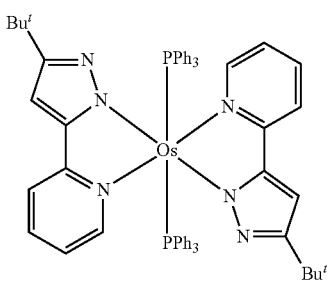

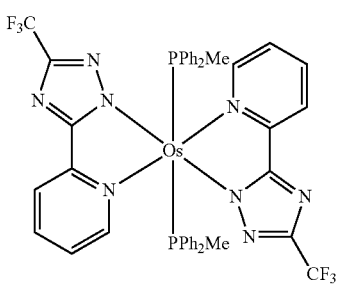
PD73

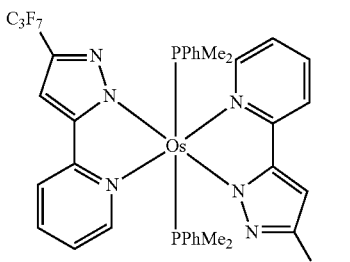
PD74

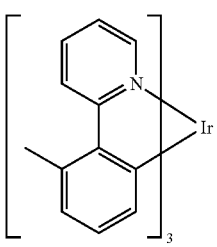
PD75

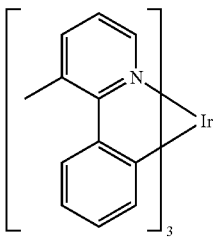
PD76

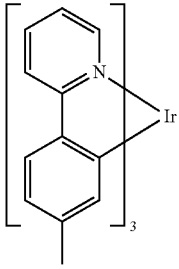
PD77

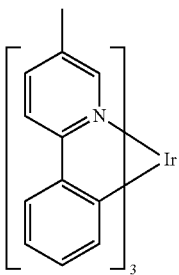
PD78

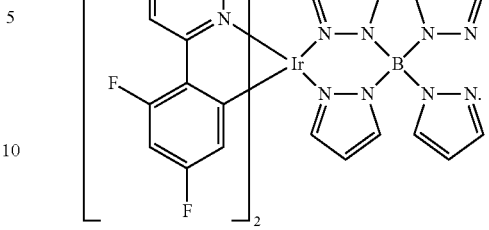
FIr6

In an embodiment, i) the organic light-emitting device may further include the organometallic compound represented by Formula 81, and the emission layer of the organic light-emitting device may include a host and a dopant, wherein the host may include the condensed cyclic compound represented by Formula 1 (for example, the host may consist of the condensed cyclic compound represented by Formula 1) and the dopant may include the organometallic compound represented by Formula 81;

ii) the organic light-emitting device may further include the second compound (for example, the compound represented by Formula H-1), and the emission layer of the organic light-emitting device may include a host and a dopant, wherein the host may include the condensed cyclic compound represented by Formula 1 and the second compound (for example, the compound represented by Formula H-1), or iii) the organic light-emitting device may further include the second compound (for example, the compound represented by Formula H-1) and the organometallic compound represented by Formula 81, the emission layer of the organic light-emitting device may include a host and a dopant, wherein the host may include the condensed cyclic compound represented by Formula 1 and the second compound (for example, the compound represented by Formula H-1), and the dopant may include the organometallic compound represented by Formula 81.

The expression that "(an organic layer) includes at least one condensed cyclic compound" as used herein may include a case in which "(an organic layer) includes at least one condensed cyclic compound identical to the condensed cyclic compound represented by Formula 1" or a case in which (an organic layer) includes two or more condensed cyclic compounds different from the condensed cyclic compound represented by Formula 1".

For example, the organic layer may include, as the condensed cyclic compound, only Compound 1. Here, Compound 1 may be in the emission layer of the organic light-emitting device. In various embodiments, the organic layer may include, as the condensed cyclic compound, Compound 1 and Compound 2. Here, Compound 1 and Compound 2 may be in an identical layer (for example, Compound 1 and Compound 2 may both be in the emission layer), or in different layers (for example, Compound 1 may be in the emission layer and Compound 2 may be in the electron blocking layer).

The first electrode may be an anode, which is a hole injection electrode, and the second electrode may be a cathode, which is an electron injection electrode. In various embodiments, the first electrode may be a cathode, which is an electron injection electrode, and the second electrode may be an anode, which is a hole injection electrode.

The term "organic layer" as used herein may refer to a single layer and/or a plurality of layers disposed between the first electrode and the second electrode of the organic light-emitting device. The "organic layer" may include not only an organic compound, but also a metal-containing organometallic complex.

The FIG. 1 is a schematic cross-sectional view of an organic light-emitting device 10 according to an embodiment. Hereinafter, the structure of an organic light-emitting device according to an embodiment and a method of manufacturing an organic light-emitting device, according to an embodiment, will be described in connection with the FIGURE. The organic light-emitting device 10 includes a first electrode 11, an organic layer 15, and a second electrode 19, which are sequentially stacked in this stated order.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water-resistance.

The first electrode 11 may be, for example, formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), and zinc oxide (ZnO). In various embodiments, metals, such as magnesium (Mg), aluminum (Al), aluminum-lithium (Al—Li), calcium (Ca), magnesium-indium (Mg—In), and magnesium-silver (Mg—Ag), may be used as the material for forming the first electrode 11.

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 may be disposed on the first electrode 11.

The organic layer 15 may include a hole transport region, an emission layer; and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In various embodiments, the hole transport region may have a structure of hole injection layer/hole transport layer, a structure of hole injection layer/hole transport layer/electron blocking layer, or a structure of hole transport layer/electron blocking layer, wherein the layers of each structure are sequentially stacked from the first electrode 11 in the stated order.

When hole transport region includes a hole injection layer, the hole injection layer may be formed on the first electrode 11 by using one or more suitable methods selected from vacuum deposition, spin coating, casting, and Langmuir-Blodgett (LB) deposition.

When the hole injection layer is formed using vacuum deposition, the deposition conditions may vary according to a material that is used to form the hole injection layer to be deposited, and the structure and thermal characteristics of the hole injection layer to be formed. For example, the deposition conditions may include a deposition temperature of about 100° C. to about 500° C., a vacuum pressure of about $10^{-8}$ torr to about $10^{-3}$ torr, and a deposition rate of about 0.01 Å/sec to about 100 Å/sec, but the deposition conditions are not limited thereto.

When the hole injection layer is formed using spin coating, the coating conditions may vary depending on a material that is used to form the hole injection layer to be deposited, and the structure and thermal characteristics of the hole injection layer to be formed. For example, a coating speed may be from about 2,000 revolutions per minute (rpm) to about 5,000 rpm and a temperature at which a heat treatment is performed to remove a solvent after coating may be from about 80° C. to about 200° C., but the coating conditions are not limited thereto.

Conditions for forming a hole transport layer and an electron blocking layer may be understood by referring to conditions for forming the hole injection layer.

The hole transport region may include, for example, at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201, and a compound represented by Formula 202:

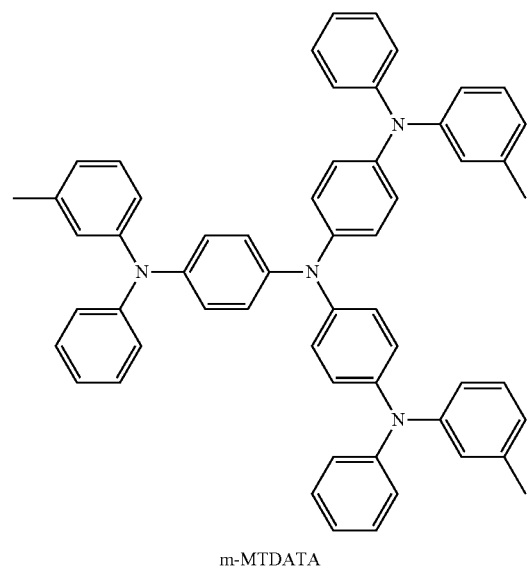

m-MTDATA

-continued
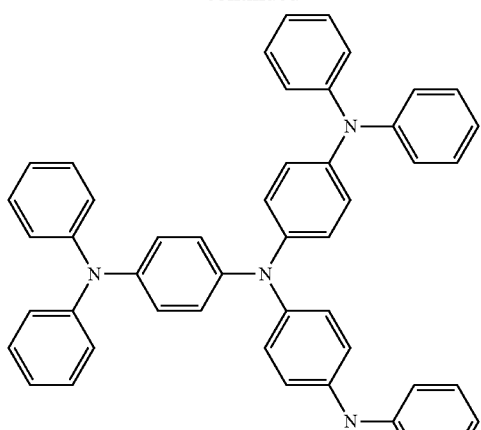
TDATA
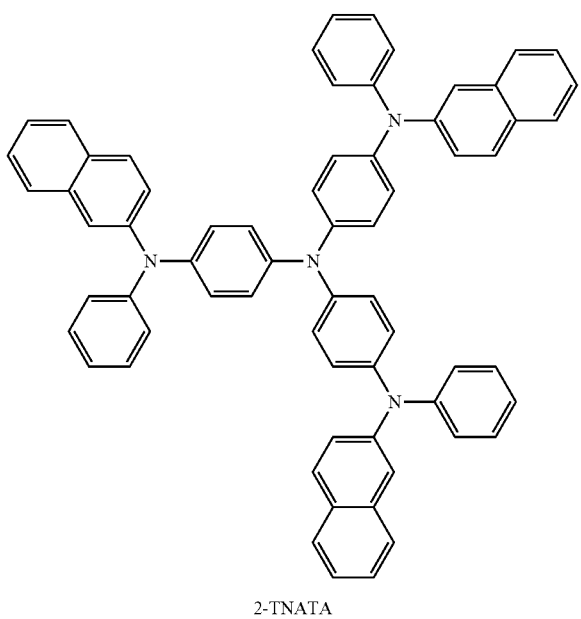
2-TNATA
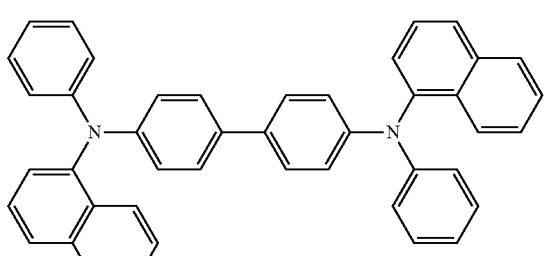
NPB
-continued
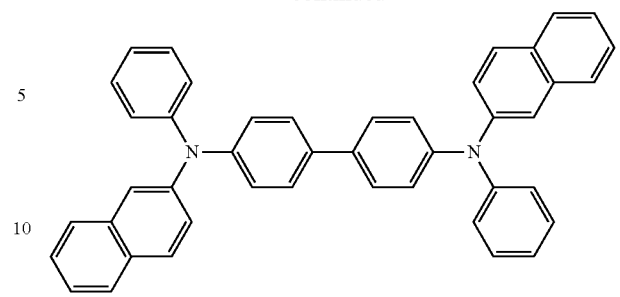
β-NPB
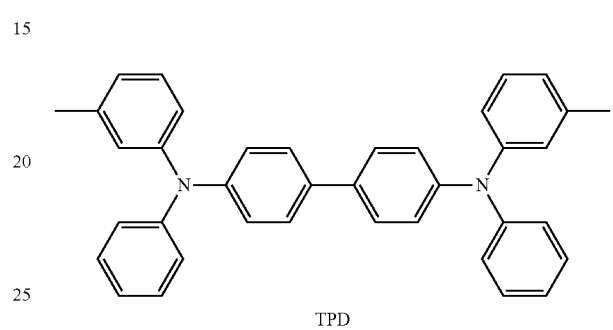
TPD
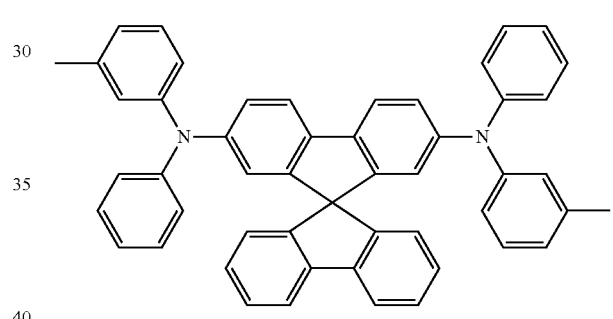
Spiro-TPD
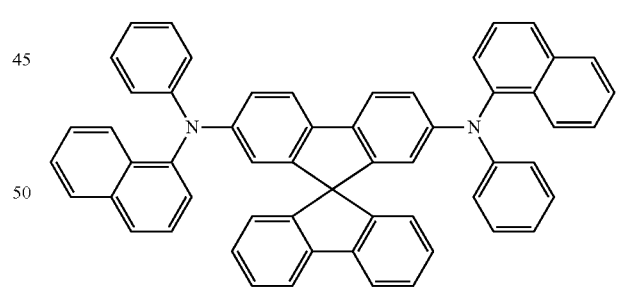
Spiro-NPB
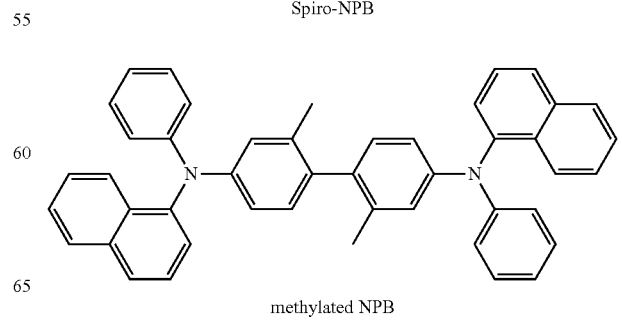
methylated NPB -continued

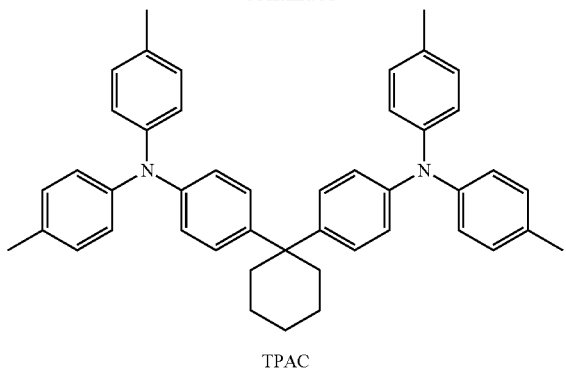

TPAC

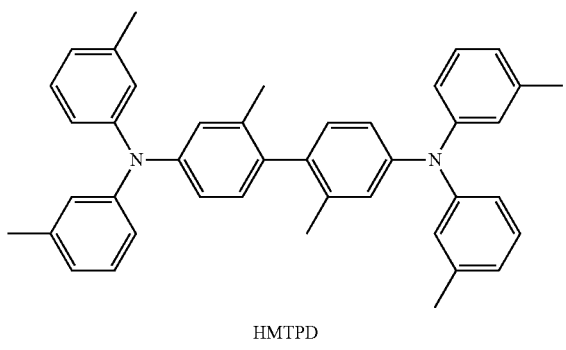

HMTPD

Formula 201

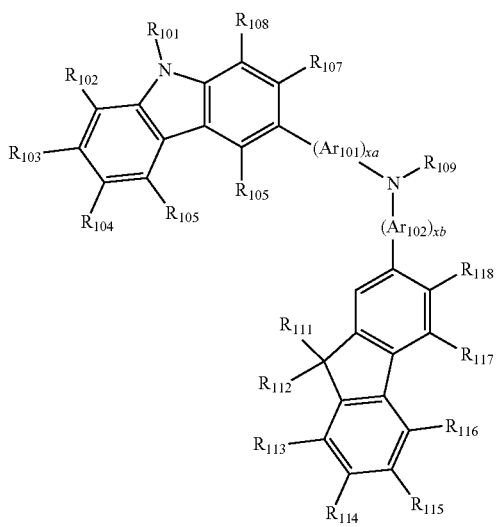

Formula 202

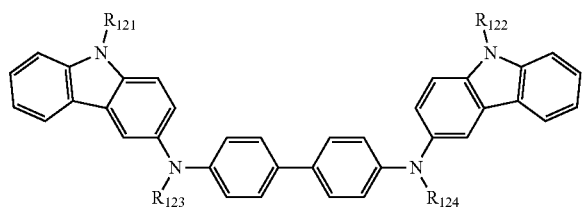

In Formula 201, $Ar_{101}$ and $Ar_{102}$ may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer selected from 0 to 5, or may each independently be 0, 1, or 2. For example, xa is 1, and xb may be 0, but embodiments are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, or a hexyl group), and a $C_1$-$C_{10}$ alkoxy group (for example, a methoxy group, an ethoxy group, a propoxy group, a butoxy group, pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

In Formula 201, $R_{109}$ may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In an embodiment, the compound represented by Formula 201 may be represented by Formula 201A, but embodiments are not limited thereto:

Formula 201A

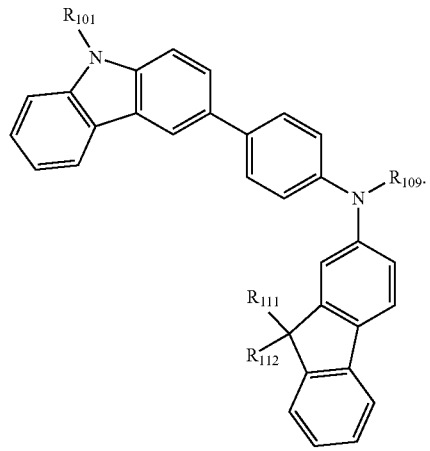

In Formula 201A, $R_{101}$, $R_{111}$, $R_{112}$, and $R_{109}$ are each independently the same as defined herein.

For example, the compound represented by Formula 201 and the compound represented by Formula 202 may each be selected from Compounds HT1 to HT20, but embodiments are not limited thereto:

HT1

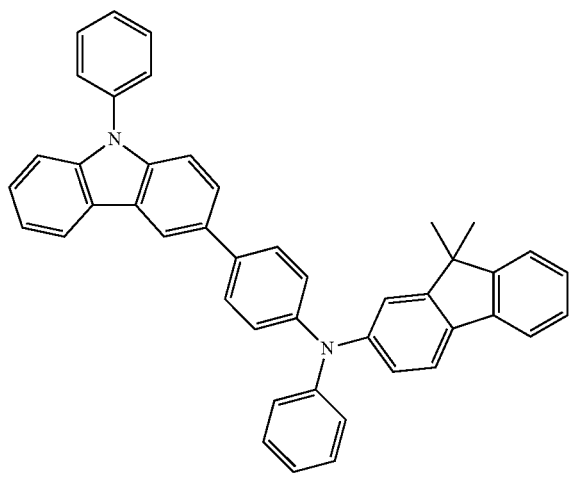

HT2

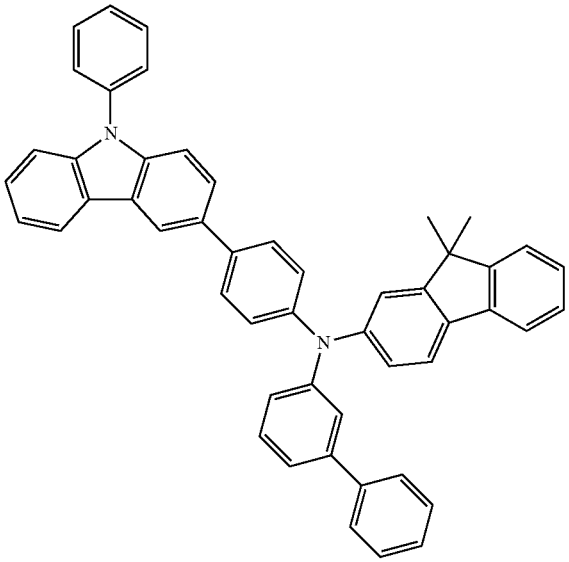

HT3

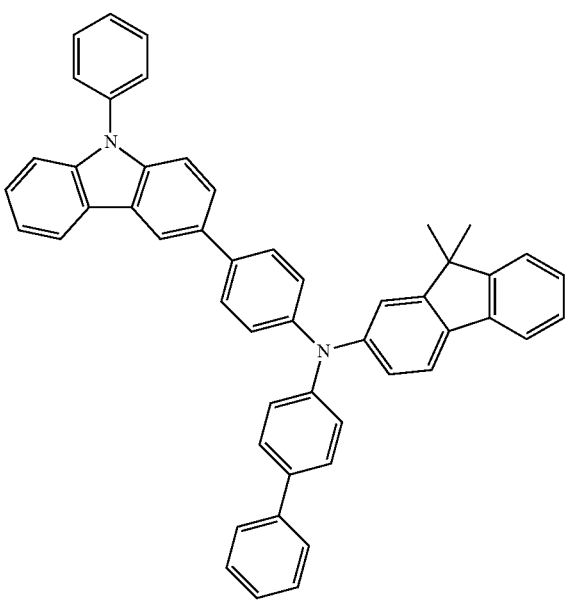

219
-continued
H3
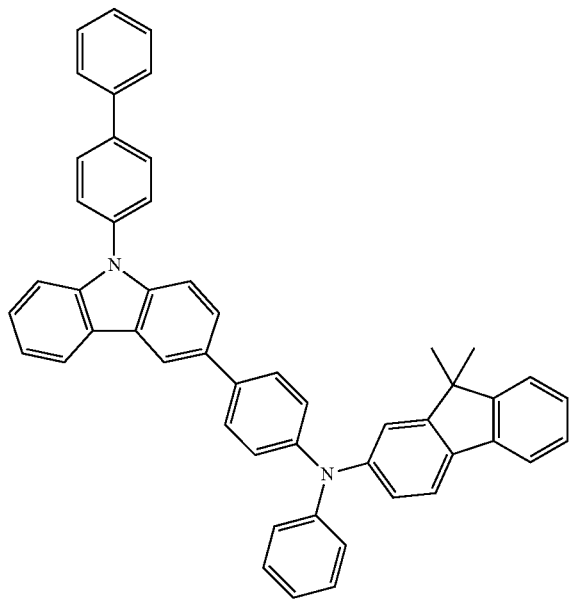
H4
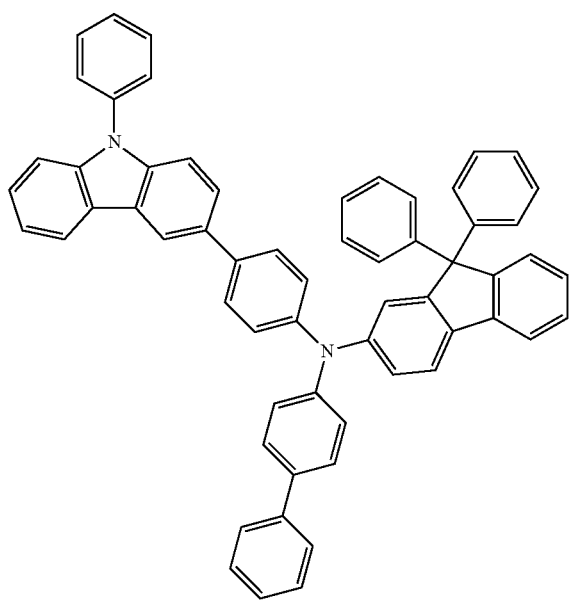
220
-continued
HT6
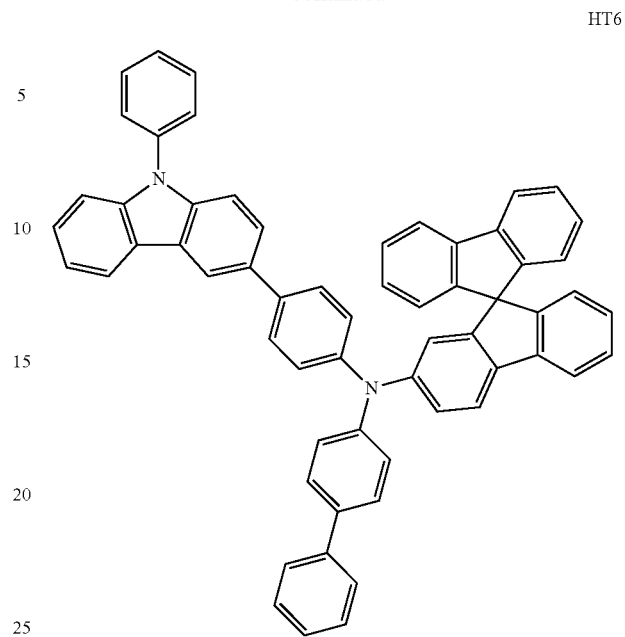
HT7

HT8
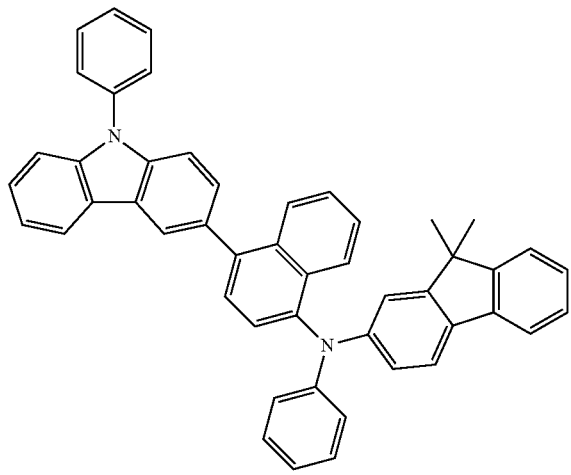
HT11
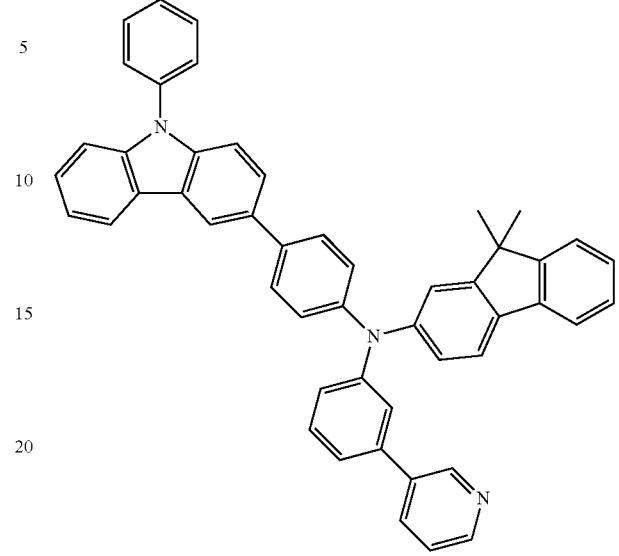
HT9
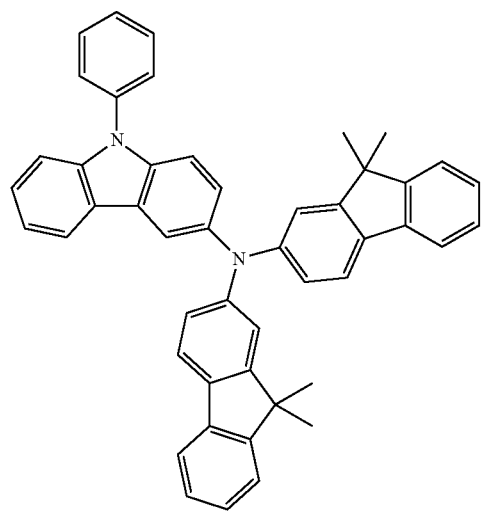
HT12
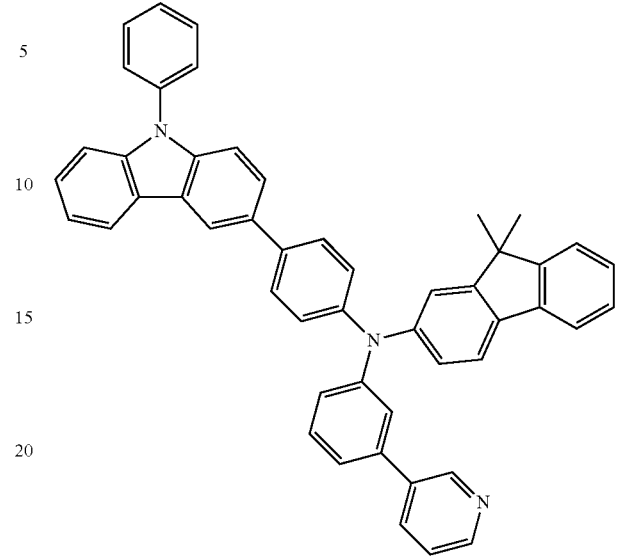
HT10
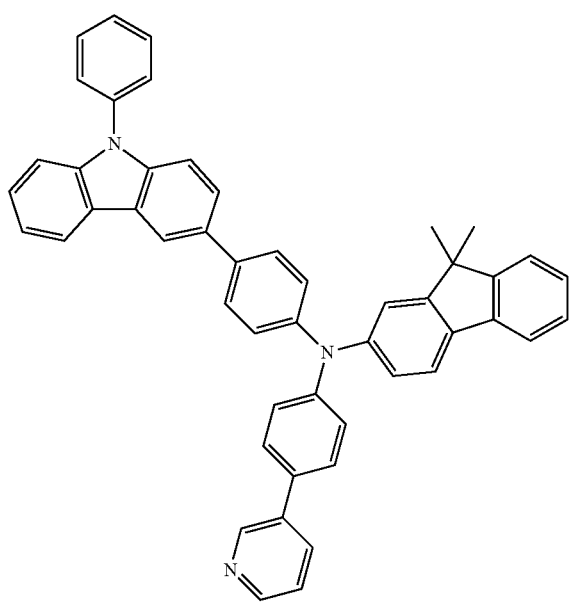
HT13
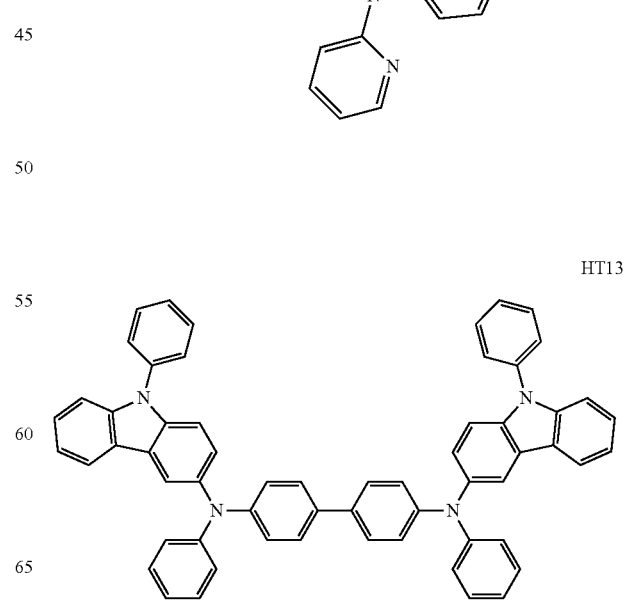

HT14

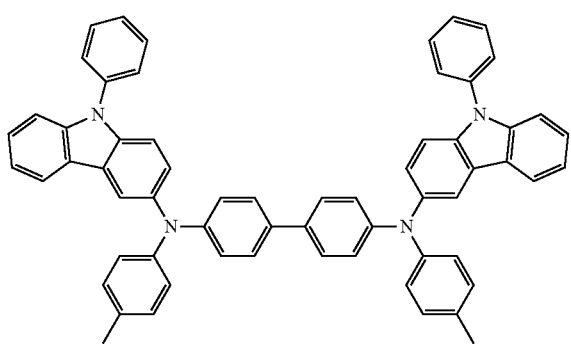

HT15

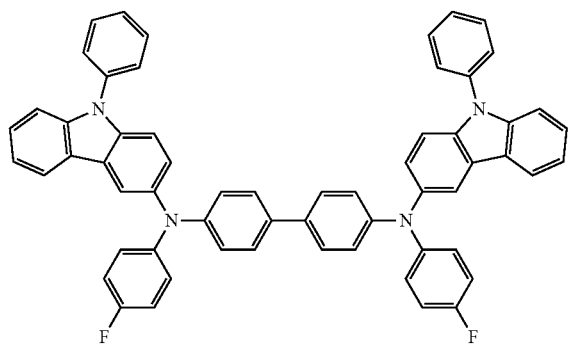

HT16

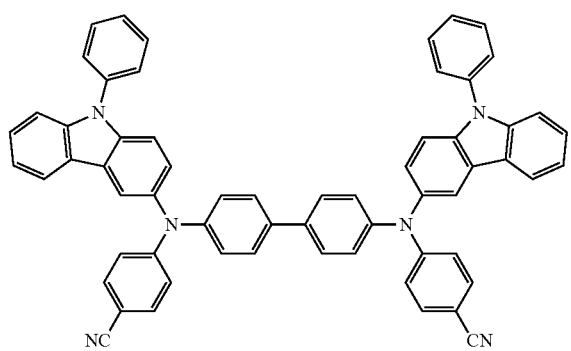

HT17

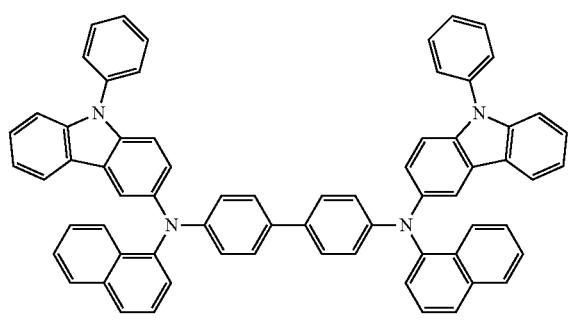

HT18

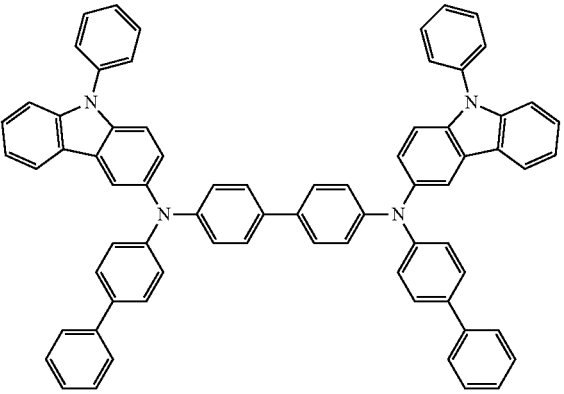

HT19

HT20

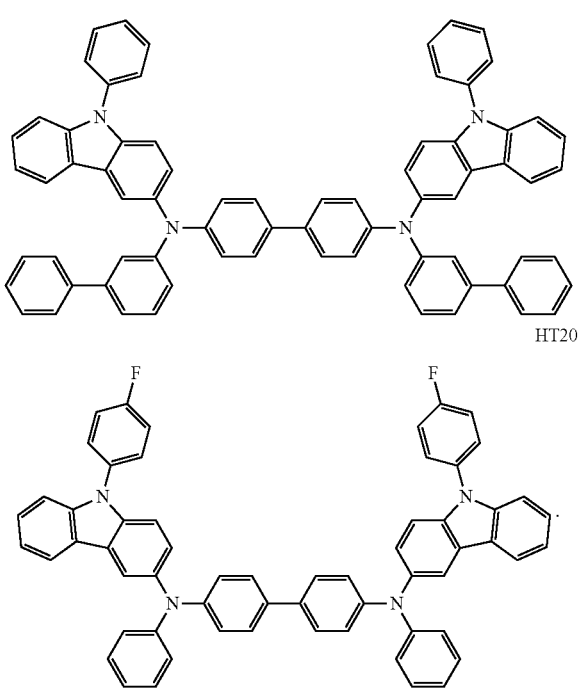

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for improving conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) and 2,3,5,6-tetrafluoro-tetracyano-1,4-benzoquinonedimethane (F4-TCNQ); a metal oxide, such as a tungsten oxide and a molybdenum oxide; and a cyano group-containing compound, such as Compounds HT-D1 and HP-1, but embodiments are not limited thereto:

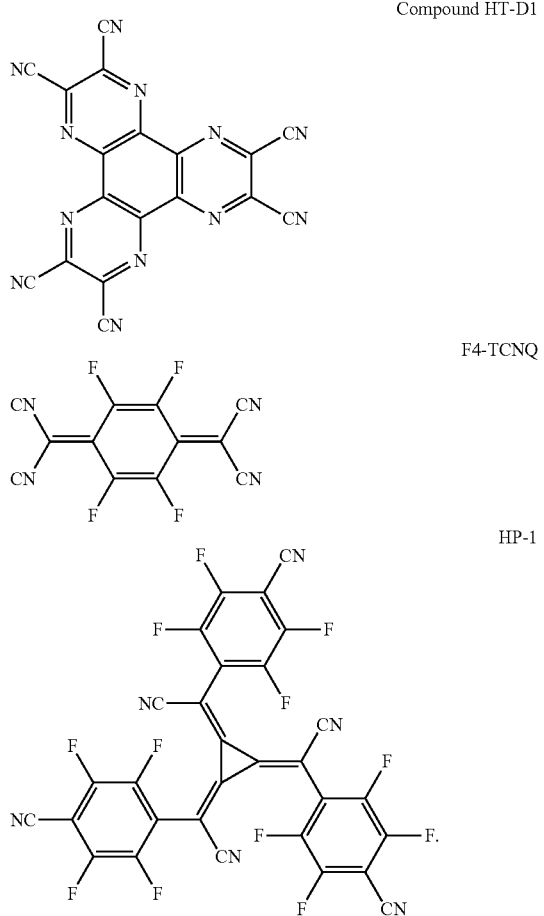

The hole transport region may further include a buffer layer.

The buffer layer may compensate for an optical resonance distance according to a wavelength of light emitted from the emission layer, and thus, the efficiency of a formed organic light-emitting device may be improved.

The emission layer may be formed on the hole transport region by using one or more suitable methods selected from vacuum deposition, spin coating, casting, and LB deposition. When the emission layer is formed using vacuum deposition and spin coating, the deposition and coating conditions for the emission layer may be similar with those for forming the hole injection layer, although deposition and coating conditions may vary according to a material that is used to form the emission layer.

The hole transport region may further include an electron blocking layer. The electron blocking layer may include a known compound, such as mCP, but embodiments are not limited thereto:

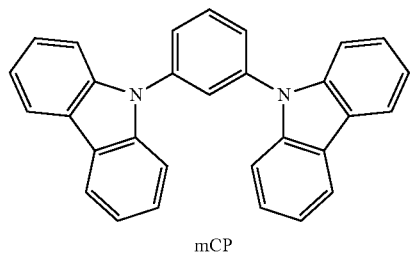

A thickness of the electron blocking layer may be in a range of about 50 Å to about 1,000 Å, for example, about 70 Å to about 500 Å. While not wishing to be bound by theory, it is understood that when the thickness of the electron blocking layer is within these ranges, satisfactory electron blocking characteristics may be obtained without a substantial increase in driving voltage.

When the organic light-emitting device 10 is a full color organic light-emitting device, the emission layer may be patterned into a red emission layer, a green emission layer, and a blue emission layer. In various embodiments, the emission layer may have a stacked structure including a red emission layer, a green emission layer and/or a blue emission layer, thereby emitting light.

The emission layer may include the condensed cyclic compound represented by Formula 1.

For example, the emission layer may only include the condensed cyclic compound represented by Formula 1.

In various embodiments, the emission layer may include the condensed cyclic compound represented by Formula 1, and may further include:

i) the second compound (for example, the compound represented by Formula H-1), ii) the organometallic compound represented by Formula 81; or iii) any combination of i) and ii).

The condensed cyclic compound represented by Formula 1, the second compound, and the organometallic compound represented by Formula 81 are each independently the same as defined herein.

In an embodiment, i) the emission layer may include the condensed cyclic compound represented by Formula 1 and the organometallic compound represented by Formula 81 wherein an amount of the condensed cyclic compound represented by Formula 1 is greater than that of the organometallic compound represented by Formula 81;

ii) the emission layer may include the condensed cyclic compound represented by Formula 1 and the second compound (for example, the compound represented by Formula H-1), wherein the emission layer optionally include a known dopant in the art; or iii) the emission layer may include the condensed cyclic compound represented by Formula 1, the second compound (for example, the compound represented by Formula H-1), and the organometallic compound represented by Formula 81, wherein the total amounts of the condensed cyclic compound represented by Formula 1 and the second compound (for example, the compound represented by Formula H-1) may be greater than the amount of the organometallic compound represented by Formula 81, but embodiments are not limited thereto.

In various embodiments, the emission layer may include a host and a dopant, wherein i) the host may include the condensed cyclic compound represented by Formula 1, and the dopant may include the organometallic compound represented by Formula 81;

ii) the host may include the condensed cyclic compound represented by Formula 1 and the second compound (for example, the compound represented by Formula H-1), and a known dopant; or iii) the host may include the condensed cyclic compound represented by Formula 1 and the second compound (for example, the compound represented by Formula H-1), and the dopant may include the organometallic compound represented by Formula 81, but embodiments are not limited thereto.

When the emission layer includes a host and a dopant, an amount of the dopant may be in a range of about 0.01 to about 20 parts by weight based on 100 parts by weight of the emission layer, but embodiments are not limited thereto. While not wishing to be bound by theory, it is understood that when the amount of the dopant is within the range above, emission may be implemented without a quenching phenomenon.

In various embodiments, when the emission layer includes the condensed cyclic compound represented by Formula 1 and the second compound, weight ratios of the condensed cyclic compound represented by Formula 1 and the second compound may be selected from ranges of 1:99 to 99:1, for example, ranges of 70:30 to 30:70. In various embodiments, the weight ratios of the condensed cyclic compound represented by Formula 1 and the second compound may be selected from ranges of 60:40 to 40:60. While not wishing to be bound by theory, it is understood that when the weight ratio of the condensed cyclic compound represented by Formula 1 and the second compound in the emission layer is within any of these ranges, the charge transport balance may be efficiently achieved in the emission layer.

A thickness of the emission layer may be in a range of about 100 Å to about 1,000 Å, for example, about 200 Å to about 600 Å. While not wishing to be bound by theory, it is understood that when the thickness of the emission layer is within any of these ranges, excellent light-emission characteristics may be obtained without a substantial increase in driving voltage.

Next, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layered structure including two or more layers.

Conditions for forming a hole transport layer, an electron blocking layer, and an electron injection layer of the electron transport region may be understood by referring to conditions for forming the hole injection layer.

When the electron transport region includes a hole blocking layer, the hole blocking layer may include, for example, at least one of BCP and Bphen, but embodiments are not limited thereto:

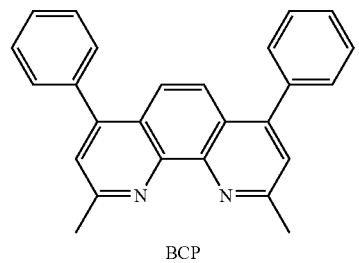

BCP

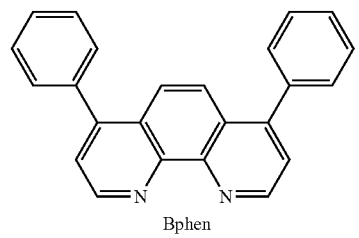

Bphen

In various embodiments, the hole blocking layer may include the condensed cyclic compound represented by Formula 1.

A thickness of the hole blocking layer may be in a range of about 20 Å to about 1,000 Å, for example, about 30 Å to about 300 Å. While not wishing to be bound by theory, it is understood that when the thickness of the hole blocking layer is within any of these ranges, excellent hole blocking characteristics may be obtained without a substantial increase in driving voltage.

The electron transport layer may further include at least one selected from BCP, Bphen, Alq$_3$, Balq, TAZ, and NTAZ:

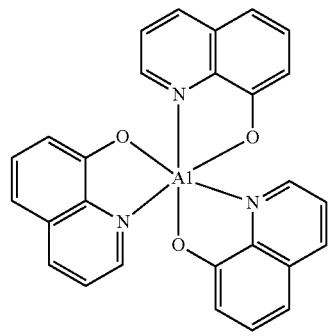

Alq$_3$

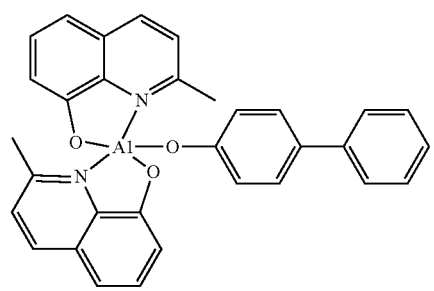

BAlq

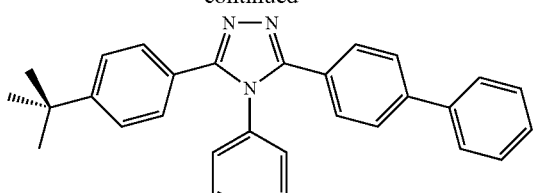

TAZ

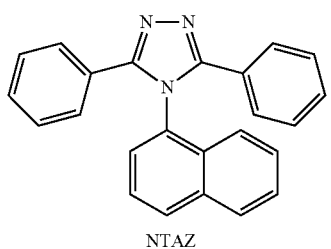

NTAZ

In various embodiments, the electron transport layer may include at least one selected from Compounds ET1, ET2, and ET3, embodiments are not limited thereto:

ET1

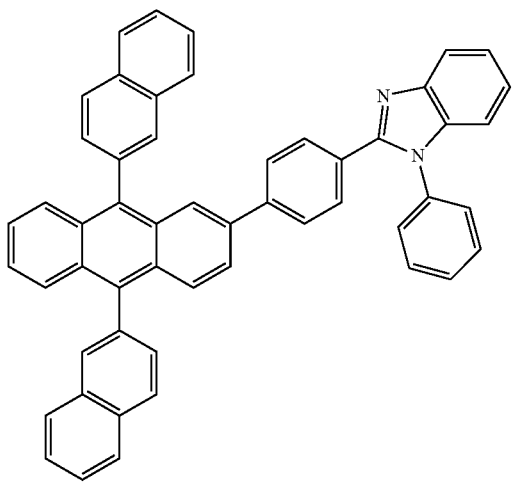

ET2

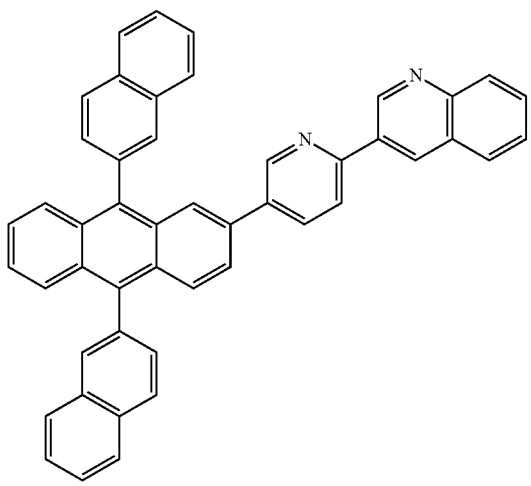

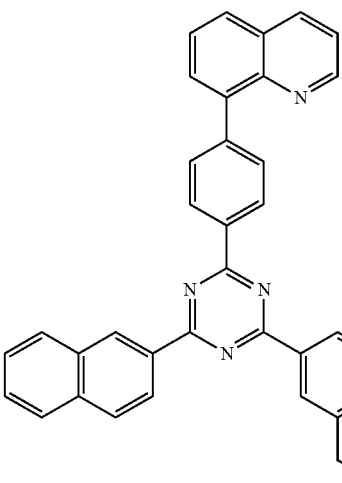

ET3

A thickness of the electron transport layer may be in a range of about 100 Å to about 1,000 Å, for example, about 150 Å to about 500 Å. While not wishing to be bound by theory, it is understood that when the thickness of the electron transport layer within any of these ranges, satisfactory electron transporting characteristics may be obtained without a substantial increase in driving voltage.

The electron transport layer may further include, in addition to these materials, a metal-containing material.

The metal-containing material may include a lithium (Li) complex. The Li complex may include, for example, Compound ET-D1 (lithium quinolate (LiQ)) or Compound ET-D2:

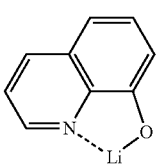

ET-D1

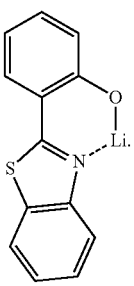

ET-D2

In addition, the electron transport region may include an electron injection layer that facilitates electron injection from the second electrode 19.

The electron injection layer may include at least one selected from LiQ, LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within any of these ranges, satisfactory electron injecting characteristics may be obtained without a substantial increase in driving voltage.

The second electrode 19 may be disposed on the organic layer 15. The second electrode 19 may be a cathode. A material for forming the second electrode 19 may be a metal having a relatively low work function, an alloy, an electrically conductive compound, and a combination thereof. For example, Li, Mg, Al, Al—Li, Ca, Mg—In, or Mg—Ag may be used as a material for forming the second electrode 19. In various embodiments, to manufacture a top emission-type light-emitting device, a transmissive electrode formed using ITO or IZO may be used as the second electrode 19.

Hereinbefore, the organic light-emitting device 10 has been described with reference to the FIGURE, but is not limited thereto.

A $C_1$-$C_{60}$ alkyl group as used herein refers to a linear or branched aliphatic saturated hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Examples thereof include a methoxy group, an ethoxy group, and an iso-propyloxy (iso-propoxy) group.

A $C_2$-$C_{60}$ alkenyl group as used herein refers to a hydrocarbon group formed by including at least one carbon-carbon double bond in the middle or at either terminal end of the $C_2$-$C_{60}$ alkyl group. Examples thereof include an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by including at least one carbon-carbon triple bond in the middle or at either terminal end of the $C_2$-$C_{60}$ alkyl group. Examples thereof include an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent saturated hydrocarbon monocyclic group having 3 to 10 carbon atoms. Examples thereof include a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent saturated monocyclic group having at least one heteroatom selected from N, O, P, Si, and S as a ring-forming atom and 1 to 10 carbon atoms. Examples thereof include a tetrahydrofuranyl group and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one carbon-carbon double bond in the ring thereof, and which is not aromatic. Examples thereof include a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one heteroatom selected from N, O, P, Si, and S as a ring-forming atom, 1 to 10 carbon atoms, and at least one carbon-carbon double bond in the ring. Examples of the $C_2$-$C_{10}$ heterocycloalkenyl group include a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Examples of the $C_6$-$C_{60}$ aryl group a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each includes two or more rings, the respective rings may be fused to each other.

A $C_1$-$C_{60}$ heteroaryl group as used herein refers to a monovalent group having a carbocyclic aromatic system that has at least one heteroatom selected from N, O, P, Si, and S as a ring-forming atom and 1 to 60 carbon atoms. A $C_1$-$C_{60}$ heteroarylene group as used herein refers to a divalent group having a carbocyclic aromatic system that has at least one heteroatom selected from N, O, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each includes two or more rings, the respective rings may be fused with each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group as used herein refers to a monovalent group (for example, a group having 8 to 60 carbon atoms) that has two or more rings condensed to each other, only carbon atoms as a ring forming atom, and which is non-aromatic in the entire molecular structure. An example of the non-aromatic condensed polycyclic group includes a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group (for example, a group having 1 to 60 carbon atoms) that has two or more rings condensed to each other, has a heteroatom selected from N, O, P, Si, and S, other than carbon atoms, as a ring-forming atom, and which is non-aromatic in the entire molecular structure. An example of the monovalent non-aromatic condensed heteropolycyclic group includes a carbazolyl group. A divalent non-aromatic condensed heteropolycyclic group as used herein refers to a divalent group having the same structure as the monovalent non-aromatic condensed heteropolycyclic group.

In Formula 1, at least one of substituents selected from the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(C)_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, and —$B(Q_{26})(Q_{27})$; and —$Si(Q_{31})(Q_{32})(Q_{33})$, —$N(Q_{34})(Q_{35})$, and —$B(Q_{36})(Q_{37})$, wherein $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one of a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

The term "biphenyl group" as used herein refers to a monovalent group in which two benzene groups are linked via a single bond.

The term "terphenyl group" as used herein refers to a monovalent group in which three benzene groups are linked via a single bond.

Unless stated otherwise in the present specification, * and *' each indicate a binding site to a neighboring atom in a formula.

Hereinafter, a compound according to embodiments and an organic light-emitting device according to embodiments will be described in detail with reference to Synthesis Examples and Examples below, but the present inventive concept is not limited thereto. The expression "B' was used instead of 'A'" used in describing Synthesis Examples below means that the number of molar equivalents of 'B' used was identical to the number of molar equivalents of 'A'.

EXAMPLES

Synthesis Example 1: Synthesis of Compound 1

Compound 1 was synthesized according to the reaction scheme shown below:

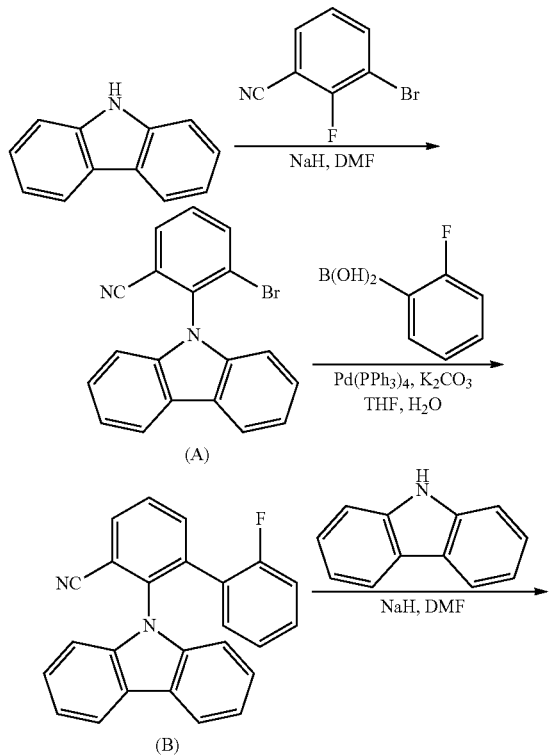

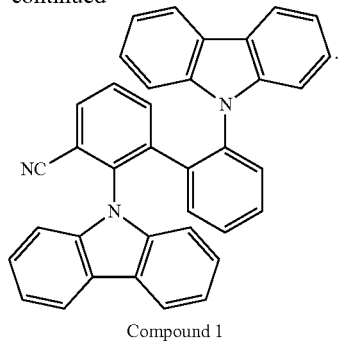

Compound 1

Synthesis of Intermediate (A)

15.0 grams (g) (89.7 millimoles, mmol) of carbazole was dissolved in 200 milliliters (ml) of dimethylformamide (DMF), and the mixed solution was cooled to a temperature of 0° C. 3.77 g (94.19 mmol) of sodium hydride (NaH, 60% dispersion in mineral oil) was slowly added thereto, the resulting mixed solution was stirred at a temperature of 0° C. for 30 minutes, and a solution in which 19.7 g (98.7 mmol) of 3-bromo-2-fluorobenzonitrile was dissolved in 50 ml of DMF was slowly added thereto for 10 minutes. Meanwhile, the reaction temperature was raised to 150° C., and an additional stirring process was performed on the reaction solution for 18 hours. After completion, the resulting reaction solution was cooled to room temperature, and saturated ammonium chloride ($NH_4Cl$) was added thereto to extract and separate an organic layer using dichloromethane (DCM). The obtained organic layer was dried with anhydrous magnesium sulfate ($MgSO_4$) to remove water therefrom, filtered, and concentrated under reduced pressure. The resulting residue was then separated by silica gel column chromatography, thereby providing a desired compound, 24.3 g (yield: 78%) of Intermediate (A).

LC-Mass (calcd: 346.01 g/mol, found: M+1=347 g/mol).

Synthesis of Intermediate (B)

20.0 g (57.6 mmol) of Intermediate (A), 9.67 g (69.1 mmol) of (2-fluorophenyl)boronic acid, 3.33 g (2.88 mmol) of tetrakistriphenylphosphine palladium (0) ($Pd(PPh_3)_4$), and 19.9 g (144 mmol) of potassium carbonate were added to a solution of 130 ml of TFT and 65 ml of water and mixed. The resulting mixed solution was stirred under reflux. After completion of the reaction, the resulting reaction solution was cooled to room temperature, and an extraction process was performed thereon to remove an aqueous solution layer therefrom. The obtained aqueous solution layer was filtered through silica gel under reduced pressure, and the filtrate was concentrated under reduced pressure. The resulting residue was then separated by silica gel column chromatography, thereby providing 15.0 g (yield: 72%) of a desired compound, Intermediate (B).

LC-Mass (cald: 362.12 g/mol, found: M+1=363 g/mol).

Synthesis of Compound 1

9.60 g (yield: 63%) of a desired compound, Compound 1, was obtained in the same manner in which Intermediate (A) was synthesized according to Synthesis Example 1, except that 11.9 g (32.9 mmol) of Intermediate (B) was used instead of 3-bromo-2-fluorobenzonitrile.

LC-Mass (cald: 509.19 g/mol, found: M+1=510 g/mol).

Synthesis Example 2: Synthesis of Compound 3

Compound 3 was synthesized according to the reaction scheme shown below:

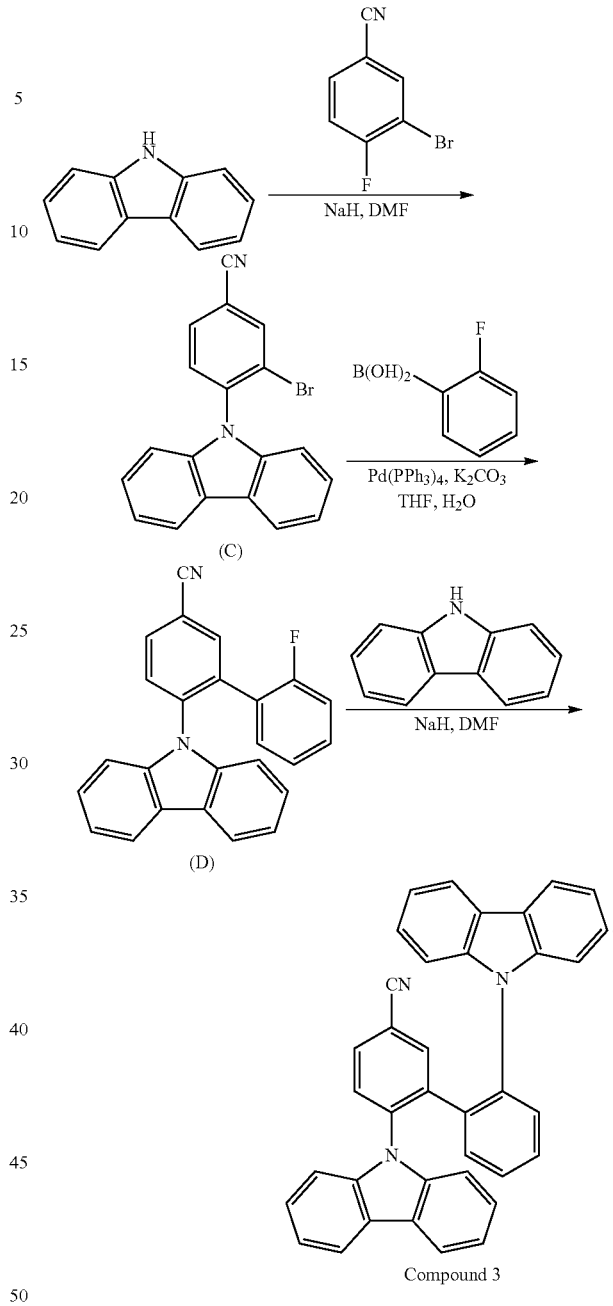

Compound 3

Synthesis of Intermediate (C)

23.4 g (yield: 75%) of a desired compound, Intermediate (C), was obtained in the same manner in which Intermediate (A) was synthesized according to Synthesis Example 1, except that 19.7 g (98.7 mmol) of 3-bromo-4-fluorobenzonitrile was used instead of 3-bromo-2-fluorobenzonitrile.

LC-Mass (cald: 346.01 g/mol, found: M+1=347 g/mol).

Synthesis of Intermediate (D)

14.4 g (yield: 69%) of a desired compound, Intermediate (D), was obtained in the same manner in which Intermediate (B) was synthesized according to Synthesis Example 1, except that 20.0 g (57.6 mmol) of Intermediate (C) was used instead of Intermediate (A).

LC-Mass (cald: 362.12 g/mol, found: M+1=363 g/mol).

Synthesis of Compound 3

8.23 g (yield: 54%) of a desired compound, Compound 3, was obtained in the same manner in which Intermediate (A)

was synthesized according to Synthesis Example 1, except that 11.9 g (32.9 mmol) of Intermediate (D) was used instead of 3-bromo-2-fluorobenzonitrile.

LC-Mass (cald: 509.19 g/mol, found: M+1=510 g/mol).

Synthesis Example 3: Synthesis of Compound 5

Compound 5 was synthesized according to the reaction scheme shown below:

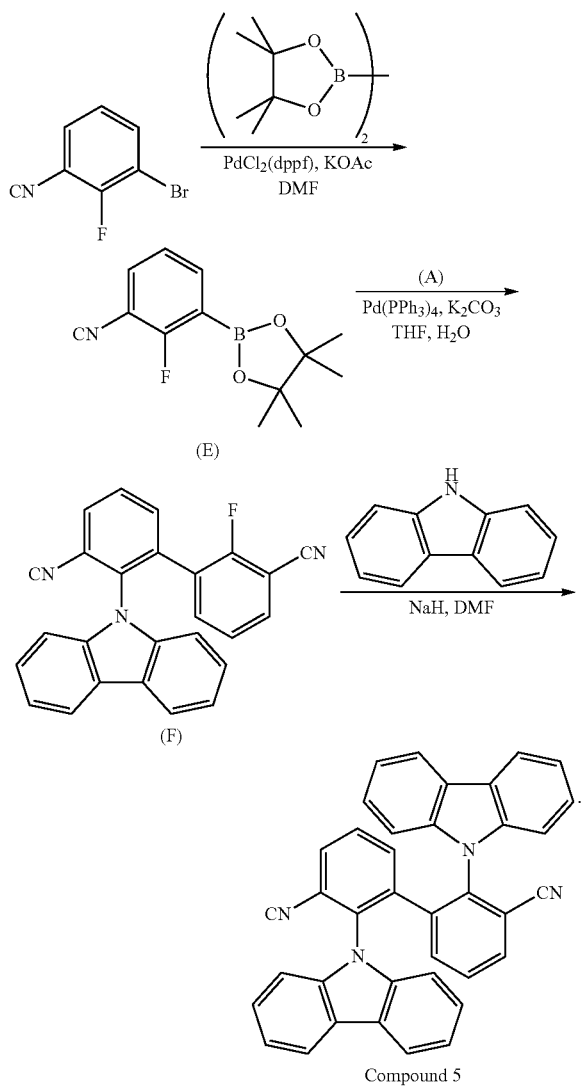

Compound 5

Synthesis of Intermediate (E)

15.0 g (75.0 mmol) of 3-bromo-2-fluorobenzonitrile, 22.9 g (90.0 mmol) of bis(pinacolato)diboron, 3.06 g (3.75 mmol) of $PdCl_2$(dppf).$CH_2Cl_2$, and 22.1 g (225 mmol) of potassium acetate were dissolved in 250 ml of DMF, and the resulting solution was stirred at a temperature of 100° C. for 24 hours. After completion of the reaction, the resulting reaction solution was cooled to room temperature and filtered through silica gel under reduced pressure, and the filtrate was concentrated under reduced pressure. The resulting residue was then separated by silica gel column chromatography, thereby providing 12.4 g (yield: 67%) of a desired compound, Intermediate (E).

LC-Mass (cald: 247.12 g/mol, found: M+1=248 g/mol).

Synthesis of Intermediate (F)

6.83 g (yield: 51%) of a desired compound, Intermediate (F), was obtained in the same manner in which Intermediate (B) was synthesized according to Synthesis Example 1, except that 10.3 g (41.5 mmol) of Intermediate (E) was used instead of (2-fluorophenyl)boronic acid.

LC-Mass (cald: 387.12 g/mol, found: M+1=388 g/mol).

Synthesis of Compound 5

5.37 g (yield: 84%) of a desired compound, Compound 5, was obtained in the same manner in which Intermediate (A) was synthesized according to Synthesis Example 1, except that 5.10 g (13.2 mmol) of Intermediate (F) was used instead of 3-bromo-2-fluorobenzonitrile.

LC-Mass (cald: 534.18 g/mol, found: M+1=535 g/mol).

Synthesis Example 4: Synthesis of Compound 7

Compound 7 was synthesized according to the reaction scheme shown below:

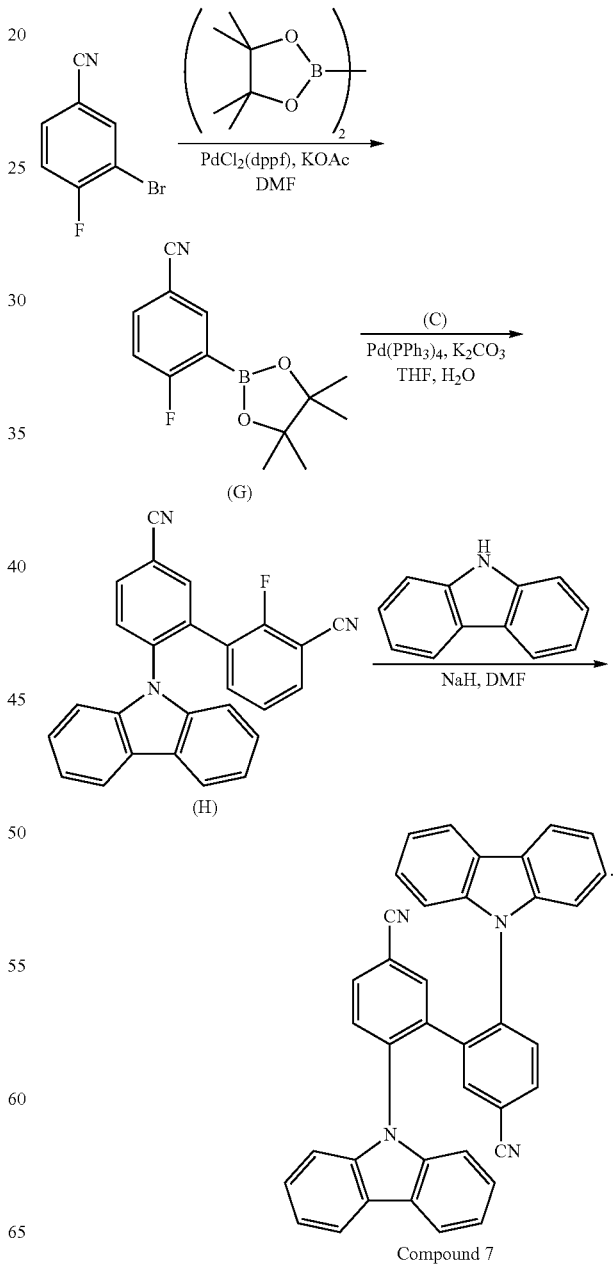

Compound 7

Synthesis of Intermediate (G)

10.5 g (yield: 57%) of a desired compound, Intermediate (G), was obtained in the same manner in which Intermediate (E) was synthesized according to Synthesis Example 3, except that 15.0 g (75.0 mmol) of 3-bromo-4-fluorobenzonitrile was used instead of 3-bromo-2-fluorobenzonitrile.

LC-Mass (cald: 247.12 g/mol, found: M+1=248 g/mol).

Synthesis of Intermediate (H)

8.30 g (yield: 62%) of a desired compound, Intermediate (H), was obtained in the same manner in which Intermediate (B) was synthesized according to Synthesis Example 1, except that 10.3 g (41.5 mmol) of Intermediate (G) was used instead of (2-fluorophenyl)boronic acid.

LC-Mass (cald: 387.12 g/mol, found: M+1=388 g/mol).

Synthesis of Compound 7

7.19 g (yield: 75%) of a desired compound, Compound 7, was obtained in the same manner as in which Intermediate (A) was synthesized according to Synthesis Example 1, except that 7.65 g (19.7 mmol) of Intermediate (H) was used instead of 3-bromo-2-fluorobenzonitrile.

LC-Mass (cald: 534.18 g/mol, found: M+1=535 g/mol).

Synthesis Example 5: Synthesis of Compound 26

Compound 26 was synthesized according to the reaction scheme shown below:

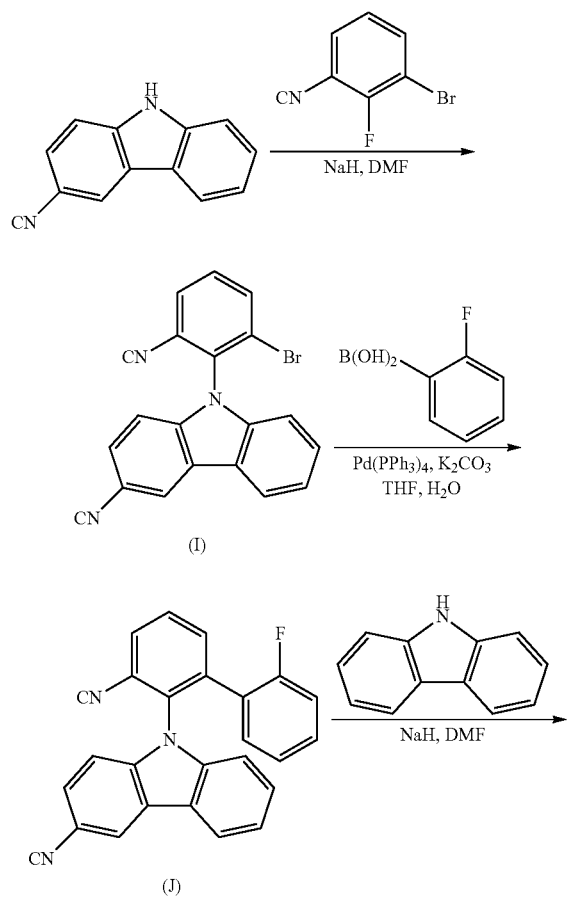

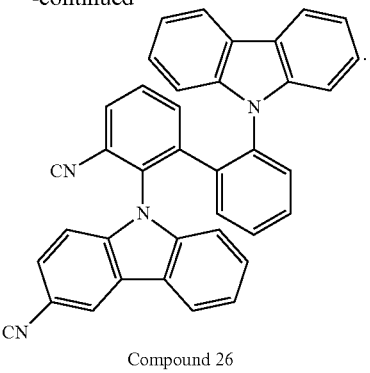

Compound 26

Synthesis of Intermediate (I)

17.8 g (yield: 46%) of a desired compound, Intermediate (I), was obtained in the same manner in which Intermediate (A) was synthesized according to Synthesis Example 1, except that 20.0 g (104 mmol) of 9H-carbazole-3-carbonitrile was used instead of carbazole.

LC-Mass (cald: 371.01 g/mol, found: M+1=372 g/mol).

Synthesis of Intermediate (J)

11.9 g (yield: 67%) of a desired compound, Intermediate (J), was obtained in the same manner in which Intermediate (A) was synthesized according to Synthesis Example 1, except that 17.0 g (45.7 mmol) of Intermediate (I) was used instead of Intermediate (A).

LC-Mass (cald: 387.12 g/mol, found: M+1=388 g/mol).

Synthesis of Compound 26

6.14 g (yield: 48%) of a desired compound, Compound 26, was obtained in the same manner in which Intermediate (A) was synthesized according to Synthesis Example 1, except that 10.2 g (26.3 mmol) of Intermediate (J) was used instead of 3-bromo-2-fluorobenzonitrile.

LC-Mass (cald: 534.18 g/mol, found: M+1=535 g/mol).

Synthesis Example 6: Synthesis of Compound 46

Compound 46 was synthesized according to the reaction scheme shown below:

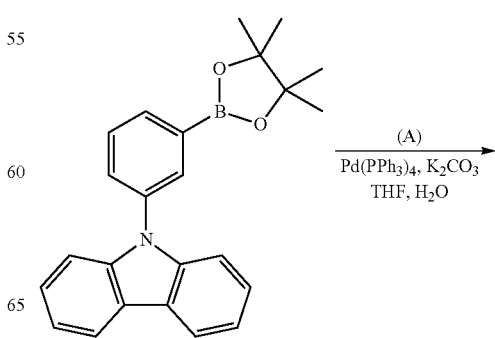

-continued

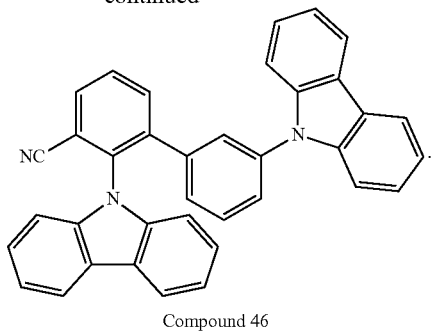

Compound 46

12.2 g (yield: 83%) of a desired compound, Compound 46, was obtained in the same manner in which Intermediate (B) was synthesized according to Synthesis Example 1, except that 12.8 g (34.6 mmol) of 9-(3-(4,4,5,5-tetramethyl-1,3,2-dioxaborolan-2-yl)phenyl)-9H-carbazole was used instead of (2-fluorophenyl)boronic acid.

LC-Mass (cald: 509.19 g/mol, found: M+1=510 g/mol).

Synthesis Example 7: Synthesis of Compound 52

Compound 52 was synthesized according to the reaction scheme shown below:

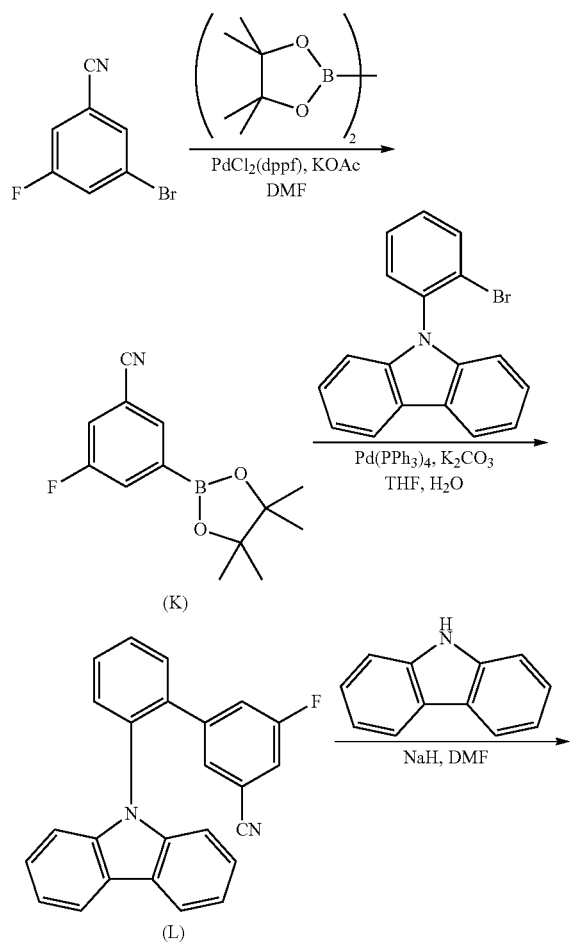

-continued

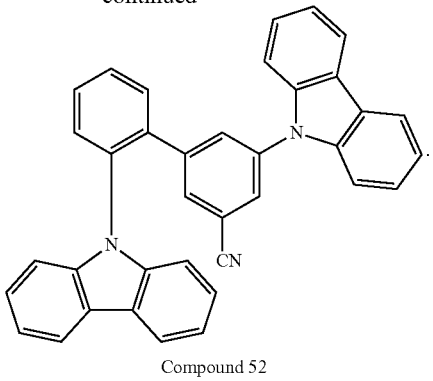

Compound 52

Synthesis of Intermediate (K)

14.7 g (yield: 80%) of a desired compound, Intermediate (G), was obtained in the same manner in which Intermediate (E) was synthesized according to Synthesis Example 3, except that 15.0 g (75.0 mmol) of 3-bromo-5-fluorobenzonitrile was used instead of 3-bromo-2-fluorobenzonitrile.

LC-Mass (cald: 247.12 g/mol, found: M+1=248 g/mol).

Synthesis of Intermediate (L)

8.60 g (yield: 51%) of a desired compound, Intermediate (L), was obtained in the same manner in which Intermediate (B) was synthesized according to Synthesis Example 1, except that 15.0 g (46.6 mmol) of 9-(2-bromophenyl)-9H-carbazole was used instead of Intermediate (A) and 13.8 g (55.9 mmol) of Intermediate (G) was used instead of (2-fluorophenyl)boronic acid.

LC-Mass (cald: 362.12 g/mol, found: M+1=363 g/mol).

Synthesis of Compound 52

6.86 g (yield: 75%) of a desired compound, Compound 52, was obtained in the same manner in which Intermediate (A) was synthesized according to Synthesis Example 1, except that 7.15 g (19.7 mmol) of Intermediate (L) was used instead of 3-bromo-2-fluorobenzonitrile.

LC-Mass (cald: 509.19 g/mol, found: M+1=510 g/mol).

Synthesis Example 8: Synthesis of Compound 55

Compound 55 was synthesized according to the reaction scheme shown below:

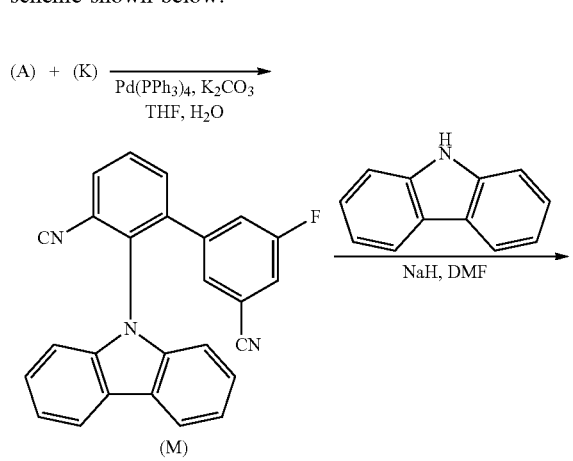

-continued

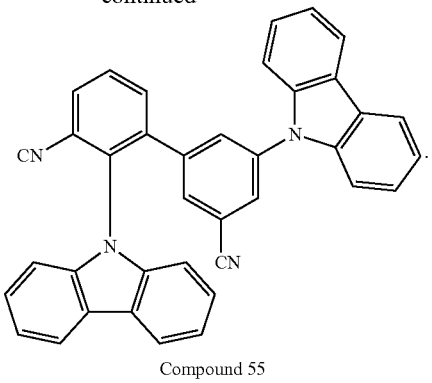

Compound 55

Synthesis of Intermediate (M)

7.20 g (yield: 43%) of a desired compound, Intermediate (M), was obtained in the same manner in which Intermediate (B) was synthesized according to Synthesis Example 1, except that 12.8 g (51.8 mmol) of Intermediate (K) was used instead of (2-fluorophenyl)boronic acid.

LC-Mass (cald: 387.12 g/mol, found: M+1=388 g/mol).

Synthesis of Compound 55

5.68 g (yield: 71%) of a desired compound, Compound 55, was obtained in the same manner in which Intermediate (A) was synthesized according to Synthesis Example 1, except that 6.37 g (16.5 mmol) of Intermediate (M) was used instead of 3-bromo-2-fluorobenzonitrile.

LC-Mass (cald: 534.18 g/mol, found: M+1=535 g/mol).

Synthesis Example 9: Synthesis of Compound 95

Compound 95 was synthesized according to the reaction scheme shown below:

Compound 95

5.28 g (yield: 38%) of a desired compound, Compound 95, was obtained in the same manner in which Intermediate (A) was synthesized according to Synthesis Example 1, except that 5.00 g (26.0 mmol) of 9H-carbazole-3-carbonitrile was used instead of carbazole and 10.4 g (28.6 mmol) of Intermediate (L) was used instead of 3-bromo-2-fluorobenzonitrile.

LC-Mass (cald: 534.18 g/mol, found: M+1=535 g/mol).

Synthesis Example 10: Synthesis of Compound 97

Compound 97 was synthesized according to the reaction scheme shown below:

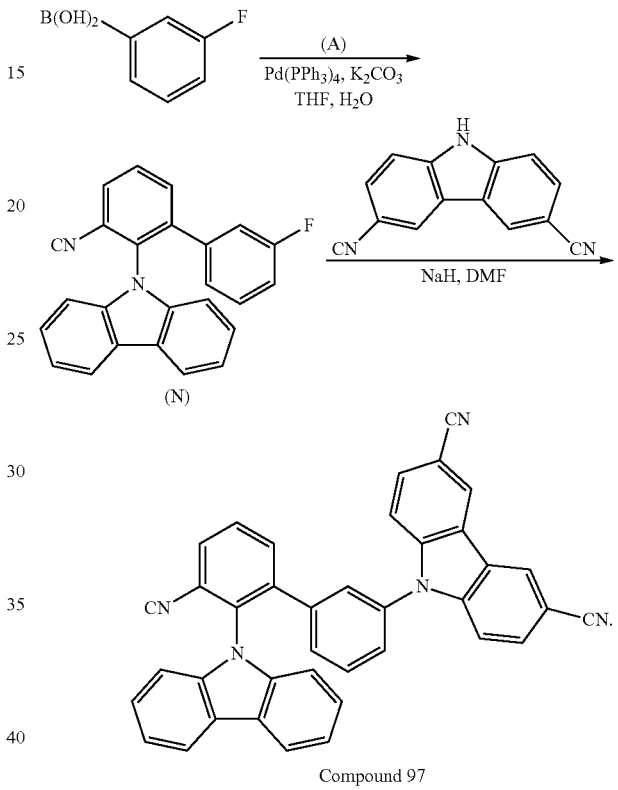

Compound 97

Synthesis of Intermediate (N)

8.56 g (yield: 82%) of a desired compound, Intermediate (N), was obtained in the same manner in which Intermediate (B) was synthesized according to Synthesis Example 1, except that 4.84 g (34.6 mmol) of (3-fluorophenyl)boronic acid was used instead of (2-fluorophenyl)boronic acid.

LC-Mass (cald: 362.12 g/mol, found: M+1=363 g/mol).

Synthesis of Compound 97

3.19 g (yield: 31%) of a desired compound, Compound 97, was obtained in the same manner in which Intermediate (A) was synthesized according to Synthesis Example 1, except that 4.00 g (18.4 mmol) of 9H-carbazole-3,6-dicarbonitrile was used instead of carbazole and 7.34 g (20.3 mmol) of Intermediate (N) was used instead of 3-bromo-2-fluorobenzonitrile.

LC-Mass (cald: 559.18 g/mol, found: M+1=560 g/mol).

Synthesis Example 11: Synthesis of Compound 106

Compound 106 was synthesized according to the reaction scheme shown below:

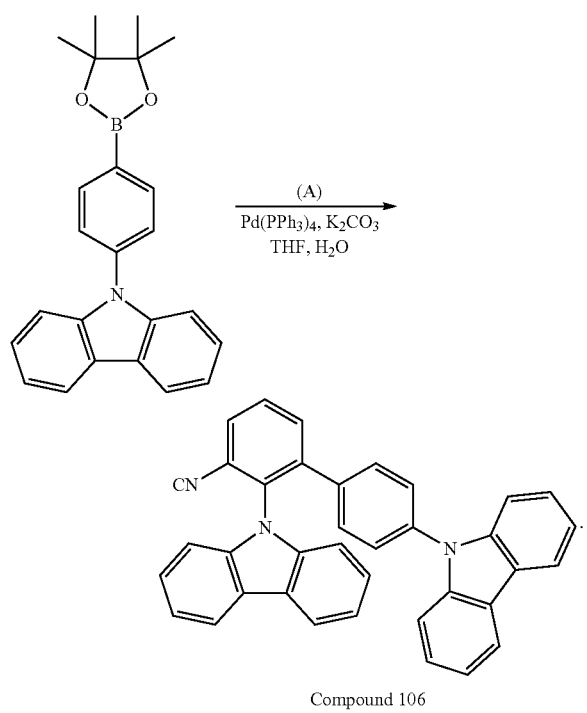

Compound 106

10.9 g (yield: 74%) of a desired compound, Compound 106, was obtained in the same manner in which Intermediate (B) was synthesized according to Synthesis Example 1, except that 12.8 g (34.6 mmol) of 9-(4-(4,4,5,5-tetramethyl-1,3,2-dioxaborolan-2-yl)phenyl)-9H-carbazole was used instead of (2-fluorophenyl)boronic acid.

LC-Mass (cald: 509.19 g/mol, found: M+1=510 g/mol).

Synthesis Example 12: Synthesis of Compound 176

Compound 176 was synthesized according to the reaction scheme shown below:

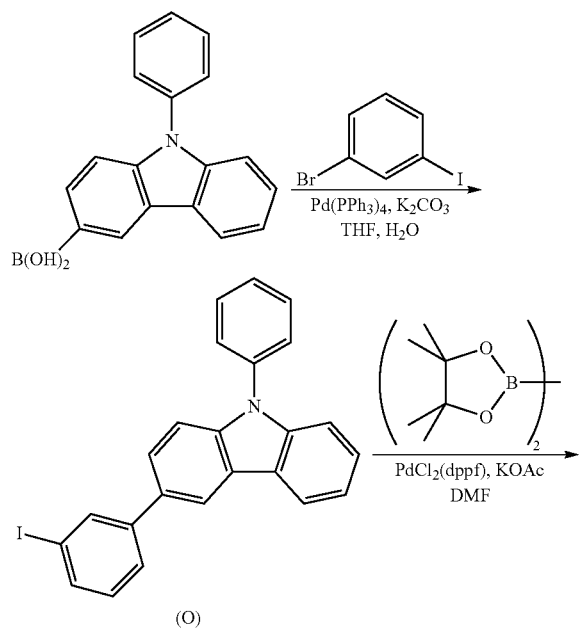

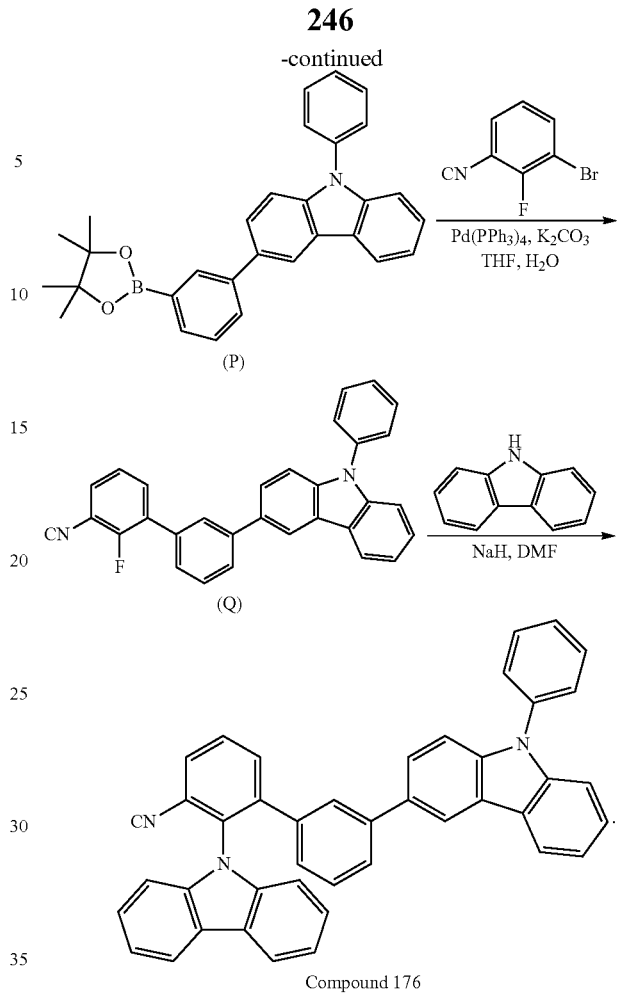

Compound 176

Synthesis of Intermediate (O)

15.0 g (52.2 mmol) of (9-phenyl-9H-carbazol-3-yl)boronic acid, 19.2 g (67.9 mmol) of 1-bromo-3-iodobenzene, 3.02 g (2.61 mmol) of tetrakistriphenylphosphine palladium (0) (Pd(PPh$_3$)$_4$), and 18.1 g (131 mmol) of potassium carbonate were added to a solution of 120 ml of THF and 60 ml of water and mixed. The mixed solution was then stirred under reflux. After completion of the reaction, the resulting reaction solution was cooled to room temperature, and an extraction process was performed thereon to remove an aqueous solution layer therefrom. The obtained residue was filtered through silica gel under reduced pressure, and the filtrate was concentrated under reduced pressure. The resulting residue was then separated by silica gel column chromatography, thereby providing 17.2 g (yield: 74%) of a desired compound, Intermediate (O).

LC-Mass (cald: 445.03 g/mol, found: M+1=446 g/mol).

Synthesis of Intermediate (P)

11.2 g (yield: 65%) of a desired compound, Intermediate (P), was obtained in the same manner in which Intermediate (E) was synthesized according to Synthesis Example 3, except that 17.2 g (38.6 mmol) of Intermediate (O) was used instead of 3-bromo-2-fluorobenzonitrile.

LC-Mass (cald: 445.36 g/mol, found: M+1=246 g/mol).

Synthesis of Intermediate (Q)

5.99 g (yield: 65%) of a desired compound, Intermediate (Q), was obtained in the same manner in which Intermediate (B) was synthesized according to Synthesis Example 1, except that 4.20 g (21.0 mmol) of 3-bromo-2-fluorobenzonitrile was used instead of Intermediate (A) and 11.2 g (25.2 mmol) of Intermediate (P) was used instead of (2-fluorophenyl)boronic acid.

LC-Mass (cald: 438.15 g/mol, found: M+1=439 g/mol).

Synthesis of Compound 176

5.39 g (yield: 77%) of a desired compound, Compound 176, was obtained in the same manner in which Intermediate (A) was synthesized according to Synthesis Example 1, except that 5.77 g (13.2 mmol) of Intermediate (Q) was used instead of 3-bromo-2-fluorobenzonitrile.

LC-Mass (cald: 585.22 g/mol, found: M+1=586 g/mol).

Synthesis Example 13: Synthesis of Compound 179

Compound 179 was synthesized according to the reaction scheme shown below:

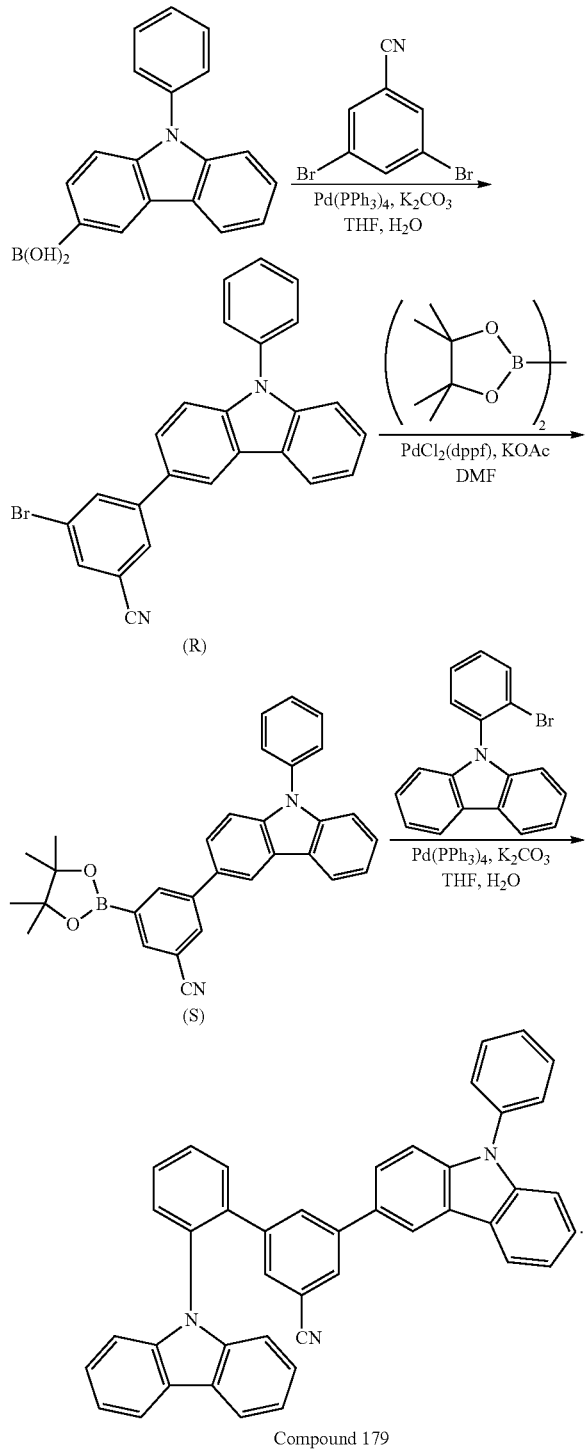

Synthesis of Intermediate (R)

15.0 g (52.2 mmol) of (9-phenyl-9H-carbazol-3-yl)boronic acid, 27.3 g (104 mmol) of 3,5-dibromobenzonitrile, 3.02 g (2.61 mmol) of tetrakistriphenylphosphine palladium (0) (Pd(PPh$_3$)$_4$), and 18.1 g (131 mmol) of potassium carbonate were added to a solution of 120 ml of THF and 60 ml of water and mixed. The mixed solution was then stirred under reflux. After completion of the reaction, the resulting reaction solution was cooled to room temperature, and an extraction process was performed thereon to remove an aqueous solution layer therefrom. The obtained residue was filtered through silica gel under reduced pressure, and the filtrate was concentrated under reduced pressure. The resulting residue was then separated by silica gel column chromatography, thereby providing 11.9 g (yield: 54%) of a desired compound, Intermediate (R).

LC-Mass (cald: 422.04 g/mol, found: M+1=423 g/mol).

Synthesis of Intermediate (S)

7.67 g (yield: 58%) of a desired compound, Intermediate (S), was obtained in the same manner in which Intermediate (E) was synthesized according to Synthesis Example 3, except that 11.9 g (28.1 mmol) of Intermediate (R) was used instead of 3-bromo-2-fluorobenzonitrile.

LC-Mass (cald: 470.22 g/mol, found: M+1=471 g/mol).

Synthesis of Compound 179

6.49 g (yield: 83%) of a desired compound, Compound 179, was obtained in the same manner in which Intermediate (B) was synthesized according to Synthesis Example 1, except that 4.30 g (13.4 mmol) of 9-(2-bromophenyl)-9H-carbazole was used instead of Intermediate (A) and 7.53 g (16.0 mmol) of Intermediate (S) was used instead of (2-fluorophenyl)boronic acid.

LC-Mass (cald: 585.22 g/mol, found: M+1=586 g/mol).

Synthesis Example 14: Synthesis of Compound 216

Compound 216 was synthesized according to the reaction scheme shown below:

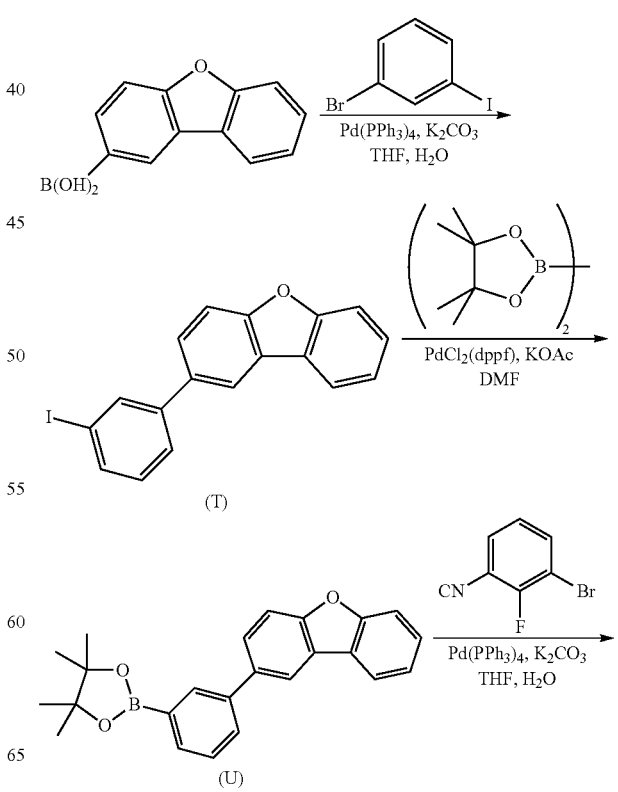

-continued

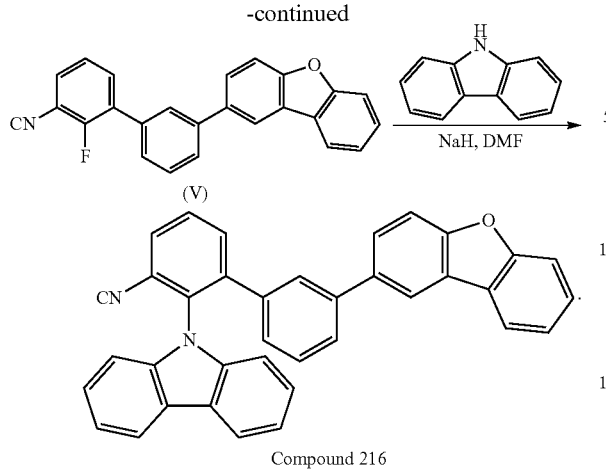

Compound 216

Synthesis of Intermediate (T)

13.0 g (yield: 85%) of a desired compound, Intermediate (T), was obtained in the same manner in which Intermediate (O) was synthesized according to Synthesis Example 12, except that 12.0 g (56.6 mmol) of dibenzo[b,d]furan-2-ylboronic acid was used instead of (9-phenyl-9H-carbazol-3-yl)boronic acid.

LC-Mass (cald: 369.99 g/mol, found: M+1=371 g/mol).

Synthesis of Intermediate (U)

8.06 g (yield: 62%) of a desired compound, Intermediate (U), was obtained in the same manner in which Intermediate (E) was synthesized according to Synthesis Example 3, except that 13.0 g (35.1 mmol) of Intermediate (T) was used instead of 3-bromo-2-fluorobenzonitrile.

LC-Mass (cald: 370.17 g/mol, found: M+1=371 g/mol).

Synthesis of Intermediate (V)

4.84 g (yield: 74%) of a desired compound, Intermediate (V), was obtained in the same manner in which Intermediate (B) was synthesized according to Synthesis Example 1, except that 3.60 g (18.0 mmol) of 3-bromo-2-fluorobenzonitrile was used instead of Intermediate (A) and 8.00 g (21.6 mmol) of Intermediate (U) was used instead of (2-fluorophenyl)boronic acid.

LC-Mass (cald: 363.11 g/mol, found: M+1=364 g/mol).

Synthesis of Compound 216

4.89 g (yield: 80%) of a desired compound, Compound 216, was obtained in the same manner in which Intermediate (A) was synthesized according to Synthesis Example 1, except that 4.78 g (13.2 mmol) of Intermediate (V) was used instead of 3-bromo-2-fluorobenzonitrile.

LC-Mass (cald: 510.17 g/mol, found: M+1=511 g/mol).

Synthesis Example 15: Synthesis of Compound 219

Compound 219 was synthesized according to the reaction scheme shown below:

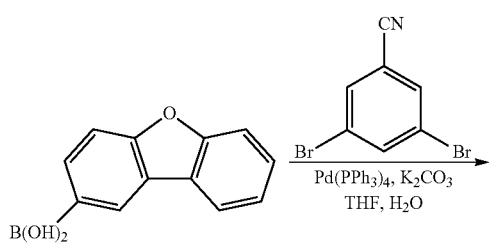

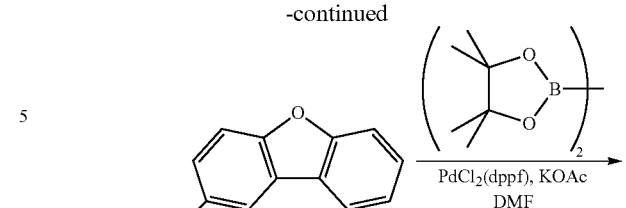

Synthesis of Intermediate (W)

15.2 g (yield: 77%) of a desired compound, Intermediate (W), was obtained in the same manner in which Intermediate (R) was synthesized according to Synthesis Example 13, except that 12.0 g (56.6 mmol) of dibenzo[b,d]furan-2-ylboronic acid was used instead of (9-phenyl-9H-carbazol-3-yl)boronic acid.

LC-Mass (cald: 346.99 g/mol, found: M+1=348 g/mol).

Synthesis of Intermediate (X)

11.4 g (yield: 66%) of a desired compound, Intermediate (X), was obtained in the same manner in which Intermediate (E) was synthesized according to Synthesis Example 3, except that 15.2 g (43.7 mmol) of Intermediate (W) was used instead of 3-bromo-2-fluorobenzonitrile.

LC-Mass (cald: 395.17 g/mol, found: M+1=396 g/mol).

Synthesis of Compound 219

5.99 g (yield: 54%) of a desired compound, Compound 219, was obtained in the same manner in which Intermediate (B) was synthesized according to Synthesis Example 1, except that 7.00 g (21.7 mmol) of 9-(2-bromophenyl)-9H-carbazole was used instead of Intermediate (A) and 10.3 g (26.1 mmol) of Intermediate (X) was used instead of (2-fluorophenyl)boronic acid.

LC-Mass (cald: 510.17 g/mol, found: M+1=511 g/mol).

Synthesis Example 16: Synthesis of Compound A

Compound A was synthesized according to the reaction scheme shown below:

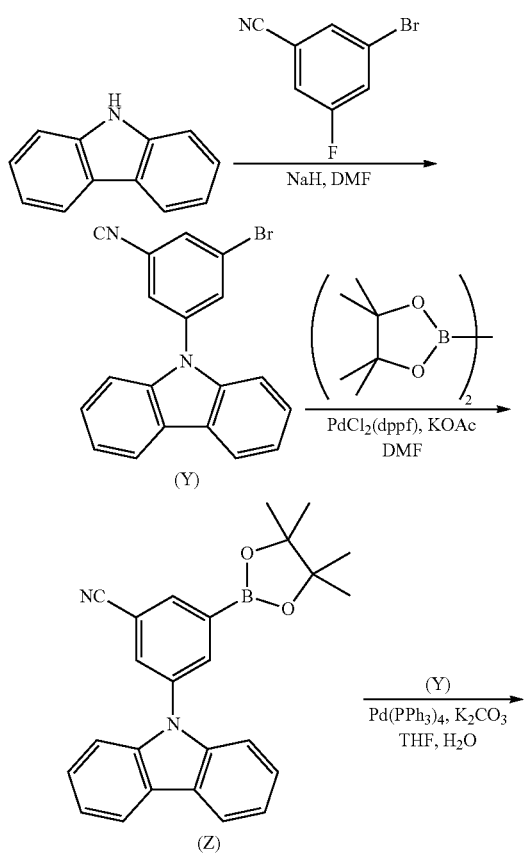

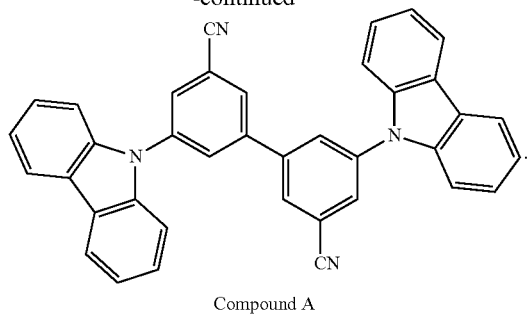

Compound A

Synthesis of Intermediate (Y)

35.3 g (yield: 85%) of a desired compound, Intermediate (Y), was obtained in the same manner in which Intermediate (A) was synthesized according to Synthesis Example 1, except that 26.3 g (132 mmol) of 3-bromo-5-fluorobenzonitrile was used instead of 3-bromo-2-fluorobenzonitrile.

LC-Mass (cald: 346.01 g/mol, found: M+1=347 g/mol).

Synthesis of Intermediate (Z)

15.7 g (yield: 69%) of a desired compound, Intermediate (Z), was obtained in the same manner in which Intermediate (E) was synthesized according to Synthesis Example 3, except that 20.0 g (57.6 mmol) of Intermediate (Y) was used instead of 3-bromo-2-fluorobenzonitrile.

LC-Mass (cald: 394.19 g/mol, found: M+1=395 g/mol).

Synthesis of Compound A 15.4 g (yield: 91%) of a desired compound, Compound A, was obtained in the same manner in which Intermediate (B) was synthesized according to Synthesis Example 1, except that 11.0 g (31.7 mmol) of Intermediate (Y) was used instead of Intermediate (A) and 15.0 g (38.0 mmol) of Intermediate (Z) was used instead of (2-fluorophenyl)boronic acid.

LC-Mass (cald: 534.18 g/mol, found: M+1=535 g/mol).

Synthesis Example 17: Synthesis of Compound B

Compound B was synthesized according to the reaction scheme shown below:

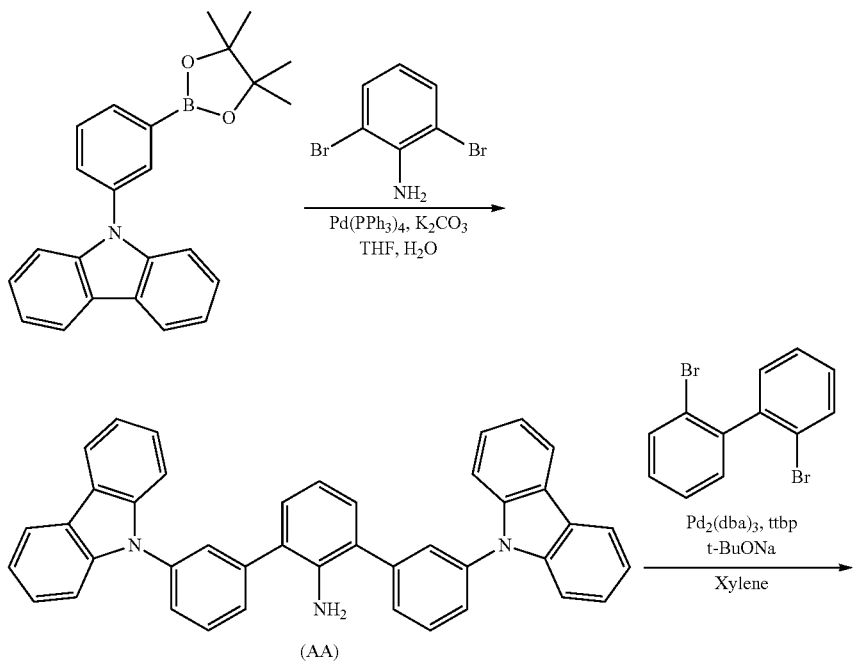

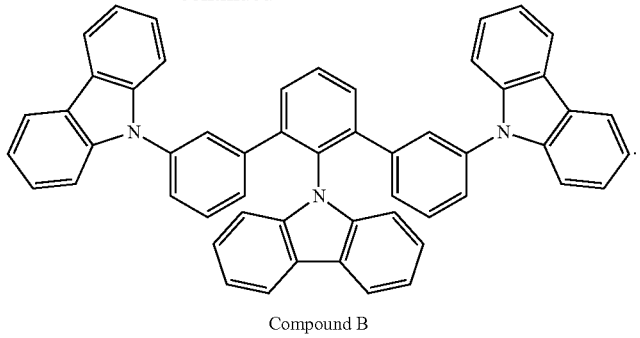

Compound B

Synthesis of Intermediate (AA)

15.0 g (59.8 mmol) of Intermediate (2,6-dibromoaniline), 53.0 g (143 mmol) of 9-(3-(4,4,5,5-tetramethyl-1,3,2-dioxaborolan-2-yl)phenyl)-9H-carbazole, 6.91 g (5.98 mmol) of tetrakistriphenylphosphine palladium(0) (Pd(PPh$_3$)$_4$), and 41.3 g (299 mmol) of potassium carbonate were added to a solution of 260 ml of THF and 130 ml of water and mixed. The mixed solution was stirred under reflux. After completion of the reaction, the resulting reaction solution was cooled to room temperature, and an extraction process was performed thereon to remove an aqueous solution layer therefrom. The obtained residue was filtered through silica gel under reduced pressure, and the filtrate was concentrated under reduced pressure. The resulting residue was then separated by silica gel column chromatography, thereby providing 14.8 g (yield: 43%) of a desired compound, Intermediate (AA).

LC-Mass (cald: 575.24 g/mol, found: M+1=576 g/mol).

Synthesis of Compound B 14.5 g (25.2 mmol) of Intermediate (AA), 11.8 g (37.8 mmol) of 2,2'-dibromo-1,1'-biphenyl, 1.45 g (2.52 mmol) of Pd$_2$(dba)$_3$, 2.52 ml (50% in toluene, 5.04 mmol) of tri-tert-butylphosphine (ttbp), and 4.84 g (50.4 mmol) of sodium tert-butoxide were added to 85 ml of xylene and mixed. The mixed solution was heated and stirred at a temperature of 120° C. After completion of the reaction, the resulting reaction solution was cooled to room temperature, filtered through silica gel under reduced pressure. The filtrate was concentrated under reduced pressure. The resulting residue was then separated by silica gel column chromatography, thereby providing 2.74 g (yield: 15%) of a desired compound, Compound B.

LC-Mass (cald: 725.28 g/mol, found: M+1=726 g/mol).

Example 1

A glass substrate with an indium tin oxide (ITO) electrode (i.e., a first electrode or an anode) having a thickness of 1,500 Å thereon was ultrasonically cleaned by using distilled water. After completing the washing of the glass substrate using distilled water, the glass substrate was ultrasonically washed again using iso-propyl alcohol, acetone, and methanol, and then dried. The glass substrate was transported to a plasma washing machine, washed using oxygen plasma for 5 minutes, and then transported to a vacuum evaporator.

Compounds HT3 and HP-1 were co-deposited on the ITO electrode of the glass substrate to form a hole injection layer having a thickness of 100 Å, Compound HT3 was deposited on the hole injection layer to form a hole transport layer having a thickness of 1,300 Å, and mCP was deposited on the hole transport layer to form an electron blocking layer having a thickness of 100 Å, thereby forming a hole transport region.

Compound 1 (as a host) and Compound FIr6 (as a dopant having an amount of 10 percent by weight, wt %) were co-deposited on the hole transport region to form an emission layer having a thickness of 400 Å.

BCP was vacuum-deposited on the emission layer to form a hole blocking layer having a thickness of 100 Å, Compound ET3 and Liq were vacuum-deposited together on the hole blocking layer to form an electron transport layer having a thickness of 300 Å, and Liq was deposited on the electron transport layer to form an electron injection layer having a thickens of 10 Å. Then, Al was deposited on the electron injection layer to form an Al second electrode (i.e., a cathode) having a thickness of 1,200 Å, thereby completing the manufacture of an organic light-emitting device.

Examples 2 to 15 and Comparative Examples 1 and 2

Organic light-emitting devices were each manufactured in the same manner as in Example 1, except that compounds shown in Table 2 were each used as a host for forming the emission layer.

Evaluation Example 1: Evaluation of Characteristics of Organic Light-Emitting Device Changes in the voltage-dependent current density, the voltage-dependent luminescence, and the voltage-dependent current efficiency of the organic light-emitting devices of Examples 1 to 15 and Comparative Examples 1 and 2 were each measured. Specific measurement methods are shown below, and the measurement results are summarized in Table 2.

(1) Measurement of Changes in Voltage-Dependent Current Density

Regarding the prepared organic light-emitting devices, voltages thereof increased from 0 volts (V) to 10 V, and current values flowing across unit devices were measured using a Keithley 2400 current-voltage meter. The results were obtained by dividing the measured current values by the area.

(2) Measurement of Changes in Voltage-Dependent Luminescence

Regarding the prepared organic light-emitting devices, voltages thereof increased from 0 V to 10 V, and results were obtained by measuring luminescence at the increased voltages using a Minolta Cs-1000A luminance meter.

(3) Measurement of Current Efficiency

Based on voltages and the luminescence and current density measured in (1) and (2), the current efficiency (candelas per ampere, cd/A) was calculated at the same current density (10 milliamperes per square centimeters, mA/cm$^2$).

(4) Measurement of Durability

The time taken for the luminescence of the organic light-emitting devices to reach about 95% of the initial luminescence (100%) was evaluated.

In Table 2, the driving voltage, the current efficiency, and the durability values are provided in a relative manner with respect to those of the organic light-emitting device of Comparative Example 1.

TABLE 2

| | Host | Driving voltage (relative value) (%) | Current efficiency (relative value) (%) | Durability (relative value) (%) | Color |
|---|---|---|---|---|---|
| Example 1 | Compound 1 | 102 | 104 | 105 | Blue |
| Example 2 | Compound 3 | 104 | 103 | 105 | Blue |
| Example 3 | Compound 5 | 91 | 114 | 121 | Blue |
| Example 4 | Compound 7 | 94 | 117 | 117 | Blue |
| Example 5 | Compound 26 | 87 | 121 | 124 | Blue |
| Example 6 | Compound 46 | 101 | 110 | 109 | Blue |
| Example 7 | Compound 52 | 95 | 106 | 114 | Blue |
| Example 8 | Compound 55 | 84 | 134 | 138 | Blue |
| Example 9 | Compound 95 | 85 | 140 | 134 | Blue |
| Example 10 | Compound 97 | 94 | 124 | 131 | Blue |
| Example 11 | Compound 106 | 105 | 110 | 111 | Blue |
| Example 12 | Compound 176 | 94 | 104 | 102 | Blue |
| Example 13 | Compound 179 | 95 | 107 | 104 | Blue |
| Example 14 | Compound 216 | 81 | 109 | 115 | Blue |
| Example 15 | Compound 219 | 83 | 108 | 121 | Blue |
| Comparative Example 1 | Compound A | 100 | 100 | 100 | Blue |
| Comparative Example 2 | Compound B | 176 | 54 | 12 | Blue |

TABLE 2-continued
| Host | Driving voltage (relative value) (%) | Current efficiency (relative value) (%) | Durability (relative value) (%) | Color |
|---|---|---|---|---|
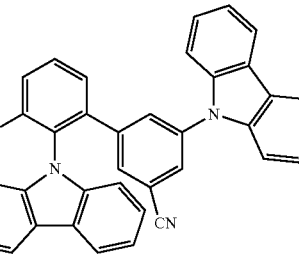

Referring to Table 2, it was confirmed that the organic light-emitting devices of Examples 1 to 15 had good driving voltage, current efficiency, and lifespan characteristics, and at levels as high as those of the organic light-emitting devices of Comparative Examples 1 and 2.

As described above, a condensed cyclic compound has excellent electric characteristics and thermal stability, and thus, an organic light-emitting device including the condensed cyclic compound exhibits low driving voltage, high emission efficiency, high current efficiency, high quantum emission efficiency, and long lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. A condensed cyclic compound represented by Formula 1:

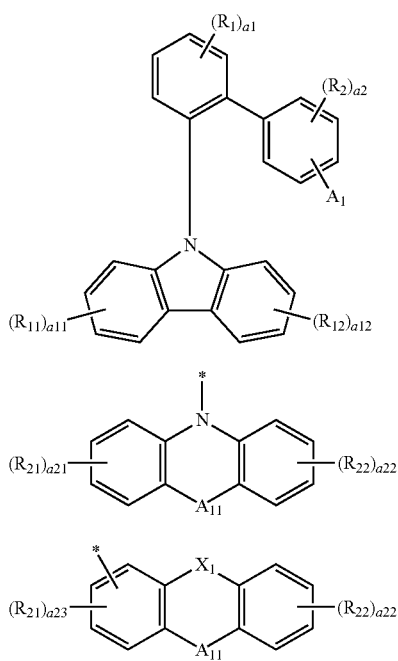

wherein, in Formulae 1, 2A, and 2B,
$A_1$ is a group represented by Formula 2A or 2B,
$A_{11}$ is a single bond or *—$C(R_{27})(R_{28})$—*',
$X_1$ is $N(R_{29})$, O, or S,
$R_1$ and $R_2$ are each independently selected from:
hydrogen, deuterium, —F, —Cl, —Br, —I, a cyano group, a $C_1$-$C_{60}$ alkyl group, and a $C_1$-$C_{60}$ alkoxy group; and
a $C_1$-$C_{60}$ alkyl group and a $C_1$-$C_{60}$ alkoxy group, each substituted with at least one selected from deuterium, —F, —Cl, —Br, —I, and a cyano group, a1 and a2 are each independently an integer selected from 0 to 4, wherein the sum of a1 and a2 is 1 or more,
1, 2, 3, or 4 groups selected from $R_1$ in the number of a1 and $R_2$ in the number of a2 are a cyano group,
$R_{11}$, $R_{12}$, $R_{21}$, $R_{22}$, and $R_{27}$ to $R_{29}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_4)(Q_5)$, and —$B(Q_6)(Q_7)$,
a11, a12, a21, and a22 are each independently an integer selected from 0 to 4, and a23 is an integer selected from 0 to 3,
* and *' each indicate a binding site to a neighboring atom in a corresponding formula,
at least one substituent selected from substituent(s) of the substituted $C_1$-$C_{60}$ alkyl group, the substituted $C_2$-$C_{60}$ alkenyl group, the substituted $C_2$-$C_{60}$ alkynyl group, the substituted $C_2$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:
deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, wherein "monovalent non-aromatic condensed polycyclic group" refers to a monovalent group that has two or more rings condensed to each other, only carbon atoms as a ring forming atom, and which is non-aromatic in the entire molecular structure, and wherein "monovalent non-aromatic condensed heteropolycyclic group" refers to a monovalent group that has two or more rings condensed to each other, has a heteroatom selected from N, O, P, Si, and S, other than carbon atoms, as a ring-forming atom, and which is non-aromatic in the entire molecular structure.

2. The condensed cyclic compound of claim 1, wherein $R_1$ and $R_2$ are each independently selected from:

hydrogen, deuterium, —F, a cyano group, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from deuterium, —F, and a cyano group.

3. The condensed cyclic compound of claim 1, wherein 1 or 2 groups selected from $R_1$ in the number of a1 are a cyano group, and $R_2$ is not a cyano group; or 1 or 2 groups selected from $R_1$ in the number of a1 are a cyano group, and 1 or 2 groups selected from $R_2$ in the number of a2 are cyano groups; or $R_1$ is not a cyano group, and 1 or 2 groups selected from $R_2$ in the number of a2 are a cyano group.

4. The condensed cyclic compound of claim 1, wherein $R_{11}$, $R_{12}$, $R_{21}$, $R_{22}$, and $R_{27}$ to $R_{29}$ are each independently selected from:

hydrogen, deuterium, —F, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a cyano group, —F, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, —F, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from hydrogen, a $C_1$-$C_{20}$ alkyl group, a $C_1$-$C_{20}$ alkoxy group, a phenyl group, a biphenyl group, a terphenyl group, and a naphthyl group.

5. The condensed cyclic compound of claim 1, wherein the total number of cyano group(s) in the condensed cyclic compound represented by Formula 1 is 1, 2, 3, or 4.

6. The condensed cyclic compound of claim 1, wherein $A_1$ in Formula 1 is selected from groups represented by Formulae 2A-1 and 2B-1 to 2B-4:

Formula 2A-1

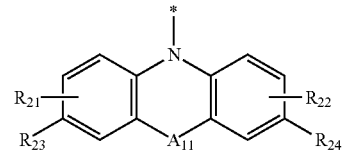

Formula 2B-1

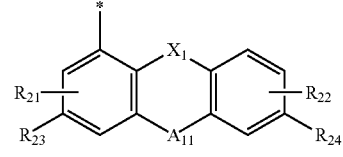

Formula 2B-2

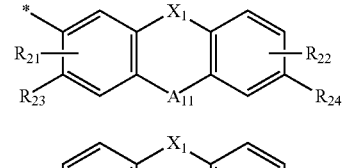

Formula 2B-3

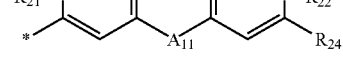

-continued

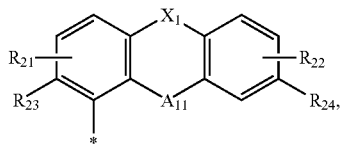
Formula 2B-4 wherein, in Formulae 2A-1 and 2B-1 to 2B-4, $A_{11}$, $X_1$, $R_{21}$, $R_{22}$, and * are each independently the same as defined in claim 1, $R_{23}$ is the same as defined in connection with $R_{21}$ in claim 1, and $R_{24}$ is the same as defined in connection with $R_{22}$ in claim 1.

7. The condensed cyclic compound of claim 1, wherein the condensed cyclic compound is represented by one selected from Formulae 1A to 1C:

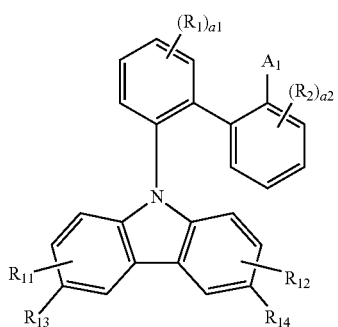
Formula 1A

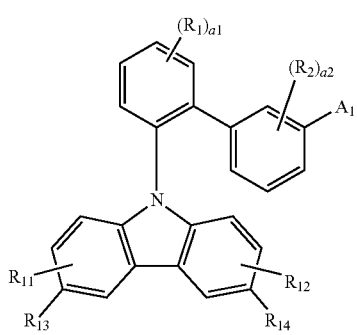
Formula 1B

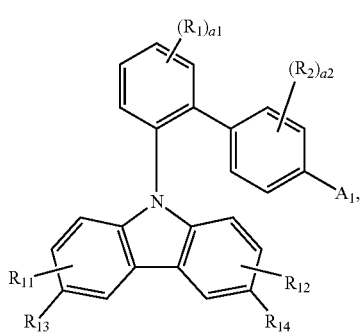
Formula 1C wherein, in Formulae 1A to 1C, $A_1$, $R_1$, $R_2$, a1, a2, $R_{11}$, and $R_{12}$ are each independently the same as defined in claim 1, $R_{13}$ is the same as defined in connection with $R_{11}$ in claim 1, and $R_{14}$ is the same as defined in connection with $R_{12}$ in claim 1.

8. The condensed cyclic compound of claim 7, wherein $A_1$ in Formulae 1A to 1C is selected from groups represented by Formulae 2A-1 and 2B-1 to 2B-4:

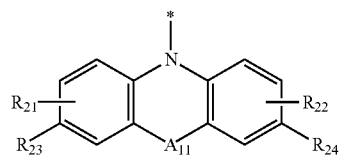
Formula 2A-1

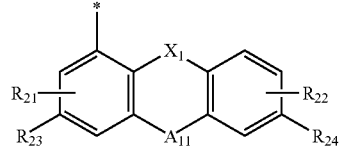
Formula 2B-1

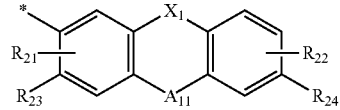
Formula 2B-2

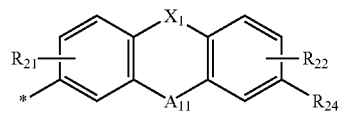
Formula 2B-3

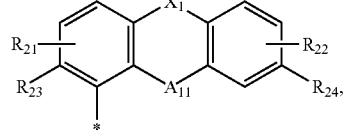
Formula 2B-4 wherein, in Formulae 2A-1 and 2B-1 to 2B-4, $A_{11}$, $X_1$, $R_{21}$, $R_{22}$, and * are each independently the same as defined in claim 1, $R_{23}$ is the same as defined in connection with $R_{21}$ in claim 1, and $R_{24}$ is the same as defined in connection with $R_{22}$ in claim 1.

9. The condensed cyclic compound of claim 8, wherein $A_1$ is selected from groups represented by Formulae 2A-1, 2B-1, 2B-2, and 2B-4, and at least one selected from $R_{13}$, $R_{14}$, $R_{23}$, and $R_{24}$ is a cyano group; or $A_1$ is a group represented by Formula 2B-3, and at least one selected from $R_{13}$, $R_{14}$, and $R_{24}$ is a cyano group.

10. The condensed cyclic compound of claim 1, wherein the condensed cyclic compound is represented by one selected from Formulae 1A-1 to 1A-76, 1B-1 to 1B-76, and 1C-1 to 1C-76:

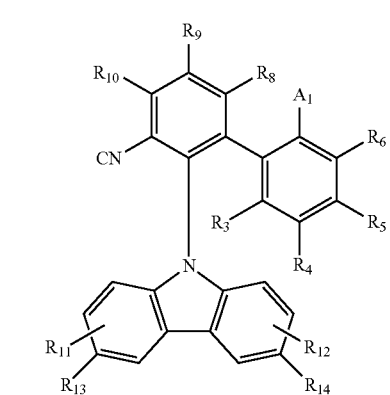
Formula 1A-1

Formula 1A-2
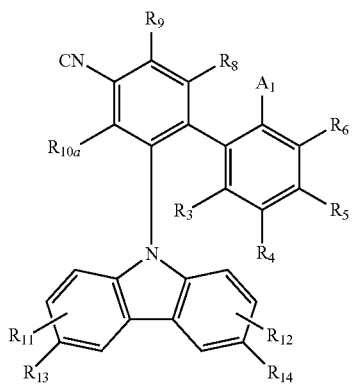
Formula 1A-3
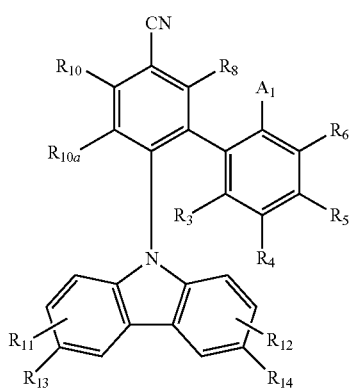
Formula 1A-4
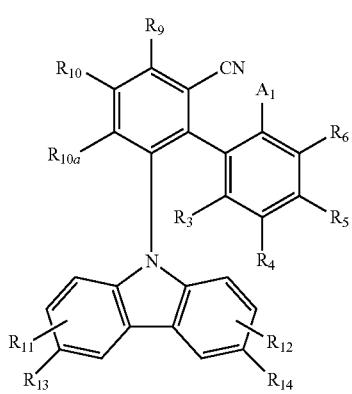
Formula 1A-5
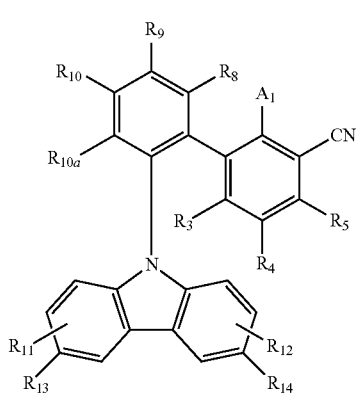
Formula 1A-6
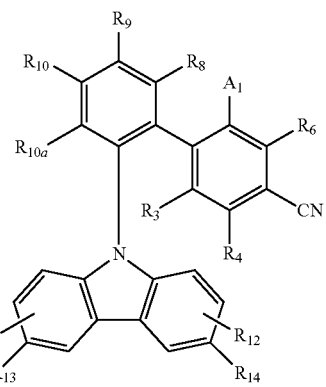
Formula 1A-7
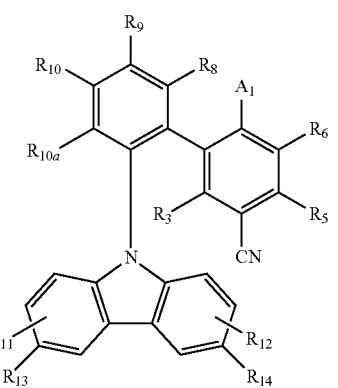
Formula 1A-8
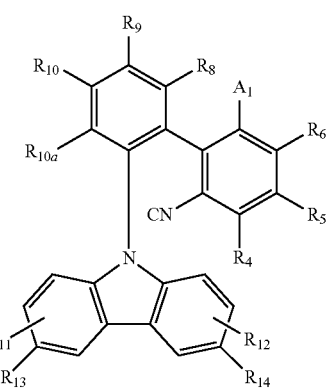
Formula 1A-9
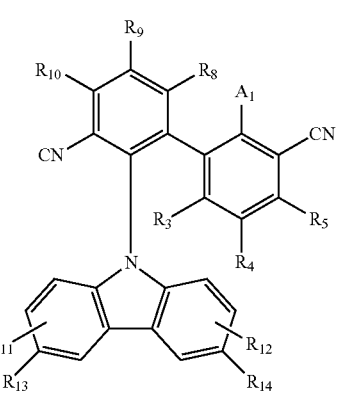

Formula 1A-10
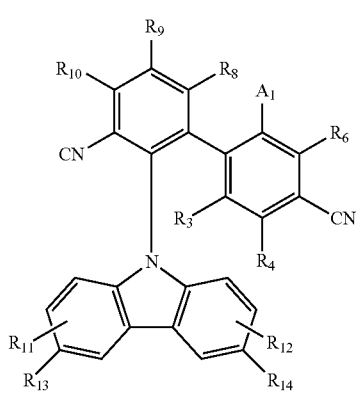
Formula 1A-11
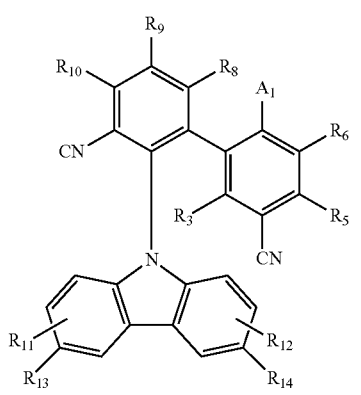
Formula 1A-12
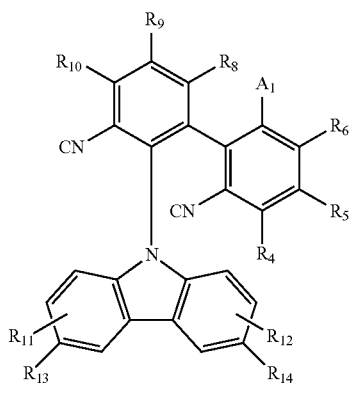
Formula 1A-13
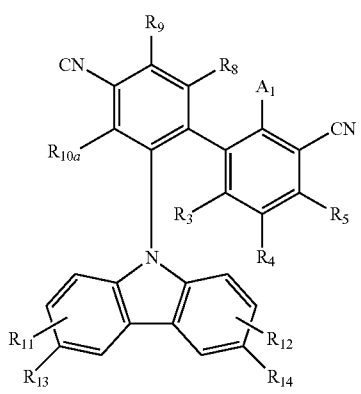
Formula 1A-14
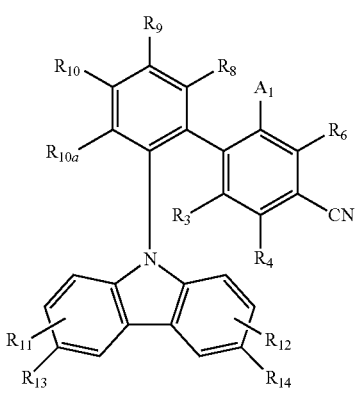
Formula 1A-15
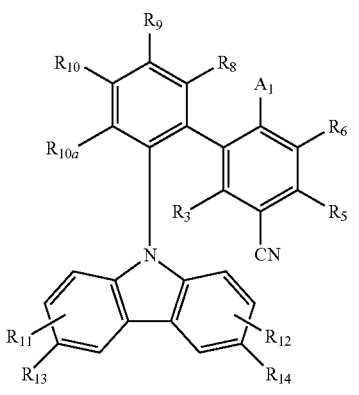
Formula 1A-16
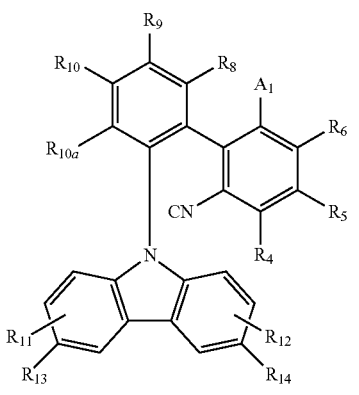
Formula 1A-17
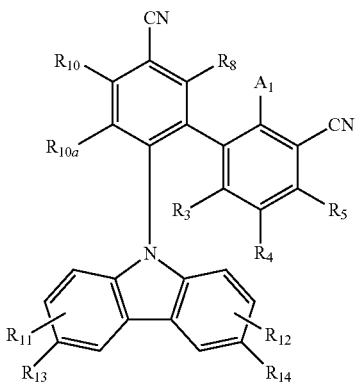

Formula 1A-18
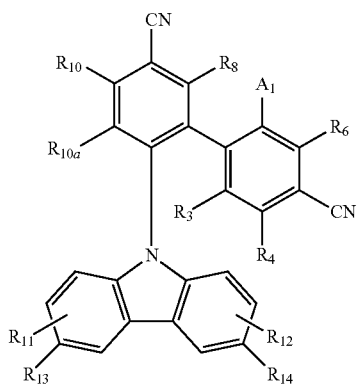
Formula 1A-19
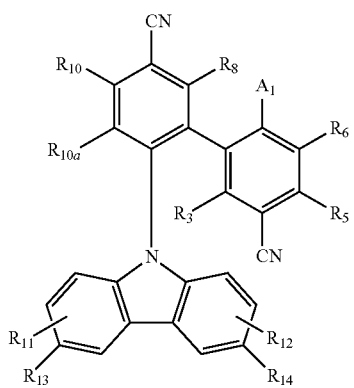
Formula 1A-20
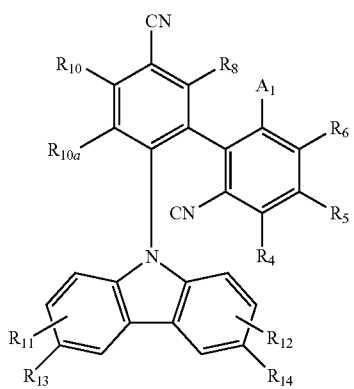
Formula 1A-21
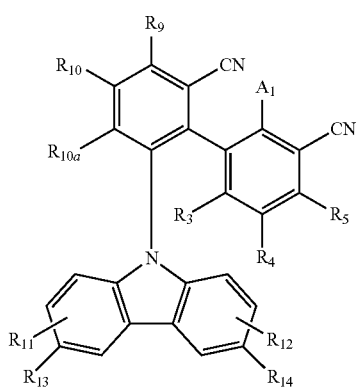
Formula 1A-22
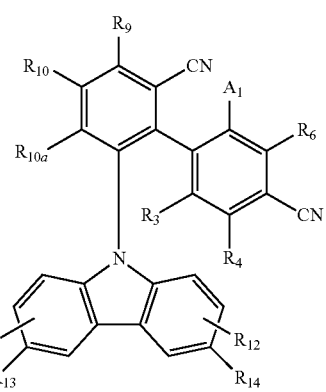
Formula 1A-23
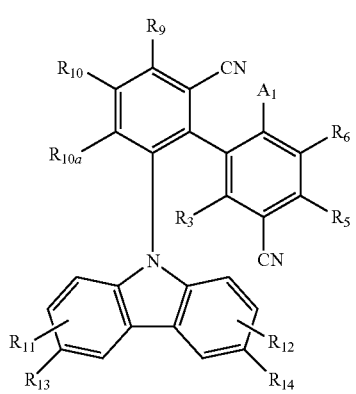
Formula 1A-24
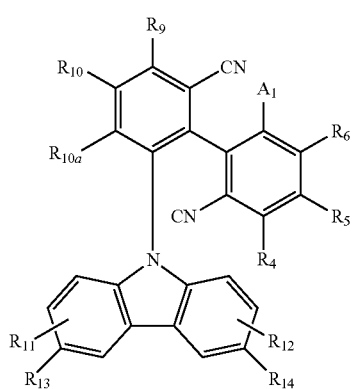
Formula 1A-25
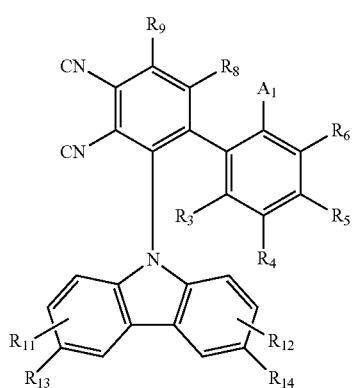

Formula 1A-26
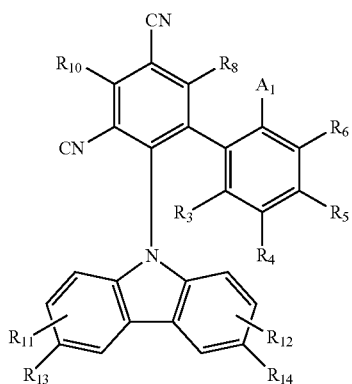
Formula 1A-27
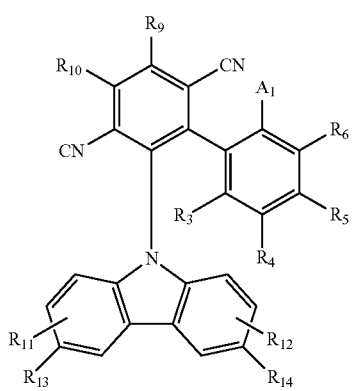
Formula 1A-28
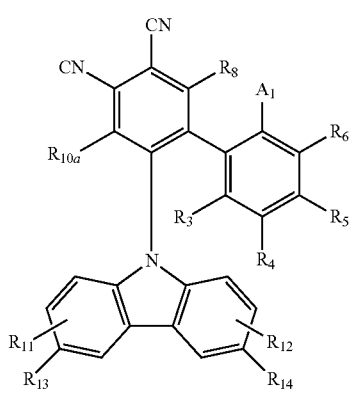
Formula 1A-29
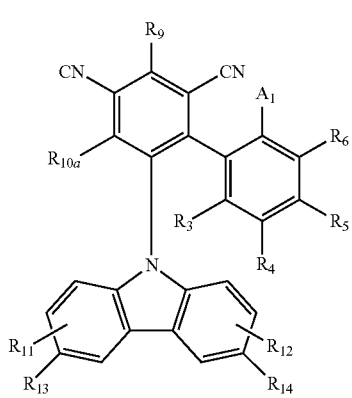
Formula 1A-30
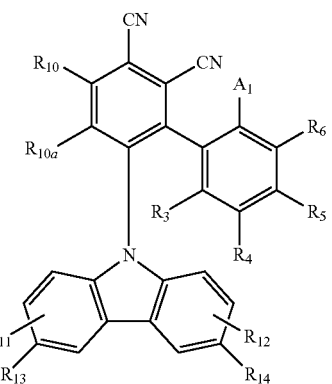
Formula 1A-31
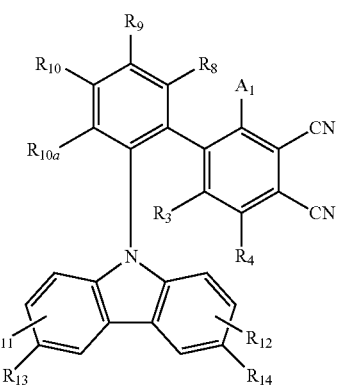
Formula 1A-32
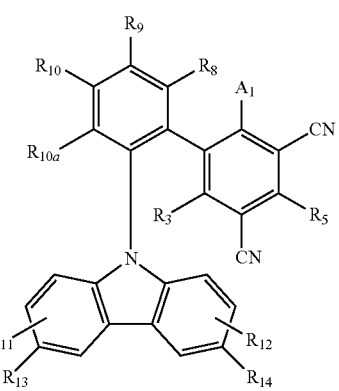
Formula 1A-33
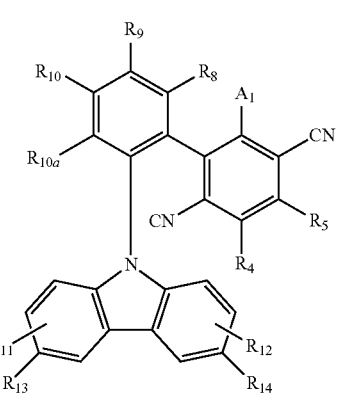

Formula 1A-34
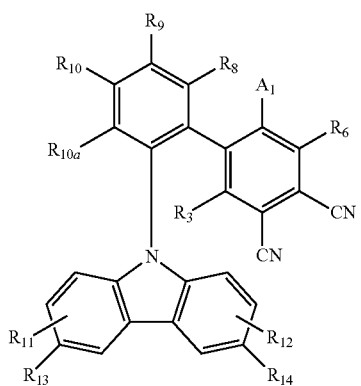
Formula 1A-35
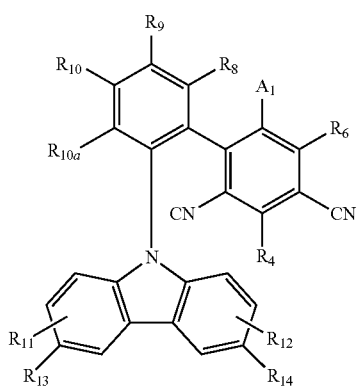
Formula 1A-36
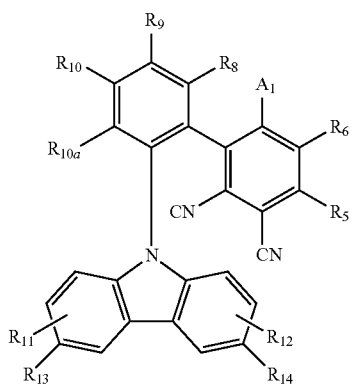
Formula 1A-37
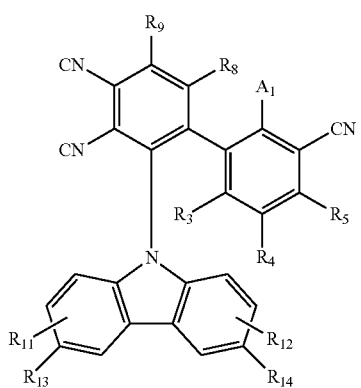
Formula 1A-38
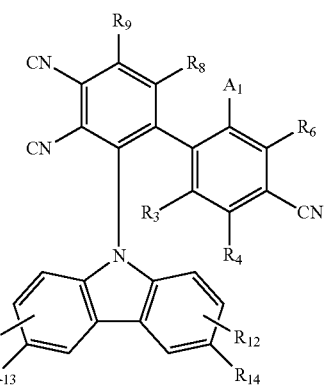
Formula 1A-39
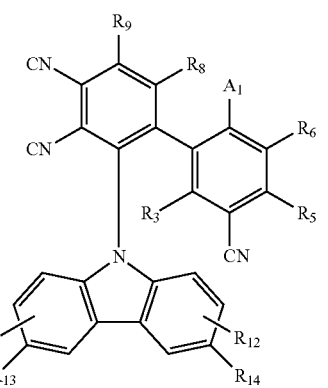
Formula 1A-40
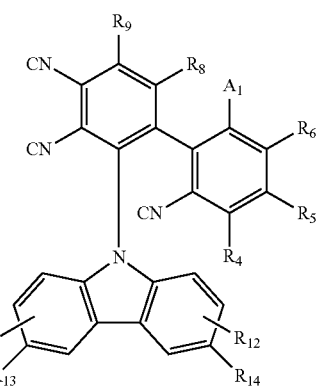
Formula 1A-41
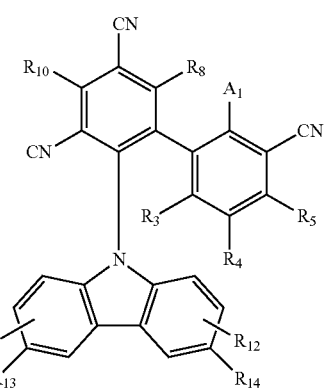

-continued
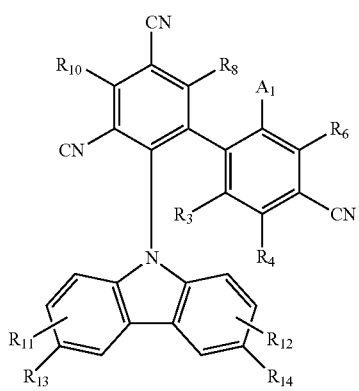
Formula 1A-42
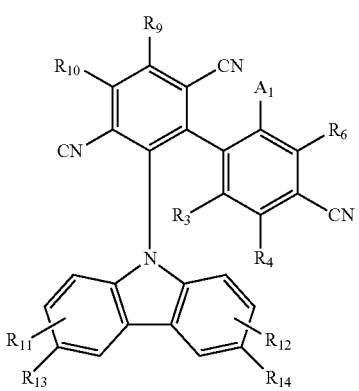
Formula 1A-46
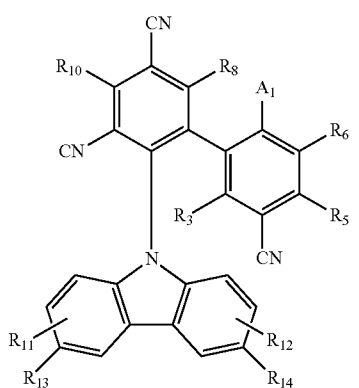
Formula 1A-43
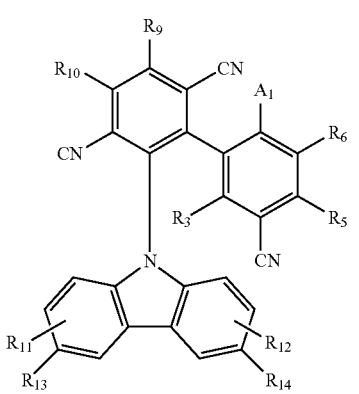
Formula 1A-47
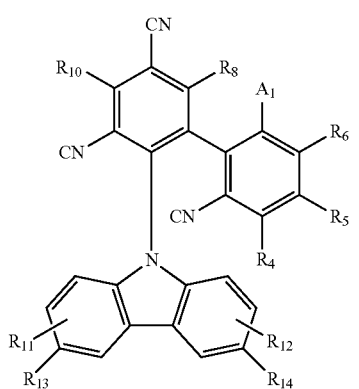
Formula 1A-44
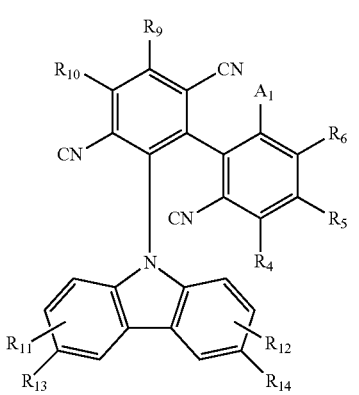
Formula 1A-48
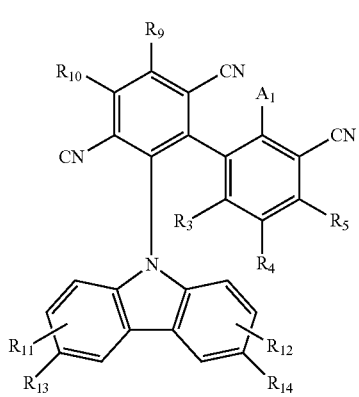
Formula 1A-46
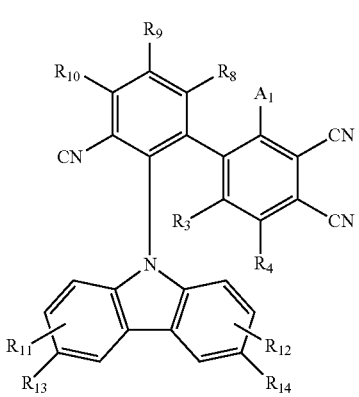
Formula 1A-49

-continued
Formula 1A-50
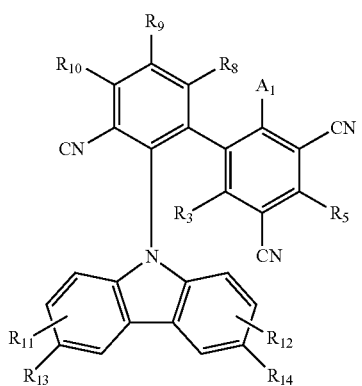
Formula 1A-51
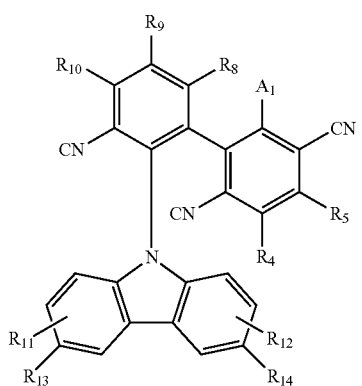
Formula 1A-52
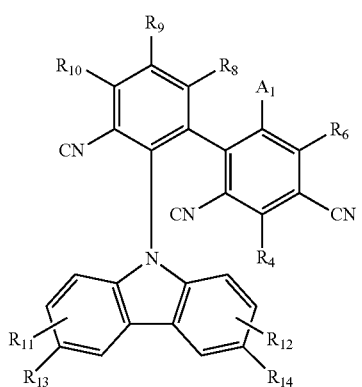
Formula 1A-53
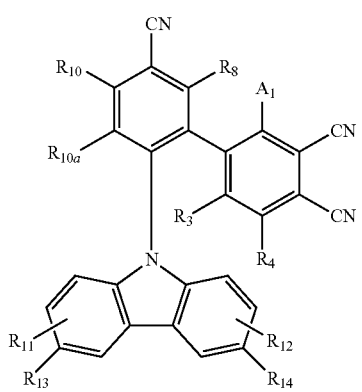
Formula 1A-54
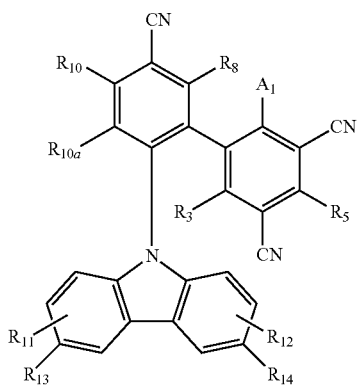
Formula 1A-55
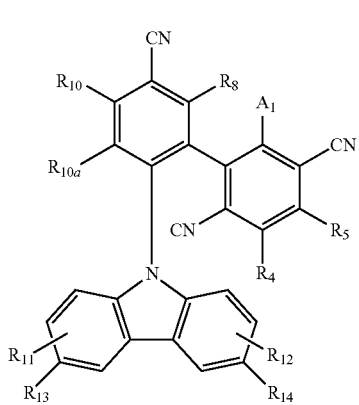
Formula 1A-56
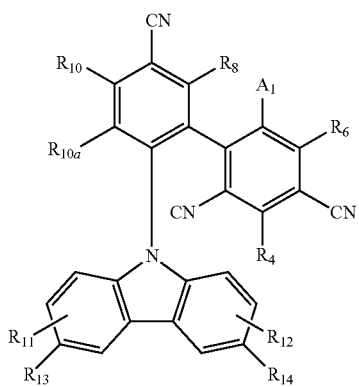
Formula 1A-57
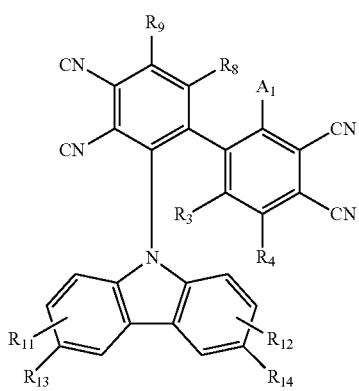

-continued
Formula 1A-58
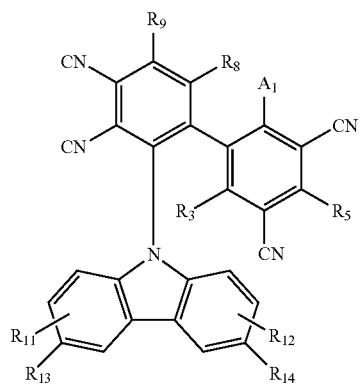
Formula 1A-59
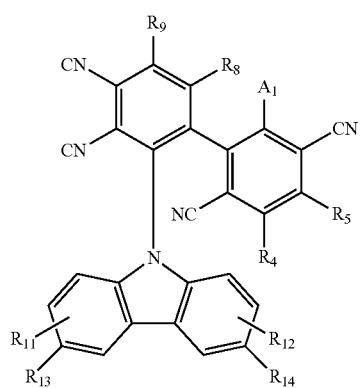
Formula 1A-60
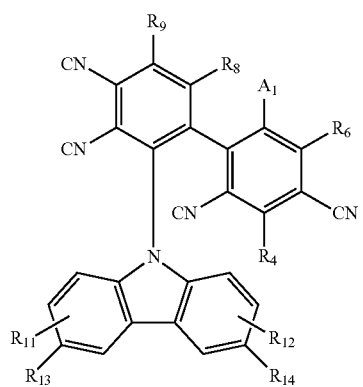
Formula 1A-61
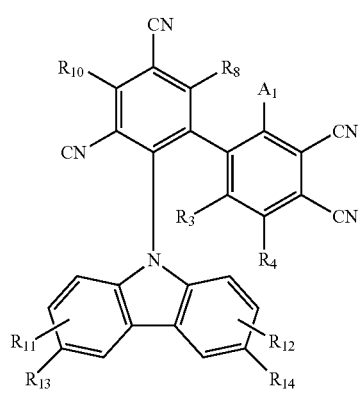
Formula 1A-62
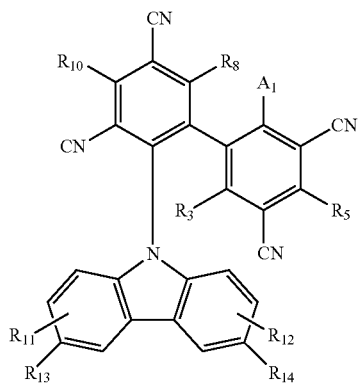
Formula 1A-63
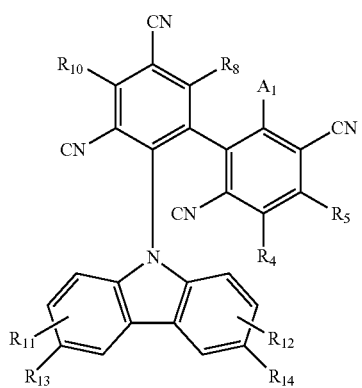
Formula 1A-64
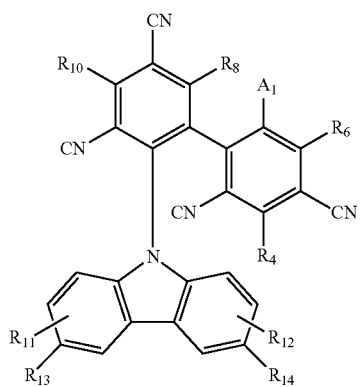
Formula 1A-65
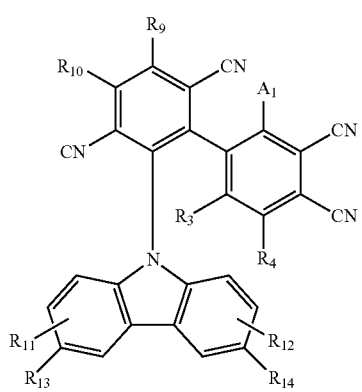

Formula 1A-66
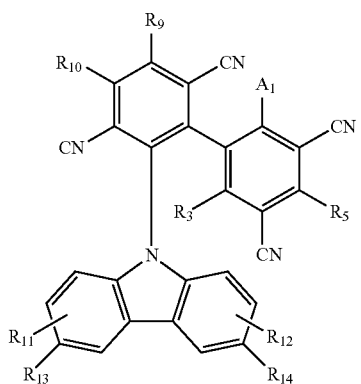
Formula 1A-67
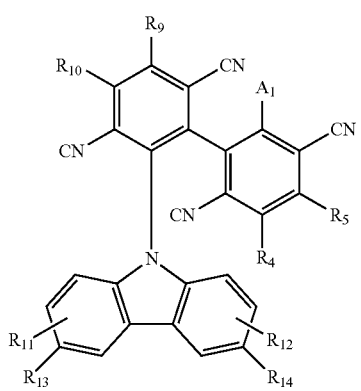
Formula 1A-68
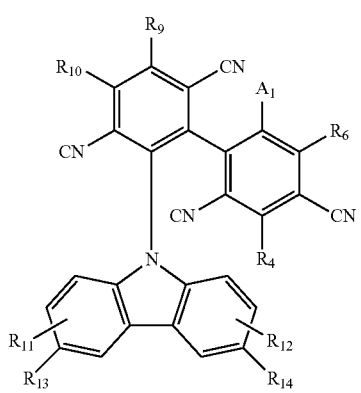
Formula 1A-69
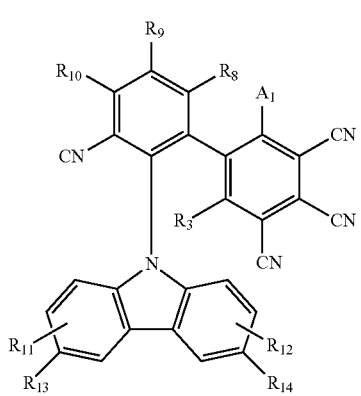
Formula 1A-70
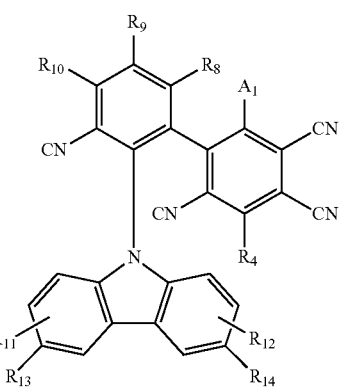
Formula 1A-71
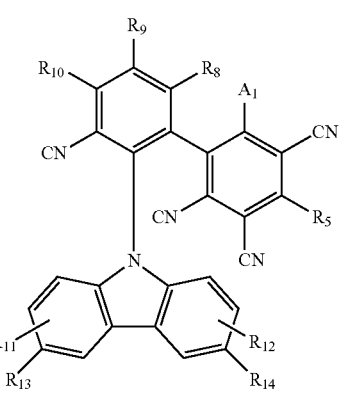
Formula 1A-72
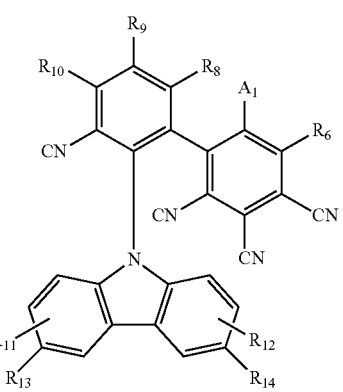
Formula 1A-73
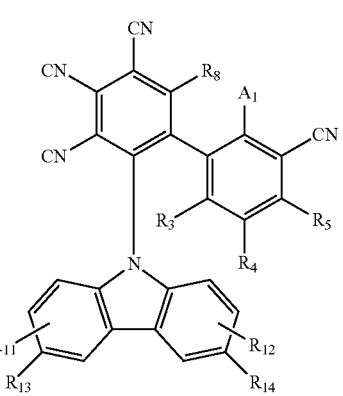

Formula 1A-74
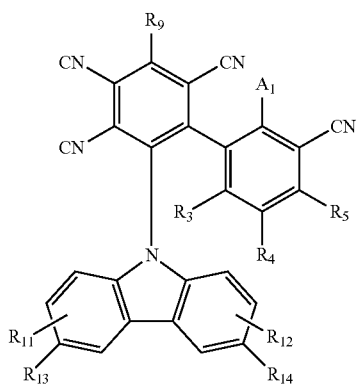
Formula 1A-75
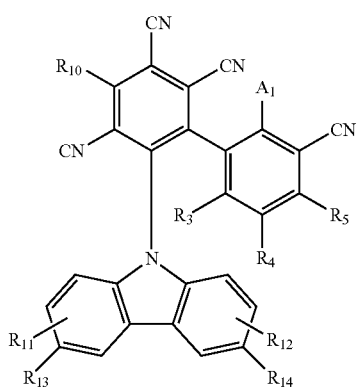
Formula 1A-76
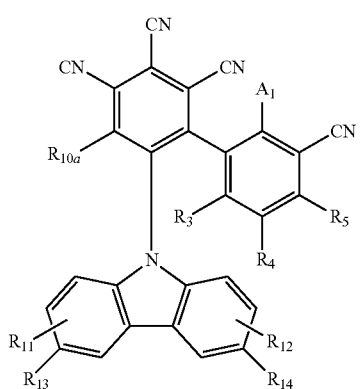
Formula 1B-1
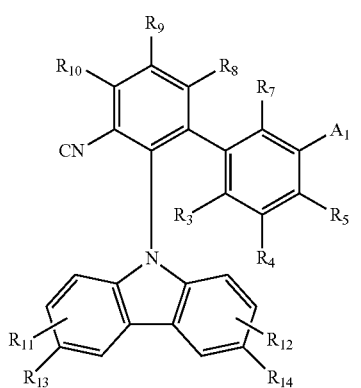
Formula 1B-2
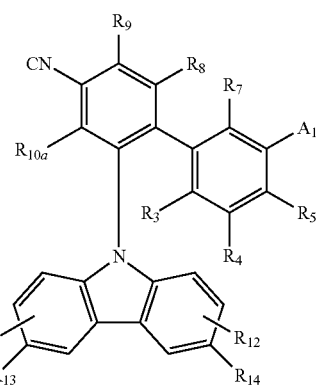
Formula 1B-3
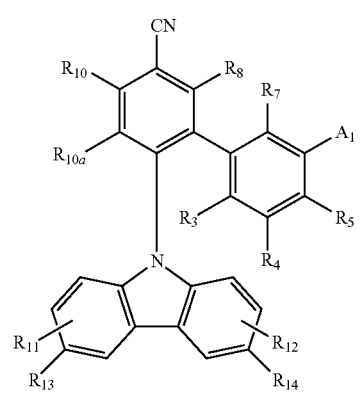
Formula 1B-4
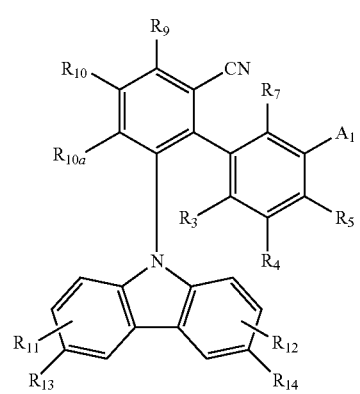
Formula 1B-5
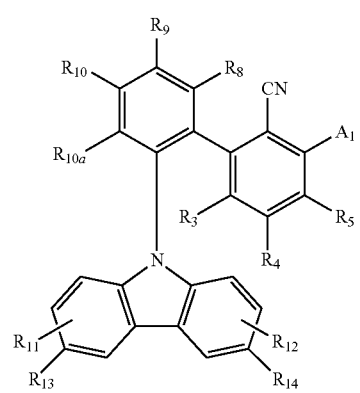

Formula 1B-6
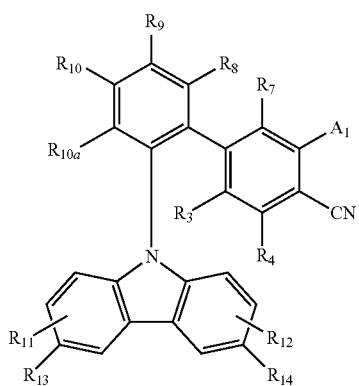
Formula 1B-7
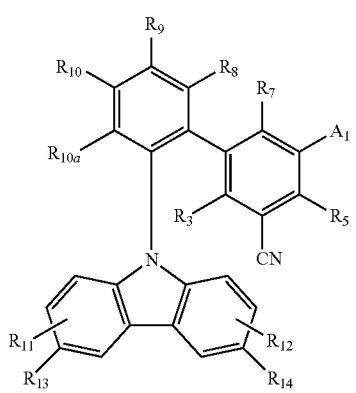
Formula 1B-8
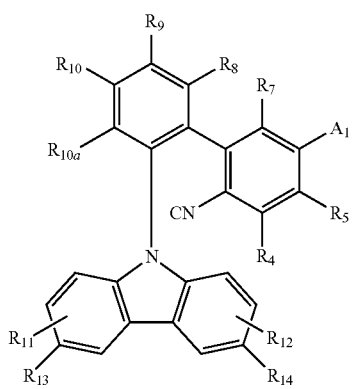
Formula 1B-9
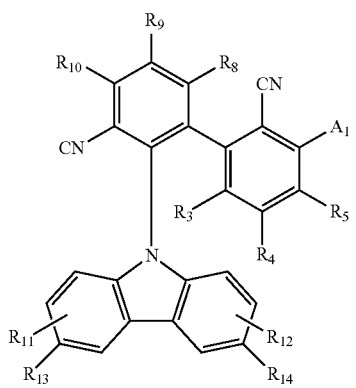
Formula 1B-10
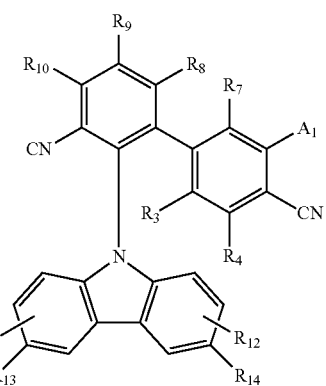
Formula 1B-11
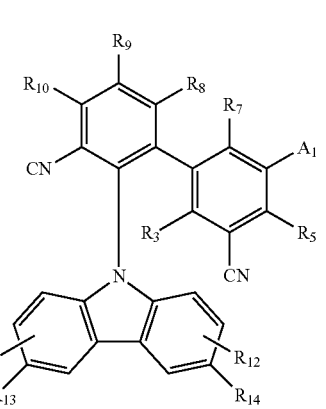
Formula 1B-12
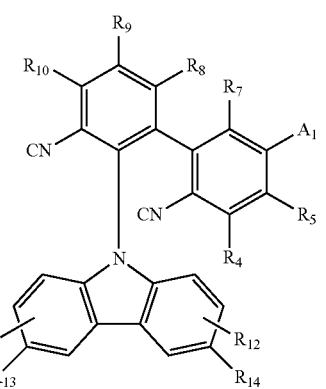
Formula 1B-13
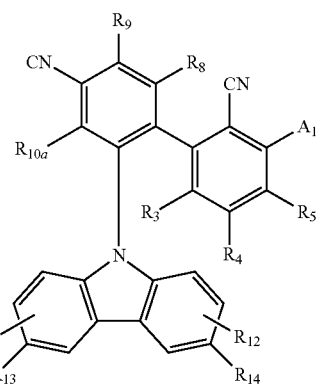

-continued
Formula 1B-14
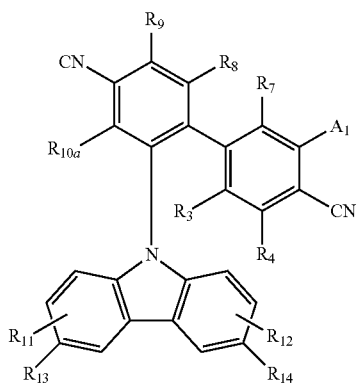
Formula 1B-15
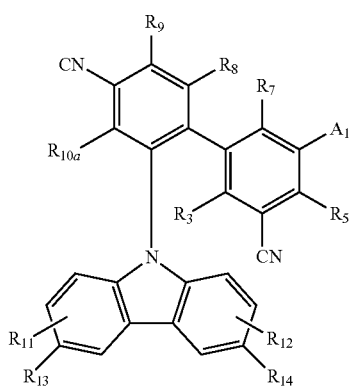
Formula 1B-16
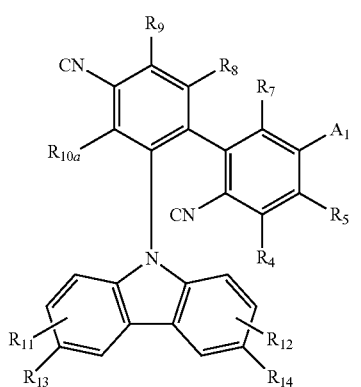
Formula 1B-17
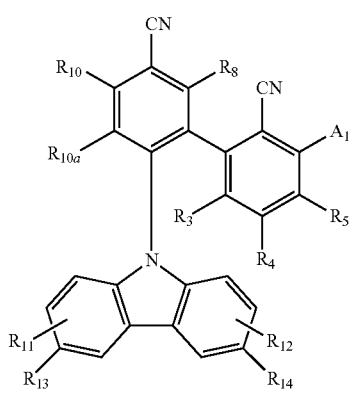
Formula 1B-18
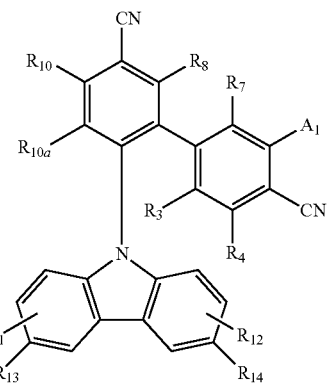
Formula 1B-19
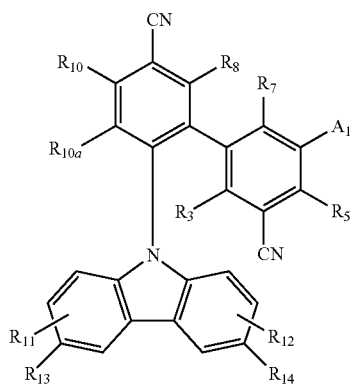
Formula 1B-20
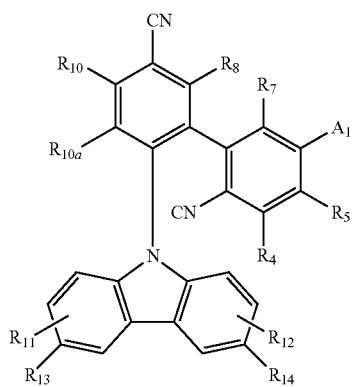
Formula 1B-21
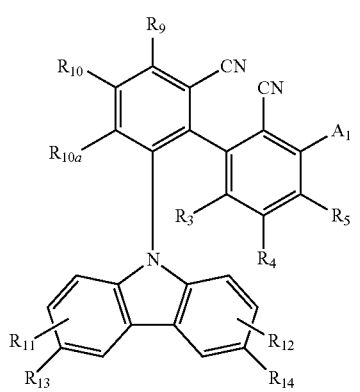

Formula 1B-22
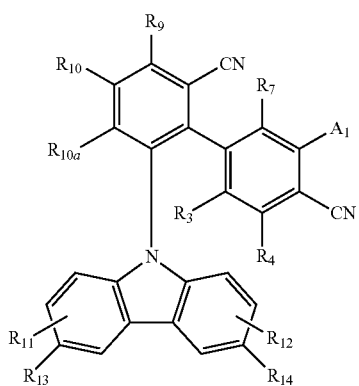
Formula 1B-23
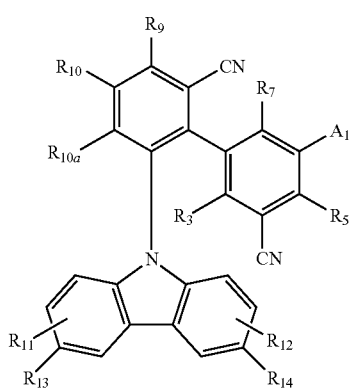
Formula 1B-24
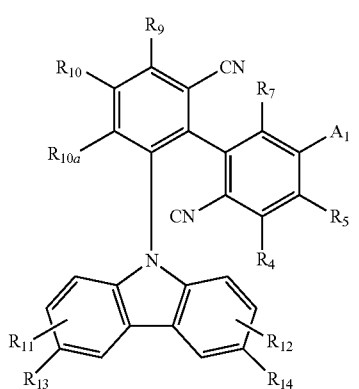
Formula 1B-25
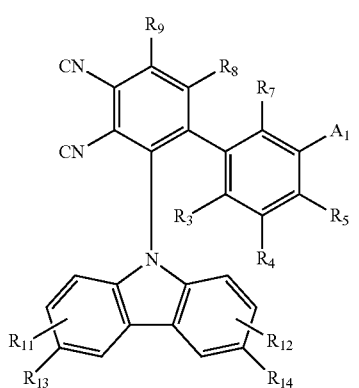
Formula 1B-26
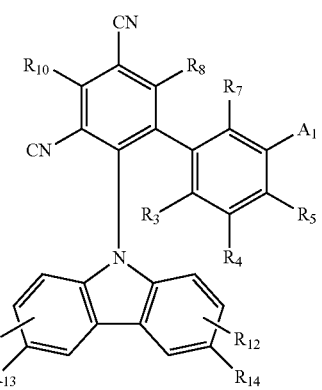
Formula 1B-27
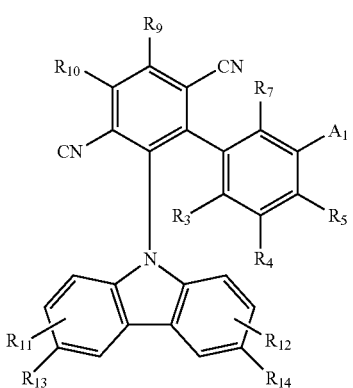
Formula 1B-28
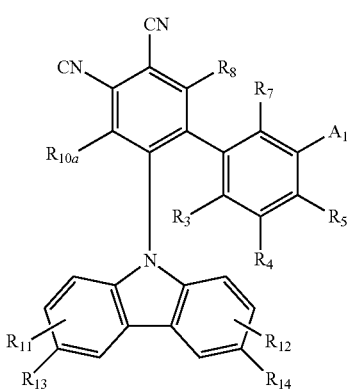
Formula 1B-29
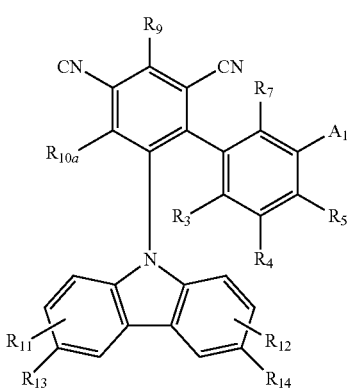

-continued
Formula 1B-30
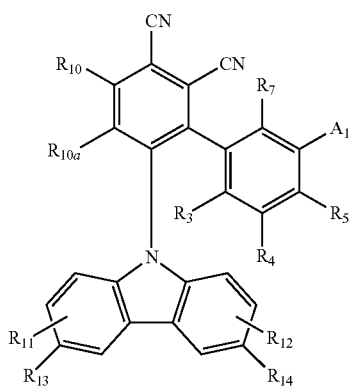
Formula 1B-31
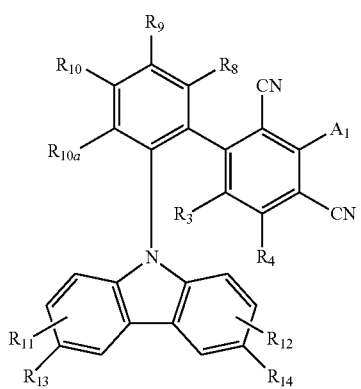
Formula 1B-32
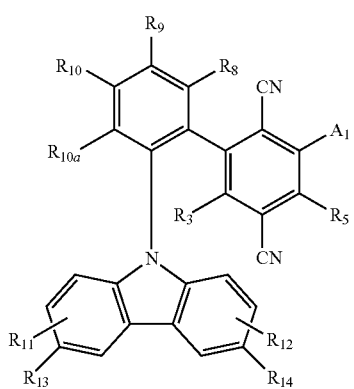
Formula 1B-33
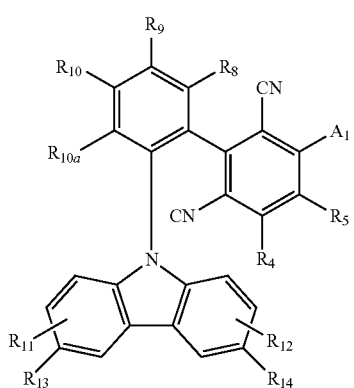
Formula 1B-34
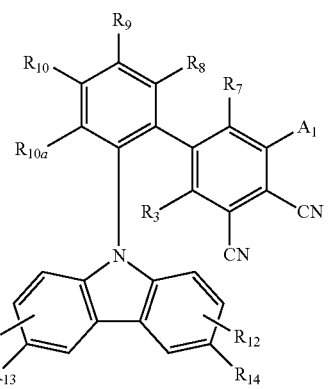
Formula 1B-35
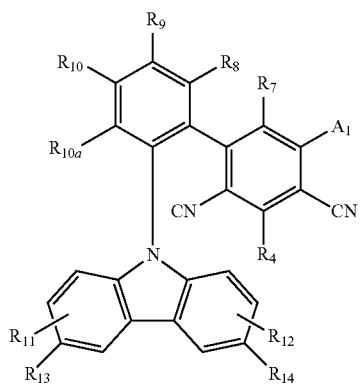
Formula 1B-36
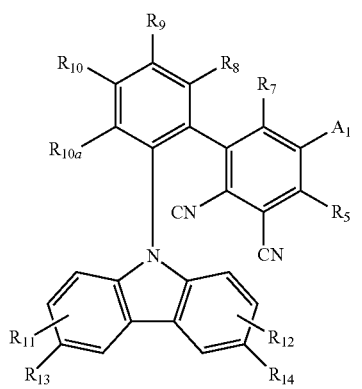
Formula 1B-37
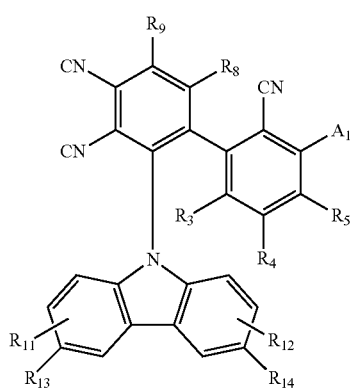

Formula 1B-38
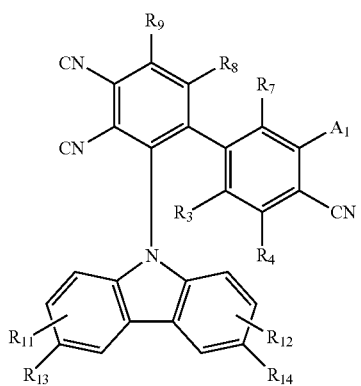
Formula 1B-39
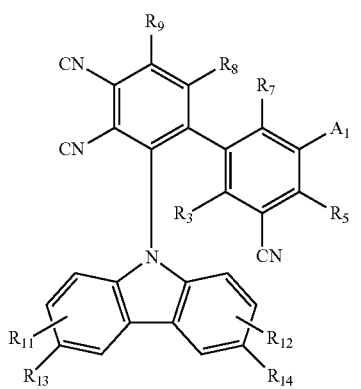
Formula 1B-40
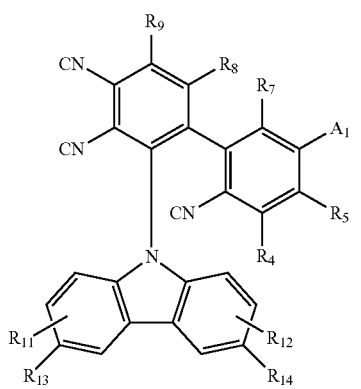
Formula 1B-41
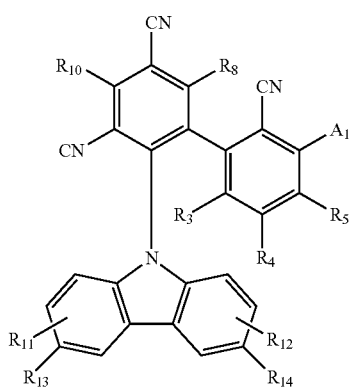
Formula 1B-42
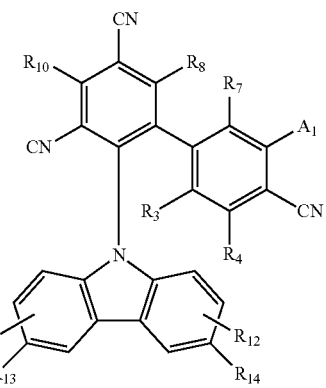
Formula 1B-43
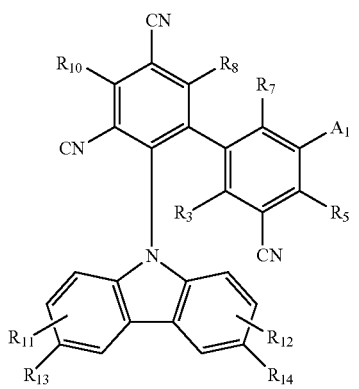
Formula 1B-44
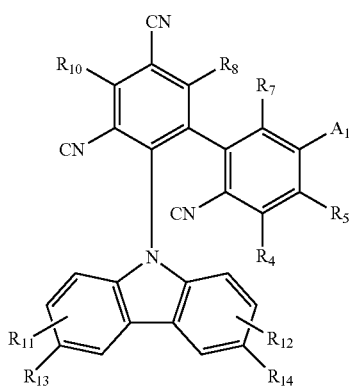
Formula 1B-45
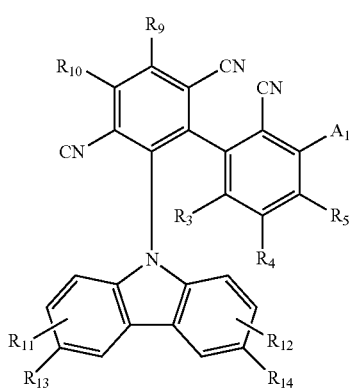

Formula 1B-46
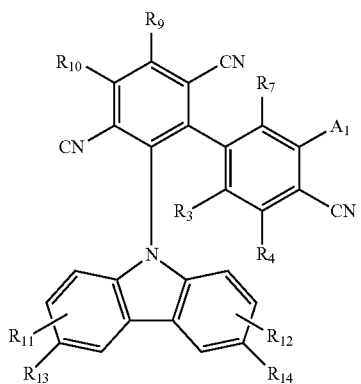
Formula 1B-47
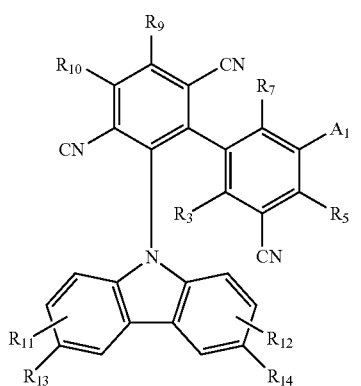
Formula 1B-48
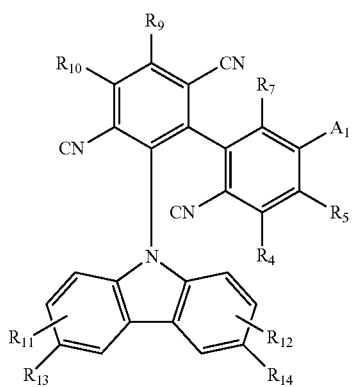
Formula 1B-49
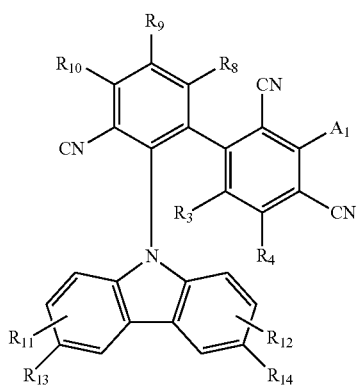
Formula 1B-50
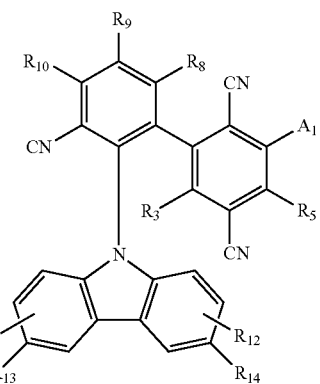
Formula 1B-51
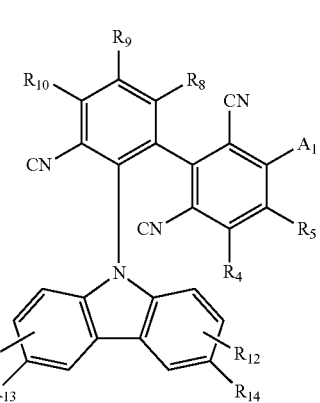
Formula 1B-52
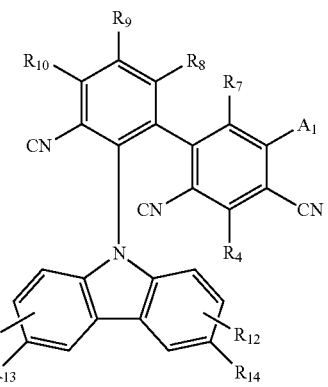
Formula 1B-53
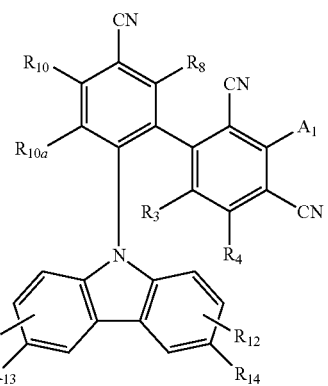

Formula 1B-54
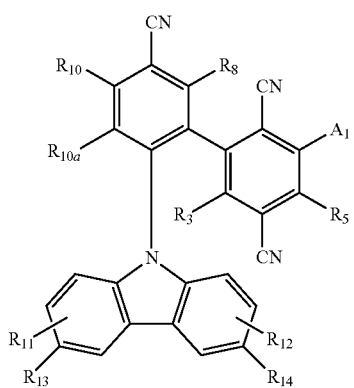
Formula 1B-55
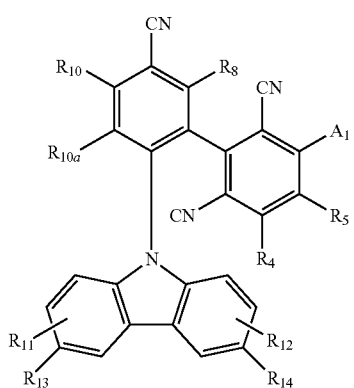
Formula 1B-56
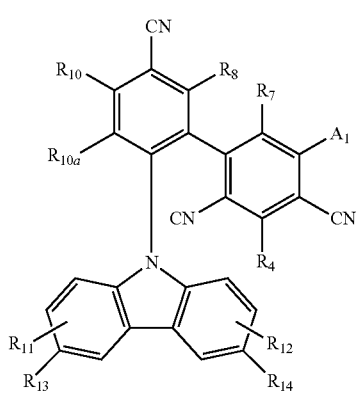
Formula 1B-57
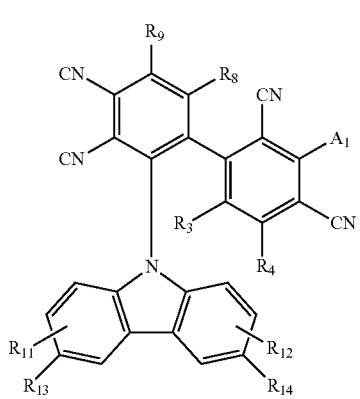
Formula 1B-58
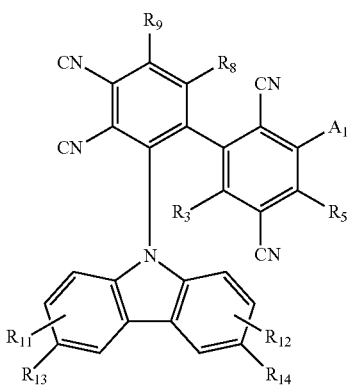
Formula 1B-59
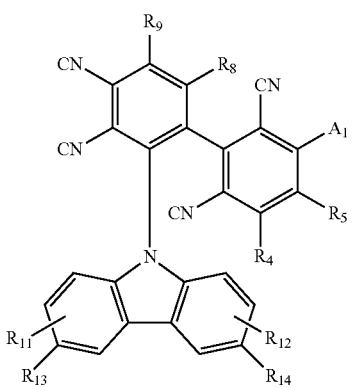
Formula 1B-60
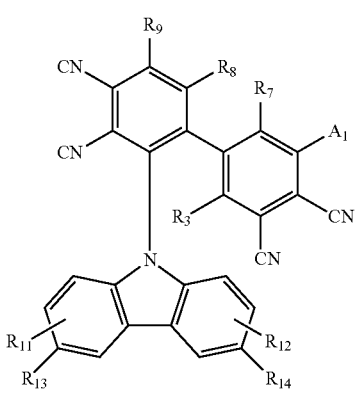
Formula 1B-61
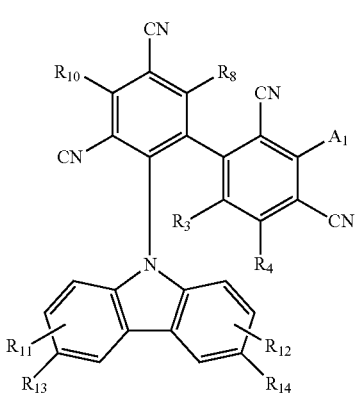

Formula 1B-62
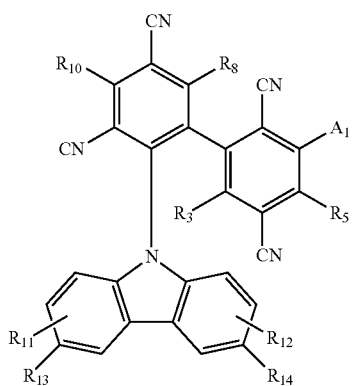
Formula 1B-63
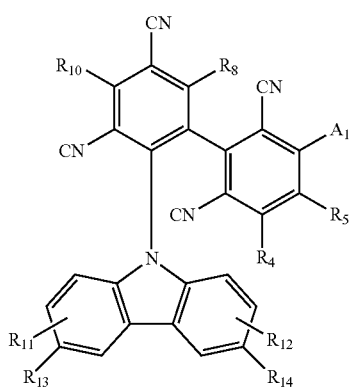
Formula 1B-64
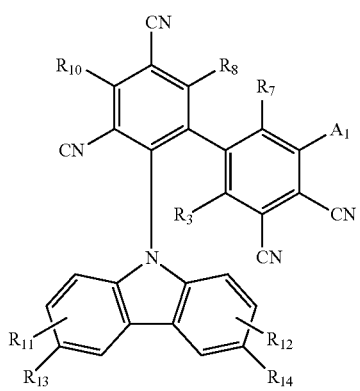
Formula 1B-65
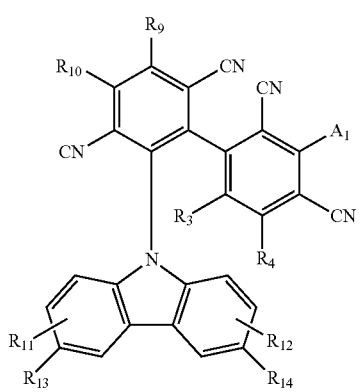
Formula 1B-66
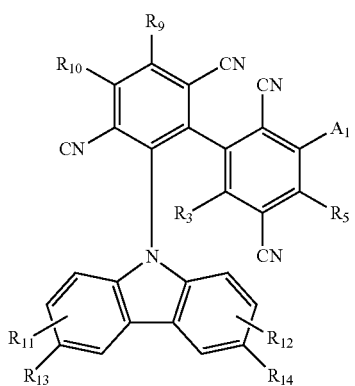
Formula 1B-67
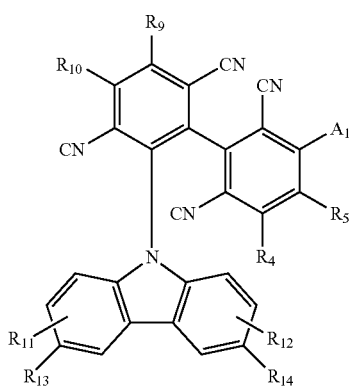
Formula 1B-68
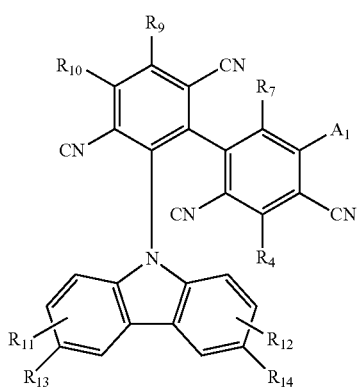
Formula 1B-69
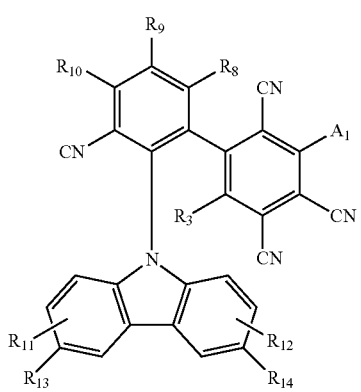

Formula 1B-70

Formula 1B-71

Formula 1B-72

Formula 1B-73

Formula 1B-74

Formula 1B-75

Formula 1B-76

Formula 1C-1

Formula 1C-2
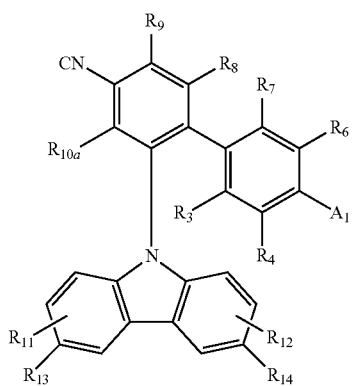
Formula 1C-3
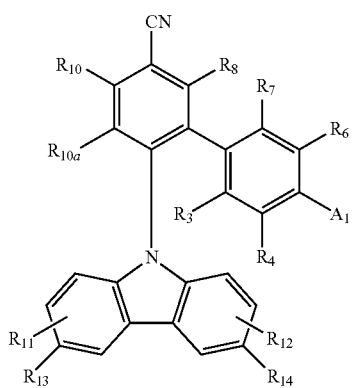
Formula 1C-4
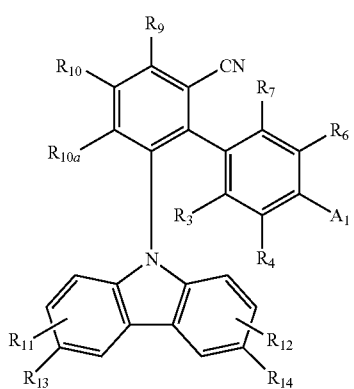
Formula 1C-5
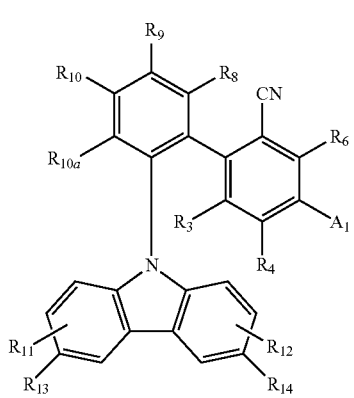
Formula 1C-6
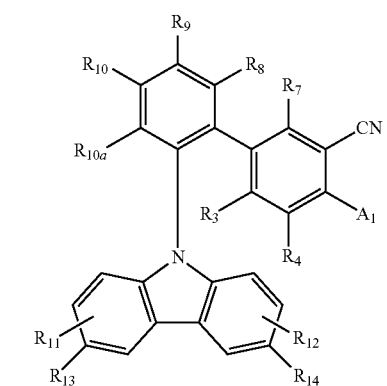
Formula 1C-7
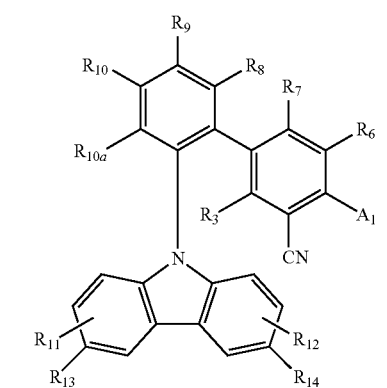
Formula 1C-8
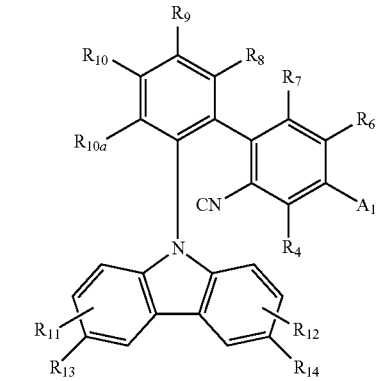
Formula 1C-9
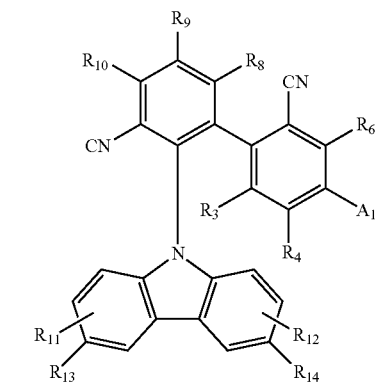

Formula 1C-10
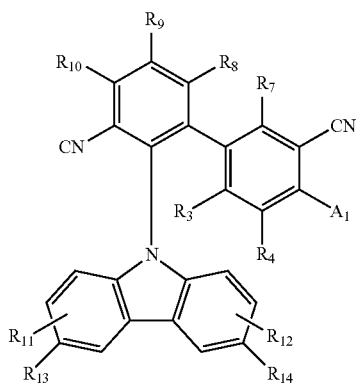
Formula 1C-14
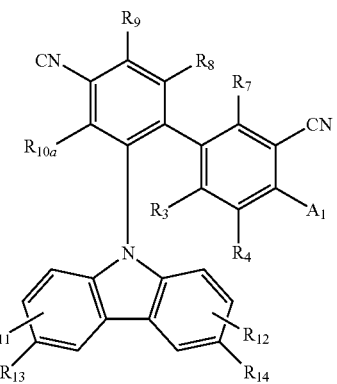
Formula 1C-11
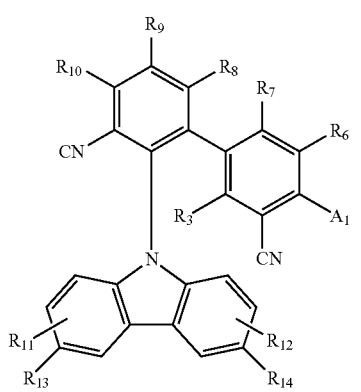
Formula 1C-15
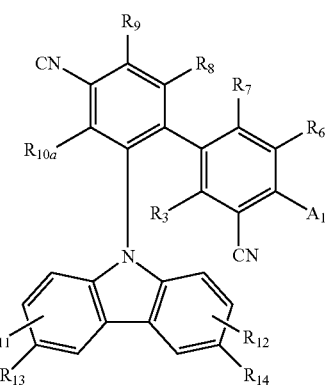
Formula 1C-12
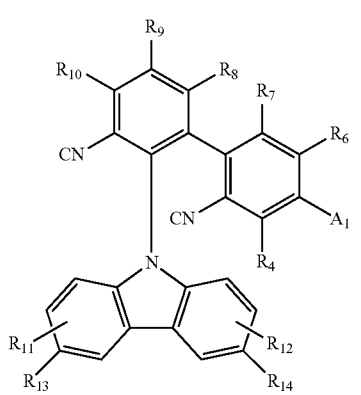
Formula 1C-16
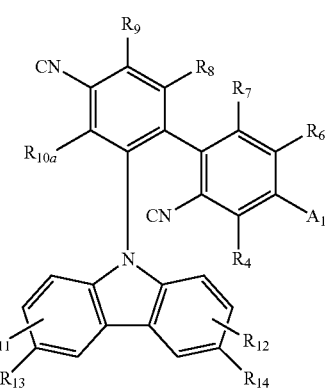
Formula 1C-13
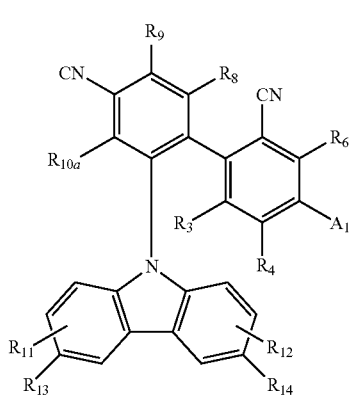
Formula 1C-17
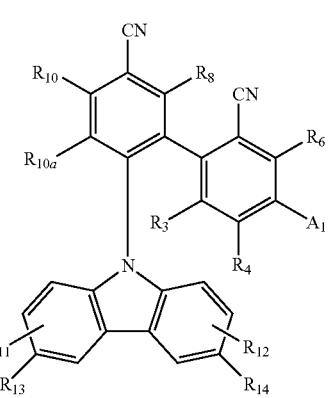

Formula 1C-18
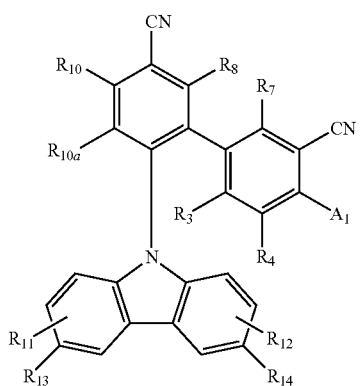
Formula 1C-19
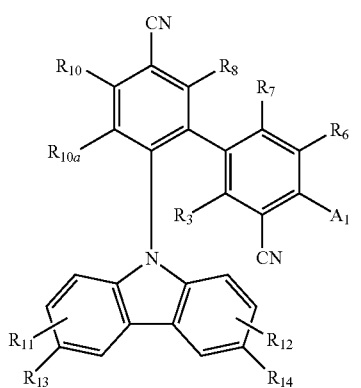
Formula 1C-20
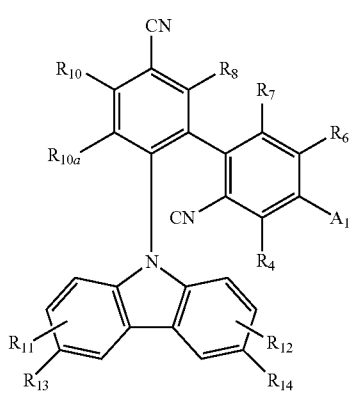
Formula 1C-21
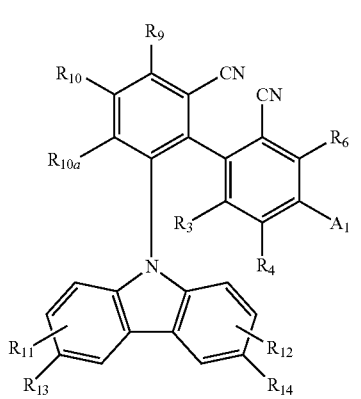
Formula 1C-22
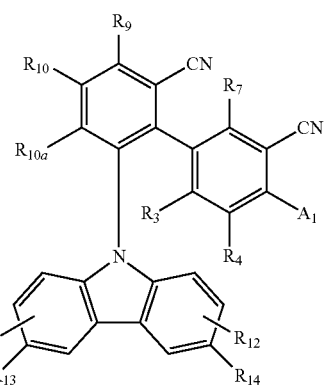
Formula 1C-23
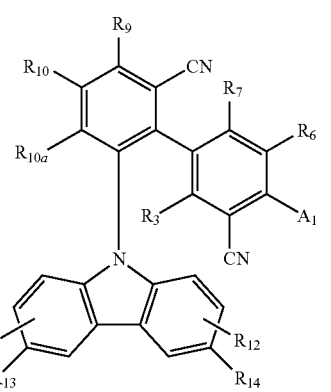
Formula 1C-24
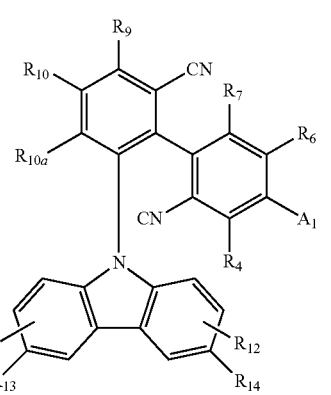
Formula 1C-25
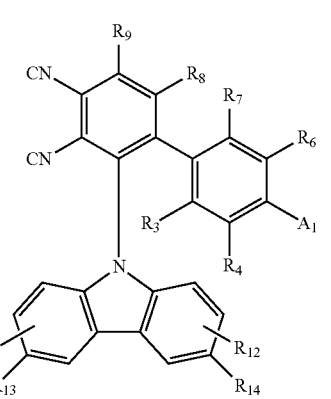

Formula 1C-26
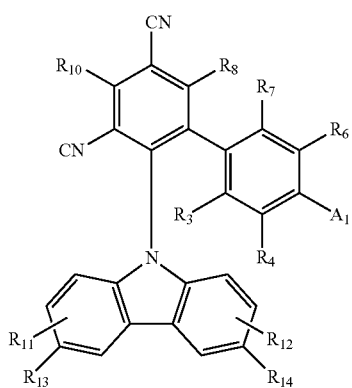
Formula 1C-27
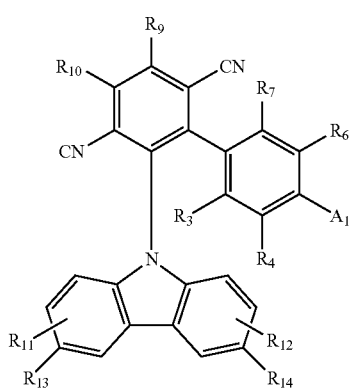
Formula 1C-28
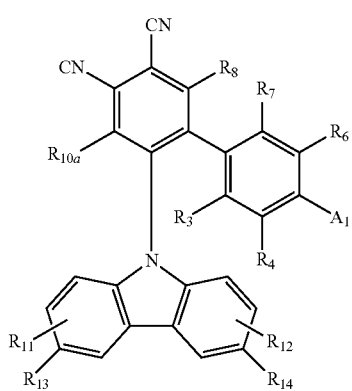
Formula 1C-29
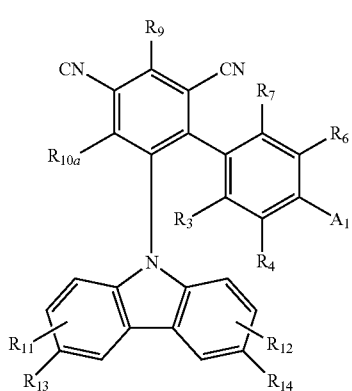
Formula 1C-30
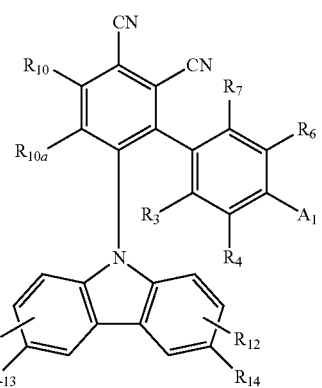
Formula 1C-31
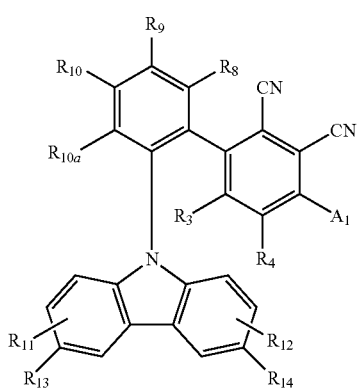
Formula 1C-32
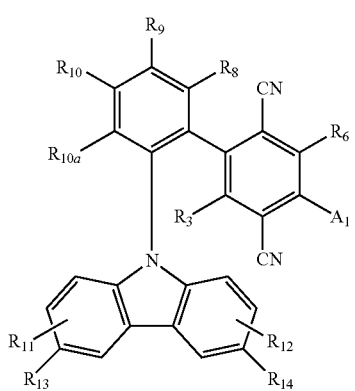
Formula 1C-33
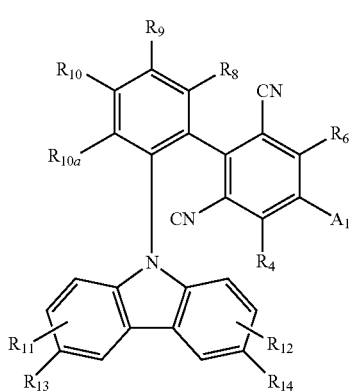

Formula 1C-34
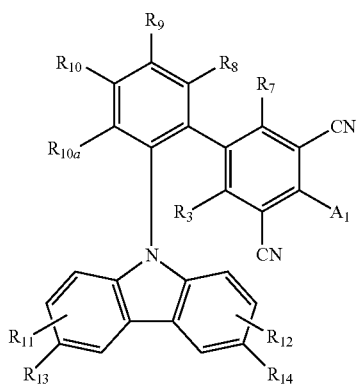
Formula 1C-35
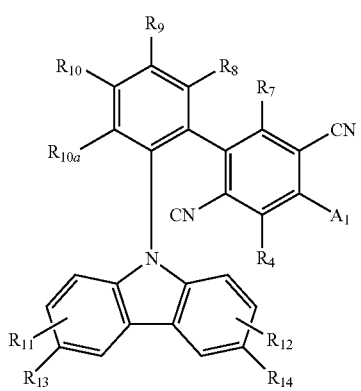
Formula 1C-36
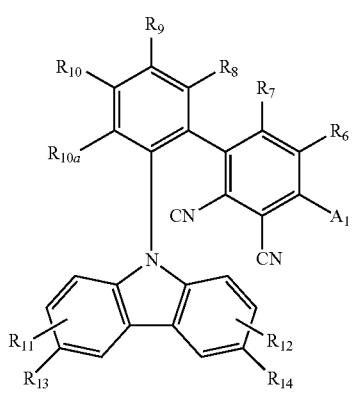
Formula 1C-37
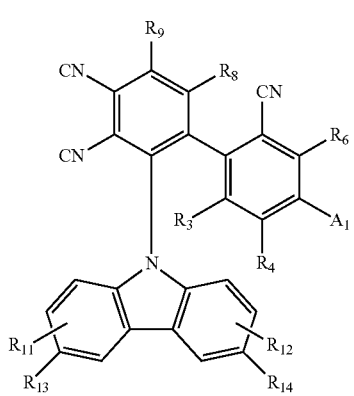
Formula 1C-38
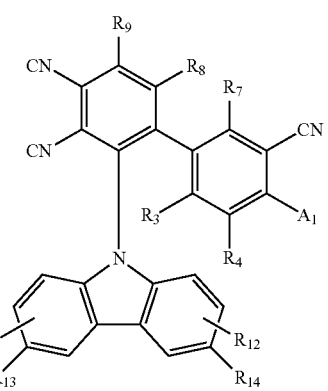
Formula 1C-39
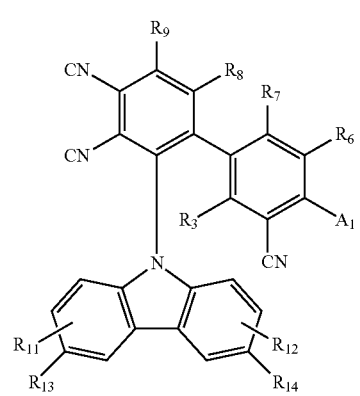
Formula 1C-40
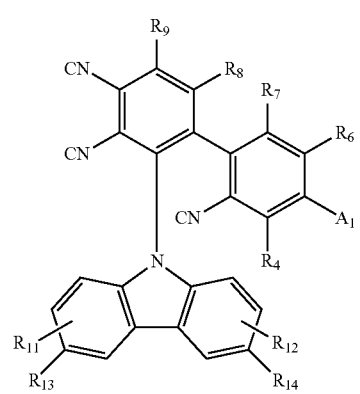
Formula 1C-41
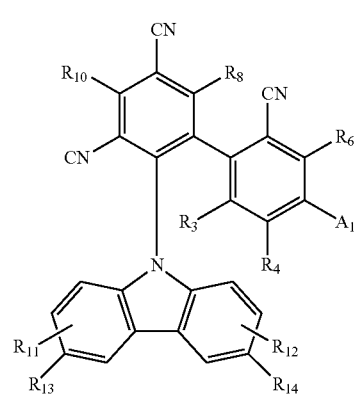

Formula 1C-42
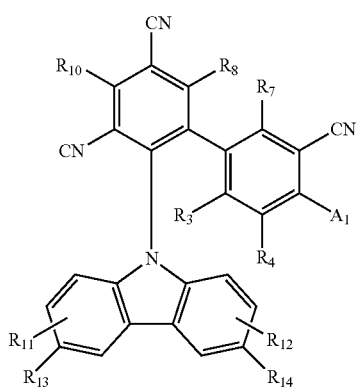
Formula 1C-43
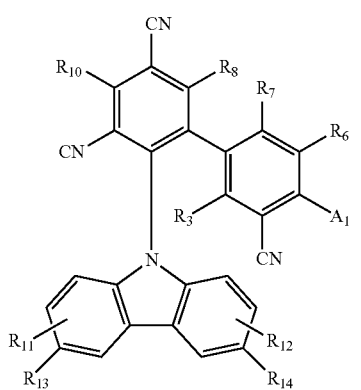
Formula 1C-44
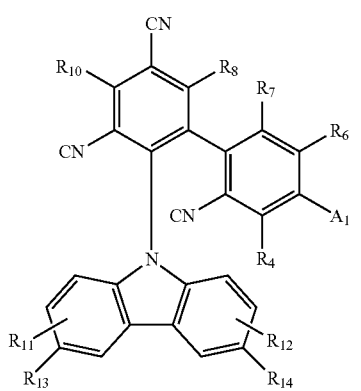
Formula 1C-45
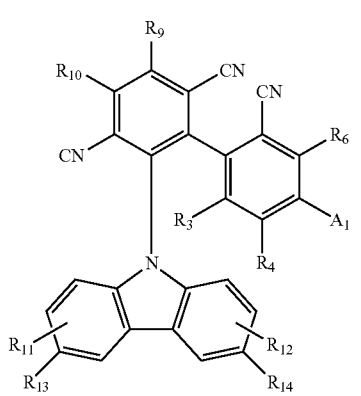
Formula 1C-46
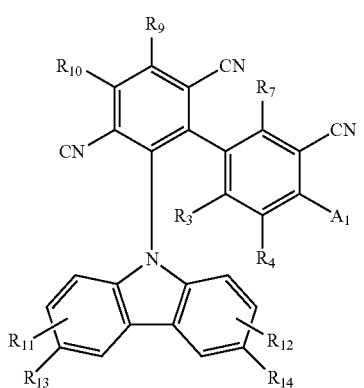
Formula 1C-47
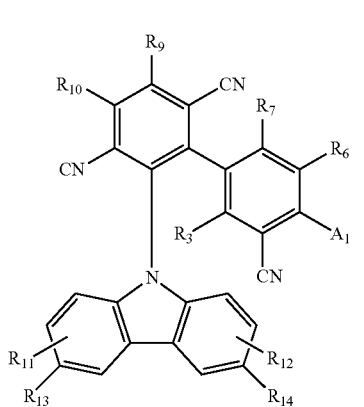
Formula 1C-48
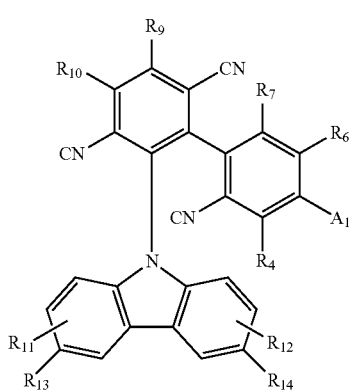
Formula 1B-49
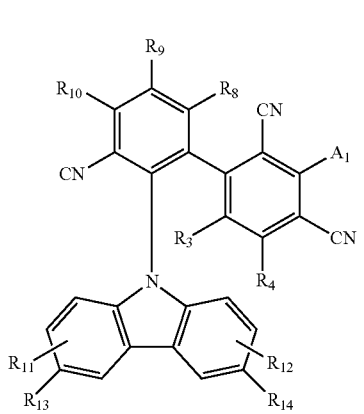

Formula 1B-50
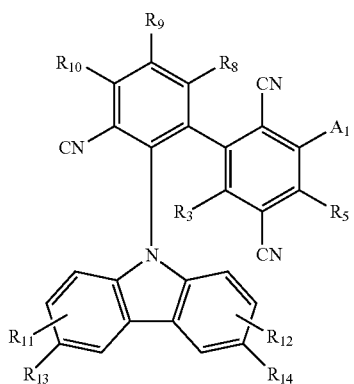
Formula 1B-51
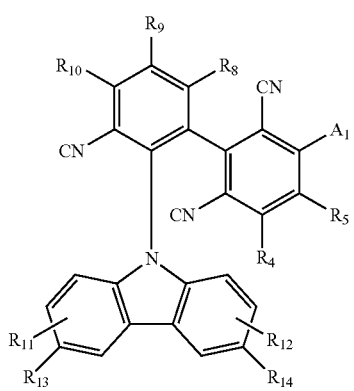
Formula 1B-52
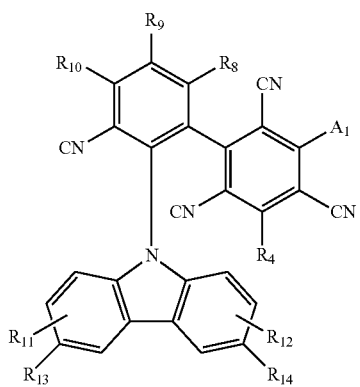
Formula 1B-53
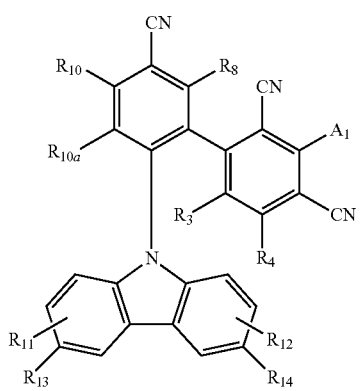
Formula 1B-54
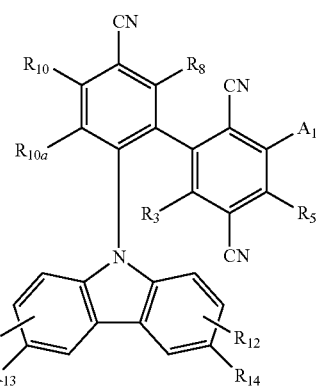
Formula 1B-55
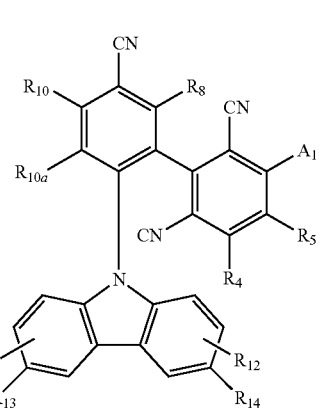
Formula 1B-56
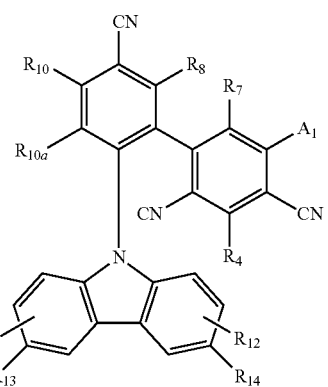
Formula 1A-57
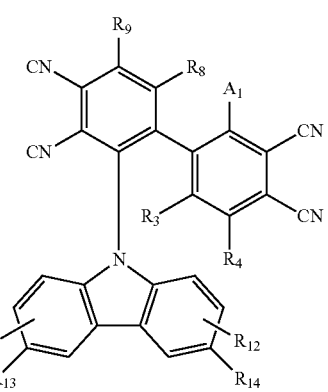

Formula 1A-58
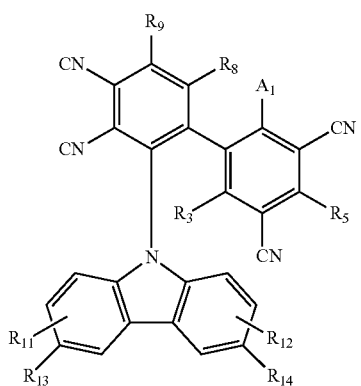
Formula 1A-59
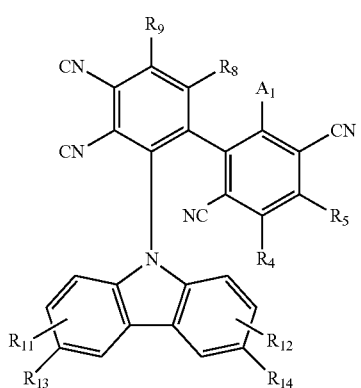
Formula 1A-60
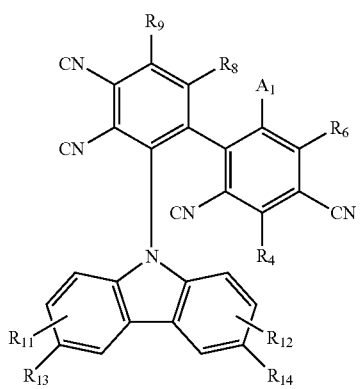
Formula 1A-61
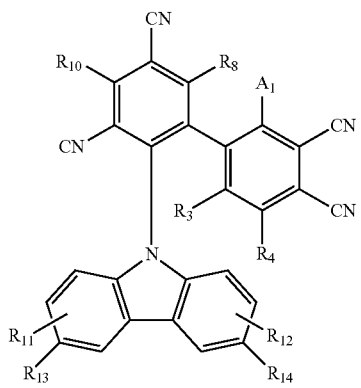
Formula 1A-62
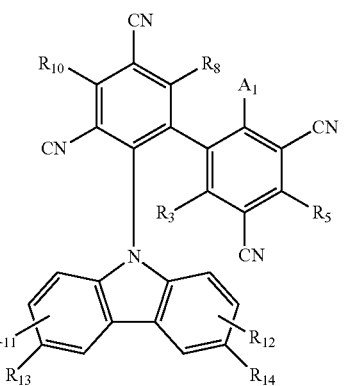
Formula 1A-63
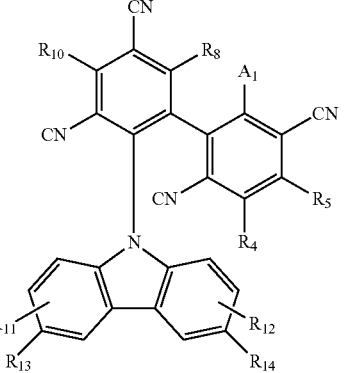
Formula 1A-64
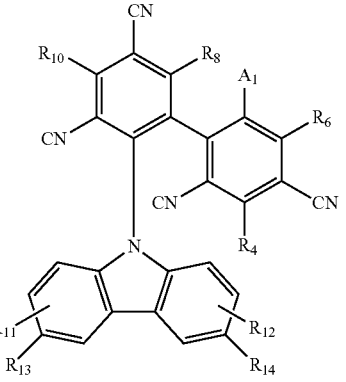
Formula 1C-65
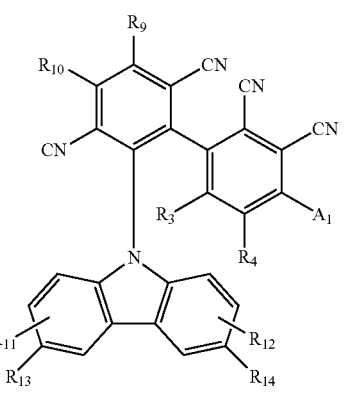

Formula 1C-66
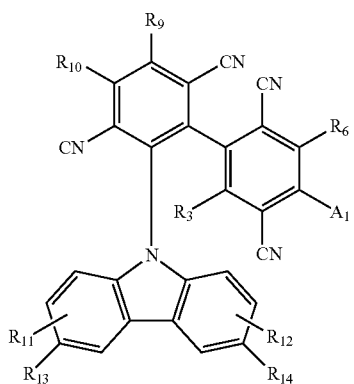
Formula 1C-67
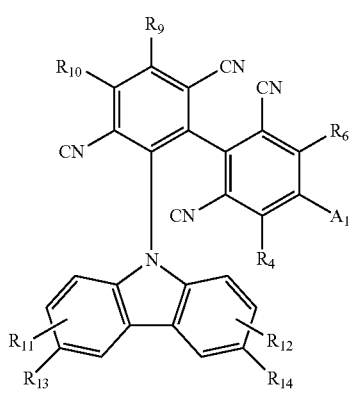
Formula 1C-68
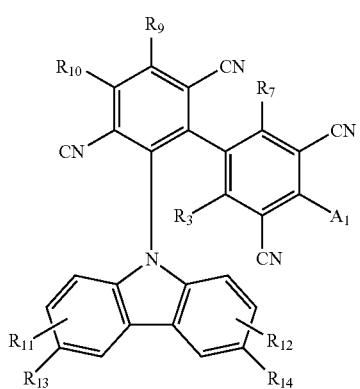
Formula 1C-69
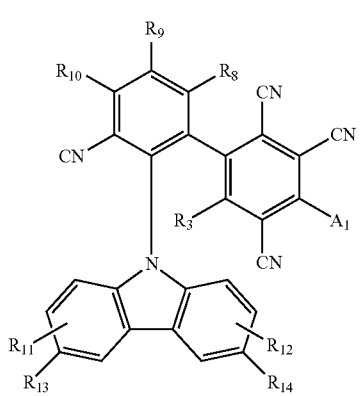
Formula 1C-70
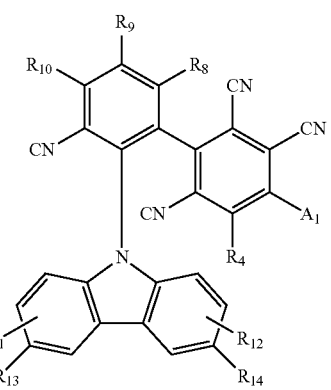
Formula 1C-71
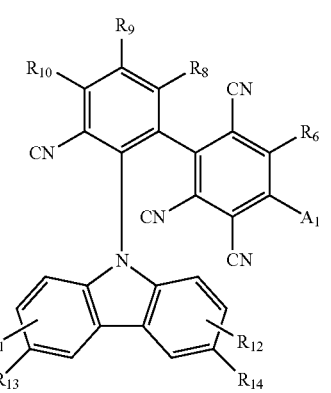
Formula 1C-72
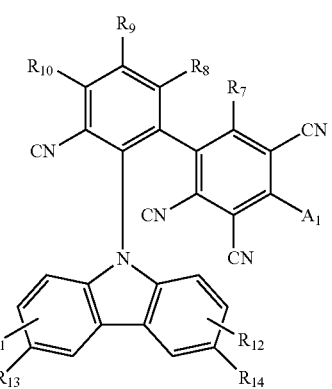
Formula 1C-73
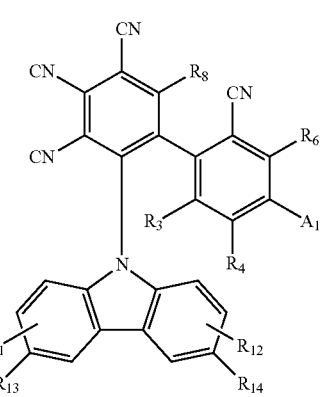

Formula 1C-74

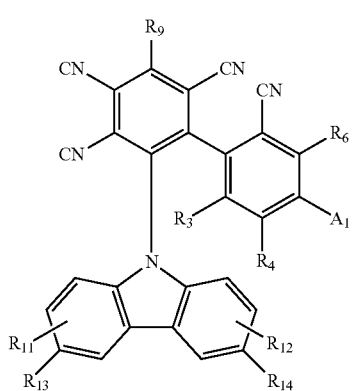

Formula 1C-75

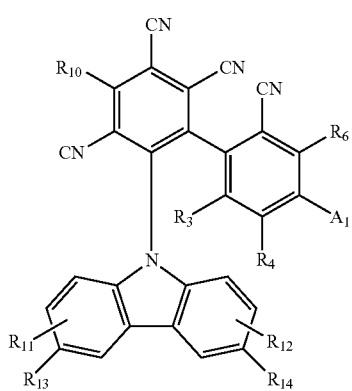

Formula 1C-76

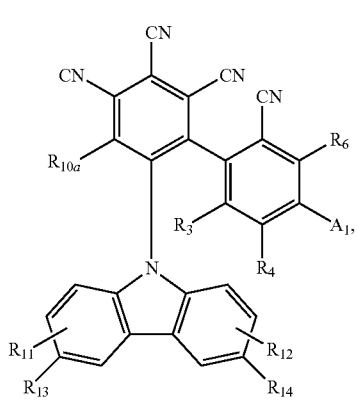

wherein, in Formulae 1A-1 to 1A-76, 1B-1 to 1B-76, and 1C-1 to 1C-76, $A_1$, $R_{11}$, and $R_{12}$ are each independently the same as defined in claim 1, $R_8$ to $R_{10}$, and $R_{10a}$ are each independently the same as defined in connection with $R_1$ in claim 1, $R_3$ to $R_7$ are each independently the same as defined in connection with $R_2$ in claim 1, $R_{13}$ is the same as defined in connection with $R_{11}$ in claim 1, and $R_{14}$ is the same as defined in connection with $R_{12}$ in claim 1.

11. The condensed cyclic compound of claim 10, wherein $R_3$ to $R_{10}$ and $R_{10a}$ in Formulae 1A-1 to 1A-76, 1B-1 to 1B-76, and 1C-1 to 1C-76 are each independently selected from:

hydrogen, deuterium, —F, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one of deuterium and —F.

12. The condensed cyclic compound of claim 1, wherein the condensed cyclic compound is selected from Compounds 1 to 330:

1

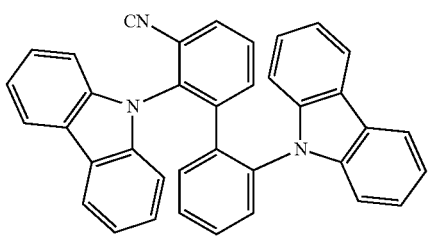

2

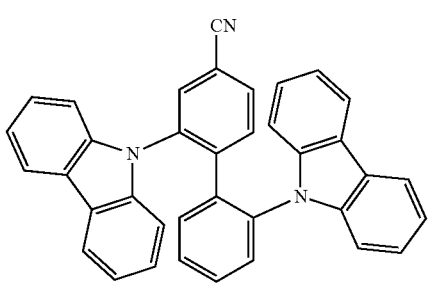

3

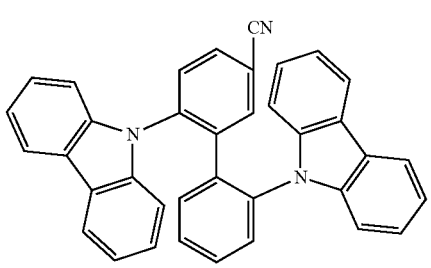

4

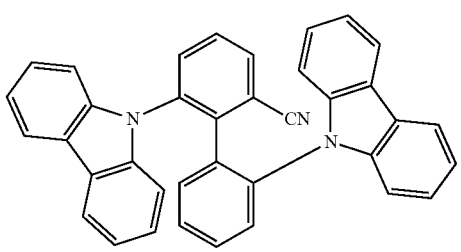

5

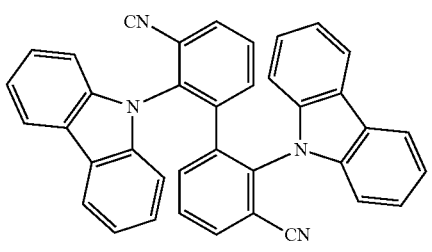

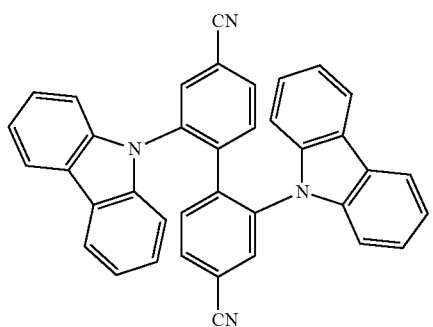
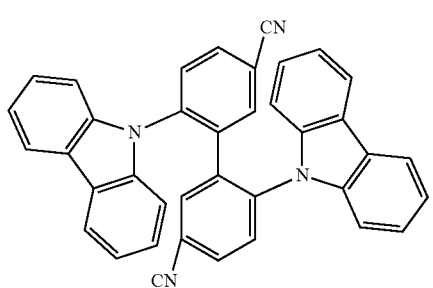
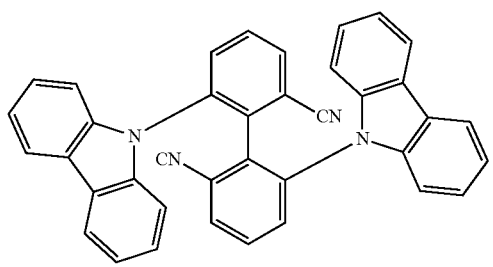
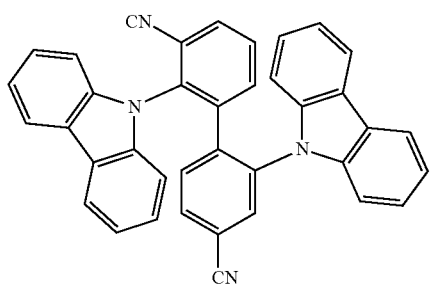
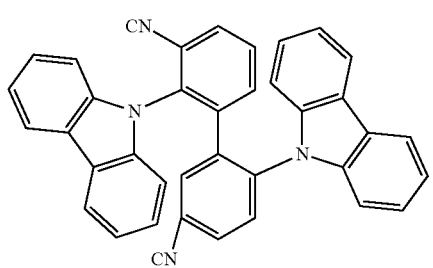
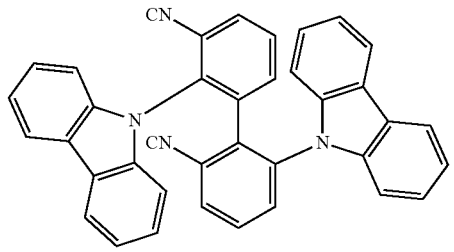
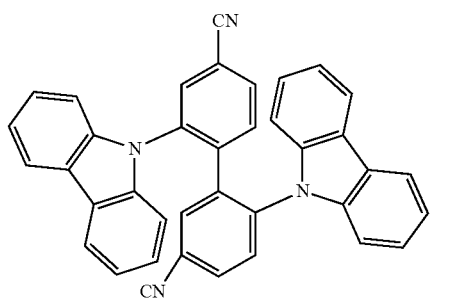
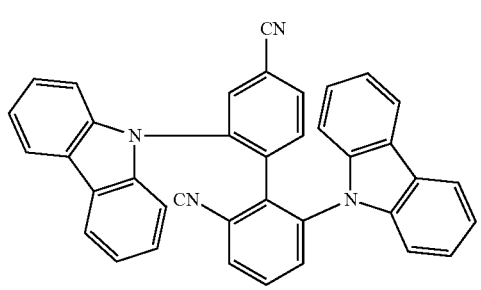
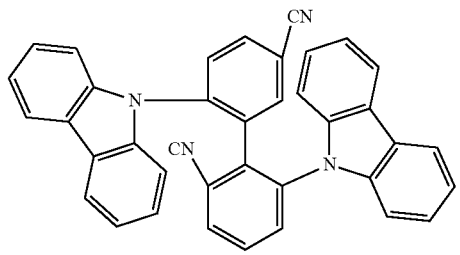
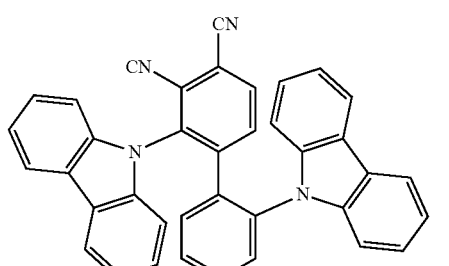
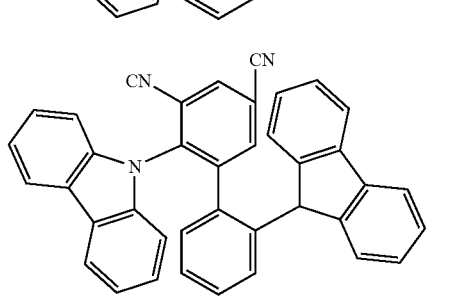

17
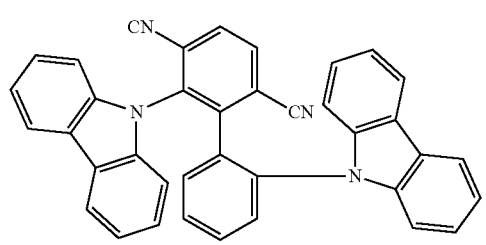
18
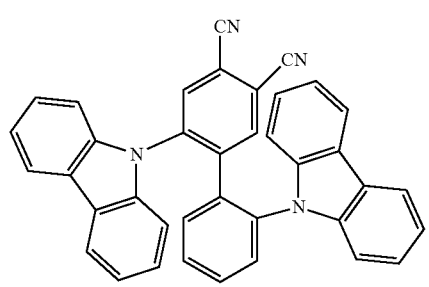
19
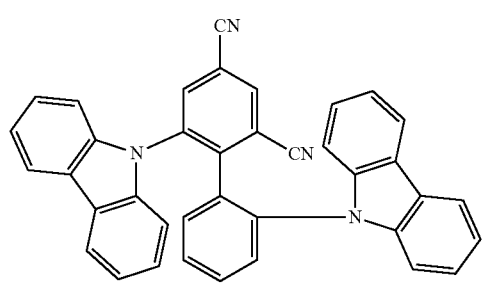
20
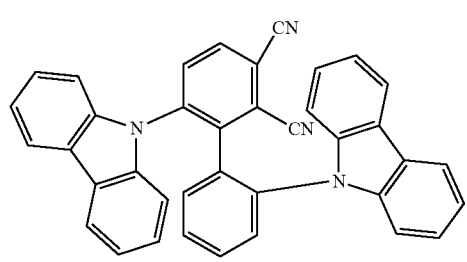
21
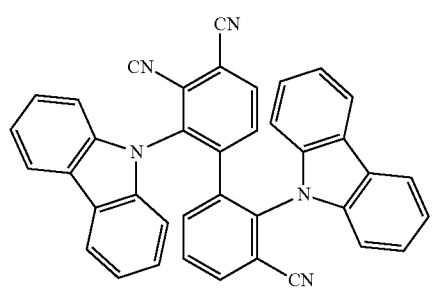
22
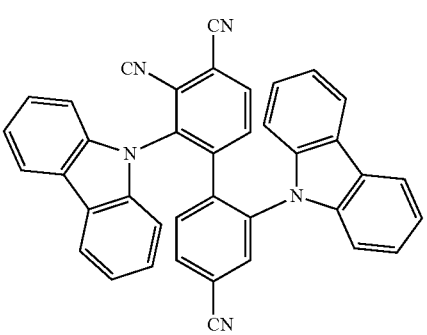
23
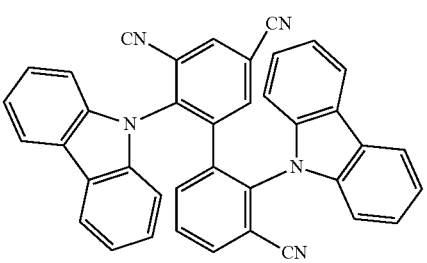
24
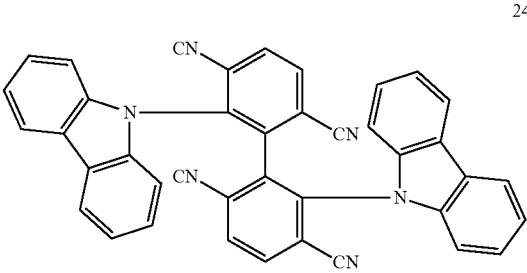
25
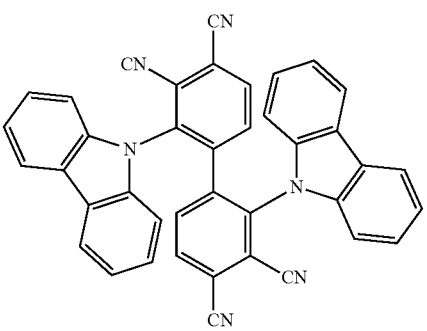
26
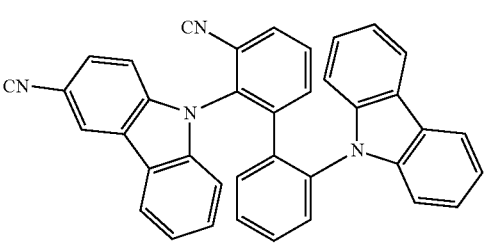

27
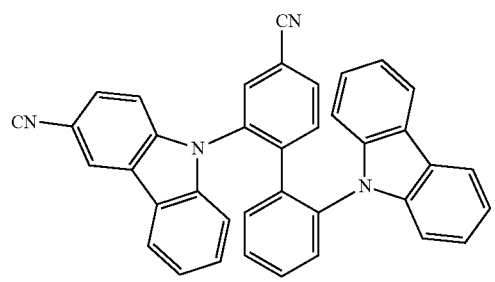
28
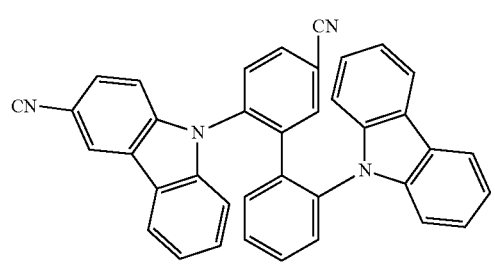
29
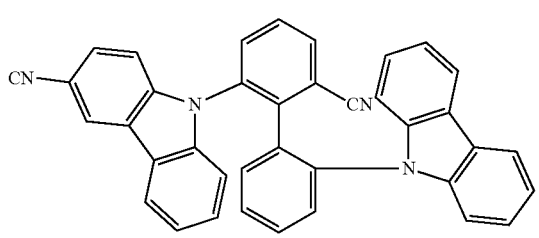
30
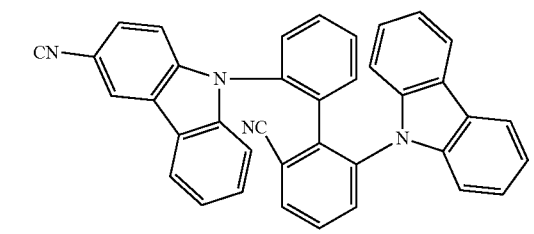
31
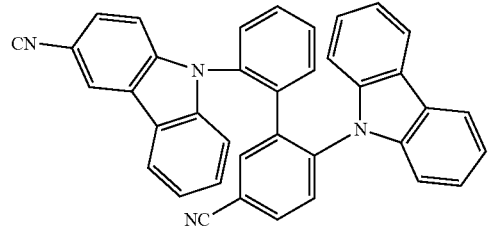
32
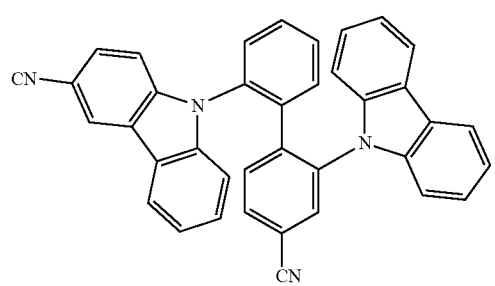
33
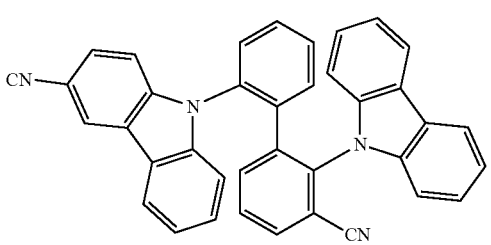
34
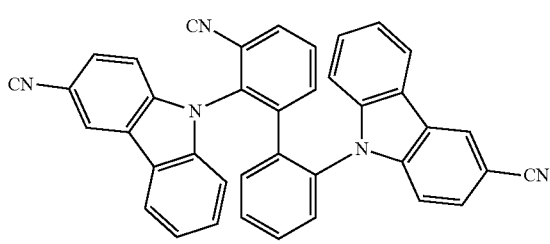
35
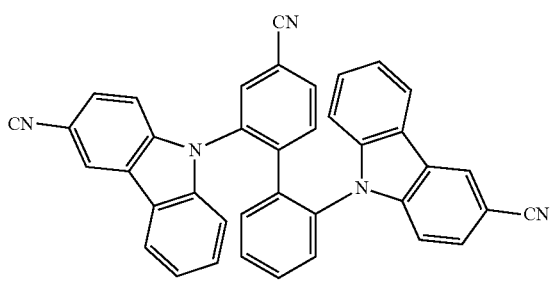
36
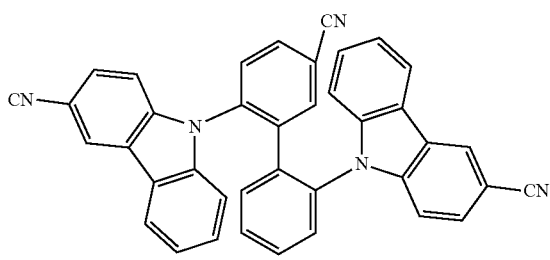
37
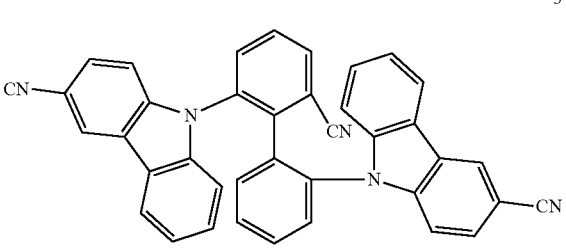
38
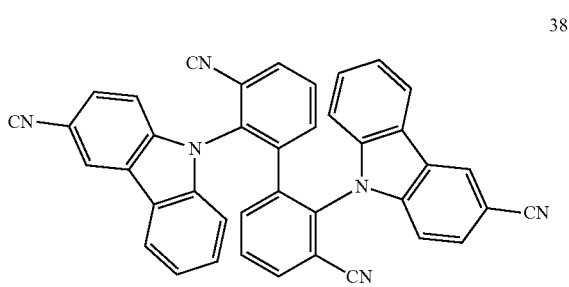

-continued
39
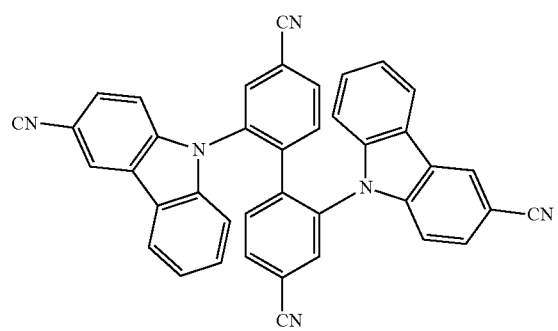
40
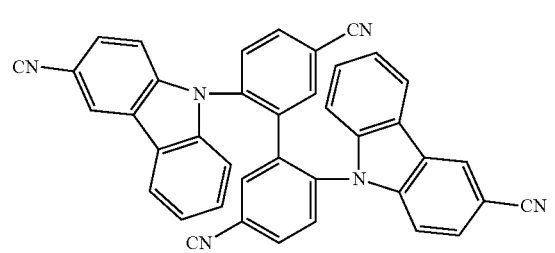
41
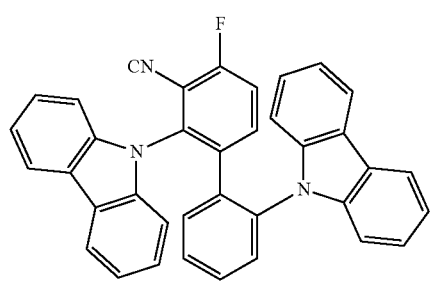
42
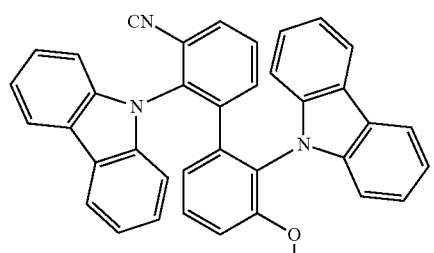
43
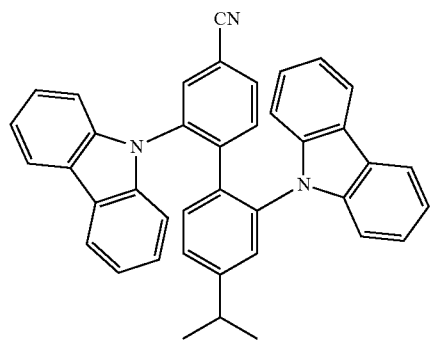
-continued
44
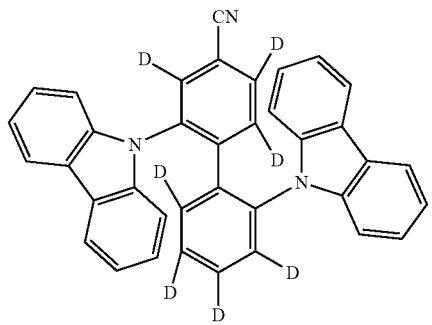
45
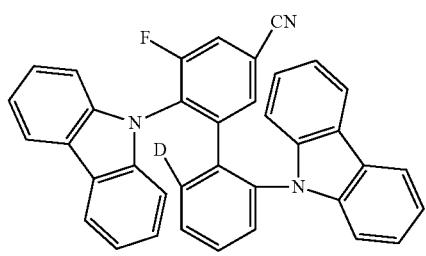
46
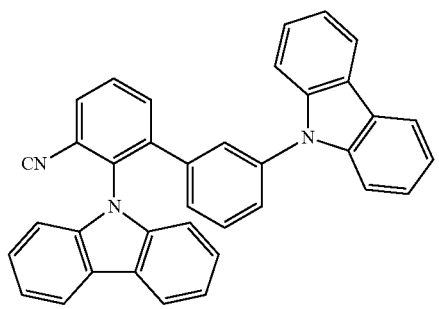
47
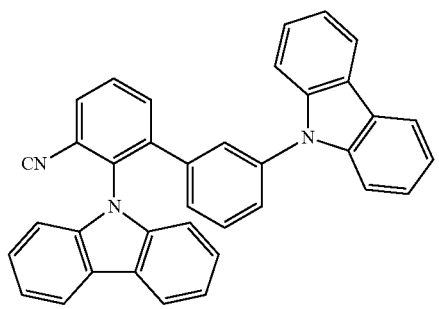
48

49
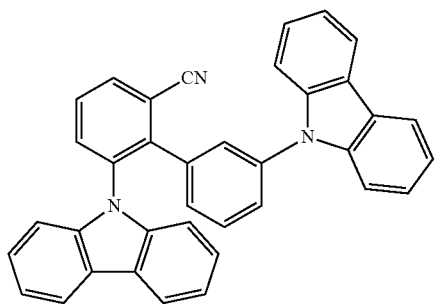
50
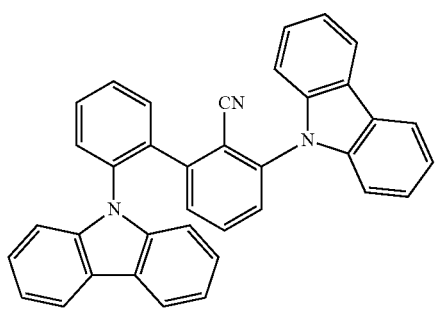
51
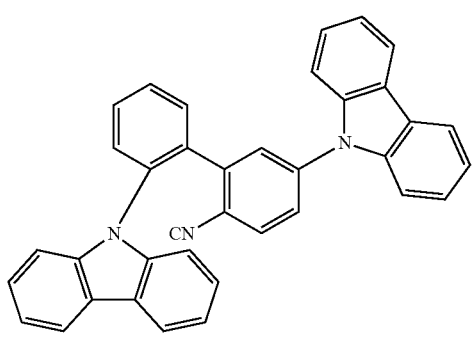
52
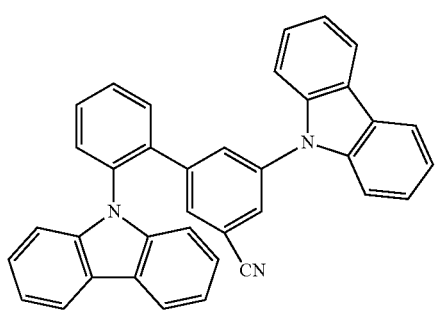
53
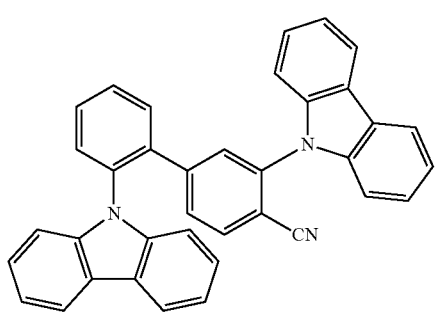
54
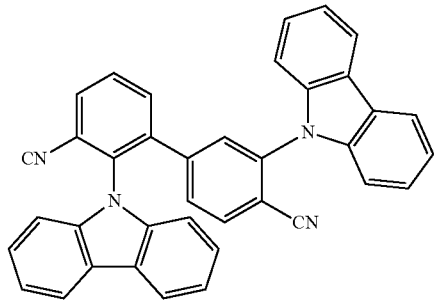
55
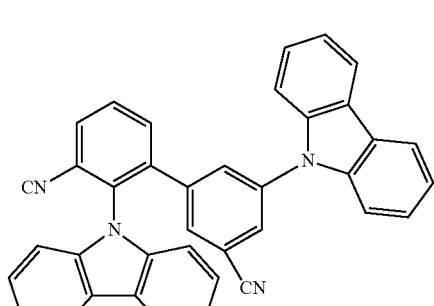
56
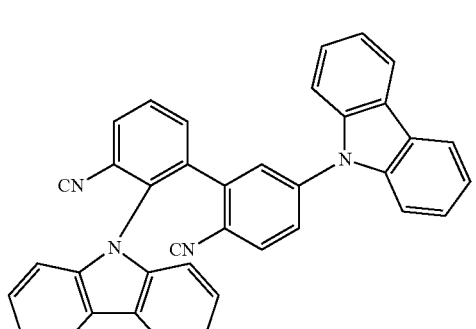
57
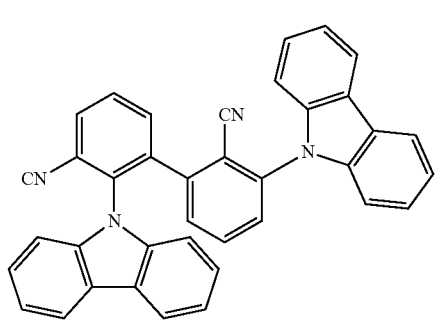
58
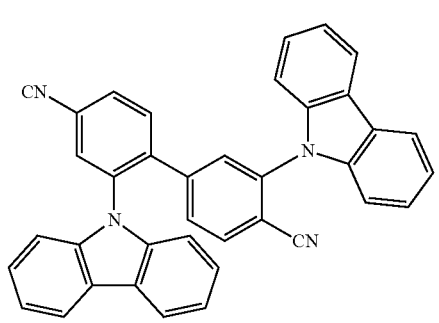

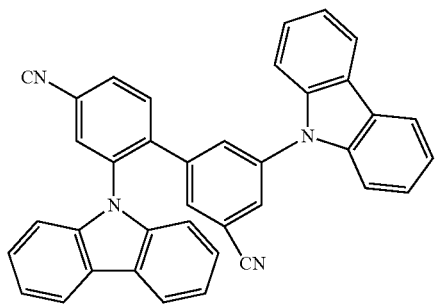
59
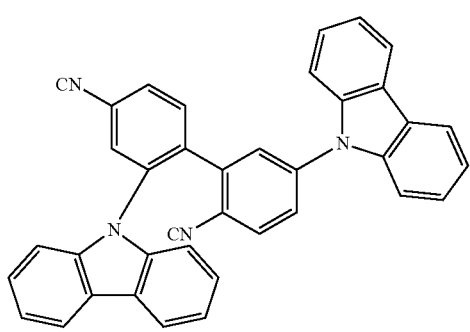
60
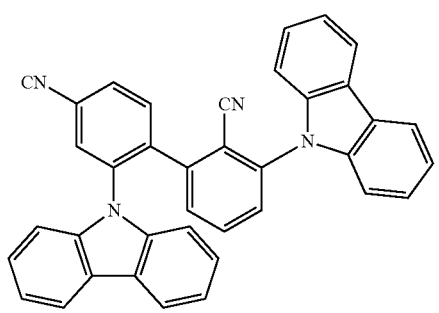
61
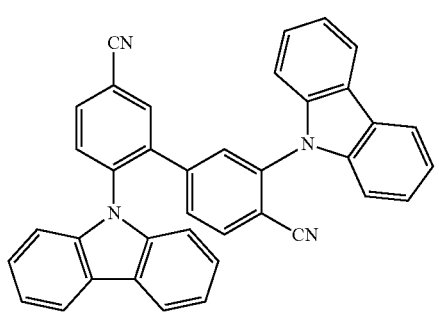
62
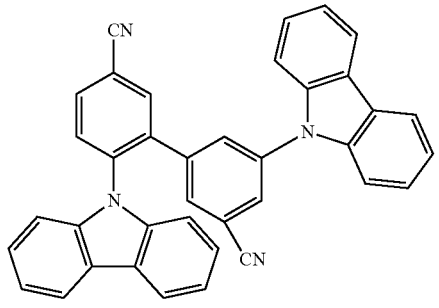
63
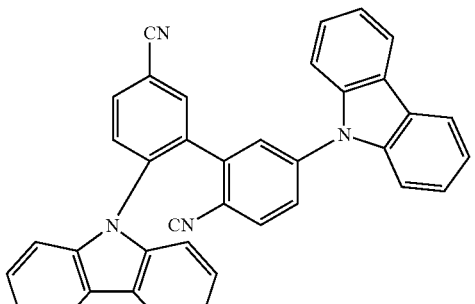
64
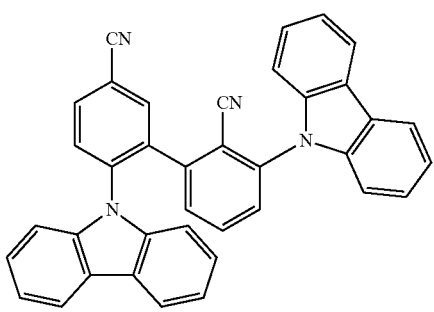
65
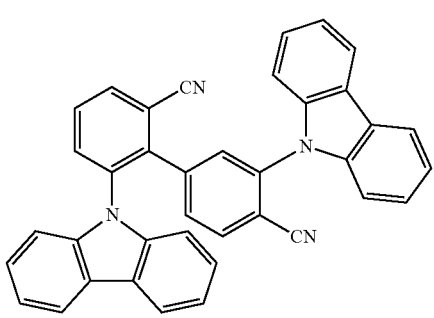
66
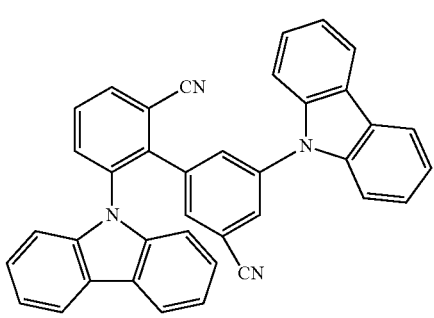
67
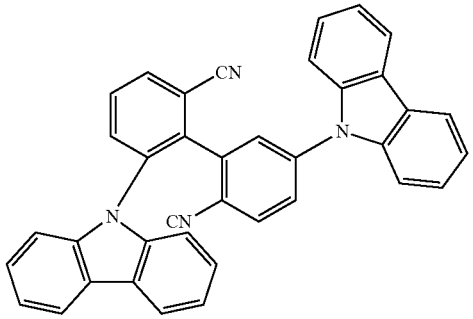
68

335
-continued
69
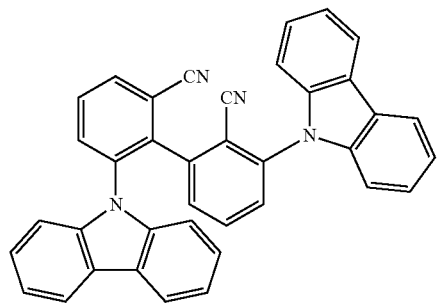
70
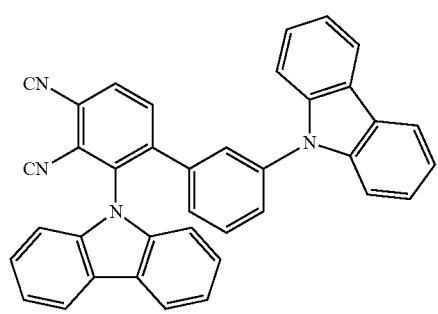
71
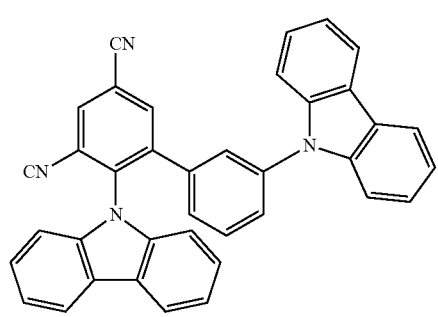
72
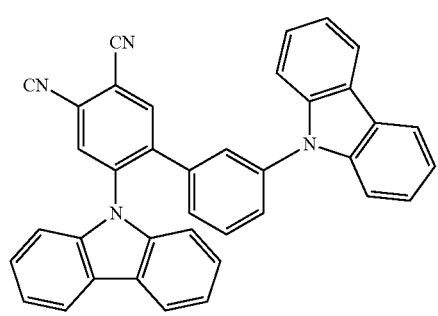
73
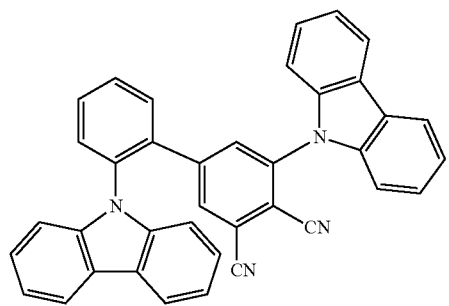
336
-continued
74
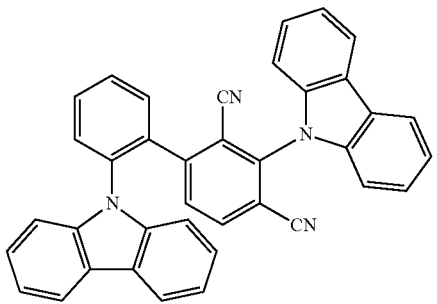
75
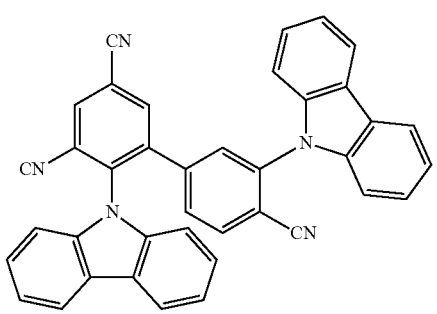
76
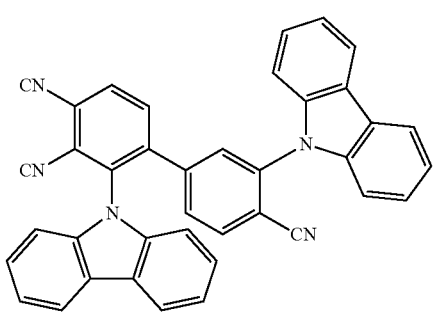
77
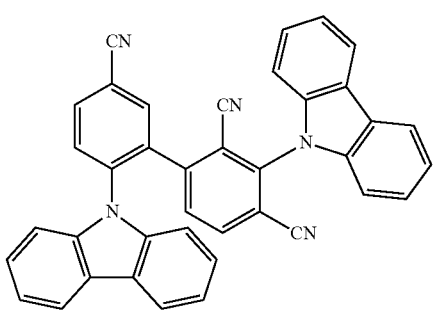
78
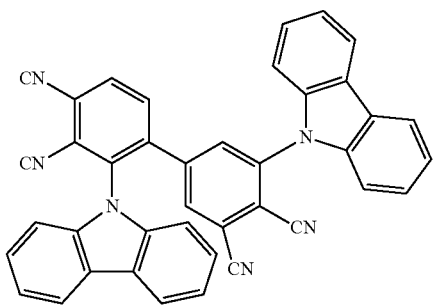

79
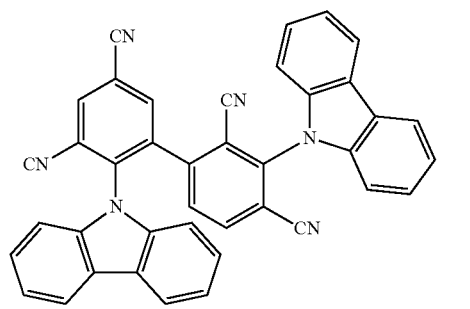
80
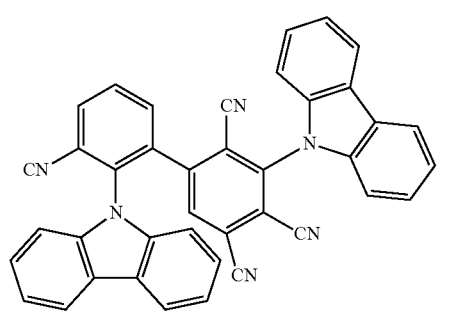
81
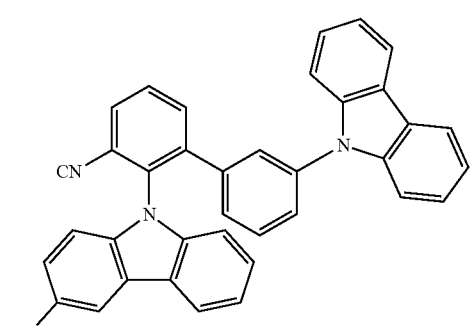
82
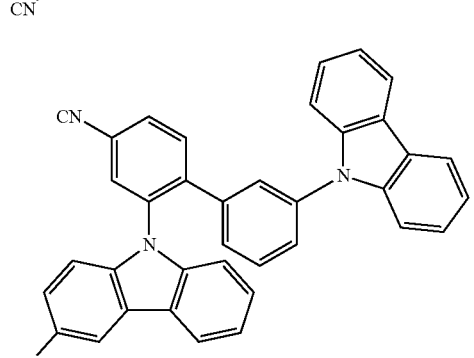
83
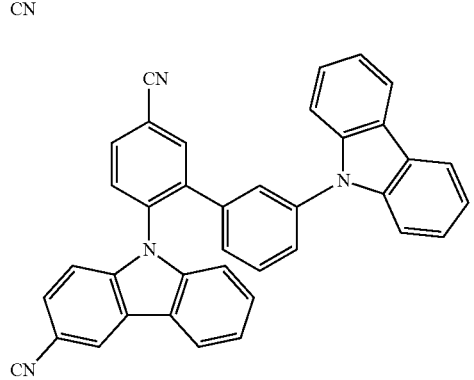
84
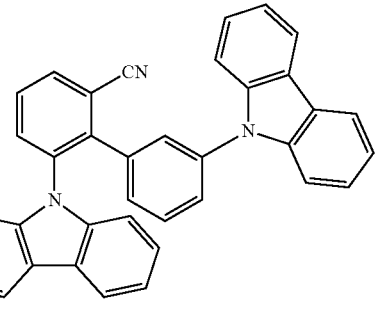
85
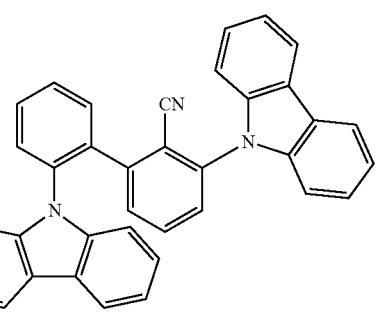
86
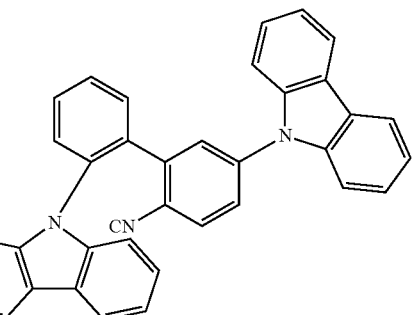
87
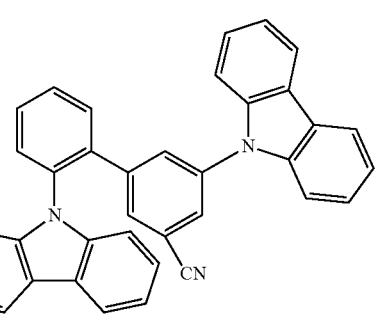

88
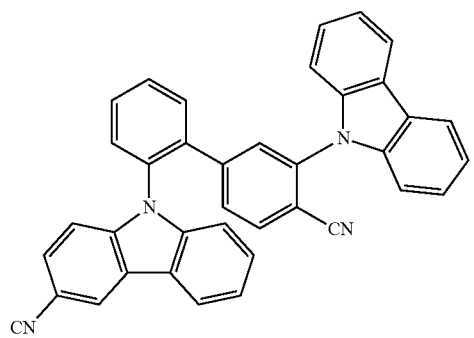
89
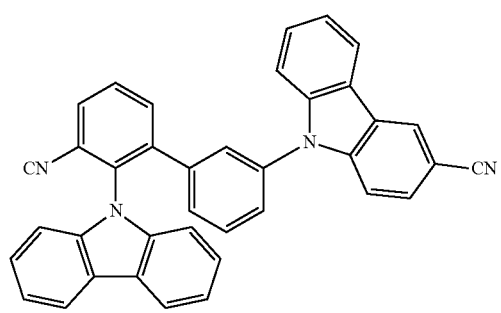
90
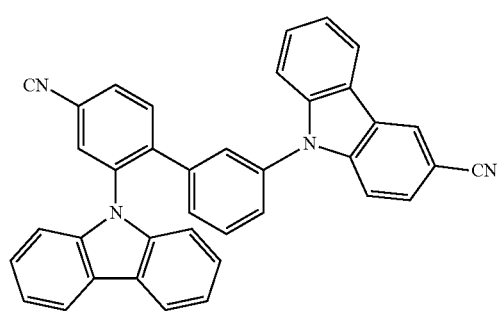
91
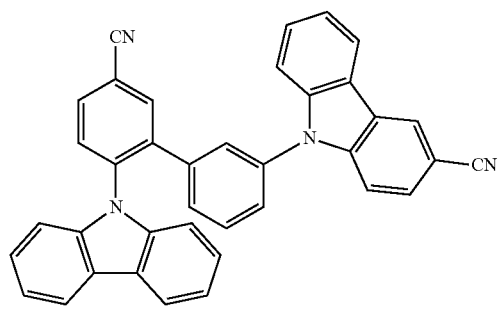
92
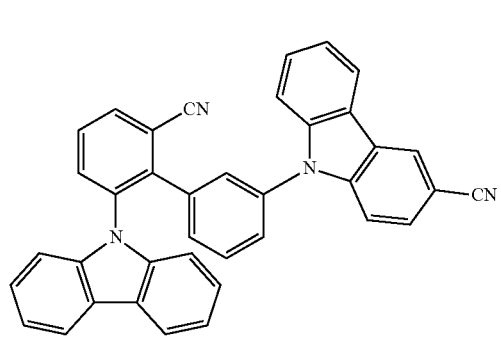
93
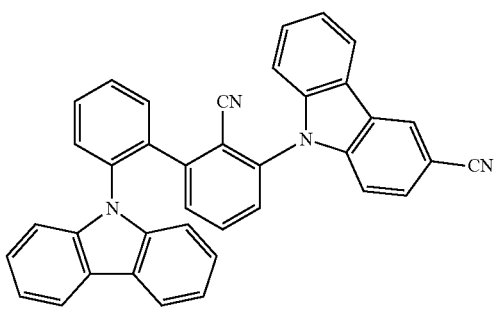
94
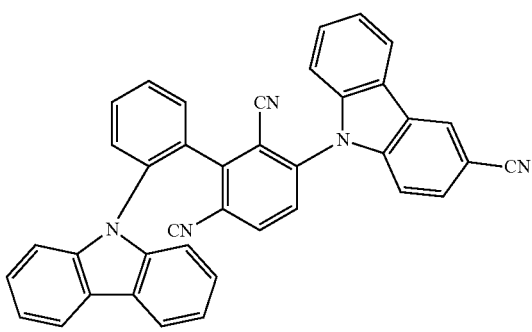
95
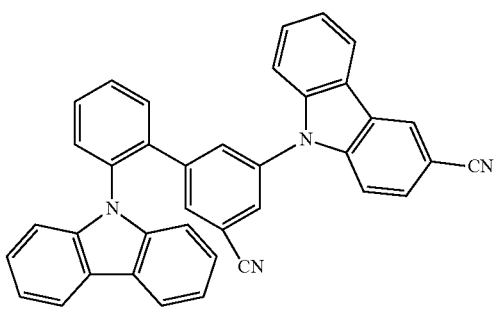
96
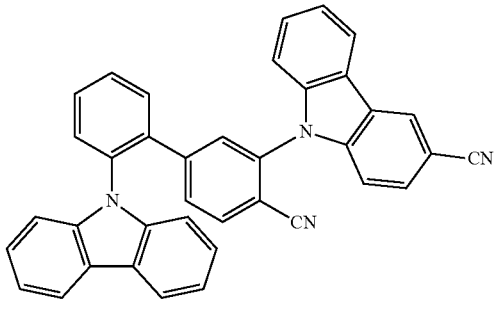
97
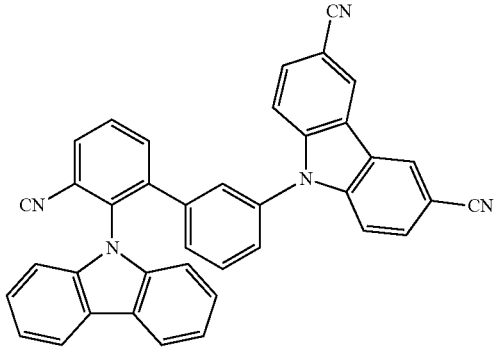

98
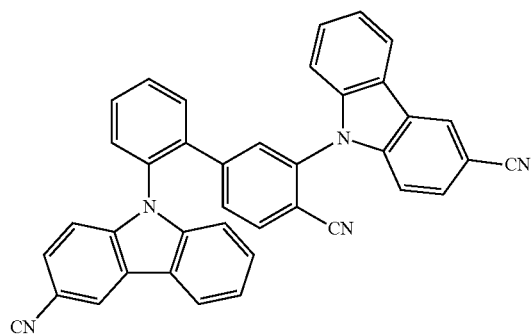
99
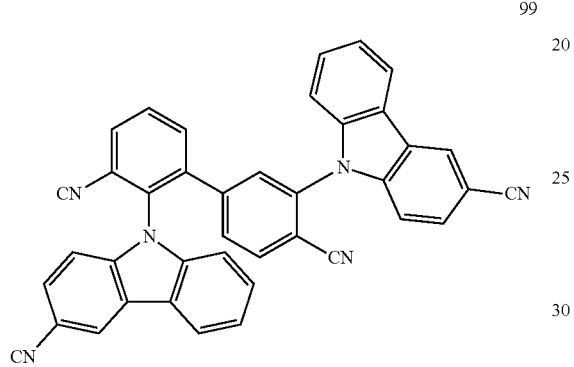
100
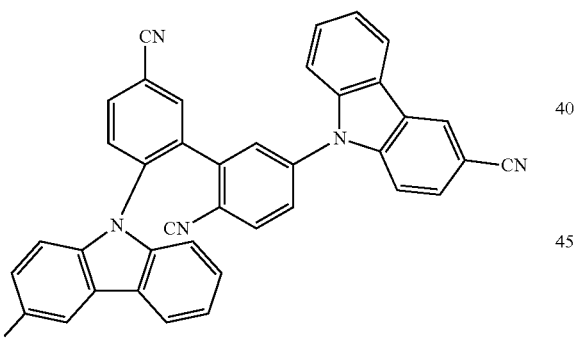
101
102
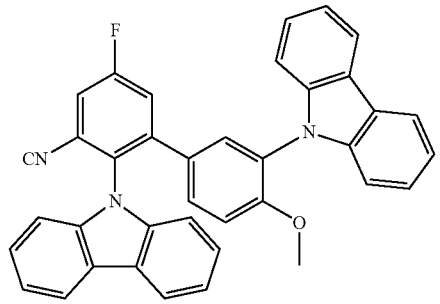
103
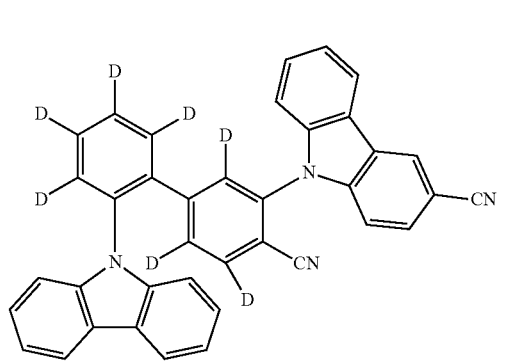
104
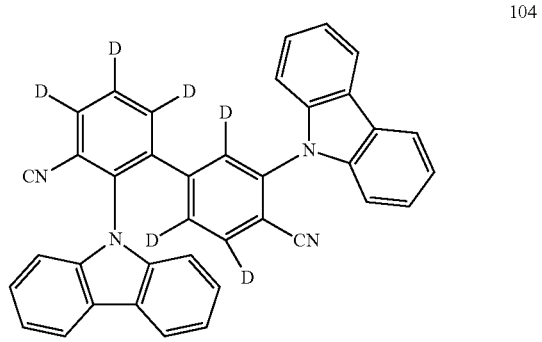
105
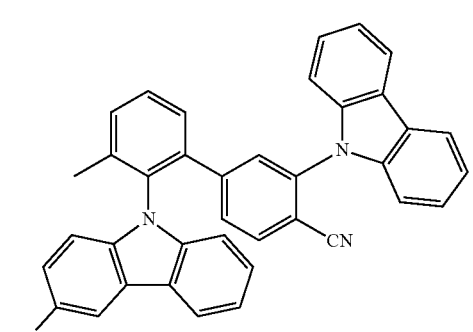
106
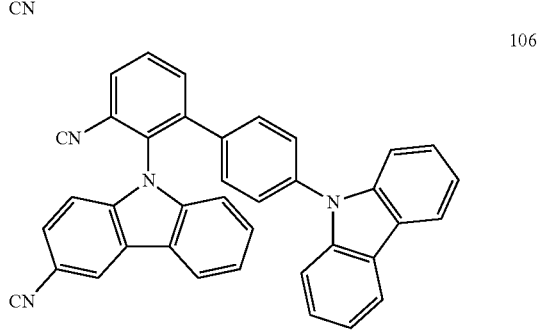

107
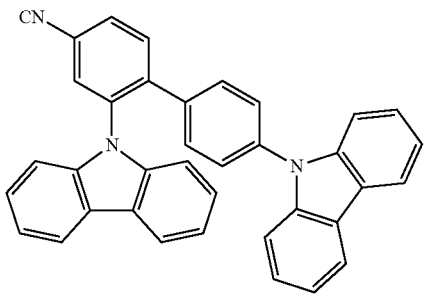
108
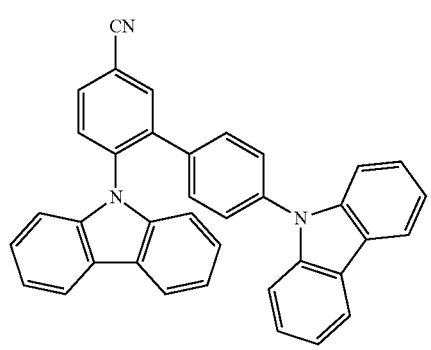
109
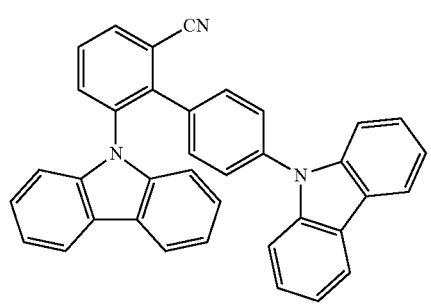
110
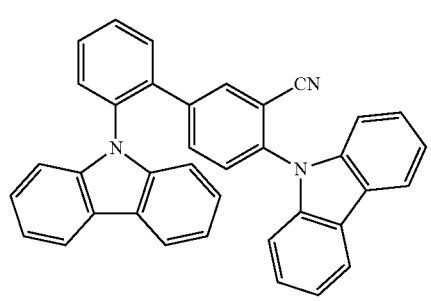
111
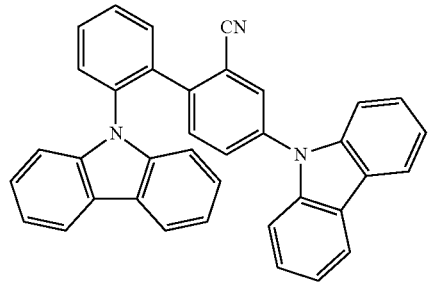
112
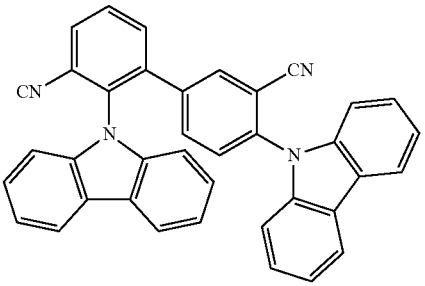
113
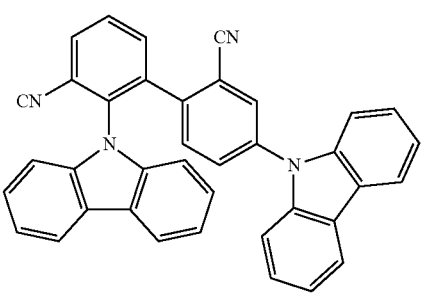
114
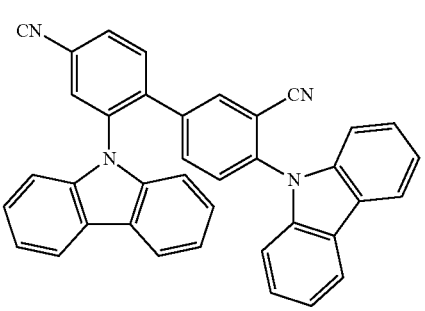
115
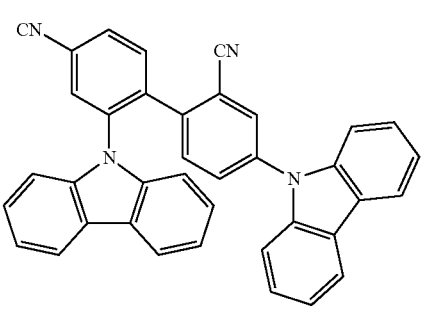
116
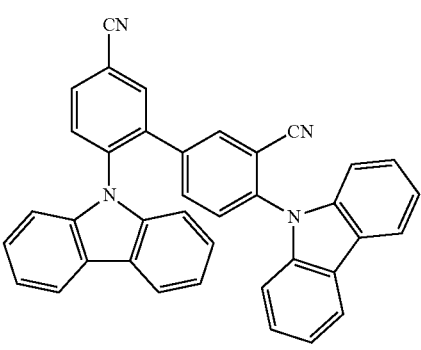

117
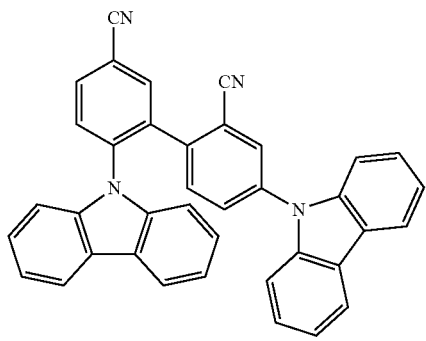
118
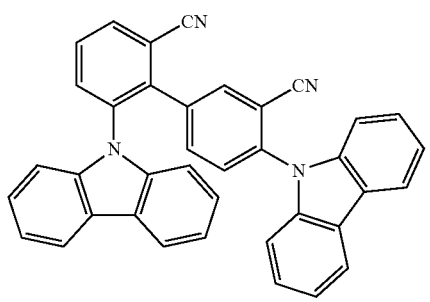
119
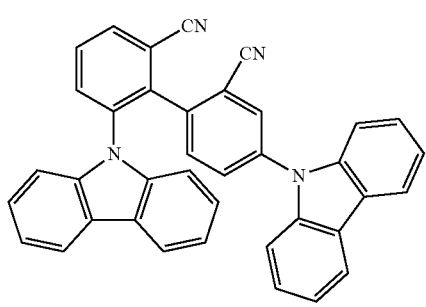
120
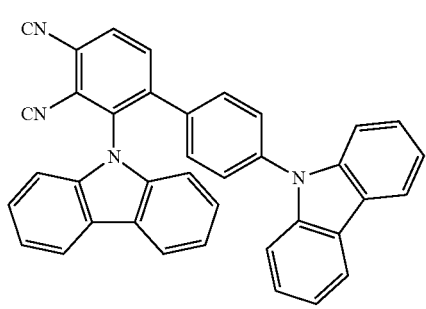
121
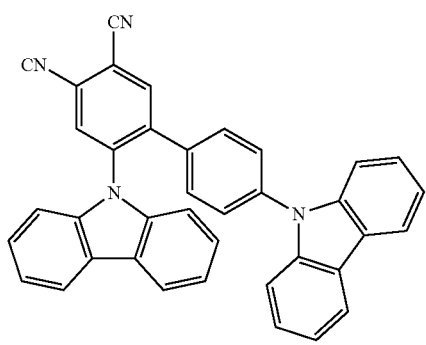
122
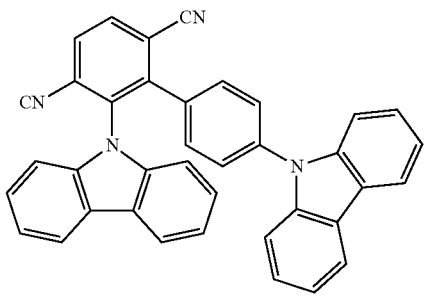
123
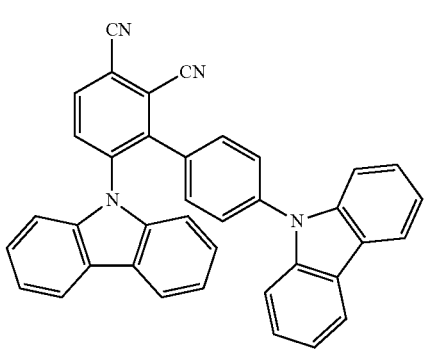
124
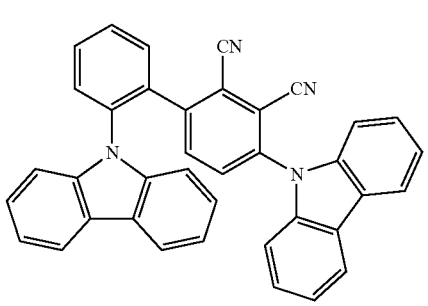
125
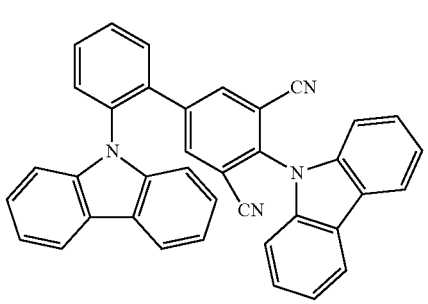
126
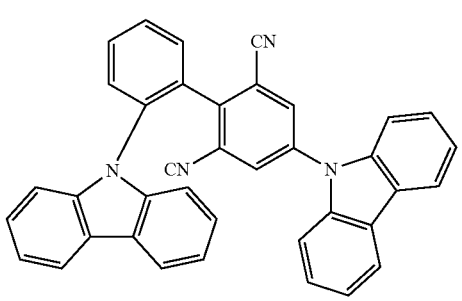

127
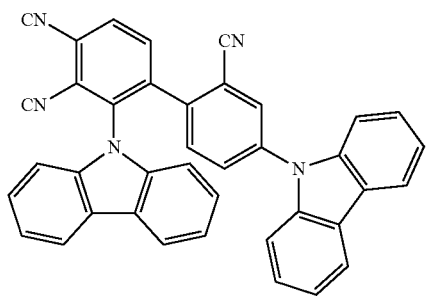
128
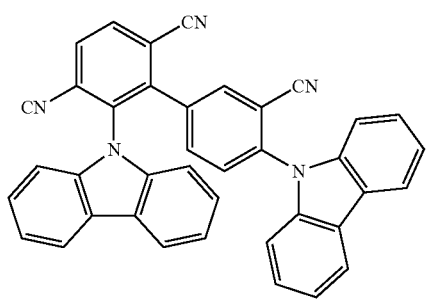
129
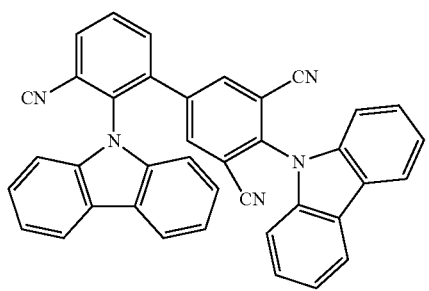
130
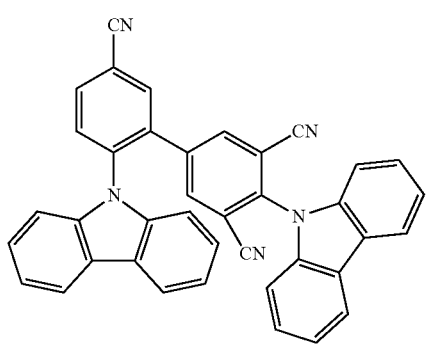
131
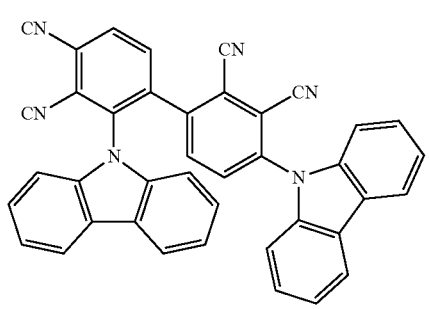
132
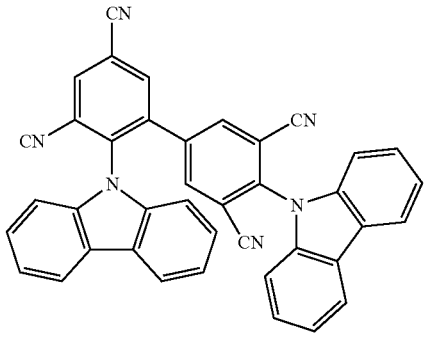
133
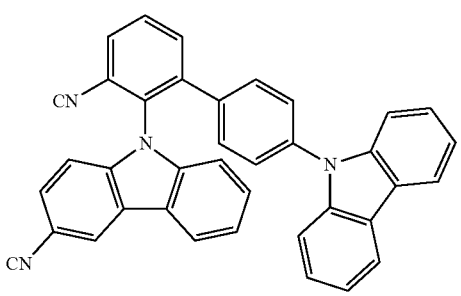
134
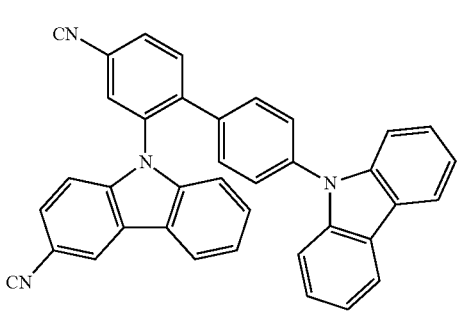
135
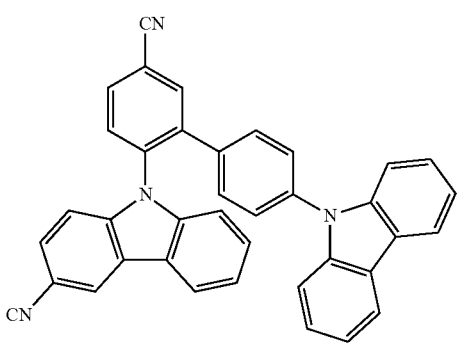
136
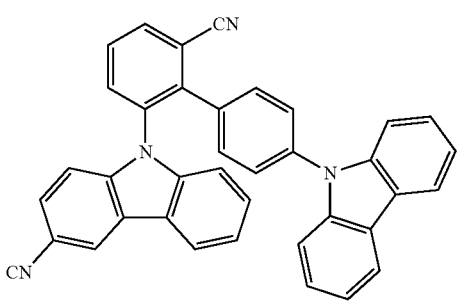

137
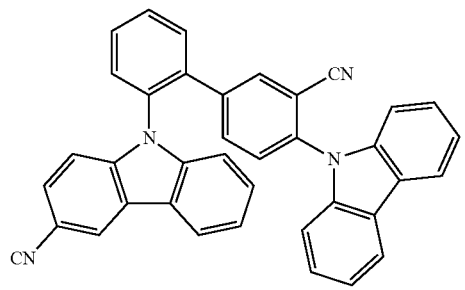
138
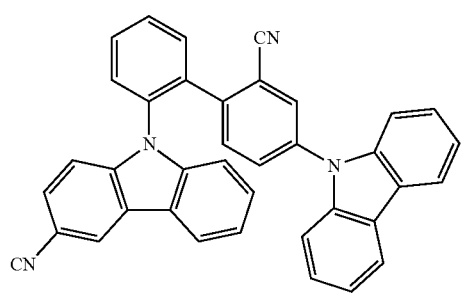
139
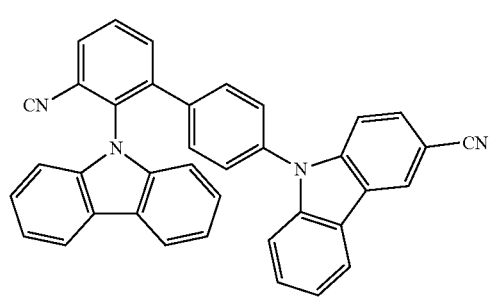
140
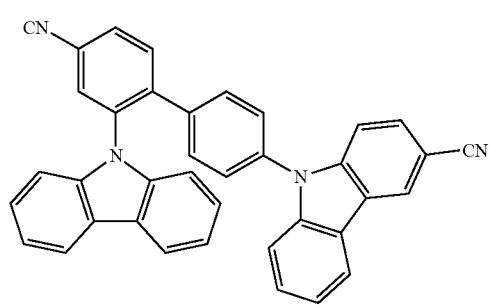
141
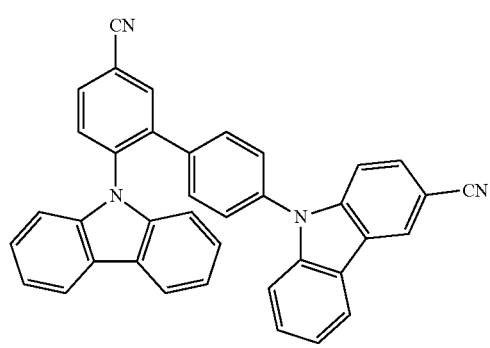
142
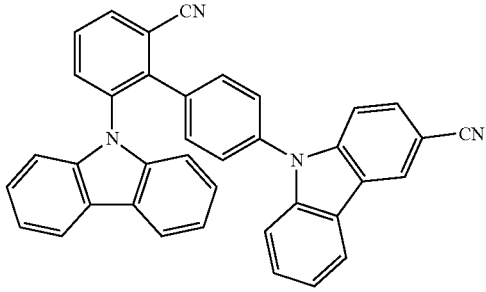
143
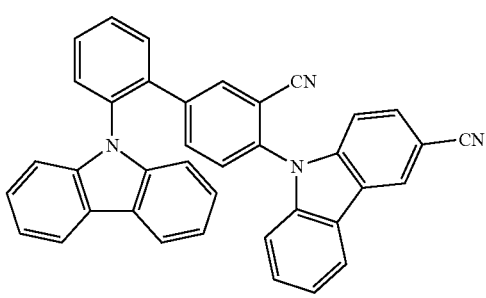
144
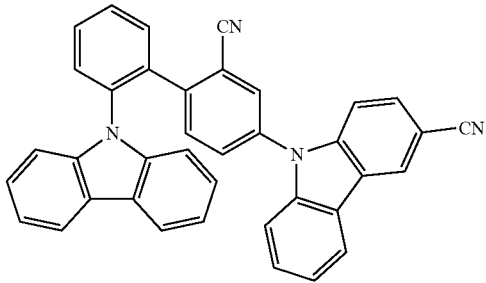
145
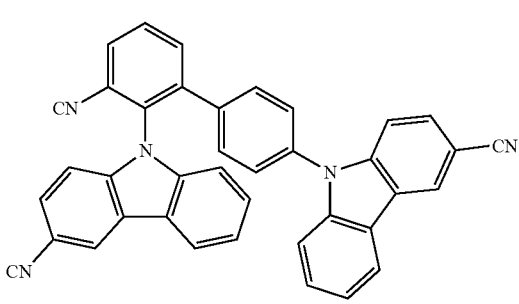
146
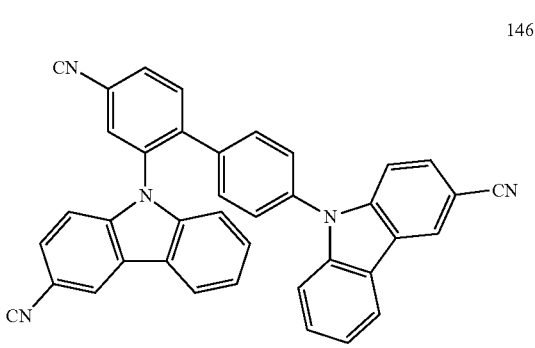

351
-continued
147
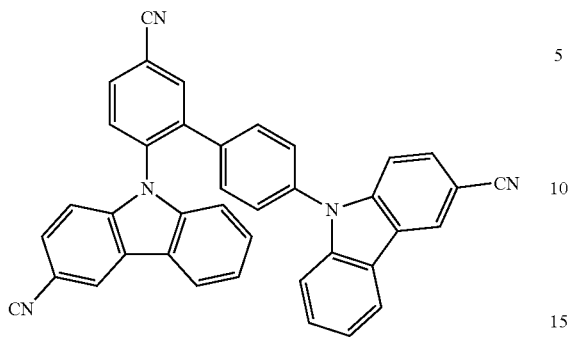
148
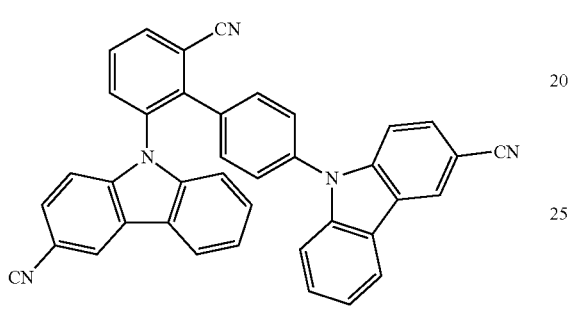
149
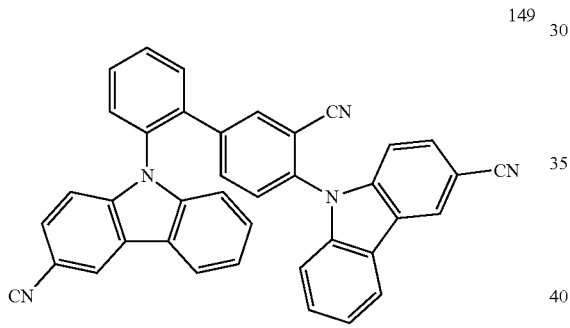
150
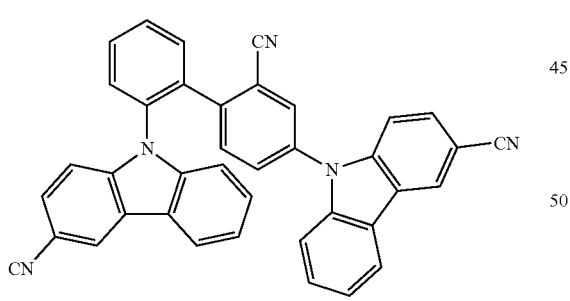
151
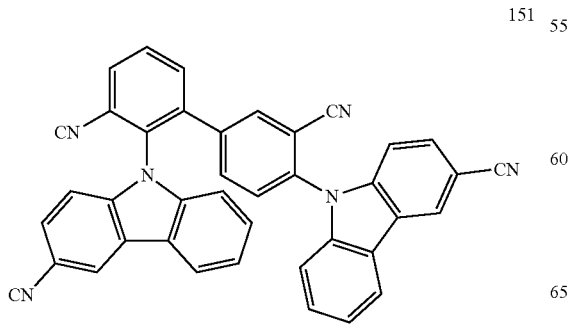
352
-continued
152
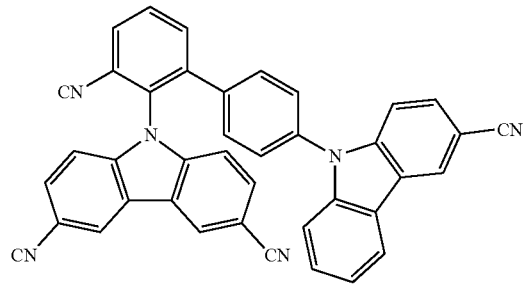
153
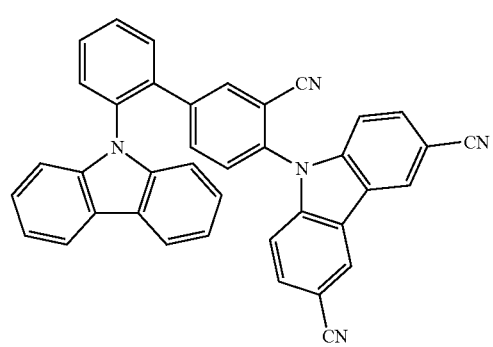
154
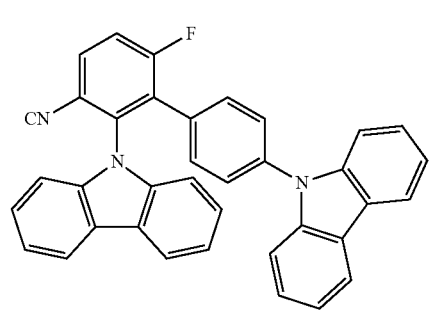
155
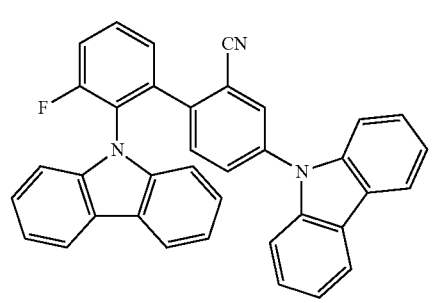
156
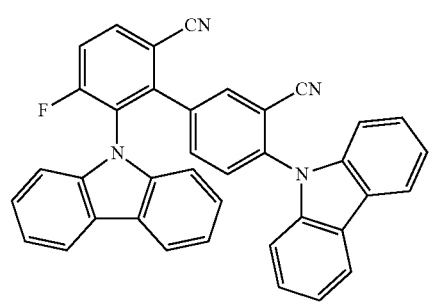

353
-continued
157
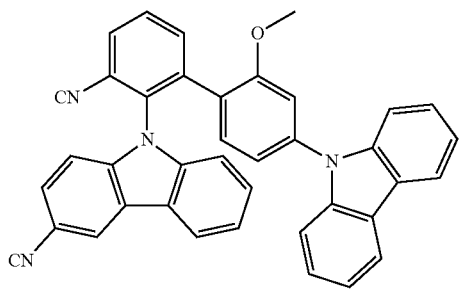
158
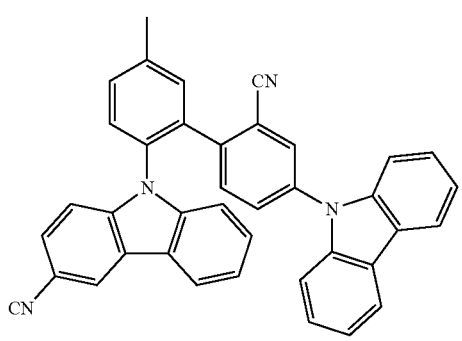
159
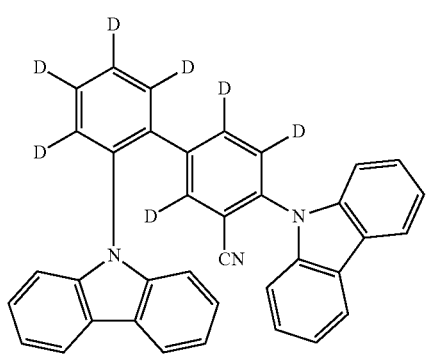
160
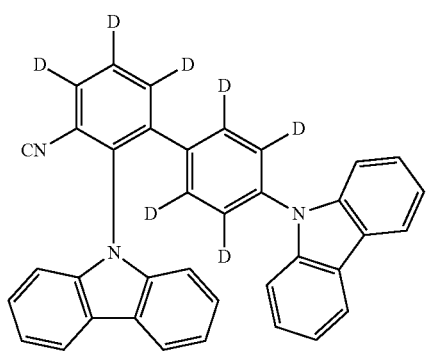
161
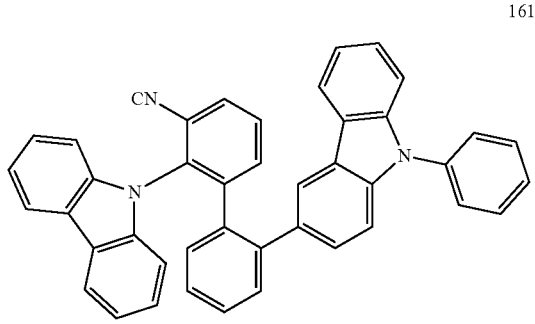
354
-continued
162
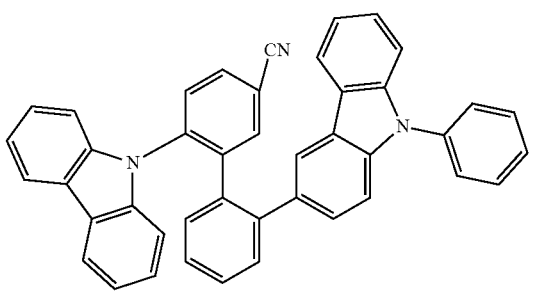
163
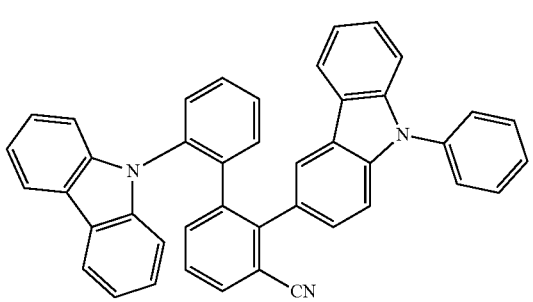
164
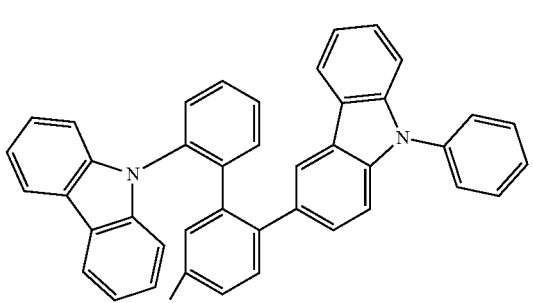
165
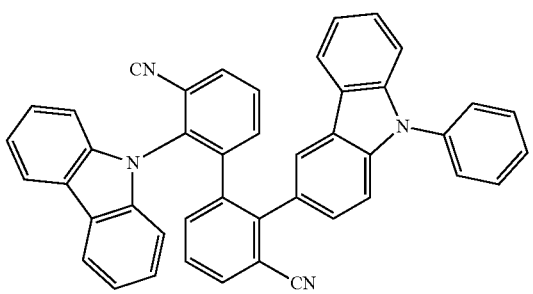
166
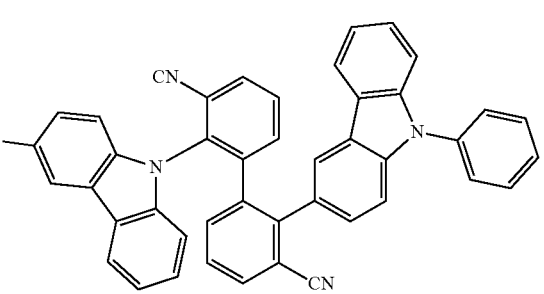

167
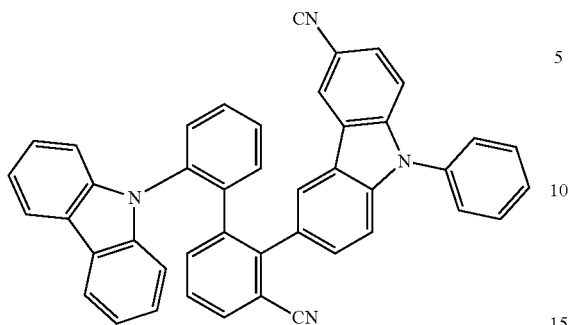
168
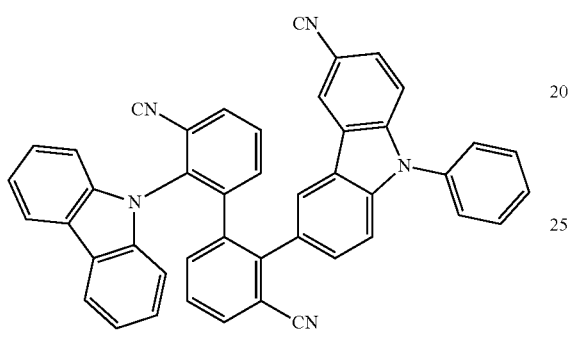
169
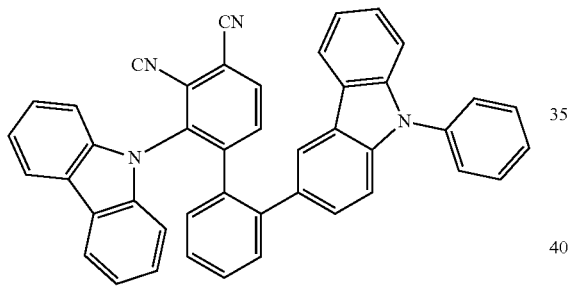
170
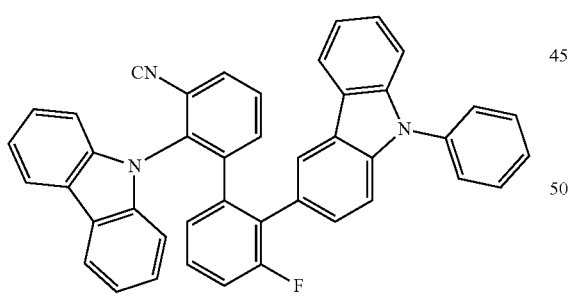
171
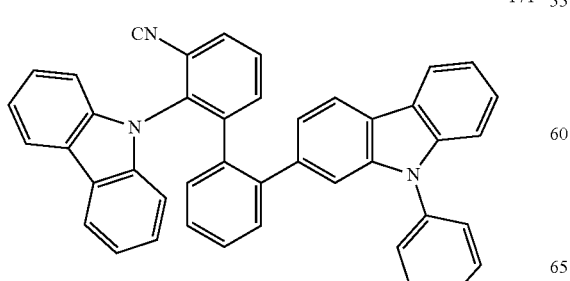
172
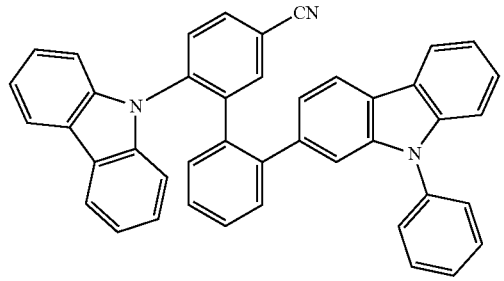
173
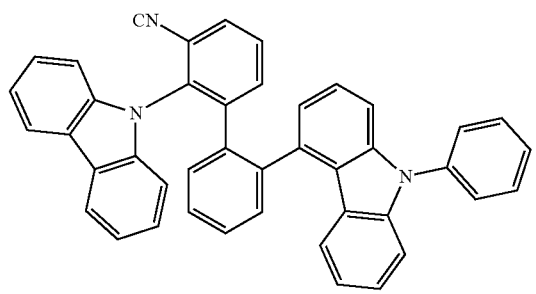
174
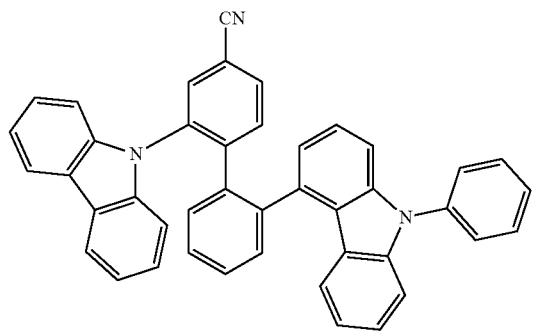
175
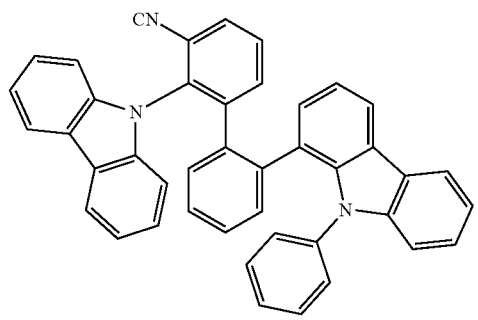

-continued
176
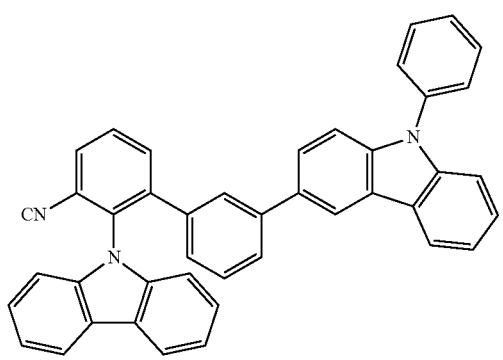
177
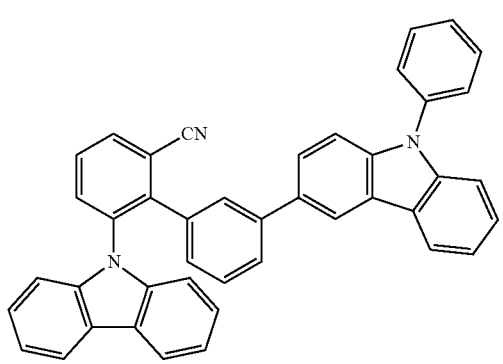
178
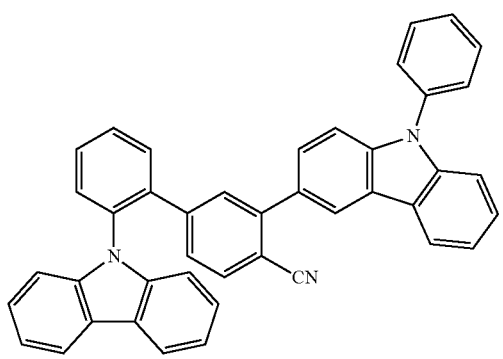
179
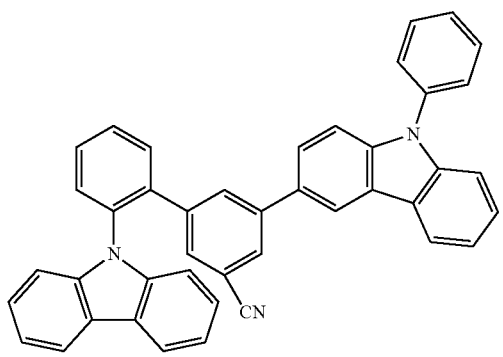
-continued
180
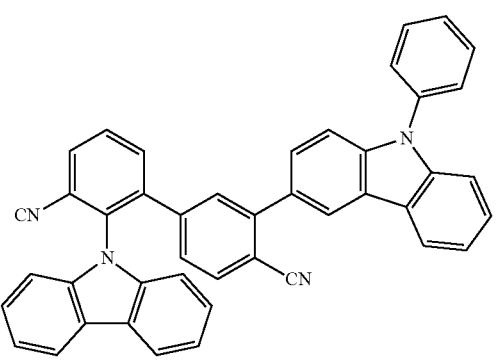
181
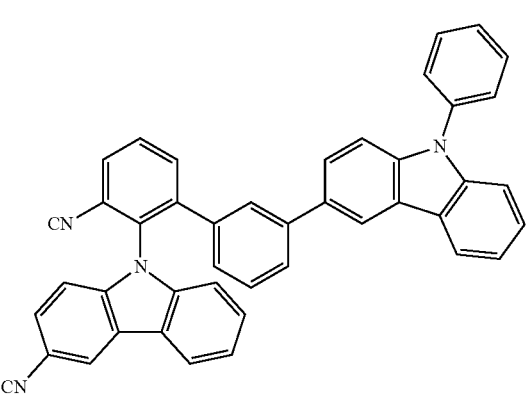
182
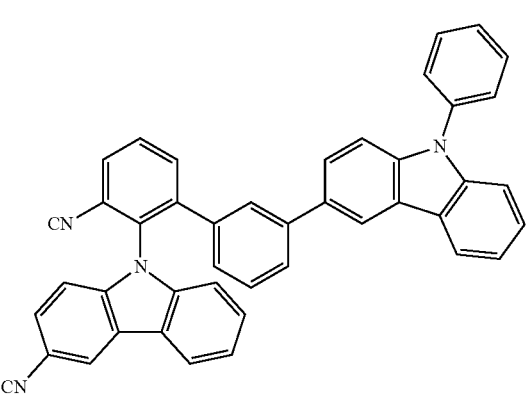
183
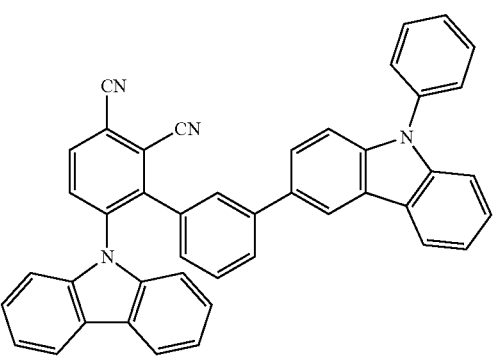

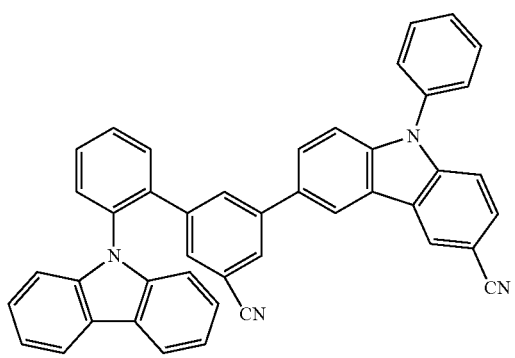
184
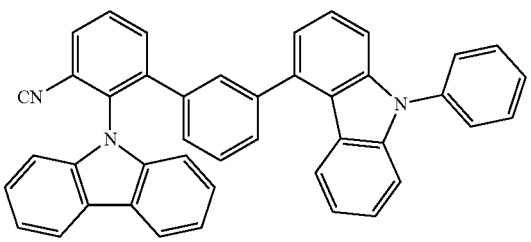
188
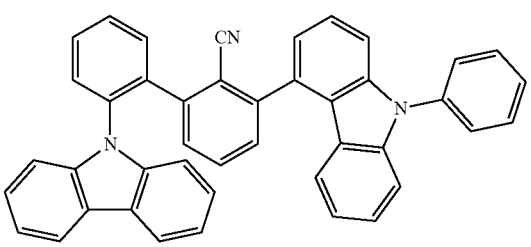
189
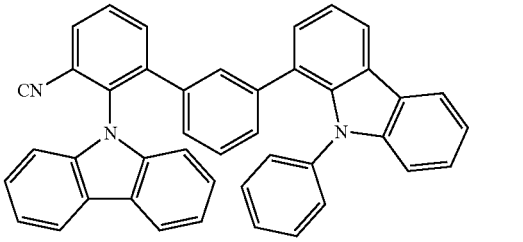
190
185
186
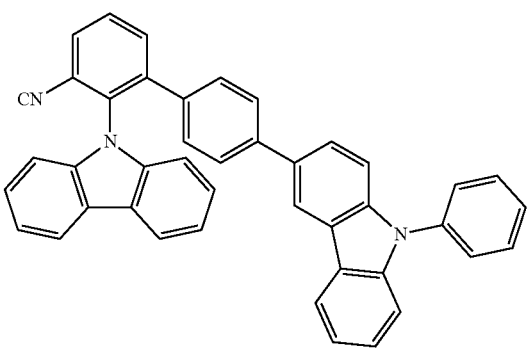
191
187
192
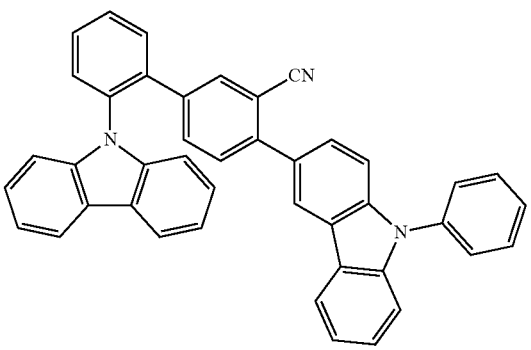

193
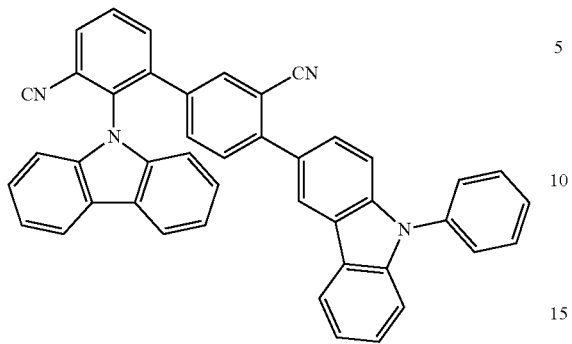
194
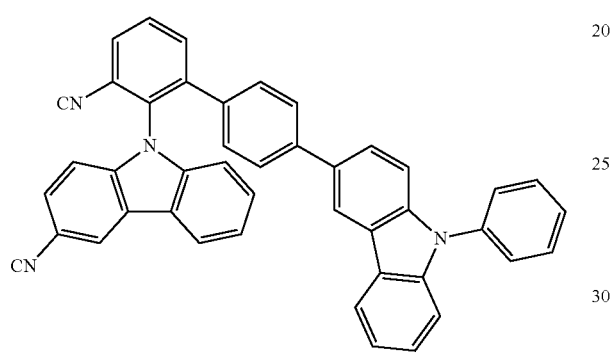
195
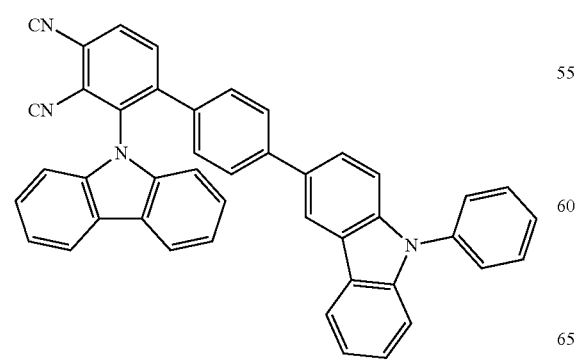
196
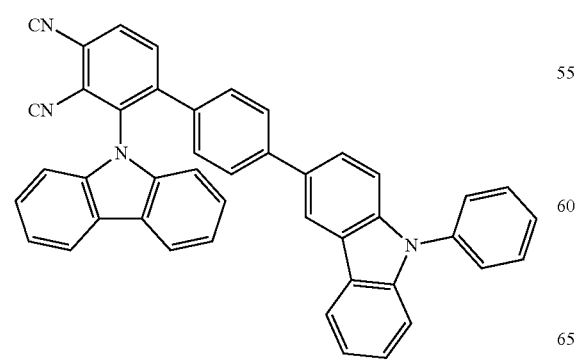
197
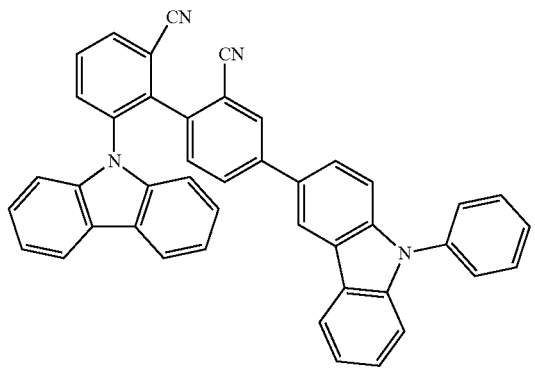
198
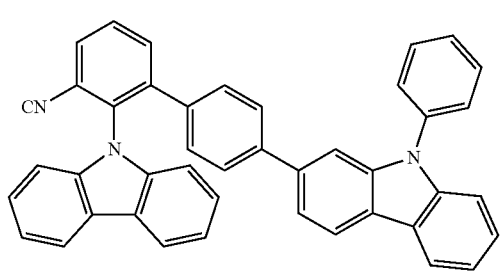
199
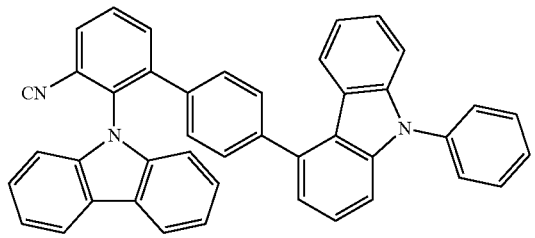
200
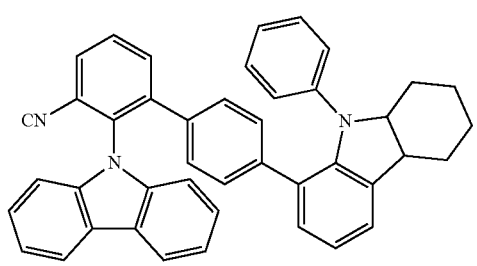
201
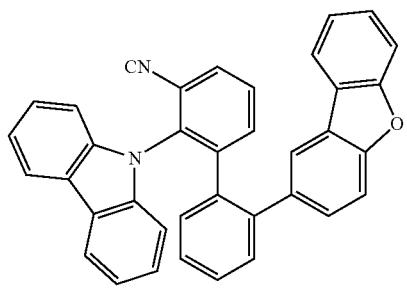

363
-continued
202
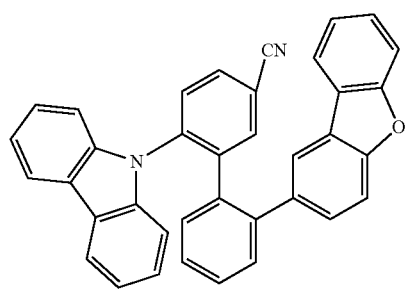
203
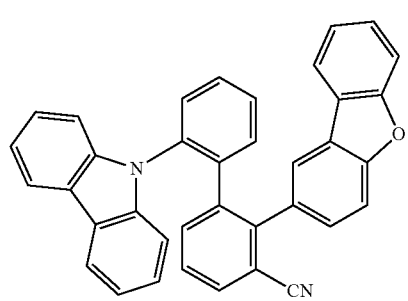
204
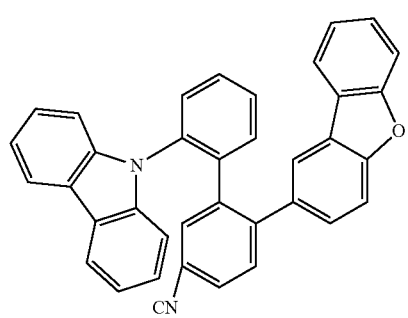
205
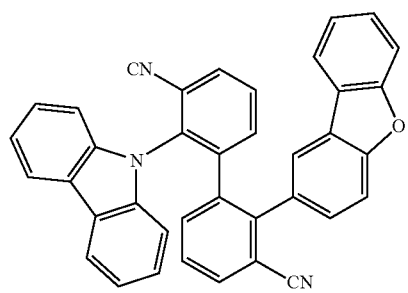
206
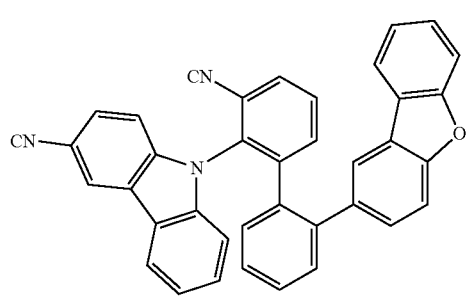
364
-continued
207
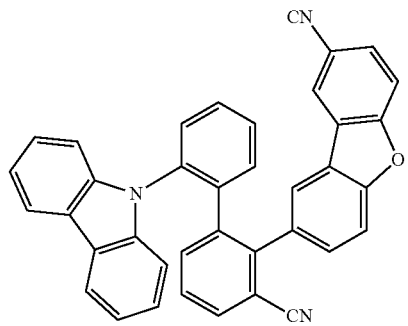
208
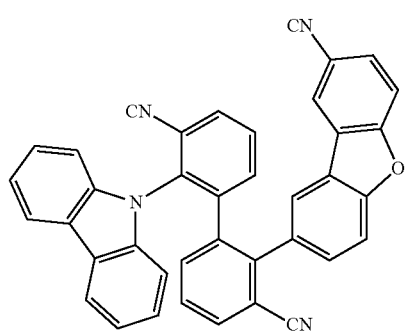
209
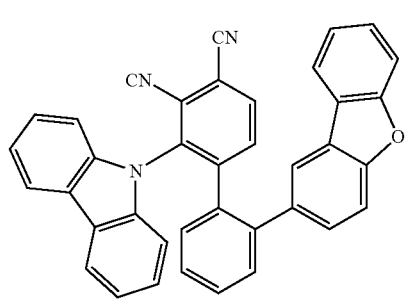
210
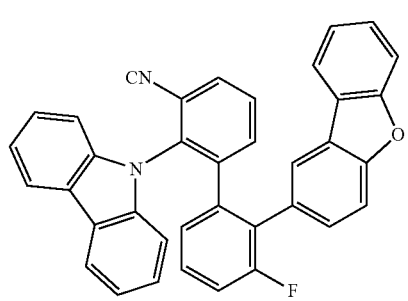
211
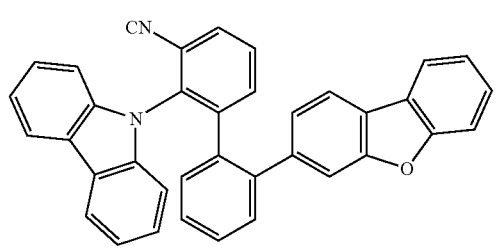

212
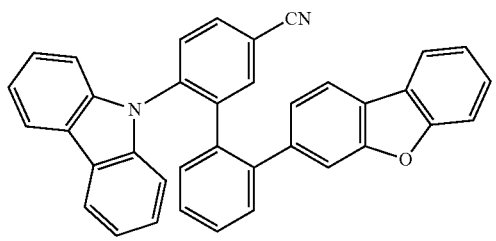
213
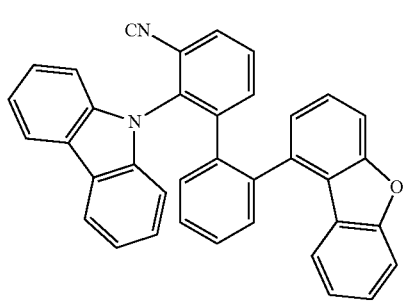
214
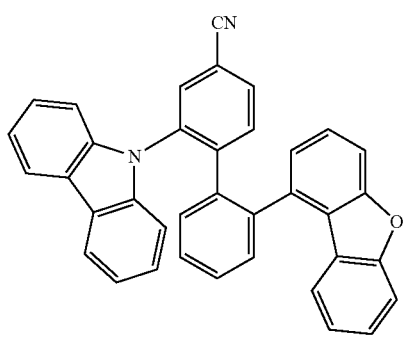
215
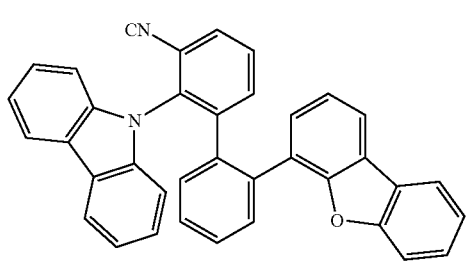
216
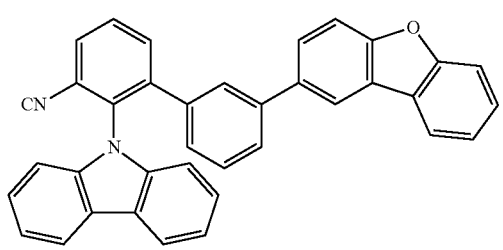
217
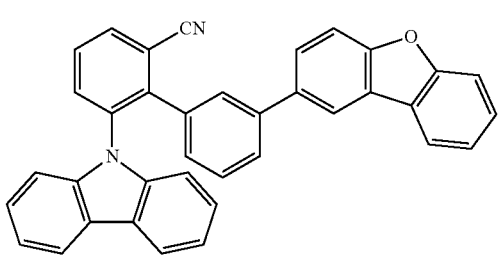
218
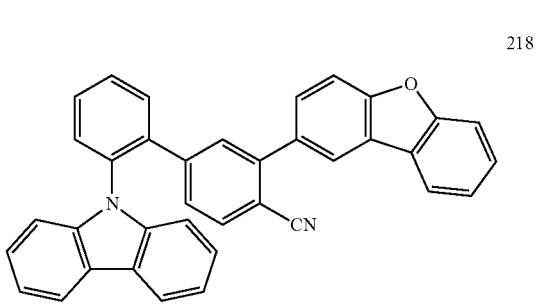
219
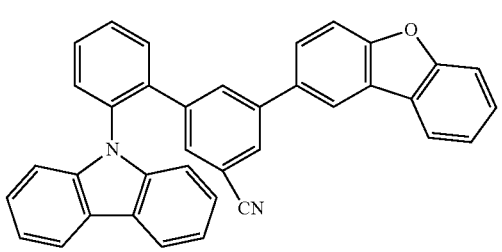
220
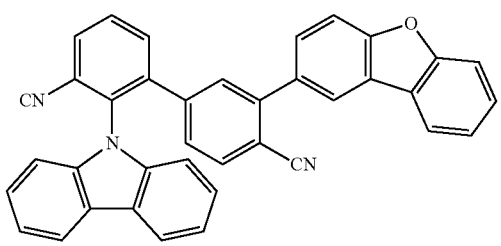
221
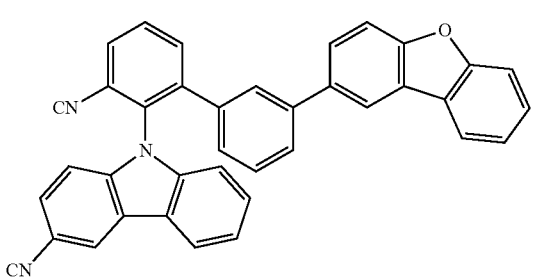

222
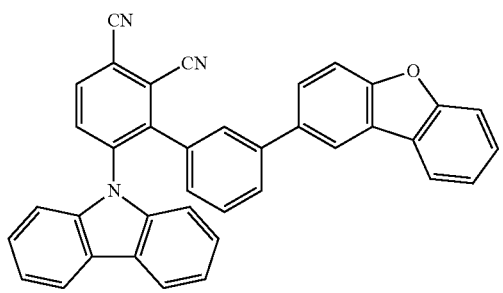
223
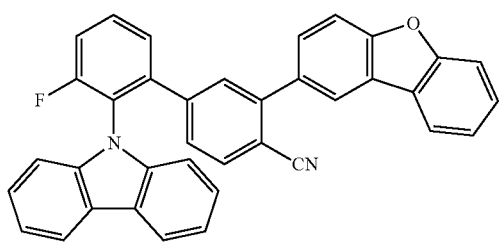
224
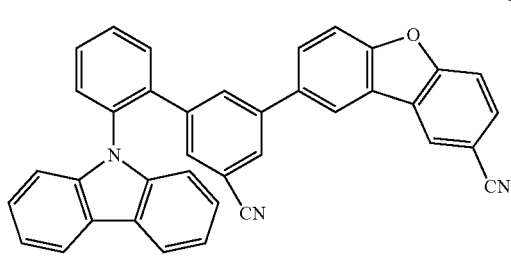
225
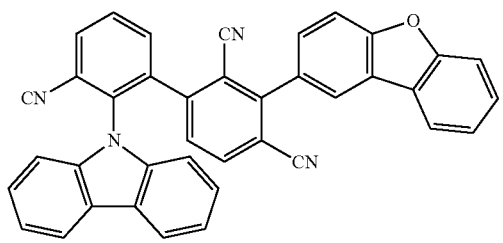
226
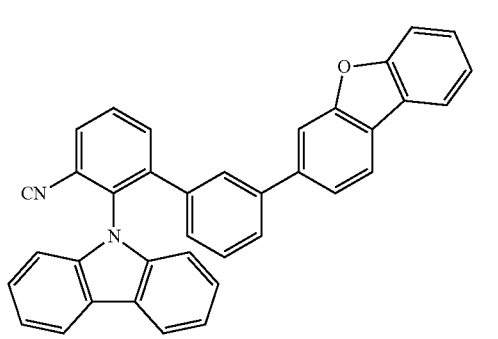
227
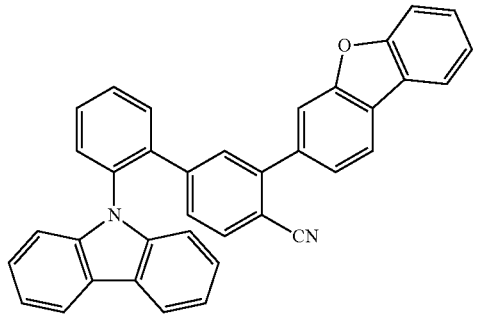
228
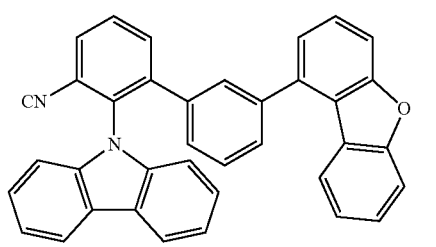
229
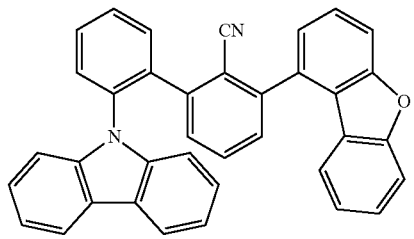
230
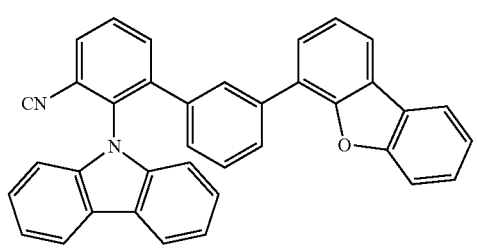
231
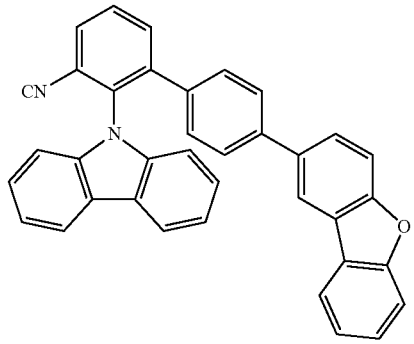

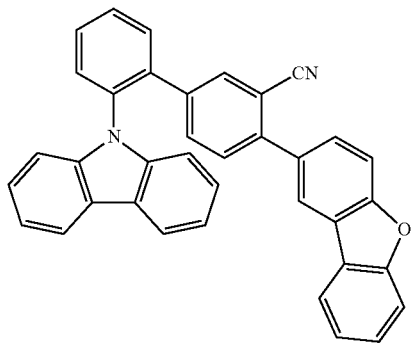
232
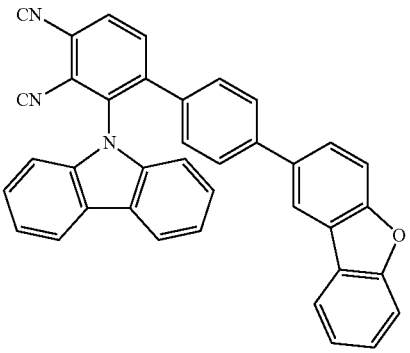
236
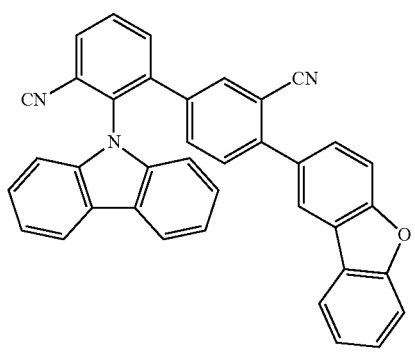
233
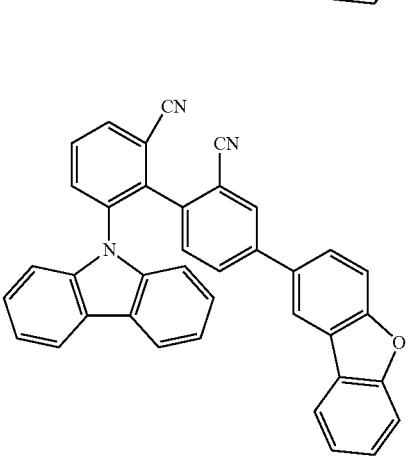
237
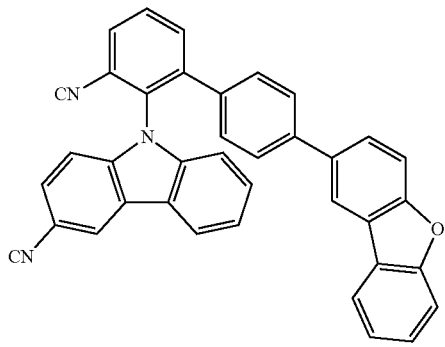
234
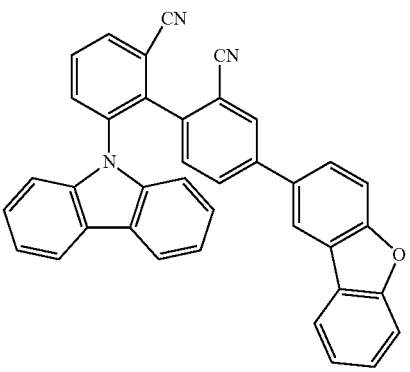
238
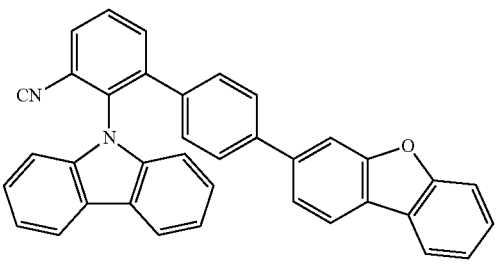
239
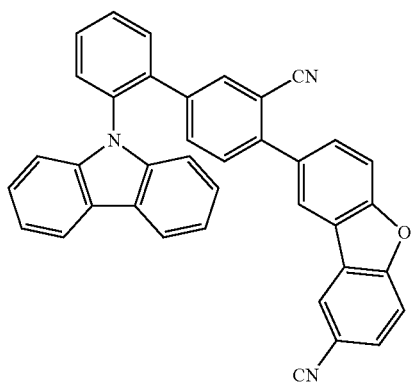
235
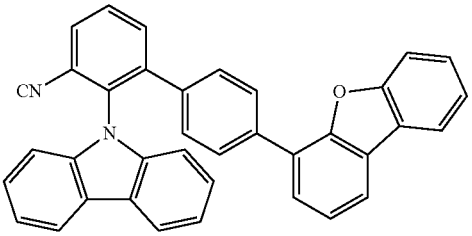
240

-continued
241
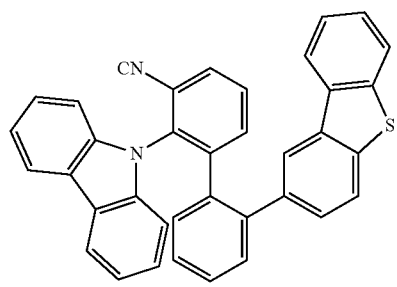
242
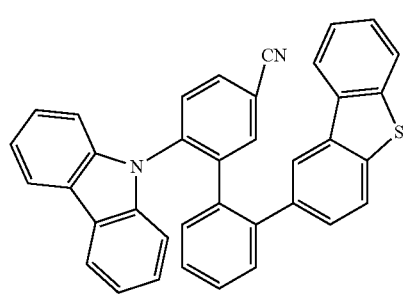
243
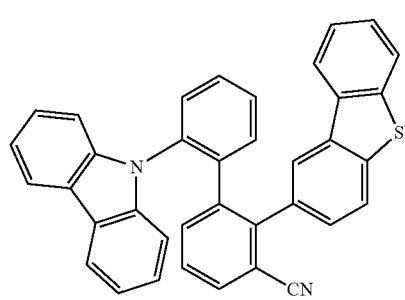
244
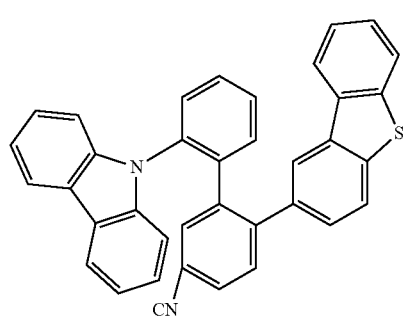
245
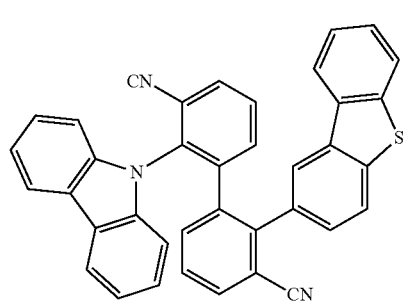
-continued
246
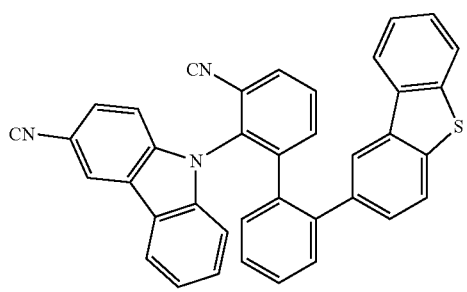
247
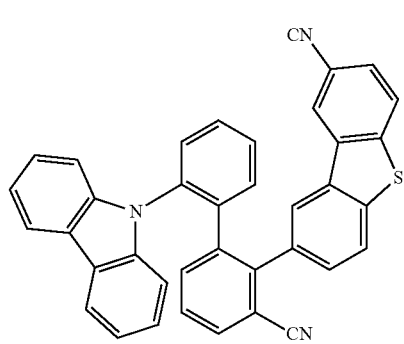
248
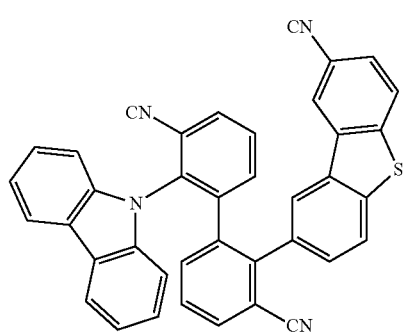
249
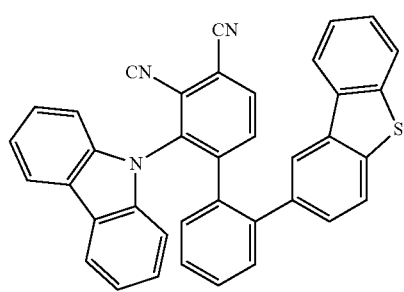
250
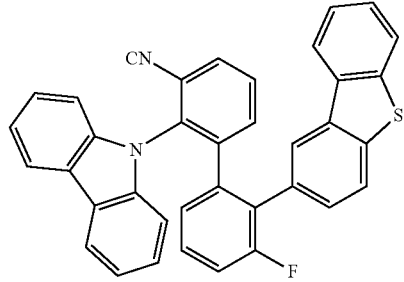

251
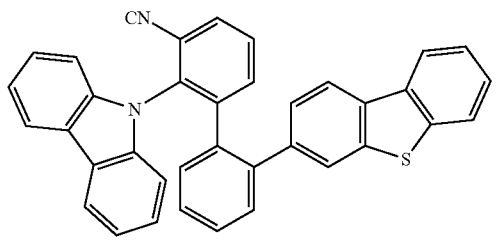
252
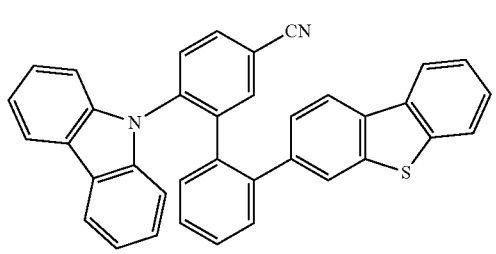
253
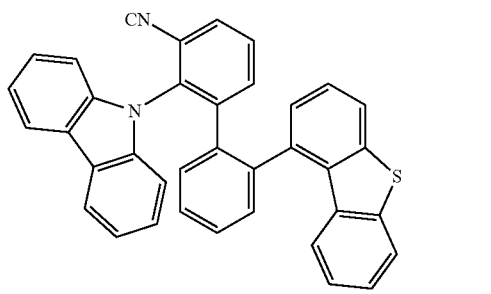
254
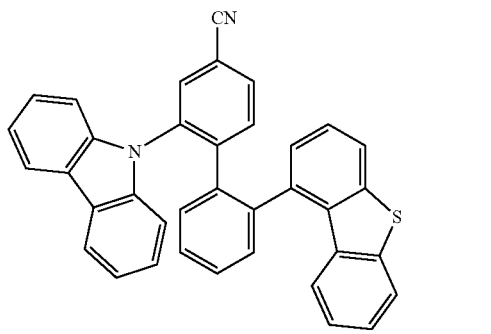
255
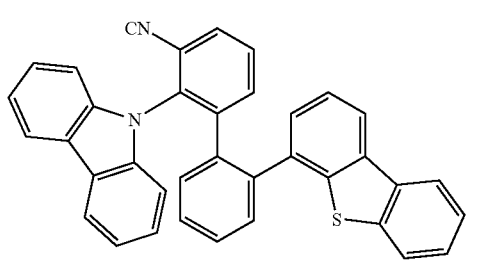
256
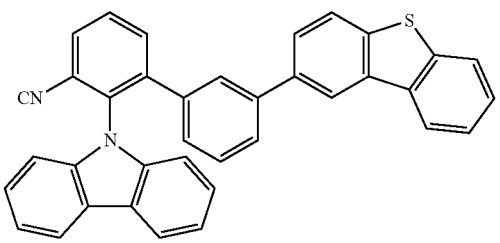
257
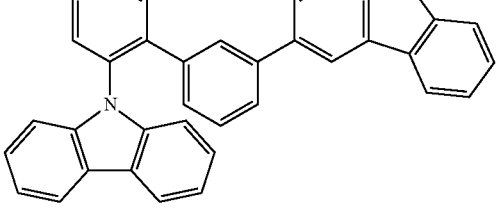
258
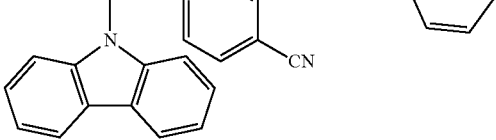
259
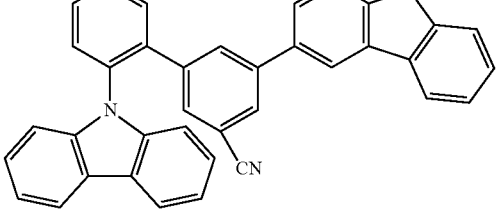
260
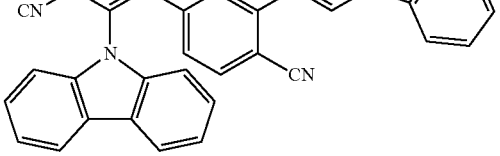
261
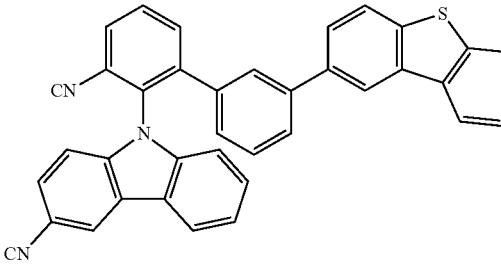

262
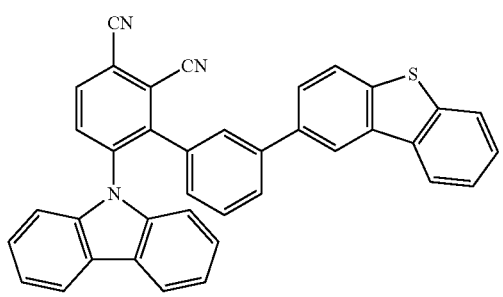
263
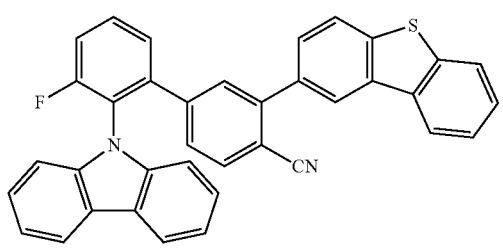
264
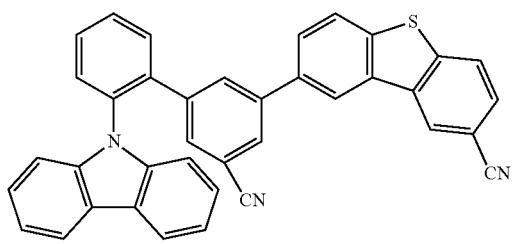
265
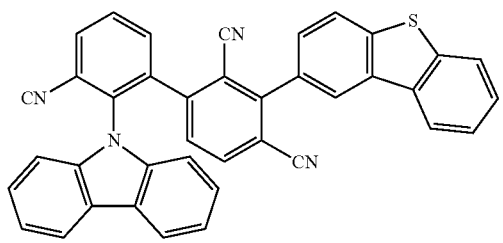
266
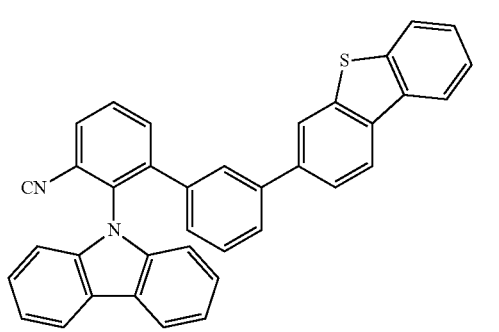
267
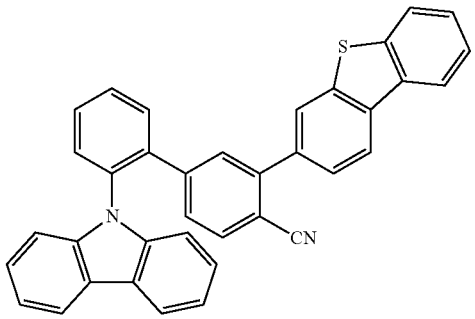
268
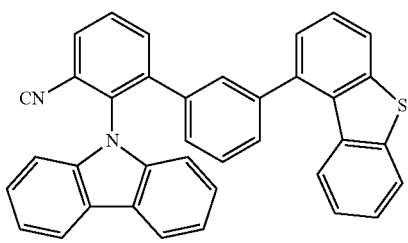
269
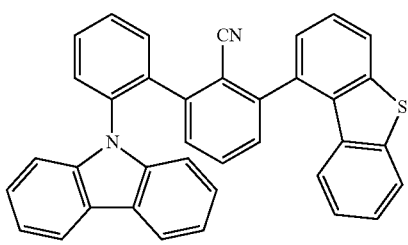
270
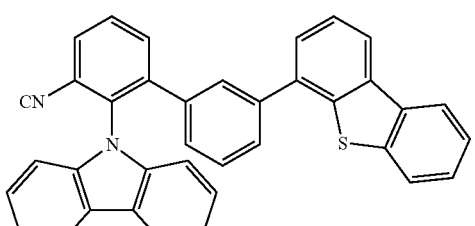
271
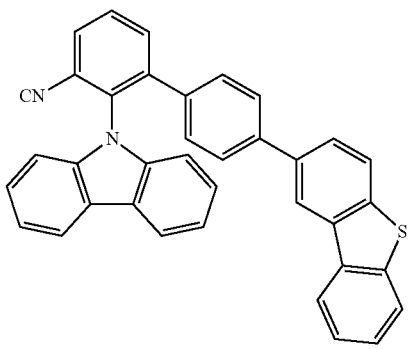

272 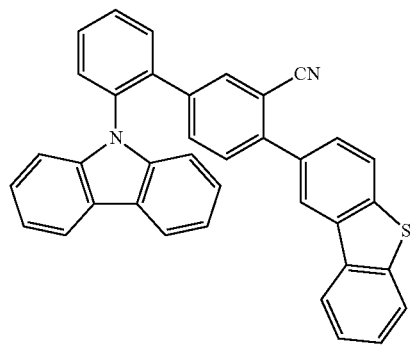
273 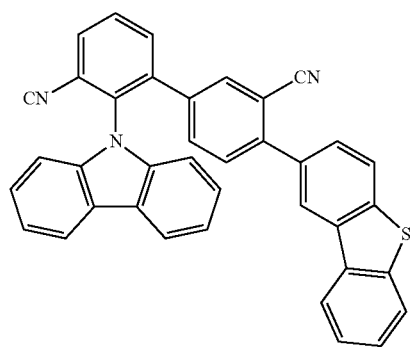
274 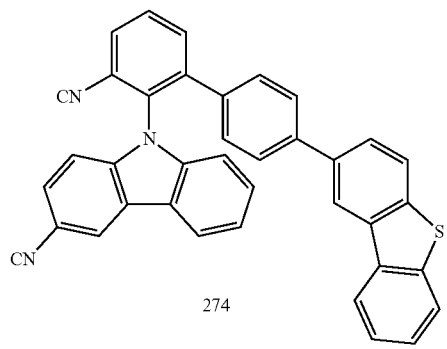
275 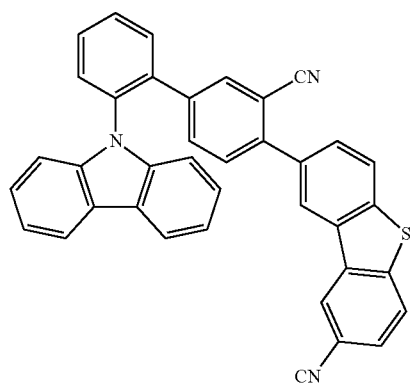
276 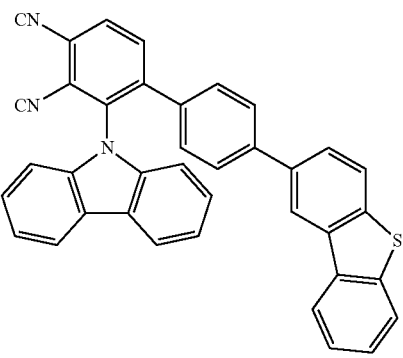
277 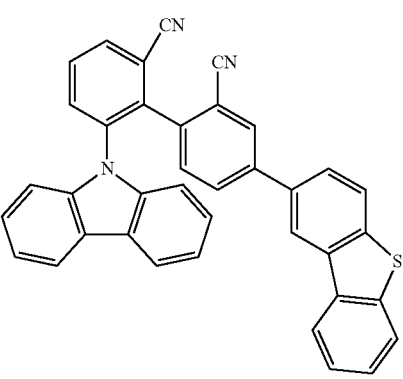
278 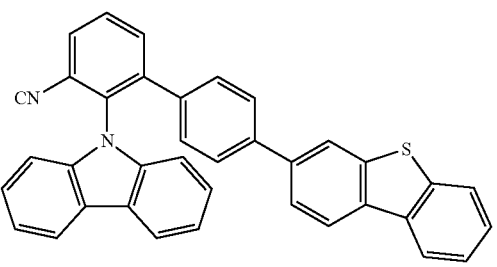
279 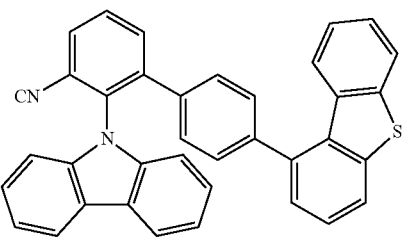
280 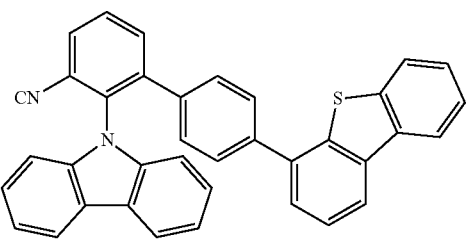

281
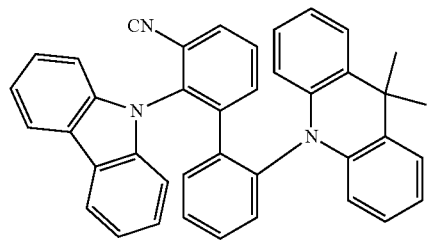
282
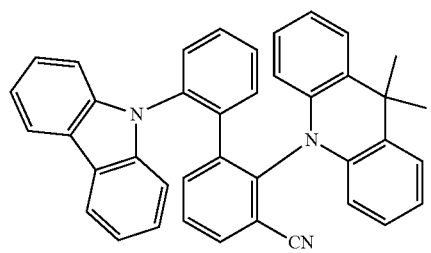
283
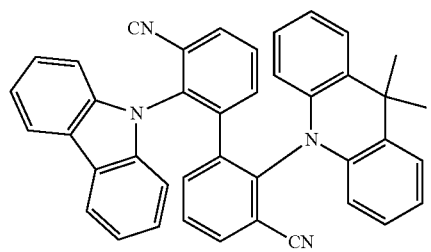
284
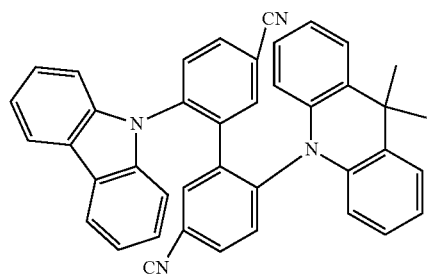
285
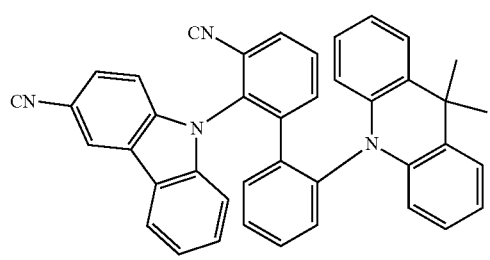
286
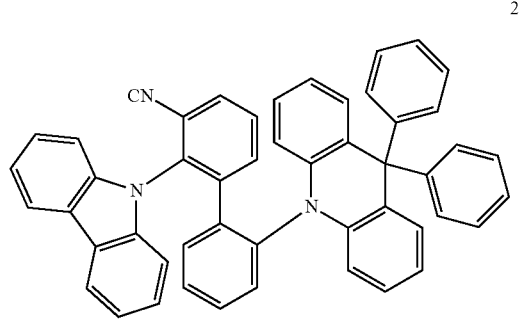
287
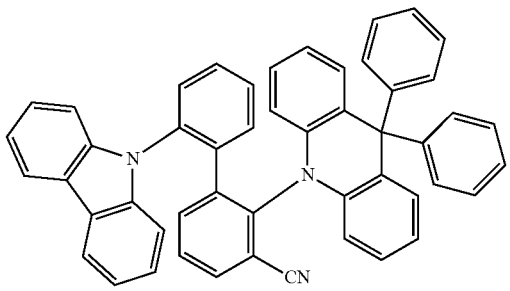
288
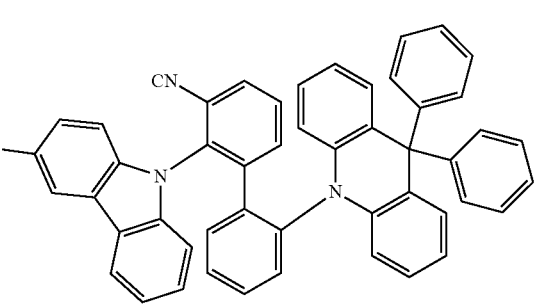
289
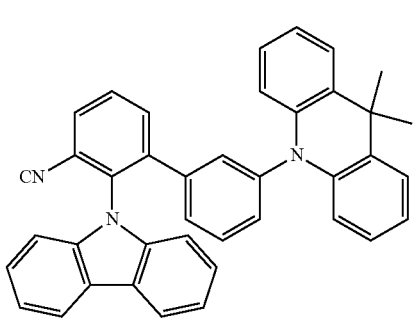
290
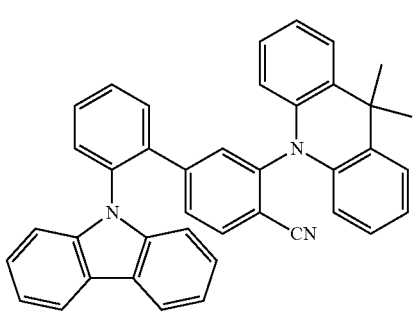
291
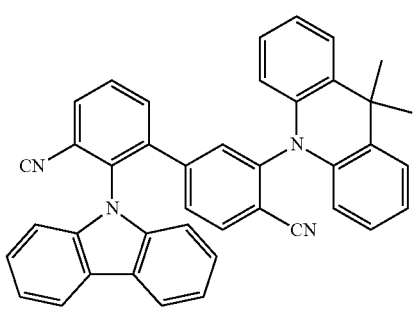

-continued
292
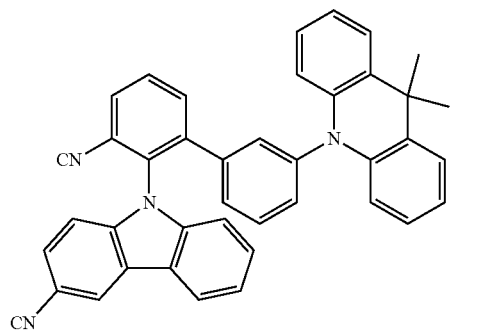
293
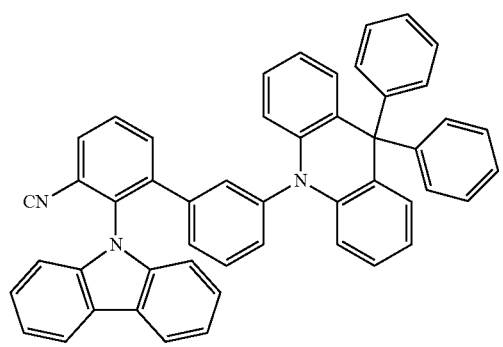
294
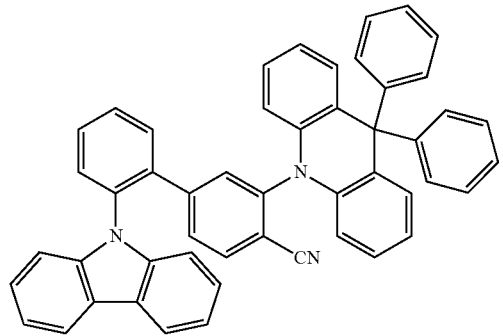
295
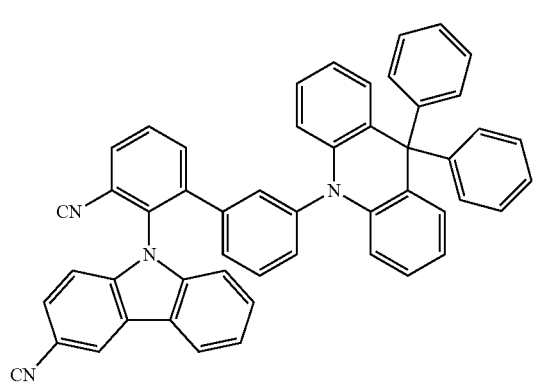
-continued
296
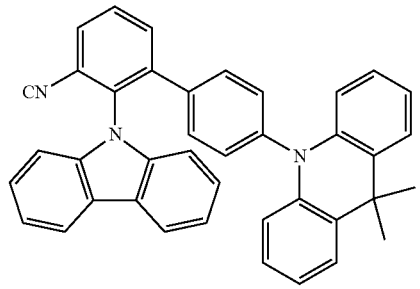
297
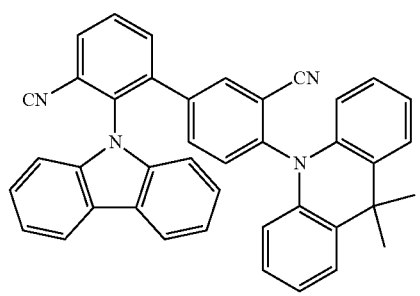
298
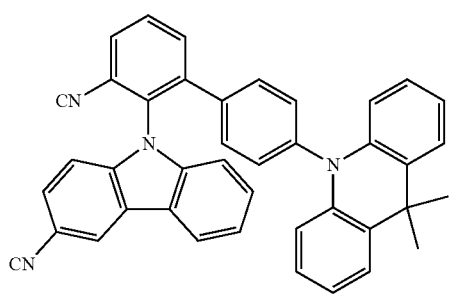
299
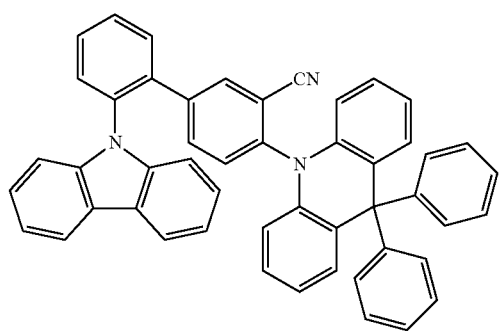
300
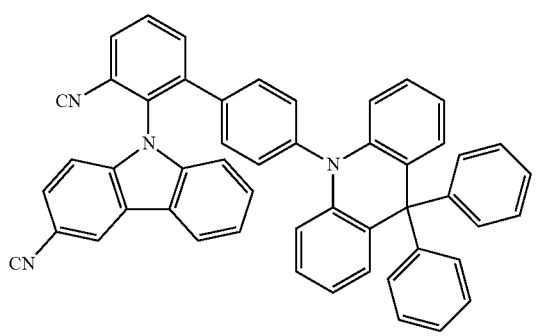

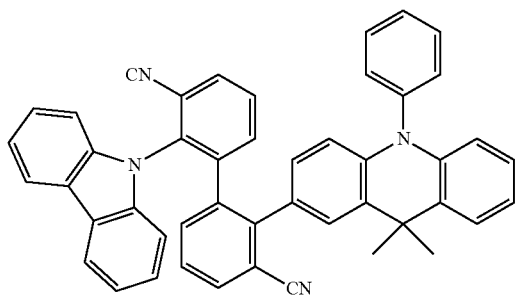
301
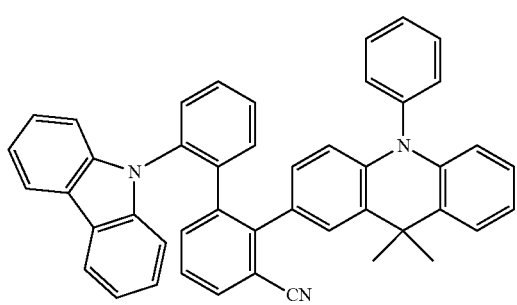
302
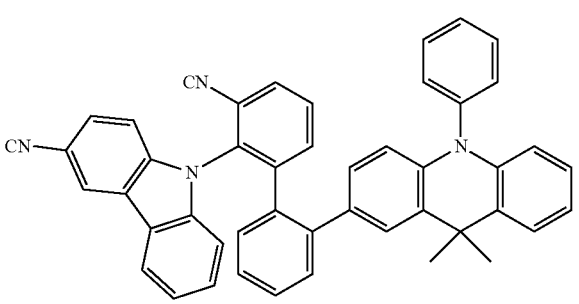
303
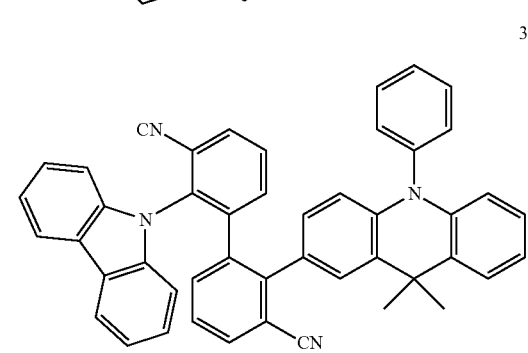
304
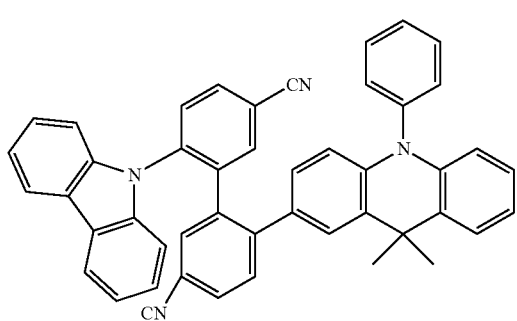
305
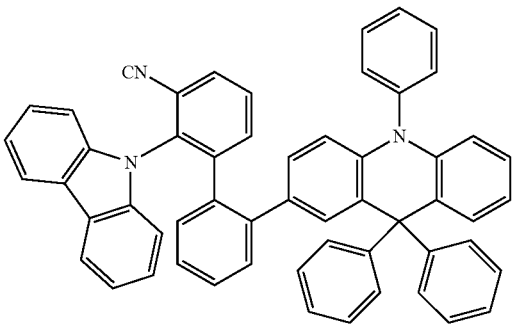
306
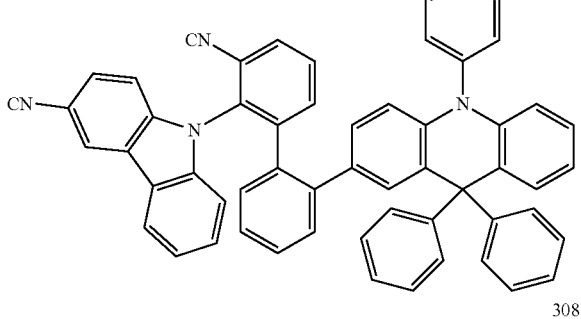
307
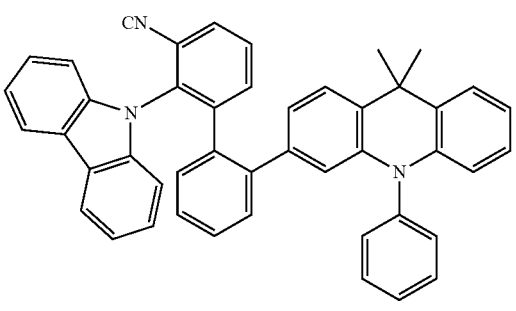
308
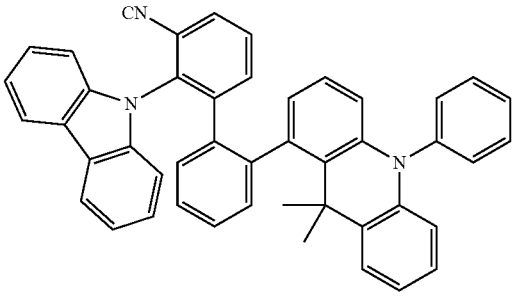
309
310

-continued
311
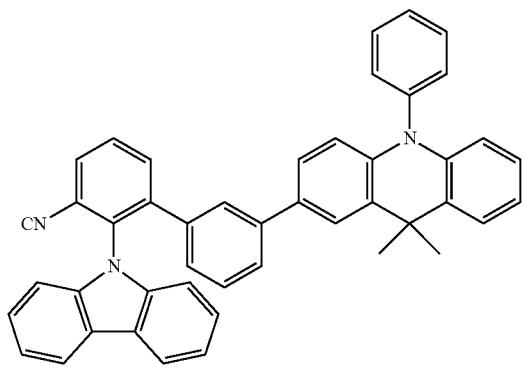
312
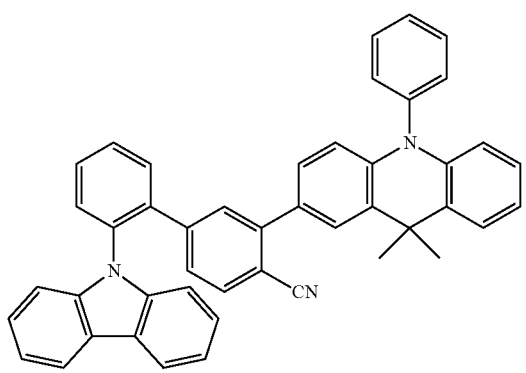
313
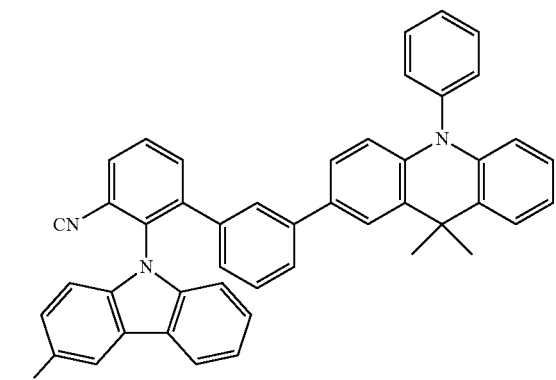
314
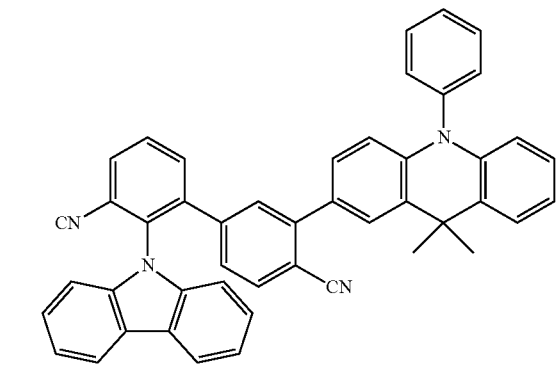
-continued
315
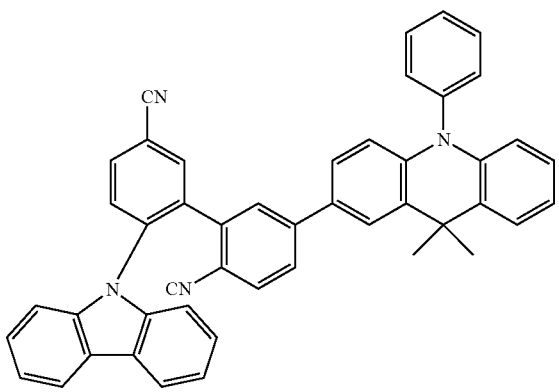
316
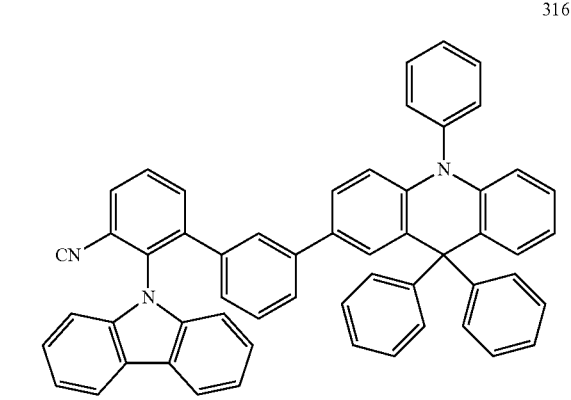
317
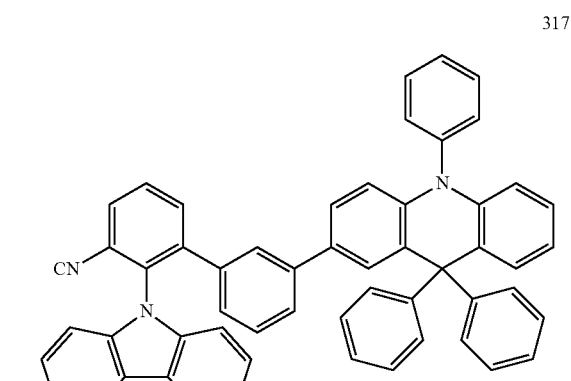
318
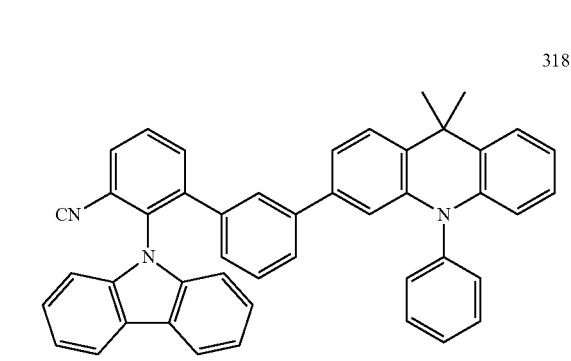

-continued
319
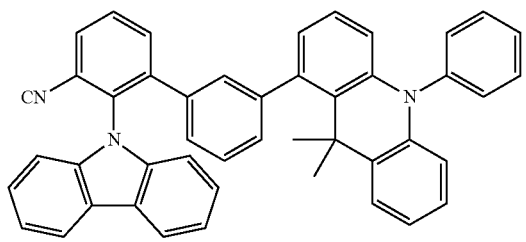
320
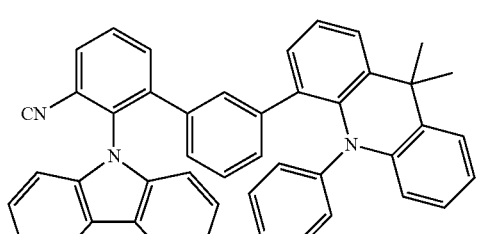
321
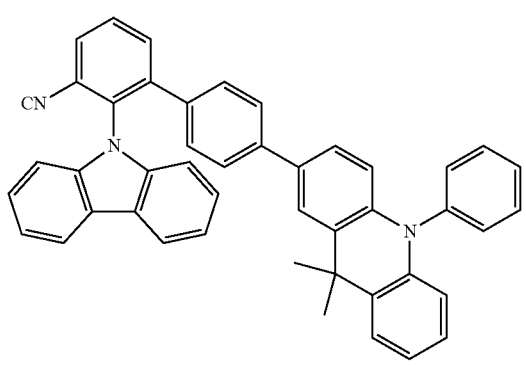
322
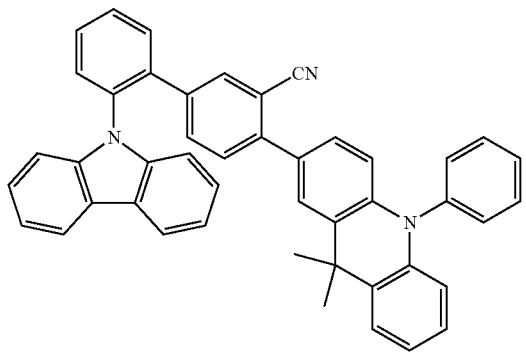
323
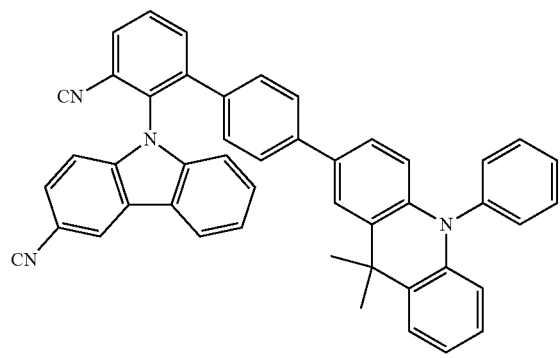
-continued
324
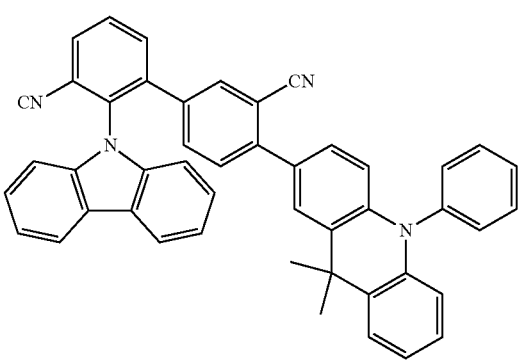
325
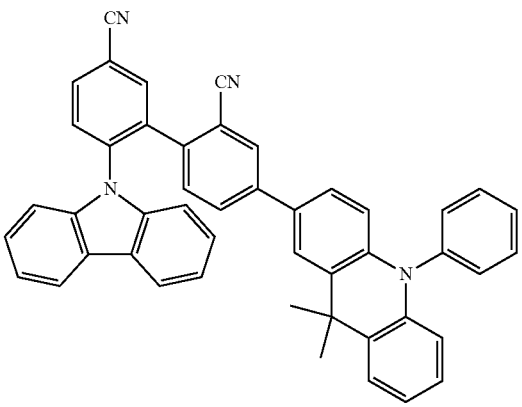
326
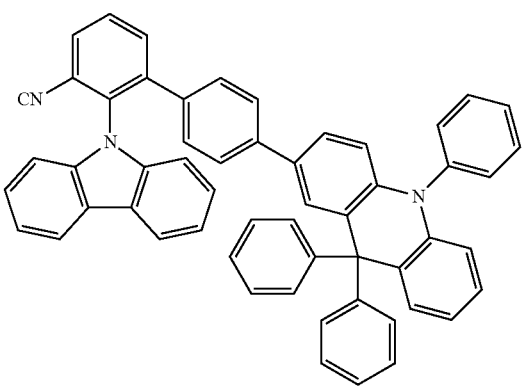
327
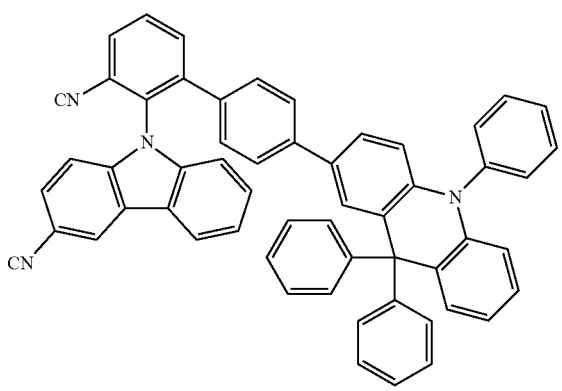

-continued

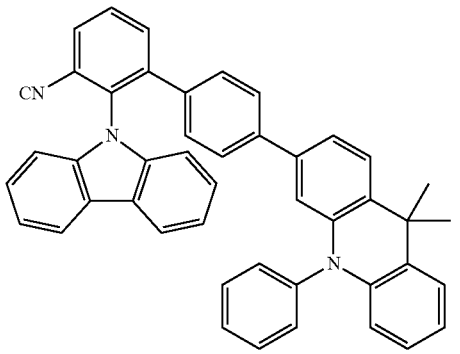

328

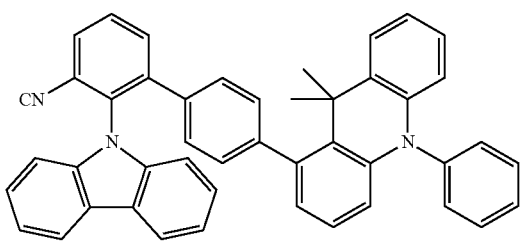

329

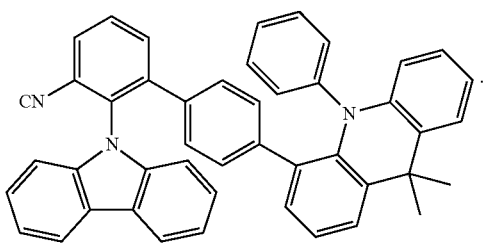

330

13. A composition comprising:
a first compound and a second compound,
wherein the first compound is the condensed cyclic compound of claim 1, and
wherein the second compound comprises at least one selected from a carbazole-containing ring, a dibenzofuran-containing ring, a dibenzothiophene-containing ring, an indenocarbazole-containing ring, an indolocarbazole-containing ring, a benzofurocarbazole-containing ring, a benzothienocarbazole-containing ring, an acridine-containing ring, a dihydroacridine-containing ring, and a triindolobenzene-containing ring, and does not comprise an electron withdrawing group,
wherein the electron withdrawing group is selected from:
F, —CFH$_2$, —CF$_2$H, —CF$_3$, —CN, and —NO$_2$;
a C$_1$-C$_{60}$ alkyl group substituted with at least one selected from —F, —CFH$_2$, —CF$_2$H, —CF$_3$, —CN, and —NO$_2$;
a C$_1$-C$_{60}$ heteroaryl group and a monovalent non-aromatic condensed polycyclic heterocyclic group that each comprise *=N—*' as a ring-forming moiety; and
a C$_1$-C$_{60}$ heteroaryl group and a monovalent non-aromatic condensed polycyclic heterocyclic group, which each comprise *=N—*' as a ring-forming moiety and are each substituted with at least one selected from deuterium, —F, —CFH$_2$, —CF$_2$H, —CF$_3$, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group,
wherein "monovalent non-aromatic condensed polycyclic group" refers to a monovalent group that has two or more rings condensed to each other, only carbon atoms as a ring forming atom and, and which is non-aromatic in the entire molecular structure, and
wherein "monovalent non-aromatic condensed heteropolycyclic group" refers to a monovalent croup that has two or more rings condensed to each other, has a heteroatom selected from N, O, P, Si and S, other than carbon atoms, as a ring-forming atom, and which is non-aromatic in the entire molecular structure.

14. The composition of claim 13, wherein the second compound is selected from a compound represented by Formula H-1:

Formula H-1

$$Ar_1 \text{——} (L_1)_{c1} \text{——} Ar_2$$

Formula 11

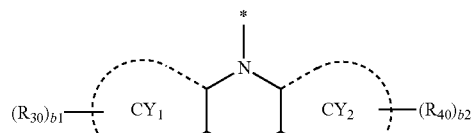

Formula 12

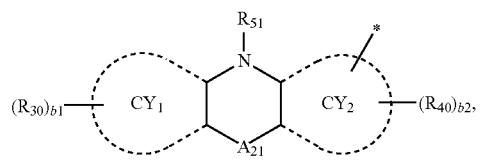

wherein, in Formulae H-1, 11, and 12,
L$_1$ is selected from:
a single bond, a phenylene group, a naphthylene group, a fluorenylene group, a carbazolylene group, a dibenzofuranylene group, and a dibenzothiophenylene group; and
a carbazolylene group, a dibenzofuranylene group, and a dibenzothiophenylene group, each substituted with at least one selected from deuterium, a C$_1$-C$_{10}$ alkyl group, a C$_1$-C$_{10}$ alkoxy group, a phenyl group, a naphthyl group, a fluorenyl group, a carbazolyl group, a dibenzofuranyl group, a dibenzothiophenyl group, a biphenyl group, and —Si(Q$_{11}$)(Q$_{12}$)(Q$_{13}$),
c1 is an integer selected from 1 to 10, wherein, when c1 is 2 or more, 2 or more L$_1$ are identical to or different from each other, Ar$_1$ is selected from groups represented by Formulae 11 and 12, Ar$_2$ is selected from:

groups represented by Formulae 11 and 12, a phenyl group, and a naphthyl group; and a phenyl group and a naphthyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a fluorenyl group, a carbazolyl group, a dibenzofuranyl group, a dibenzothiophenyl group, and a biphenyl group, CY$_1$ and CY$_2$ are each independently selected from a benzene group, a naphthalene group, a fluorene group, a carbazole group, a benzocarbazole group, an indolocarbazole group, a dibenzofuran group, and a dibenzothiophene group, A$_{21}$ is selected from:

a single bond, a C$_1$-C$_4$ alkylene group, and a C$_2$-C$_4$ alkenylene group; and a C$_1$-C$_4$ alkylene group and a C$_2$-C$_4$ alkenylene group, each substituted with at least one selected from deuterium, a C$_1$-C$_{10}$ alkyl group, a C$_1$-C$_{10}$ alkoxy group, a phenyl group, a naphthyl group, a fluorenyl group, a carbazolyl group, a dibenzofuranyl group, a dibenzothiophenyl group, a biphenyl group, and —Si(Q$_{21}$)(Q$_{22}$)(Q$_{23}$), R$_{30}$, R$_{40}$, and R$_{51}$ are each independently selected from:

hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, and a dibenzothiophenyl group;

a phenyl group, a naphthyl group, a fluorenyl group, a carbazolyl group, a dibenzofuranyl group, and a dibenzothiophenyl group;

a phenyl group, a naphthyl group, a fluorenyl group, a carbazolyl group, a dibenzofuranyl group, and a dibenzothiophenyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a fluorenyl group, a carbazolyl group, a dibenzofuranyl group, a dibenzothiophenyl group, and a biphenyl group; and Si(Q$_1$)(Q$_2$)(Q$_3$), b1 and b2 are each independently an integer selected from 0 to 10, Q$_1$ to Q$_3$, Q$_{11}$ to Q$_{13}$, and Q$_{21}$ to Q$_{23}$ are each independently selected from hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, a dibenzothiophenyl group, and a biphenyl group, and

* indicates a binding site to a neighboring atom.

15. The composition of claim 14, wherein Ar$_1$ is selected from groups represented by Formulae 11-1 to 11-8 and 12-1 to 12-16, and Ar$_2$ is selected from:

groups represented by Formulae 11-1 to 11-8 and 12-1 to 12-16, a phenyl group, and a naphthyl group; and a phenyl group and a naphthyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a fluorenyl group, a carbazolyl group, a dibenzofuranyl group, a dibenzothiophenyl group, and a biphenyl group

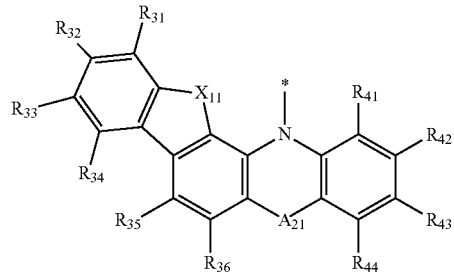

Formula 11-1

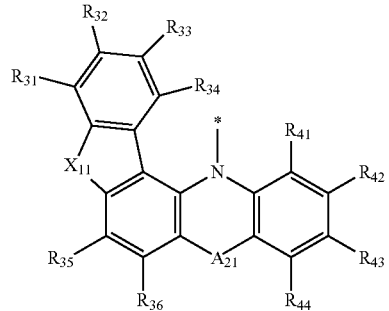

Formula 11-2

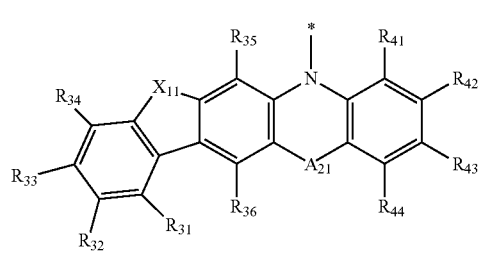

Formula 11-3

Formula 11-4
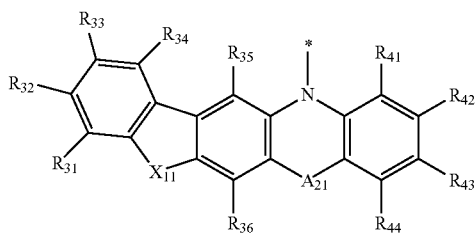
Formula 11-5
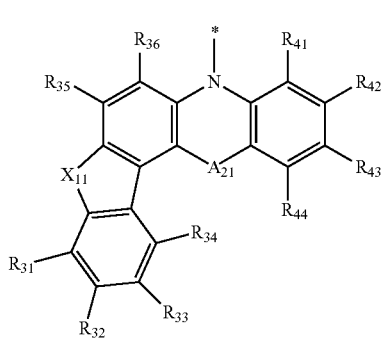
Formula 11-6
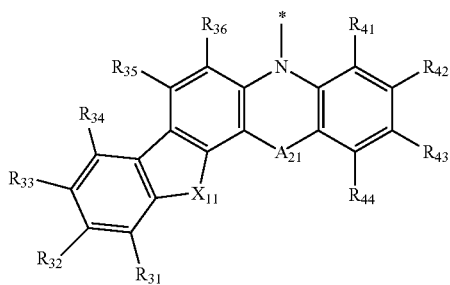
Formula 11-7
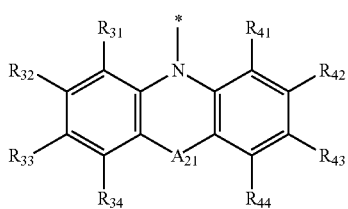
Formula 11-8
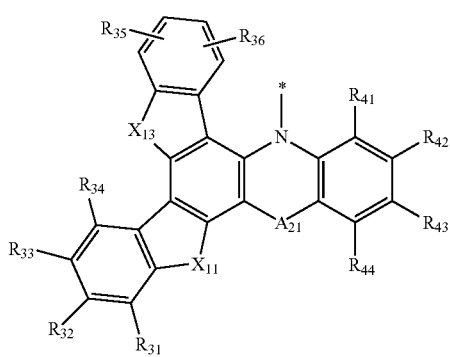
Formula 12-1
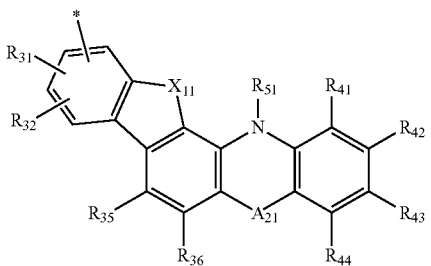
Formula 12-2
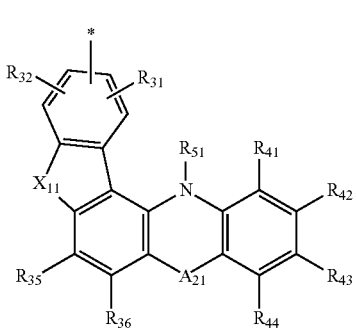
Formula 12-3
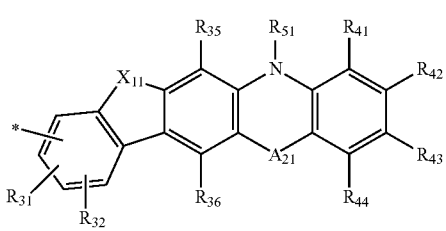
Formula 12-4
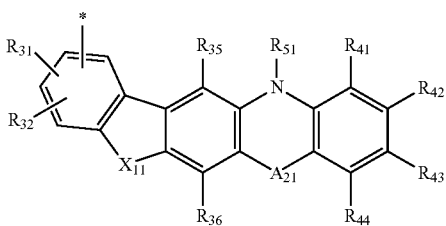
Formula 12-5
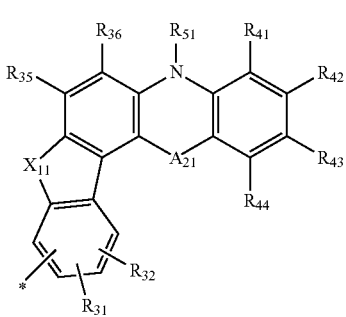

Formula 12-6
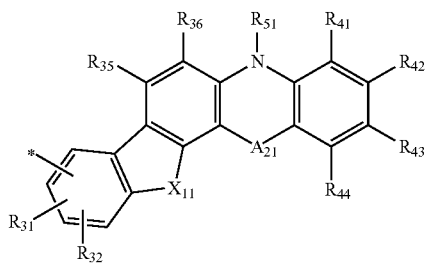
Formula 12-7
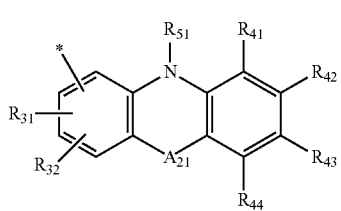
Formula 12-8
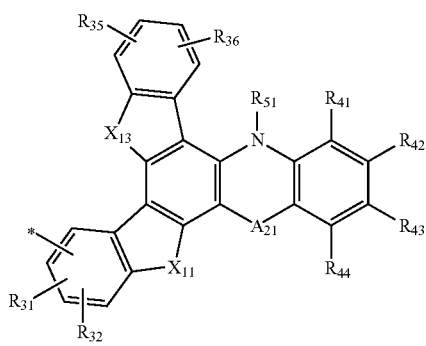
Formula 12-9
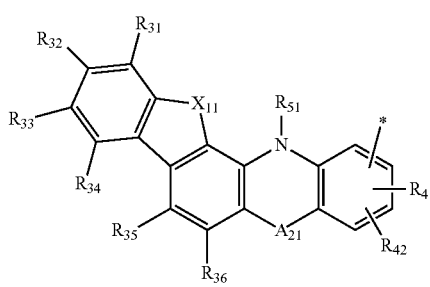
Formula 12-10
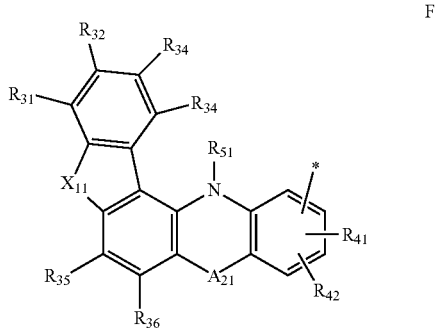
Formula 12-11
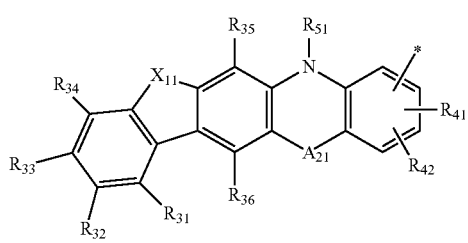
Formula 12-12
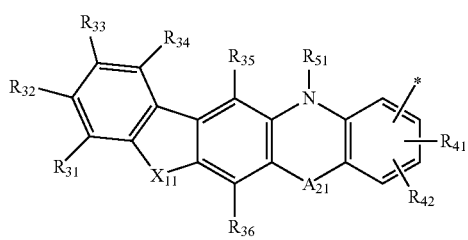
Formula 12-13
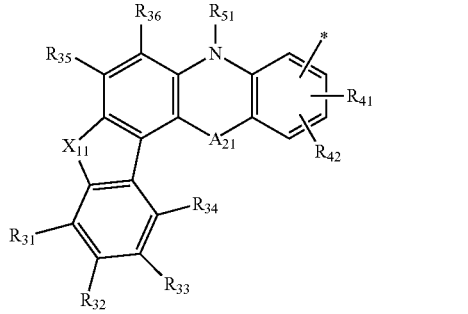
Formula 12-14
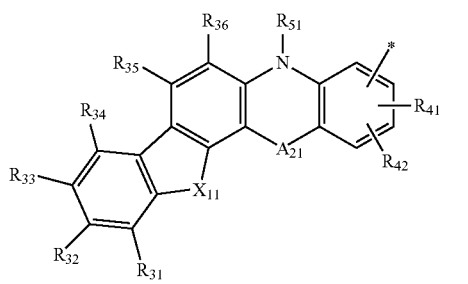
Formula 12-15
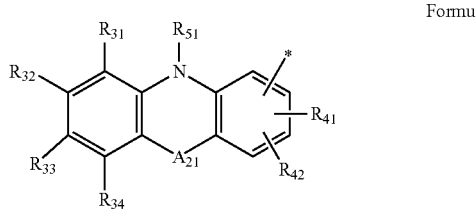

Formula 12-16

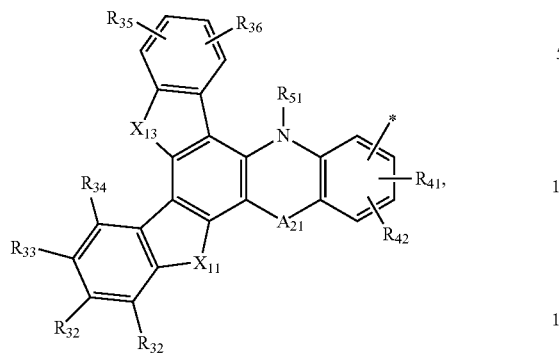

wherein, in Formulae 11-1 to 11-8 and 12-1 to 12-16, $X_{11}$ and $X_{13}$ are each independently $C(R_{37})(R_{38})$, $N(R_{39})$, O, or S, $A_{21}$, $R_{51}$, and * are each independently the same as defined in claim 14, $R_{31}$ to $R_{39}$ are each independently the same as defined in connection with $R_{30}$ in claim 14, and $R_{41}$ to $R_{44}$ are each independently the same as defined in connection with $R_{40}$ in claim 14.

16. The composition of claim 14, wherein i) the second compound is selected from a compound represented by Formula H-1, wherein $L_1$ in Formula H-1 is a single bond; or ii) the second compound is selected from compounds represented by Formulae H-1(1) to H-1(52):

Formula H-1(1)

Formula H-1(2)

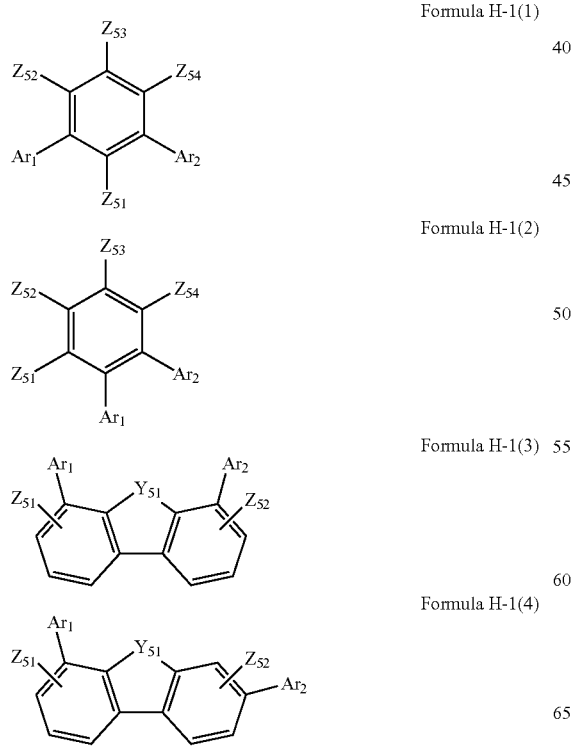

Formula H-1(3)

Formula H-1(4)

Formula H-1(5)

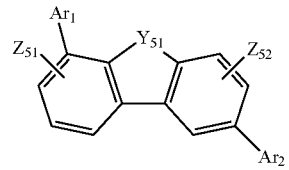

Formula H-1(6)

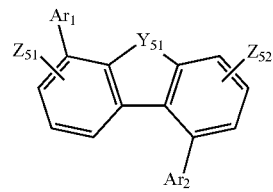

Formula H-1(7)

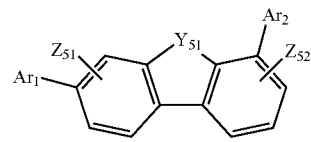

Formula H-1(8)

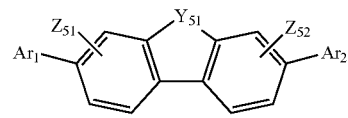

Formula H-1(9)

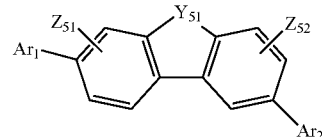

Formula H-1(10)

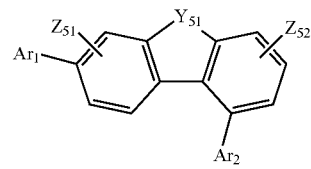

Formula H-1(11)

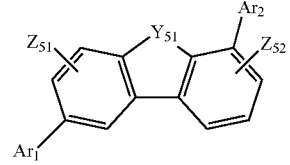

Formula H-1(12)

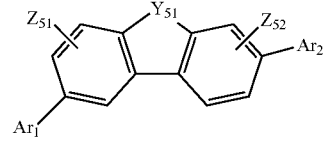

Formula H-1(13)

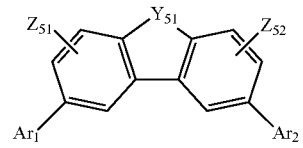

399
-continued
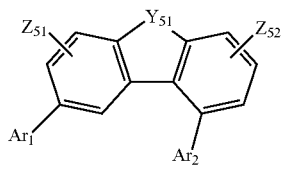
Formula H-1(14)
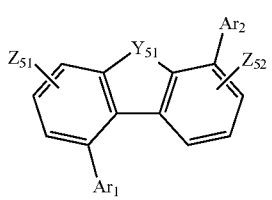
Formula H-1(15)
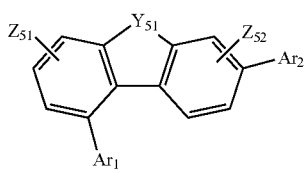
Formula H-1(16)
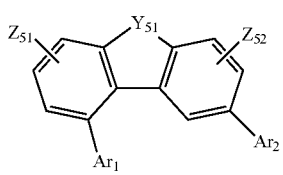
Formula H-1(17)
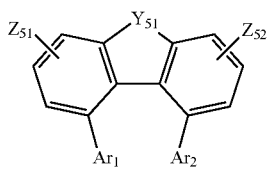
Formula H-1(18)
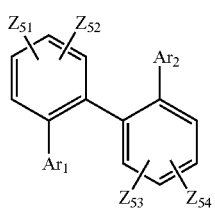
Formula H-1(19)
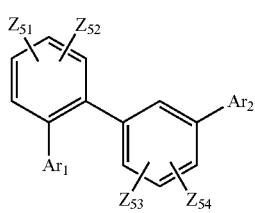
Formula H-1(20)
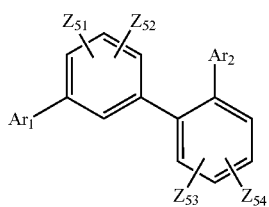
Formula H-1(21)
400
-continued
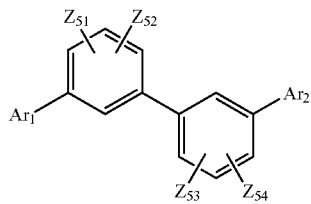
Formula H-1(22)
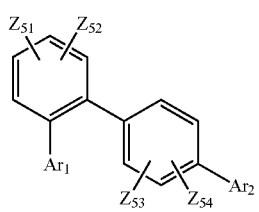
Formula H-1(23)
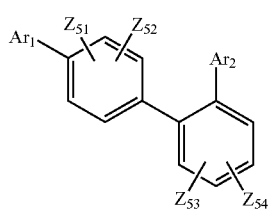
Formula H-1(24)
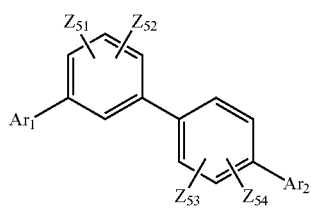
Formula H-1(25)
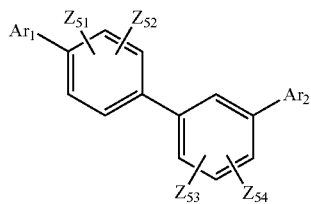
Formula H-1(26)
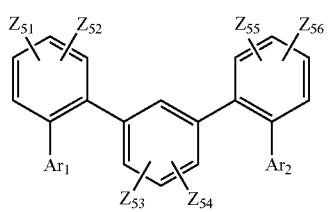
Formula H-1(27)
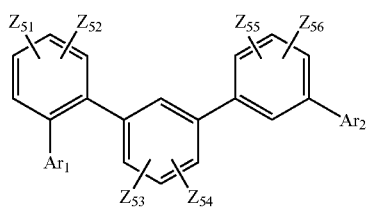
Formula H-1(28)

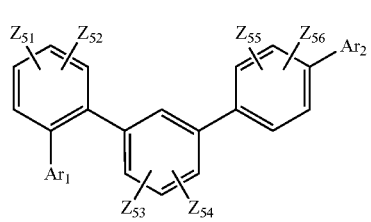
Formula H-1(29)
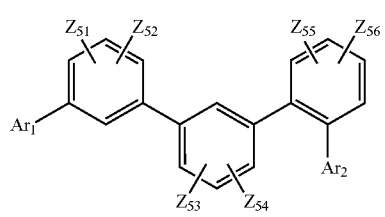
Formula H-1(30)
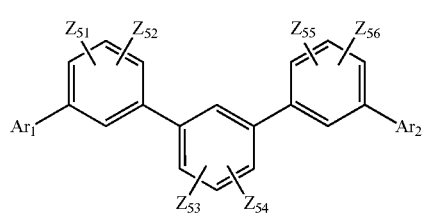
Formula H-1(31)
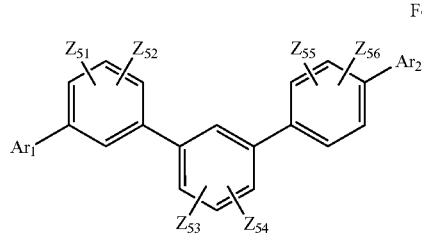
Formula H-1(32)
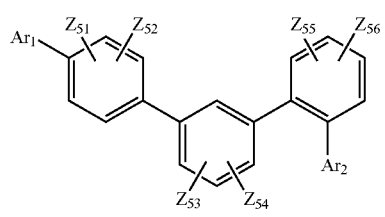
Formula H-1(33)
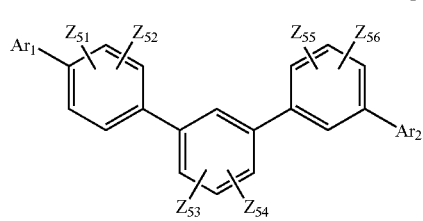
Formula H-1(34)
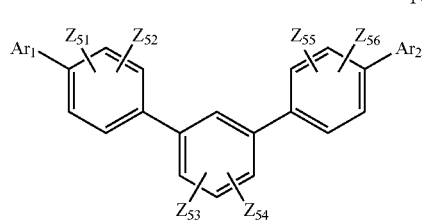
Formula H-1(35)
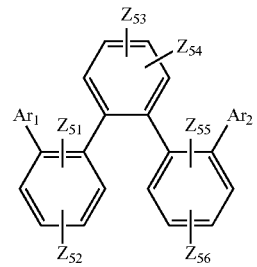
Formula H-1(36)
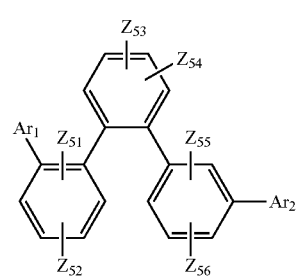
Formula H-1(37)
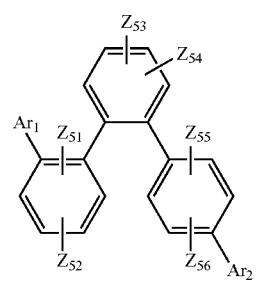
Formula H-1(38)
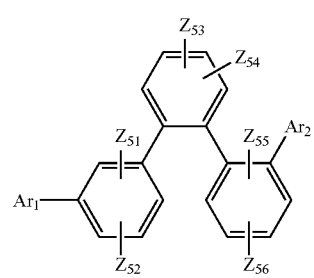
Formula H-1(39)
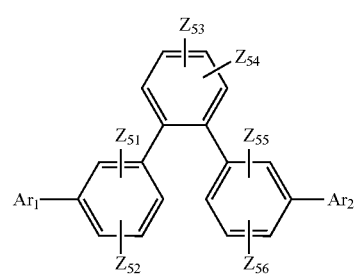
Formula H-1(40)

Formula H-1(41)
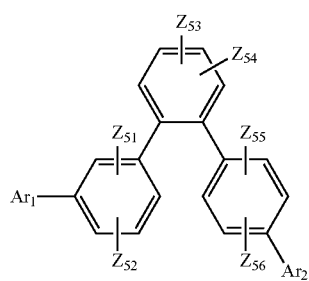
Formula H-1(42)
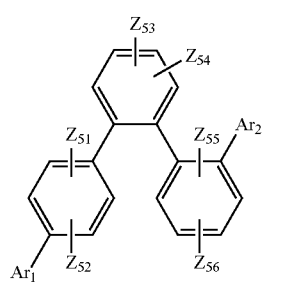
Formula H-1(43)
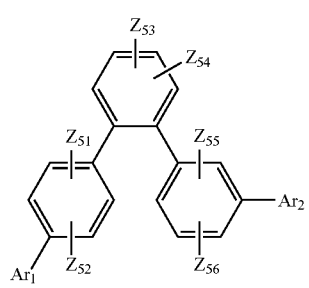
Formula H-1(44)
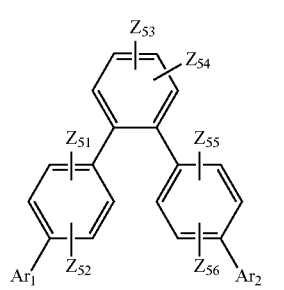
Formula H-1(45)
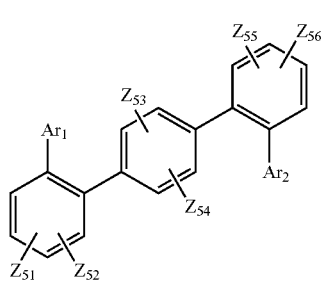
Formula H-1(46)
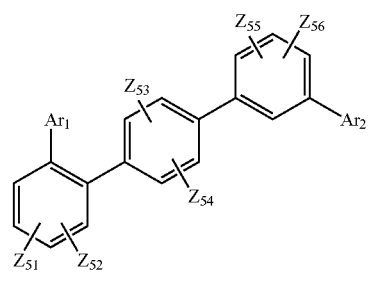
Formula H-1(47)
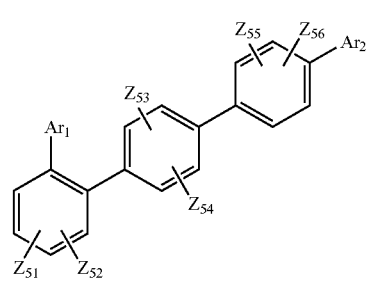
Formula H-1(48)
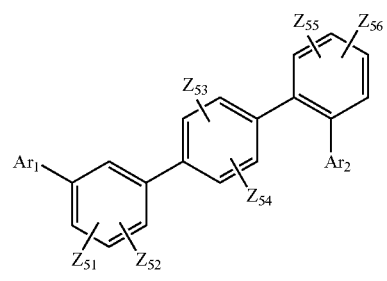
Formula H-1(49)
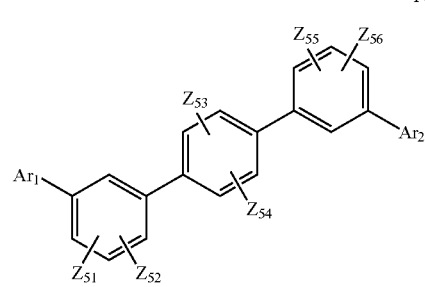
Formula H-1(50)
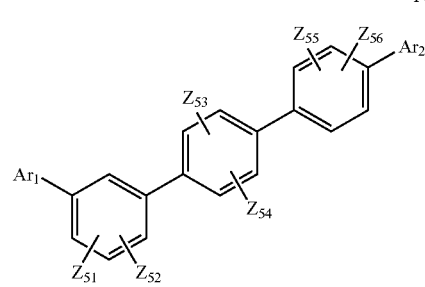

Formula H-1(51)

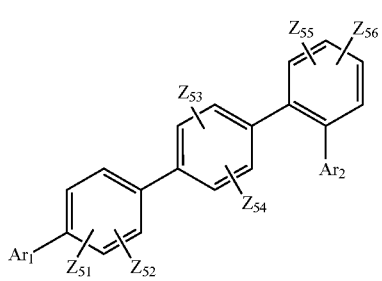

Formula H-1(52)

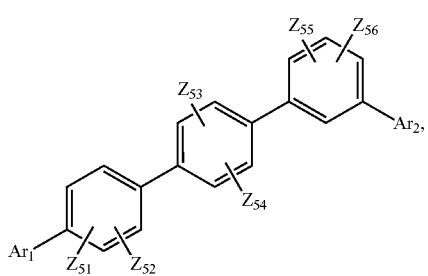

wherein, in Formulae H-1(1) to H-1(52),

Ar$_1$ and Ar$_2$ are each independently the same as defined in claim 14,

Y$_{51}$ is C(Z$_{53}$)(Z$_{54}$), N(Z$_{55}$), O, or S,

Z$_{51}$ to Z$_{56}$ are each independently selected from hydrogen, deuterium, a C$_1$-C$_{10}$ alkyl group, a C$_1$-C$_{10}$ alkoxy group, a phenyl group, a naphthyl group, a fluorenyl group, a carbazolyl group, a dibenzofuranyl group, a dibenzothiophenyl group, a biphenyl group, and —Si(Q$_{11}$)(Q$_{12}$)(Q$_{13}$), wherein Q$_{11}$ to Q$_{13}$ are each independently selected from hydrogen, a C$_1$-C$_{10}$ alkyl group, a C$_1$-C$_{10}$ alkoxy group, a phenyl group, and a naphthyl group.

17. The condensed cyclic compound of claim 13, wherein the second compound is selected from Compounds H-1 to H-32:

H-1

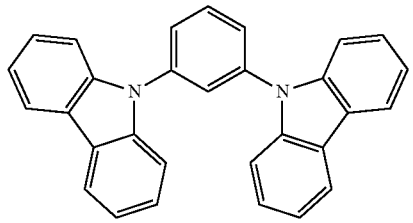

H-2

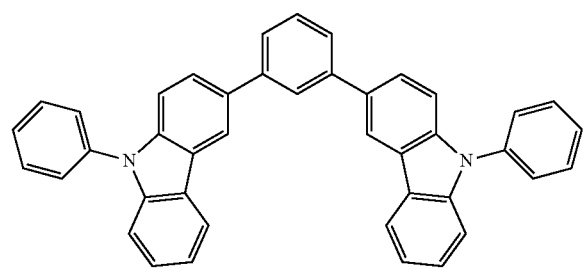

H-3

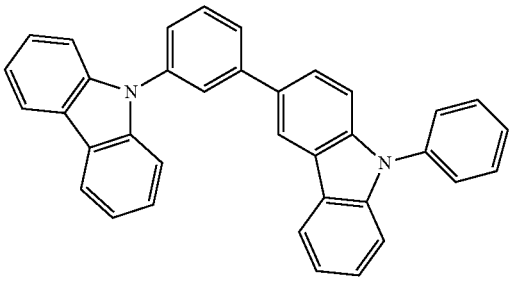

H-4

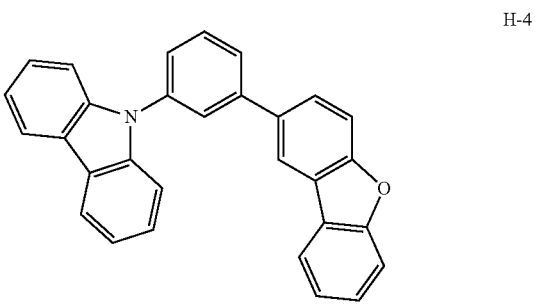

H-5

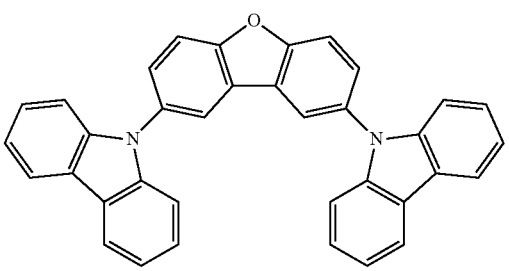

H-6

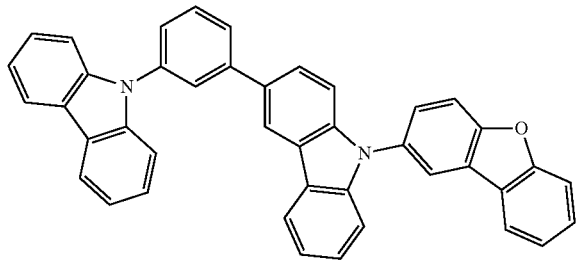

H-7

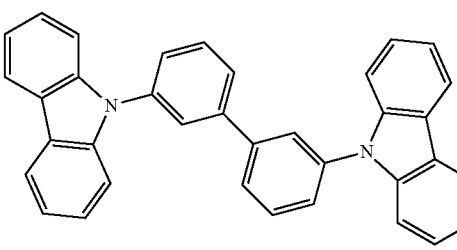

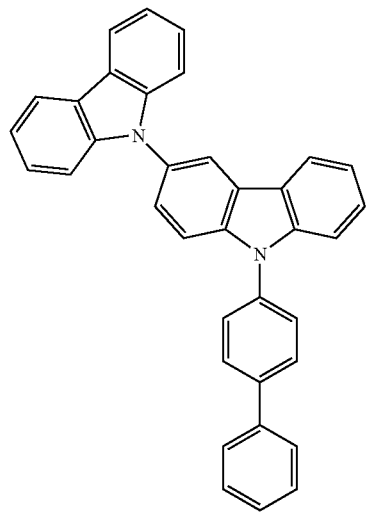
H-8
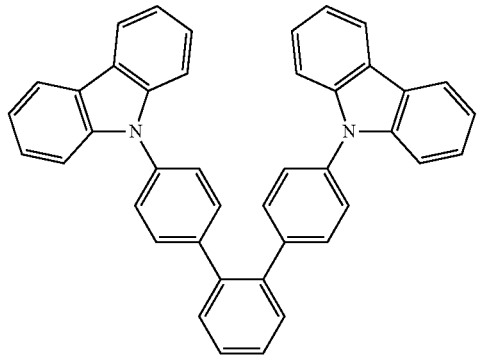
H-12
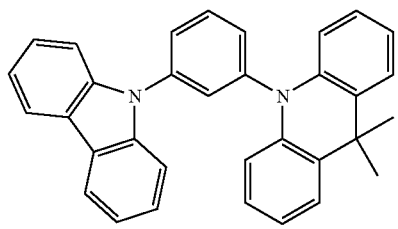
H-13
H-9
H-14
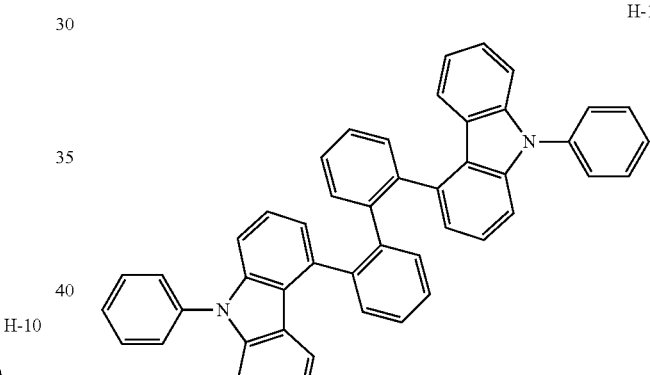
H-10
H-15
H-11
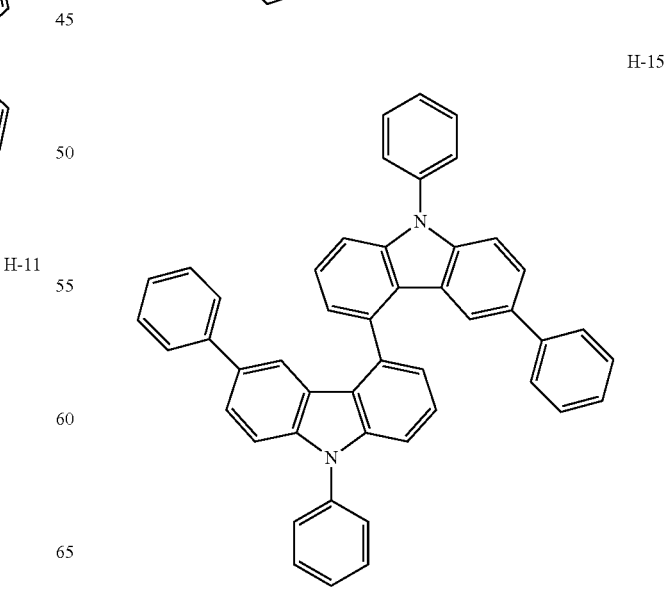

H-16
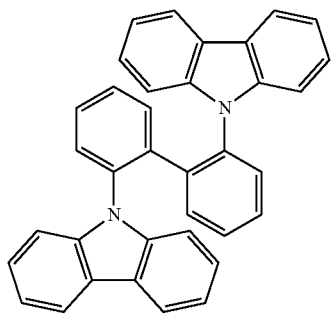
H-20
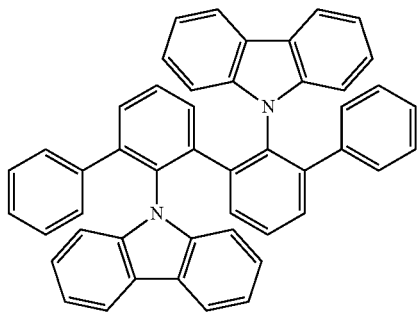
H-17
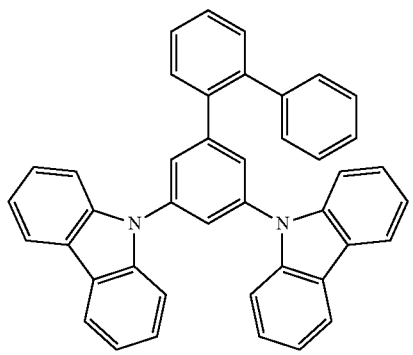
H-21
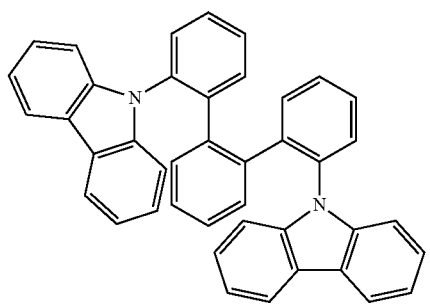
H-18
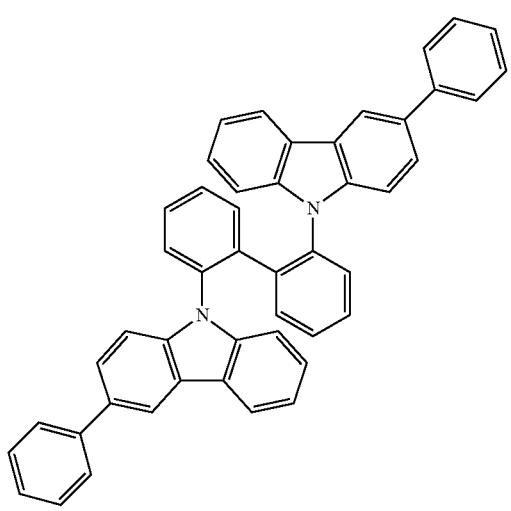
H-22
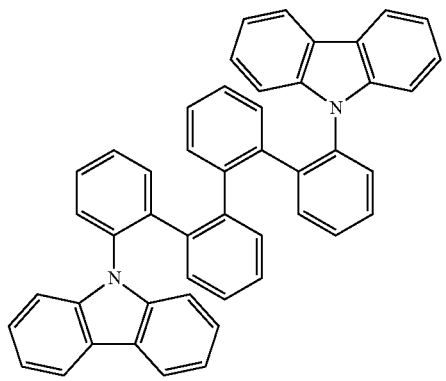
H-19
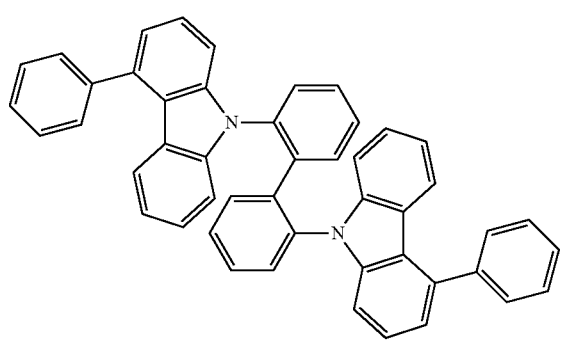
H-23
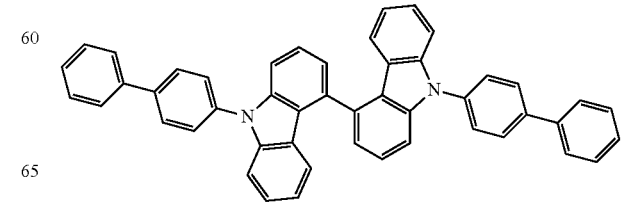

H-24
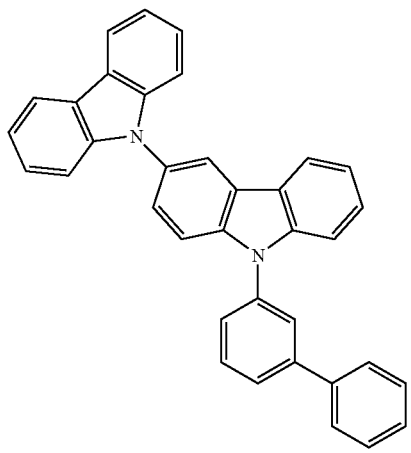
H-25
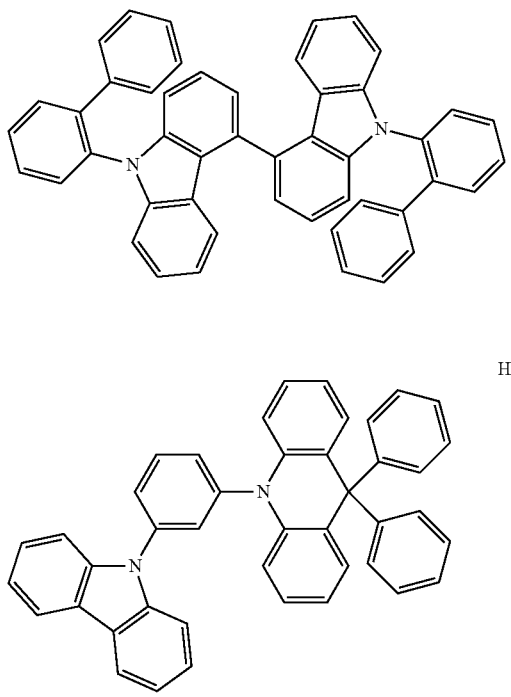
H-26
H-27
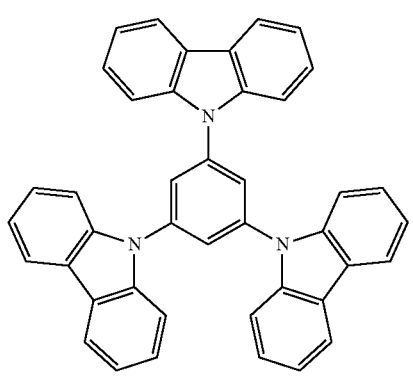
H-28
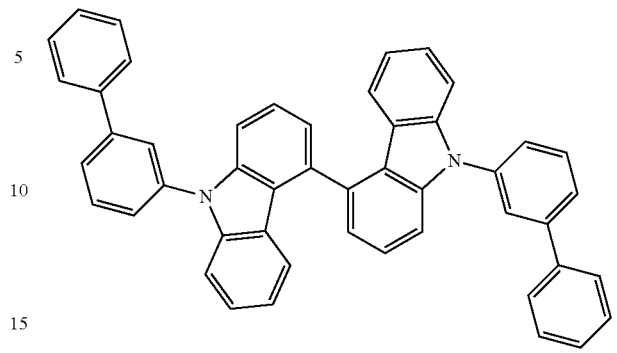
H-29
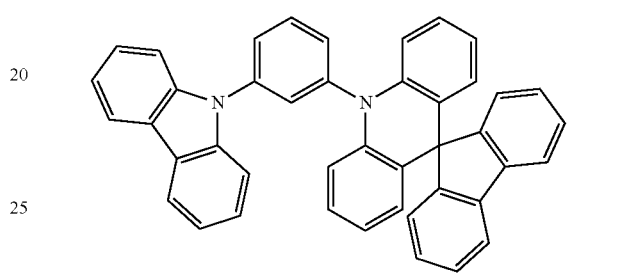
H-30
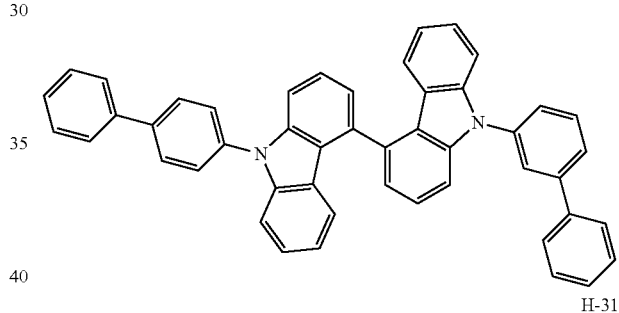
H-31
H-32
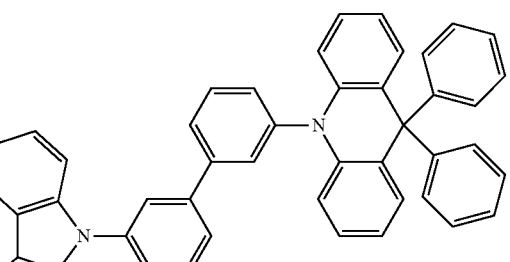

18. An organic light-emitting device comprising:
a first electrode;
a second electrode; and
an organic layer disposed between the first electrode and the second electrode,
wherein the organic layer comprises an emission layer, and
wherein the organic layer comprises the condensed cyclic compound represented by Formula 1 of claim 1.

19. The organic light-emitting device of claim 18, further comprising:
i) a second compound, wherein the second compound comprises at least one selected from a carbazole-containing ring, a dibenzofuran-containing ring, a dibenzothiophene-containing ring, an indenocarbazole-containing ring, an indolocarbazole-containing ring, a benzofurocarbazole-containing ring, a benzothienocarbazole-containing ring, an acridine-containing ring, a dihydroacridine-containing ring, and a triindolobenzene-containing ring and does not comprise an electron withdrawing group;
ii) an organometallic compound represented by Formula 81

$$M(L_{81})_{n81}(L_{82})_{n82};\ \text{or} \qquad \text{Formula 81}$$

iii) any combination thereof:

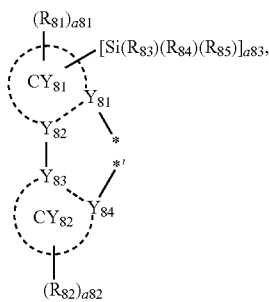

Formula 81A wherein, in Formulae 81 and 81A,
M is selected from iridium (Ir), platinum (Pt), osmium (Os), titanium (Ti), zirconium (Zr), hafnium (Hf), europium (Eu), terbium (Tb), thulium (Tm), and rhodium (Rh),
$L_{81}$ is a ligand represented by Formula 81A, and n81 is an integer selected from 1 to 3, wherein, when n81 is 2 or more, 2 or more $L_{81}$ are identical to or different from each other,
$L_{82}$ is an organic ligand, and n82 is an integer selected from 0 to 4, wherein, when n82 is 2 or more, 2 or more $L_{82}$ are identical to or different from each other,
$Y_{81}$ to $Y_{84}$ are each independently carbon (C) or nitrogen (N),
$Y_{81}$ and $Y_{82}$ are linked via a single bond or a double bond, and $Y_{83}$ and $Y_{84}$ are linked via a single bond or a double bond,
$CY_{81}$ and $CY_{82}$ are each independently selected from a $C_5$-$C_{30}$ carbocyclic group and a $C_3$-$C_{30}$ heterocarbocyclic group,
$CY_{81}$ and $CY_{82}$ are optionally further linked via an organic linking group,
$R_{81}$ to $R_{85}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q$_{81}$)(Q$_{82}$)(Q$_{83}$), —N(Q$_{84}$)(Q$_{85}$), —B(Q$_{86}$)(Q$_{87}$) and —P(=O)(Q$_{88}$)(Q$_{89}$),
a81 to a83 are each independently an integer selected from 0 to 5,
wherein, when a81 is 2 or more, 2 or more $R_{81}$ are identical to or different from each other; when a82 is 2 or more, 2 or more $R_{82}$ are identical to or different from each other; when a81 is 2 or more, 2 or more adjacent $R_{81}$ are optionally linked to each other to form a saturated or unsaturated $C_2$-$C_{30}$ ring or a saturated or unsaturated $C_2$-$C_{30}$ ring substituted with at least one $R_{88}$; when a82 is 2 or more, 2 or more adjacent $R_{82}$ are optionally linked to each other to form a saturated or unsaturated $C_2$-$C_{30}$ ring or a saturated or unsaturated $C_2$-$C_{30}$ ring substituted with at least one $R_{89}$,
$R_{88}$ is the same as defined in connection with $R_{81}$,
$R_{89}$ is the same as defined in connection with $R_{82}$,
and *' in Formula 81A each independently indicate a binding site to M of Formula 81,
at least one substituent selected from substituent(s) of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si(Q$_{91}$)(Q$_{92}$)(Q$_{93}$),
$Q_{81}$ to $Q_{89}$ and $Q_{91}$ to $Q_{93}$ are each independently selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and the electron withdrawing group is selected from:
—F, —$CFH_2$, —$CF_2H$, —$CF_3$, —CN, and —$NO_2$;
a $C_1$-$C_{60}$ alkyl group substituted with at least one selected from —F, —$CFH_2$, —$CF_2H$, —$CF_3$, —CN, and —$NO_2$;
a $C_1$-$C_{60}$ heteroaryl group and a monovalent non-aromatic condensed polycyclic heterocyclic group that each comprise *=N—*' as a ring-forming moiety; and
a $C_1$-$C_{60}$ heteroaryl group and a monovalent non-aromatic condensed polycyclic heterocyclic group that each comprises *=N—*' as a ring-forming moiety and are each substituted with at least one selected from deuterium, —F, —$CFH_2$, —$CF_2H$, —$CF_3$, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein "monovalent non-aromatic condensed polycyclic group" refers to a monovalent arm that has two or more rings condensed to each other, only carbon atoms as a ring forming atom, and which is non-aromatic in the entire molecular structure, and wherein "monovalent non-aromatic condensed heteropolycyclic group" refers to a monovalent group that has two or more rings condensed to each other, has a heteroatom selected from N, O, P, Si, and S, other than carbon atoms, as a ring-forming atom, and which is non-aromatic in the entire molecular structure.

20. The organic light-emitting device of claim 19, wherein $Y_{81}$ is N, $Y_{82}$ and $Y_{83}$ are each independently C, and $Y_{84}$ is N or C, $CY_{81}$ and $CY_{82}$ are each independently selected from a cyclopentadiene group, a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, a hexacene group, a pentacene group, a rubicene group, a corozene group, an ovalene group, a pyrrole group, an isoindole group, an indole group, an indazole group, a pyrazole group, an imidazole group, a triazole group, an oxazole group, an isoxazole group, an oxadiazole group, a thiazole group, an isothiazole group, thiadiazole group, a purine group, a furan group, a thiophene group, a pyridine group, a pyrimidine group, a quinoline group, an isoquinoline group, a benzoquinoline group, a phthalazine group, naphthyridine group, a quinoxaline group, a quinazoline group, a cinnoline group, a phenentrididine group, an acridine group, phenanthroline group, a phenazine group, a benzimidazole group, a benzofuran group, a benzothiophene group, an isobenzothiazole group, a benzoxazole group, an isobenzoxazole group, a benzocarbazole group, a dibenzocarbazole group, an imidazopyridine group, an imidazopyrimidine group, a dibenzofuran group, a dibenzothiophene group, a dibenzothiophene sulfone group, a carbazole group, a dibenzosilol group, and a 2,3-dihydro-1H-imidazole group, $R_{81}$ and $R_{82}$ are each independently selected from:
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B(Q$_{86}$)(Q$_{87}$) and —P(=O)(Q$_{88}$)(Q$_{89}$), and Q$_{86}$ to Q$_{89}$ are each independently selected from: —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group and a naphthyl group, each substituted with at least one selected from deuterium, a C$_1$-C$_{10}$ alkyl group, and a phenyl group.

21. The organic light-emitting device of claim 19, wherein, in Formula 81A, at least one selected from R$_{81}$ in the number of a81 and R$_{82}$ in the number of a82 is a cyano group or deuterium.

22. The organic light-emitting device of claim 19, wherein the emission layer comprises a host and a dopant, wherein i) the host comprises the condensed cyclic compound represented by Formula 1, and the dopant comprises the organometallic compound represented by Formula 81;

ii) the host comprises the condensed cyclic compound represented by Formula 1 and the second compound; or iii) the host comprises the condensed cyclic compound represented by Formula 1 and the second compound, and the dopant comprises the organometallic compound represented by Formula 81.

* * * * *